US011253839B2

(12) United States Patent
Terrian et al.

(10) Patent No.: US 11,253,839 B2
(45) Date of Patent: Feb. 22, 2022

(54) SHAPED POROUS CARBON PRODUCTS

(71) Applicant: Archer-Daniels-Midland Company, Decatur, IL (US)

(72) Inventors: Joshua Terrian, Lovington, IL (US); Andrew J. Ingram, Champaign, IL (US); Eric L. Dias, Belmont, CA (US); Alfred Hagemeyer, Sunnyvale, CA (US); Hong X. Jiang, Palo Alto, CA (US); James Longmire, San Jose, CA (US); James A. W. Shoemaker, Gilroy, CA (US); Valery Sokolovskii, Santa Clara, CA (US); Guang Zhu, Union City, CA (US); Vincent J. Murphy, San Jose, CA (US); Gary M. Diamond, Menlo Park, CA (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 16/877,222

(22) Filed: May 18, 2020

(65) Prior Publication Data
US 2020/0346188 A1 Nov. 5, 2020

Related U.S. Application Data

(60) Continuation-in-part of application No. 16/520,869, filed on Jul. 24, 2019, now Pat. No. 10,654,027,
(Continued)

(51) Int. Cl.
*C04B 35/638* (2006.01)
*C04B 38/06* (2006.01)
(Continued)

(52) U.S. Cl.
CPC ............... *B01J 21/18* (2013.01); *B01J 23/40* (2013.01); *B01J 23/42* (2013.01); *B01J 23/52* (2013.01);
(Continued)

(58) Field of Classification Search
CPC .................................................. C07C 29/132
(Continued)

(56) References Cited

U.S. PATENT DOCUMENTS 2,382,586 A 8/1945 Solomon et al.
2,719,779 A 1/1950 Bray et al.
(Continued)

FOREIGN PATENT DOCUMENTS

CN 101102904 A 1/2008
CN 101147847 A 3/2008
(Continued)

OTHER PUBLICATIONS

Dasari, M.A., et al., "Low-pressure hydrogenolysis of glycerol to propylene glycol," Applied Catalysis A: General, vol. 281, pp. 225-231. (Year: 2005).*
(Continued)

*Primary Examiner* — Patricia L. Hailey
(74) *Attorney, Agent, or Firm* — Stinson LLP

(57) ABSTRACT

Shaped porous carbon products and processes for preparing these products are provided. The shaped porous carbon products can be used, for example, as catalyst supports and adsorbents. Catalyst compositions including these shaped porous carbon products, processes of preparing the catalyst compositions, and various processes of using the shaped porous carbon products and catalyst compositions are also provided.

26 Claims, 17 Drawing Sheets

Related U.S. Application Data which is a division of application No. 15/996,756, filed on Jun. 4, 2018, now Pat. No. 10,384,192, which is a division of application No. 15/441,732, filed on Feb. 24, 2017, now Pat. No. 9,993,802, which is a division of application No. 14/699,942, filed on Apr. 29, 2015, now Pat. No. 9,682,368.

(60) Provisional application No. 61/985,988, filed on Apr. 29, 2014, provisional application No. 61/986,009, filed on Apr. 29, 2014.

(51) Int. Cl.

| | |
|---|---|
| C09C 1/48 | (2006.01) |
| C09C 1/56 | (2006.01) |
| B01J 35/04 | (2006.01) |
| C04B 111/00 | (2006.01) |
| B01J 23/06 | (2006.01) |
| B01J 23/18 | (2006.01) |
| B01J 23/22 | (2006.01) |
| B01J 23/28 | (2006.01) |
| B01J 23/34 | (2006.01) |
| B01J 23/70 | (2006.01) |
| B01J 23/755 | (2006.01) |
| B01J 21/18 | (2006.01) |
| C07C 29/60 | (2006.01) |
| B01J 37/10 | (2006.01) |
| B01J 37/00 | (2006.01) |
| B01J 37/02 | (2006.01) |
| B01J 35/10 | (2006.01) |
| B01J 35/00 | (2006.01) |
| B01J 35/02 | (2006.01) |
| B01J 23/40 | (2006.01) |
| B01J 37/08 | (2006.01) |
| B01J 23/42 | (2006.01) |
| B01J 23/52 | (2006.01) |
| B01J 23/656 | (2006.01) |
| B01J 23/89 | (2006.01) |
| C07C 29/149 | (2006.01) |
| C07C 209/16 | (2006.01) |
| C04B 35/532 | (2006.01) |
| C07C 51/235 | (2006.01) |
| C07C 51/377 | (2006.01) |
| C04B 35/636 | (2006.01) |

(52) U.S. Cl.
CPC ......... *B01J 23/6567* (2013.01); *B01J 23/892* (2013.01); *B01J 35/002* (2013.01); *B01J 35/008* (2013.01); *B01J 35/0086* (2013.01); *B01J 35/023* (2013.01); *B01J 35/04* (2013.01); *B01J 35/1014* (2013.01); *B01J 35/1019* (2013.01); *B01J 35/1023* (2013.01); *B01J 35/1038* (2013.01); *B01J 35/1042* (2013.01); *B01J 35/1061* (2013.01); *B01J 35/1066* (2013.01); *B01J 37/0009* (2013.01); *B01J 37/0018* (2013.01); *B01J 37/0201* (2013.01); *B01J 37/0215* (2013.01); *B01J 37/084* (2013.01); *B01J 37/10* (2013.01); *C04B 35/532* (2013.01); *C04B 35/636* (2013.01); *C04B 35/638* (2013.01); *C04B 35/6365* (2013.01); *C04B 38/0615* (2013.01); *C07C 29/149* (2013.01); *C07C 29/60* (2013.01); *C07C 51/235* (2013.01); *C07C 51/377* (2013.01); *C07C 209/16* (2013.01); *C09C 1/48* (2013.01); *C09C 1/56* (2013.01); *B01J 23/06* (2013.01); *B01J 23/18* (2013.01); *B01J 23/22* (2013.01); *B01J 23/28* (2013.01); *B01J 23/34* (2013.01); *B01J 23/70* (2013.01); *B01J 23/755* (2013.01); *B01J 35/1085* (2013.01); *C04B 2111/0081* (2013.01); *C04B 2235/424* (2013.01); *C04B 2235/5409* (2013.01); *C04B 2235/6586* (2013.01); *C04B 2235/96* (2013.01)

(58) Field of Classification Search
USPC .......................................................... 568/861
See application file for complete search history.

(56) References Cited

U.S. PATENT DOCUMENTS

| | | | |
|---|---|---|---|
| 2,754,330 | A | 7/1956 | Schreyer |
| 2,850,403 | A | 9/1958 | Day et al. |
| 3,127,356 | A | 3/1964 | Hamilton et al. |
| 3,171,720 | A | 3/1965 | Shea, Jr. et al. |
| 3,268,588 | A | 8/1966 | Horlenko et al. |
| 3,270,059 | A | 8/1966 | Winderl et al. |
| 3,329,626 | A | 7/1967 | Teter et al. |
| 3,413,152 | A | 11/1968 | Folkins et al. |
| 3,859,421 | A | 1/1975 | Hucke |
| 3,978,000 | A | 8/1976 | Schmitt, Jr. et al. |
| 4,029,600 | A | 6/1977 | Schmitt, Jr. et al. |
| 4,031,137 | A | 6/1977 | Schmitt, Jr. et al. |
| 4,035,260 | A | 7/1977 | Schmitt, Jr. et al. |
| 4,399,052 | A | 8/1983 | Sugino |
| 4,591,578 | A | 5/1986 | Foley et al. |
| 4,777,303 | A | 10/1988 | Kitson et al. |
| 4,804,791 | A | 2/1989 | Kitson et al. |
| 5,015,773 | A | 5/1991 | Dobson |
| 5,149,680 | A | 9/1992 | Kitson et al. |
| 5,472,648 | A | 12/1995 | Alisch et al. |
| 5,478,952 | A | 12/1995 | Schwartz |
| 5,726,118 | A | 3/1998 | Ivey et al. |
| 5,736,481 | A | 4/1998 | Miller et al. |
| 5,846,639 | A | 12/1998 | Robinson et al. |
| 5,872,177 | A | 2/1999 | Whitehouse |
| 5,916,838 | A | 6/1999 | Wulff-Döring et al. |
| 5,958,825 | A | 9/1999 | Wulff-Döring et al. |
| 6,180,738 | B1 | 1/2001 | Wang et al. |
| 6,207,264 | B1 | 3/2001 | Robinson et al. |
| 6,258,864 | B1 | 7/2001 | Dalton et al. |
| 6,337,302 | B1 | 1/2002 | Teng et al. |
| 6,471,763 | B1 | 10/2002 | Karl |
| 6,479,713 | B1 | 11/2002 | Werpy et al. |
| 6,500,401 | B2 | 12/2002 | Reznek et al. |
| 6,573,212 | B2 | 6/2003 | McCrae et al. |
| 6,682,667 | B1 | 1/2004 | Matviya |
| 6,787,029 | B2 | 9/2004 | Gaudet et al. |
| 6,989,348 | B2 | 1/2006 | Eijsbouts |
| 6,992,037 | B2 | 1/2006 | Chen et al. |
| 7,008,534 | B2 | 3/2006 | Gaudet et al. |
| 7,195,713 | B2 | 3/2007 | Gaudet et al. |
| 7,358,004 | B2 | 4/2008 | Igarashi et al. |
| 7,651,772 | B2 | 1/2010 | Lee |
| 7,754,922 | B2 | 7/2010 | Kubanek et al. |
| 7,790,937 | B2 * | 9/2010 | Henkelmann ........... C07C 67/03 568/861 |
| 7,906,453 | B2 | 3/2011 | Ezenyilimba et al. |
| 7,922,805 | B2 | 4/2011 | Kowalski et al. |
| 7,928,148 | B2 | 4/2011 | Bloom |
| 7,951,297 | B2 | 5/2011 | Gaudet et al. |
| 8,501,989 | B2 | 8/2013 | Boussie et al. |
| 8,585,816 | B2 | 11/2013 | Shim et al. |
| 8,657,483 | B2 | 2/2014 | Nebergall et al. |
| 8,669,393 | B2 | 3/2014 | Boussie et al. |
| 8,669,397 | B2 | 3/2014 | Boussie et al. |
| 8,728,223 | B2 | 5/2014 | Shim et al. |
| 8,759,250 | B2 | 6/2014 | Robinson et al. |
| 8,759,253 | B2 | 6/2014 | De Leede et al. |
| 8,785,683 | B2 | 7/2014 | Boussie et al. |
| 9,682,368 | B2 | 6/2017 | Dias et al. |
| 9,993,802 | B2 | 6/2018 | Dias et al. |
| 10,384,192 | B2 | 8/2019 | Dias et al. |

(56) References Cited

U.S. PATENT DOCUMENTS

| | | |
|---|---|---|
| 10,464,048 B2 | 11/2019 | Sokolovskii et al. |
| 10,654,027 B2 | 5/2020 | Dias et al. |
| 10,722,867 B2 | 7/2020 | Diamond et al. |
| 10,722,869 B2 | 7/2020 | Sokolovskii et al. |
| 2002/0077504 A1 | 6/2002 | Albers et al. |
| 2003/0042205 A1 | 3/2003 | Gaudet et al. |
| 2003/0060361 A1 | 3/2003 | Chen et al. |
| 2003/0118581 A1 | 6/2003 | Sonobe et al. |
| 2003/0157014 A1 | 8/2003 | Wang et al. |
| 2003/0161781 A1 | 8/2003 | Cabasso et al. |
| 2003/0215640 A1 | 11/2003 | Ackerman et al. |
| 2004/0028901 A1 | 2/2004 | Rumpf et al. |
| 2004/0118287 A1 | 6/2004 | Jaffe et al. |
| 2004/0219363 A1 | 11/2004 | Schuch et al. |
| 2005/0150835 A1 | 7/2005 | Vo |
| 2005/0207962 A1 | 9/2005 | Dietz et al. |
| 2005/0247635 A1 | 11/2005 | Vo et al. |
| 2007/0203284 A1 | 8/2007 | Schuch et al. |
| 2007/0265161 A1 | 11/2007 | Gadkaree et al. |
| 2007/0287845 A1 | 12/2007 | Lilga et al. |
| 2008/0031972 A1 | 2/2008 | Sonobe et al. |
| 2008/0063591 A1 | 3/2008 | Im et al. |
| 2008/0132408 A1 | 6/2008 | Mitchell et al. |
| 2009/0208751 A1 | 8/2009 | Green et al. |
| 2009/0209418 A1 | 8/2009 | Watanabe et al. |
| 2010/0069507 A1 | 3/2010 | Tabata et al. |
| 2010/0173772 A1 | 7/2010 | Robinson et al. |
| 2010/0212495 A1 | 8/2010 | Gadkaree et al. |
| 2010/0298134 A1 | 11/2010 | De Leede et al. |
| 2011/0011414 A1 | 1/2011 | Hummel et al. |
| 2011/0175024 A1 | 7/2011 | Lang et al. |
| 2011/0244012 A1 | 10/2011 | Iida et al. |
| 2011/0306790 A1 | 12/2011 | Murphy et al. |
| 2012/0007027 A1 | 1/2012 | Istvan et al. |
| 2012/0204719 A1 | 8/2012 | Dubois-Brugger et al. |
| 2012/0289755 A1 | 11/2012 | Kato et al. |
| 2012/0292794 A1 | 11/2012 | Prabhu et al. |
| 2013/0211146 A1 | 8/2013 | Menne et al. |
| 2013/0295462 A1 | 11/2013 | Atanassova et al. |
| 2013/0310253 A1 | 11/2013 | Tabata et al. |
| 2013/0310605 A1 | 11/2013 | Salem et al. |
| 2013/0281581 A1 | 12/2013 | Wong et al. |
| 2014/0011666 A1 | 1/2014 | Yoshizaki et al. |
| 2014/0037536 A1 | 2/2014 | Reimerink-Schats et al. |
| 2014/0120339 A1 | 5/2014 | Nikova et al. |
| 2014/0267515 A1 | 9/2014 | Zhang et al. |
| 2014/0287306 A1 | 9/2014 | Takeshi et al. |
| 2015/0041708 A1 | 2/2015 | Wiesner et al. |
| 2015/0314273 A1 | 11/2015 | Paulus et al. |
| 2015/0321175 A1 | 11/2015 | Ohtake et al. |
| 2017/0120219 A1 | 5/2017 | Diamond et al. |
| 2017/0120233 A1 | 5/2017 | Sokolovskii et al. |
| 2017/0016564 A1 | 6/2017 | Dias et al. |
| 2020/0338530 A1 | 10/2020 | Diamond et al. |
| 2020/0353449 A1 | 11/2020 | Sokolovskii et al. |

FOREIGN PATENT DOCUMENTS

| | | |
|---|---|---|
| CN | 101385966 A | 3/2009 |
| CN | 102078753 A | 6/2011 |
| CN | 102701183 A | 10/2012 |
| CN | 103107319 A | 5/2013 |
| CN | 103638921 A | 3/2014 |
| CN | 103663450 A | 3/2014 |
| CN | 103848802 A | 11/2014 |
| DE | 202006001770 U1 | 2/2007 |
| EP | 0484176 A1 | 5/1992 |
| EP | 0729785 A1 | 9/1996 |
| EP | 0862596 B1 | 6/2001 |
| EP | 2003201417 A | 7/2003 |
| EP | 0815566 B1 | 6/2006 |
| EP | 1757362 A1 | 2/2007 |
| EP | 1567602 B1 | 8/2007 |
| EP | 2045223 A1 | 4/2009 |
| EP | 2060535 A1 | 5/2009 |
| EP | 2308591 A1 | 4/2011 |
| EP | 2429020 A1 | 3/2012 |
| EP | 2478957 A1 | 7/2012 |
| EP | 2497751 A1 | 9/2012 |
| EP | 2674214 A1 | 12/2013 |
| EP | 2728407 A1 | 5/2014 |
| GB | 828206 | 2/1960 |
| GB | 1045694 | 10/1996 |
| JP | 60225639 A | 4/1985 |
| JP | H0549921 A | 3/1993 |
| JP | H072951 B2 | 1/1995 |
| JP | H11100524 A | 4/1999 |
| JP | 3746509 B1 | 2/2006 |
| JP | 2007284337 A | 11/2007 |
| JP | 2010269994 A | 12/2010 |
| JP | 2011042569 A | 3/2011 |
| JP | 2014072497 A | 4/2014 |
| JP | 5629578 B2 | 11/2014 |
| WO | 9621698 | 7/1996 |
| WO | 9747691 A1 | 12/1997 |
| WO | 9912641 A1 | 3/1999 |
| WO | 9923174 A1 | 5/1999 |
| WO | 9931175 A1 | 6/1999 |
| WO | 9951690 A1 | 10/1999 |
| WO | 9963007 A1 | 12/1999 |
| WO | 2000022051 A1 | 4/2000 |
| WO | 2002018929 A1 | 3/2002 |
| WO | 2002072258 A1 | 9/2002 |
| WO | 02083559 A1 | 10/2002 |
| WO | 03009927 A1 | 2/2003 |
| WO | 03020639 A1 | 3/2003 |
| WO | 03041847 A1 | 5/2003 |
| WO | 03070662 A1 | 8/2003 |
| WO | 03072352 A1 | 9/2003 |
| WO | 03072640 A2 | 9/2003 |
| WO | 2003099940 A1 | 12/2003 |
| WO | 2004076360 A1 | 9/2004 |
| WO | 2007070455 A1 | 6/2007 |
| WO | 2008051540 A2 | 2/2008 |
| WO | 2008133520 A1 | 11/2008 |
| WO | 2009011590 A1 | 1/2009 |
| WO | 2009088540 A1 | 7/2009 |
| WO | 2009105172 A2 | 8/2009 |
| WO | 2010008072 A1 | 1/2010 |
| WO | 2010144862 A2 | 12/2010 |
| WO | 2012102610 A1 | 8/2012 |
| WO | 2013045894 A1 | 4/2013 |
| WO | 2014070987 A1 | 5/2014 |
| WO | 2014091447 A1 | 6/2014 |
| WO | 2014141619 A1 | 9/2014 |
| WO | 2015164088 A1 | 10/2015 |
| WO | 2017011615 A1 | 1/2017 |

OTHER PUBLICATIONS

Connor, R., et al., "Hydrogenolysis of oxygenated organic compounds," J. Am. Chem. Soc., vol. 54, pp. 4678-4690. (Year: 1932).*

Chaminand, J., et al., "Glycerol hydrogenolysis on heterogeneous catalysts," Green Chem., vol. 6, pp. 359-361. (Year: 2004).*

Antolini, E., "Carbon Supports for Low-Temperature Fuel Cell Catalysts," 2009, Applied Catalysis B: Enviommental 88:1-24.

Barrett, E.P., et al., "The Determination of Pore Volume and Area Distributions in Porous Substances. I. Computations from Nitrogen Isotherms," 1951, The Volume and Area Distributions in Porous Substances, 373-380.

Brunauer, S., et al., "Adsorption of Gases in Multimolecular Layers," 1938, JACS, 60:309-319.

Dapsens, P.Y, et al., "Biobased Chemicals from Conception Toward Industrial Reality: Lessons Learned and To Be Learned," 2012, ACS Catal, 2:1487-1499.

Gerspacher, M., DR., "Furnace Black Characterization," Presentation at the Non-Platinum Electrocatalysts Workshop held Mar. 21-22, 2003 in New Orleans, Louisiana, Sid Richardson Carbon Co., Fort Worth, Texas, 19 pages.

Haber, J., "Manual on Catalyst Characterization," 1991, International Union of Pure and Applied Chemistry, Physical Chemistry

(56) References Cited

OTHER PUBLICATIONS

Division Commission on Colloid and Surfactant Chemistry Including Catalysis, Subcommittee on Catalyst Characterization, Pure & Appl Chem, 63/9:1227-1246.
Hidayu, A.R., et al., "Characterization of Activitated Carbon Prepared from Oil Palm Empty Fruit Bunch Using BET and FT-IR Techniques," 2013, Procedia Engineering, 68: 379-387.
Kishimoto, H., et al., "Amorphous Alloy Electrodes for Electrooxidation of Propane," 1995, Sci Rep RITU A41, 83-88, 6 pages.
Kruk, M., et al., "Well-Defined Polyethylene Oxide-Polyacrylonitrile Di-Block Copolymers as Templates for Meso Porous Silicas and Precursors for Meso Porous Carbons," 2006 Chem Mater, 18/6:1417-1424.
Liu, D., et al., "Preparation of Activated Carbon Aerogels with Hierarchically Porous Structures for Electrical Double Layer Capacitors, 2013," Electrochimica Acta, 89:571-576.
Norman, D.T., "Rubber Grade Carbon Blacks," Witco Coporation, Concarb Division, Houston, Texas, 2001, 19 pages.
Walker, P.L. Jr., "Carbon—A Versatile Catalyst Support," 1978, Fifth London International Carbon and Graphite Conference, Imperial College, London, Sep. 18-22, 1978, vol. 3, 10 pages.
Yang, C-M., et al., "Desalination Effects of Capacitive Deionization Process with Porous Carbon-Nano Materials," 2004, Kongop Hwahak, 15/3:294-299 (CAPLUS Abstract Only).
Handbook of Pharmaceutical Catalysis, Johnson Matthey Catalysts, 2009, Johnson Matthey Plc, 108 pages.
IARC Monographs on the Evaluation of Carcinogenic Risks to Humans, vol. 93, Carbon Black, Titanium Dioxide, and Talc, World Health Organization, 2010, pp. 43-191.
Insights on Carbon Black Fundamentals, 2006, 8 pages, obtained from www.moderndispersions.com/CARBON_20BLACK_20FUNDAMENTALS.pdf.
English Language Abstract of JPS62223125A, 1987, 1 page.
English Language Abstract of JPS5818418A, 1983, 2 pages.
WO2007132936a1, English Language Abstract, 2007, 1 page.
International Search Report issued in PCT/US2015/028358, dated Aug. 12, 2015, 5 pages.
Written Opinion issued in PCT/US2015/028358, dated Aug. 12, 2015, 20 pages.
Patent Abstracts of Japan, JPS60-225639, published Nov. 9, 1985, 1 page.
Bathey, B.R., et al., "Review Solar-Grade Silicon," 1982, J Mat Sci, 17:3077-3096, 20 pages.
Bin, D., et al., "Controllable Oxidation of Glucose to Gluconic Acid and Glucaric Acid Using an Electrocatalytic Reactor," 2014, Electrochimica Acta, 130:170-178. 9 pages.
Colmenares, J.C., et al., Heterogeneous Photocatalytic Nanomaterials: Prospects and Challenges in Selective Transformations of Biomass-Derived Compounds, 2014, Chem Soc Rev, 765-778, 14 pages.
Delidovich, I.V., et al., Selective Oxidation of Glucose Over Carbon-Supported Pd and Pt Catalysts, 2010, Catal Lett, 140:14-21, 8 pages.
Önal, Y., et al., "Structure Sensitivity and Kinetics of D-Glucose Oxidation to D-Gluconic Acid Over Carbon-Supported Gold Catalysts," 2004, J Catalysis, 223:122-133. 12 pages.
Sokhi, R.S., et al., "PIXE Analysis of Carbon Black for Elemental Impurities," Nuclear Instruments & Methods in Physics, vol. B49 (1990), 414-417, 4 pages.

\* cited by examiner

Cross Sectional Analysis of a 1.5 mm Carbon Black Extrudate Catalyst

Platinum/Gold reside as a shell on the external surface of the extrudate

Cross Sectional Analysis of a 1.5 mm Carbon Black Extrudate Catalyst

Shell thickness ~ 100 μm

FIG. 15

```
Counts/pixel              Area      SE   Ni-KA  Re-MA
5 Ni 1 Re on Clone 7 1    165    23166      8      3
5 Ni 1 Re on Clone 7 2    165    22820      1      1
5 Ni 1 Re on Clone 7 3    304    23110      7      3
5 Ni 1 Re on Clone 7 4    240    23005     10      3
5 Ni 1 Re on Clone 7 5    380    23039     14      2
5 Ni 1 Re on Clone 7 6    135    23808      1      1
```

FIG. 17

```
Counts/pixel                        Area      SE  Ni-KA  Re-MA
5 Ni 1 Re on Clone 7 Nitric 1        160   24766      2      1
5 Ni 1 Re on Clone 7 Nitric 2        180   23949      0      1
5 Ni 1 Re on Clone 7 Nitric 3        252   23146      0      1
5 Ni 1 Re on Clone 7 Nitric 4         72   24328      2      1
5 Ni 1 Re on Clone 7 Nitric 5        154   35115      0      0
5 Ni 1 Re on Clone 7 Nitric 6        147   24952      5      1
```

SHAPED POROUS CARBON PRODUCTS

REFERENCE TO RELATED APPLICATIONS

This application is continuation-in-part of U.S. non-provisional application Ser. No. 16/520,869, filed Jul. 24, 2019, now U.S. Pat. No. 10,654,027, issued May 19, 2020, which is a division of U.S. non-provisional application Ser. No. 15/996,756, filed Jun. 4, 2018, now U.S. Pat. No. 10,384,192, issued Aug. 20, 2019, which is a division of U.S. non-provisional application Ser. No. 15/441,732, filed Feb. 24, 2017, now U.S. Pat. No. 9,993,802, issued Jun. 12, 2018, which is a division of U.S. non-provisional application Ser. No. 14/699,942, filed Apr. 29, 2015, now U.S. Pat. No. 9,682,368, issued Jun. 20, 2017, and claims priority to U.S. provisional applications Ser. Nos. 61/985,988 and 61/986,009, both filed Apr. 29, 2014, the entire disclosures of which are incorporated herein by reference.

FIELD OF THE INVENTION

The present invention generally relates to shaped porous carbon products and processes for preparing these products. The shaped porous carbon products can be used, for example, as catalyst supports, chromatographic support material, filtration media and adsorbents. The present invention also relates to catalyst compositions including these shaped porous carbon products, processes of preparing the catalyst compositions, and various processes of using the shaped porous carbon products and the catalyst compositions.

BACKGROUND OF THE INVENTION

Carbon is a material that can be deployed as a catalyst support or adsorbent. The most commonly used carbon based supports for chemical catalysis are activated carbons exhibiting high specific surface areas (e.g., over 500 $m^2/g$). Preparing activated carbon requires activating a carbonaceous material such as charcoal, wood, coconut shell or petroleum-sourced carbon black either by a chemical activation, such as contacting with an acid at high temperatures, or by steam activation. Both methods of activation produce high concentrations of micropores and consequently higher surface areas. Depending upon the source of the carbonaceous material, the resultant activated carbons may have a high residual content of inorganic ash and sulfur, and possibly oxygen or nitrogen-containing functional groups at the surface. Activated carbons are thought to possess an optimum support structure for catalytic applications as they enable good dispersion of catalytically active components and effective adsorption and reaction of chemical reagents at the catalyst surface.

In recent years, there has been a growing interest in using biorenewable materials as a feedstock to replace or supplement crude oil. See, for example, Klass, Biomass for Renewable Energy, Fuels, and Chemicals, Academic Press, 1998. This publication and all other cited publications are incorporated herein by reference. One of the major challenges for converting biorenewable resources such as carbohydrates (e.g., glucose derived from starch, cellulose or sucrose) to current commodity and specialty chemicals is the selective removal of oxygen atoms from the carbohydrate. Approaches are known for converting carbon-oxygen single bonds to carbon-hydrogen bonds. See, for example, U.S. Pat. No. 8,669,397, which describes a process for the conversion of glucose to adipic acid via the intermediate glucaric acid. One challenging aspect associated with the catalytic conversions of highly functionalized biorenewably-derived molecules and intermediates is reaching the high levels of catalytic activity, selectivity and stability necessary for commercial applications. With respect to catalytic activity and selectivity, highly functionalized, biorenewably-derived molecules and intermediates derived from carbohydrates (e.g., glucose and glucaric acid) are non-volatile and must therefore be processed as solutions in the liquid phase. When compared to gas phase catalytic processes, liquid phase catalytic processes are known to suffer from lower productivities because liquid to solid (and gas to liquid to solid) diffusion rates are slower than gas to solid diffusion rates.

Another challenging aspect associated with the catalytic conversion of highly functionalized biorenewably-derived molecules and intermediates is the use of chemically aggressive reaction conditions. For example, U.S. Pat. No. 8,669,397 describes catalytic conversion steps performed at elevated temperatures in the presence of polar solvents such as water and acetic acid. Polar solvents are typically required for the dissolution of non-volatile, highly-functionalized molecules such as glucose and glucaric acid, and elevated temperatures are required for productive and affordable catalytic conversion steps for commodity chemical applications. Therefore, a significant challenge associated with the catalytic conversion of highly functionalized biorenewably-derived molecules and intermediates is catalyst stability. Long term catalyst stability is a necessity for commodity chemical production, meaning that the catalyst must be stable, productive, and selective under reaction conditions for long periods.

The challenges associated with the development of industrial shaped catalysts, especially in the conversion of biorenewably-derived molecules and intermediates, are a) high productivity and selectivity consistent with an economically viable catalyst at industrial scale, b) mechanical and chemical stability of the shaped catalyst support and c) retention of the catalytically active components by the support and the avoidance of leaching of the catalytically active components into a polar solvent reaction medium. There remains a need for industrially scalable, highly active, selective and stable catalyst supports and catalyst compositions that can satisfy these challenges.

SUMMARY OF THE INVENTION

Briefly, in various aspects, the present invention is directed to shaped porous carbon products. In accordance with various embodiments, the shaped porous carbon products comprise carbon black and a carbonized binder comprising a carbonization product of a water soluble organic binder, wherein the shaped porous carbon products have a BET specific surface area from about 20 $m^2/g$ to about 500 $m^2/g$, a mean pore diameter greater than about 5 nm, a specific pore volume greater than about 0.1 $cm^3/g$, a radial piece crush strength greater than about 4.4 N/mm (1 lb/mm), and a carbon black content of at least about 35 wt. %. In accordance with other embodiments, the shaped porous carbon products comprise a carbon agglomerate, wherein the shaped porous carbon products have a mean diameter of at least about 50 μm, a BET specific surface area from about 20 $m^2/g$ to about 500 $m^2/g$ or from about 25 $m^2/g$ to about 250 $m^2/g$, a mean pore diameter greater than about 5 nm, a specific pore volume greater than about 0.1 $cm^3/g$, and a radial piece crush strength greater than about 4.4 N/mm (1 lb/mm).

In further aspects, the present invention is directed to methods for preparing shaped porous carbon products. In accordance with various embodiments, one method of preparing a shaped porous carbon product comprises mixing water, carbon black, and a water soluble organic binder to produce a carbon black mixture; forming the carbon black mixture to produce a shaped carbon black composite; and heating the shaped carbon black composite to carbonize the binder to a water insoluble state to produce the shaped porous carbon product.

Aspects of the present invention are also directed to various catalyst compositions and methods for preparing the catalyst compositions. For example, a catalyst composition according to various embodiments comprises a shaped porous carbon product as a catalyst support and a catalytically active component or precursor thereof at a surface of the support. Another catalyst composition comprises a shaped porous carbon support and a catalytically active component or precursor thereof comprising platinum and gold at a surface of the support. Still another catalyst composition comprises a shaped porous carbon support and a catalytically active component or precursor thereof comprising platinum and rhodium at a surface of the support. Methods of preparing a catalyst composition in accordance with the present invention comprise depositing a catalytically active component or precursor thereof on a shaped porous carbon product.

In other aspects, the present invention is further directed to various processes of using the shaped porous carbon products and the catalyst compositions. One process in accordance with the present invention is for the catalytic conversion of a reactant comprising contacting a liquid medium comprising the reactant with a catalyst composition of the present invention. Other processes include the selective oxidation of an aldose to an aldaric acid and the selective hydrodeoxygenation of aldaric acid or salt, ester, or lactone thereof to a dicarboxylic acid. Moreover, the present invention is directed to methods of preparing a reactor vessel for a liquid phase catalytic reaction. The methods comprise charging the reactor vessel with a catalyst composition of the present invention.

In further aspects, the present invention is directed to processes for the hydrogenolysis of glycerol. Some processes comprise feeding a feed composition comprising glycerol to a reaction zone and reacting the glycerol with hydrogen in the presence of a catalyst composition as described herein (e.g., comprising a shaped porous carbon product) in the reaction zone to form a reaction product comprising propylene glycol and/or ethylene glycol. Other processes for the hydrogenolysis of glycerol comprise feeding a feed composition comprising glycerol to a reaction zone and reacting the glycerol with hydrogen in the presence of a catalyst composition in the reaction zone to form a reaction product comprising propylene glycol and/or ethylene glycol, wherein the catalyst composition comprises a catalytically active component comprising a metal selected from the group consisting of chromium, cobalt, nickel, copper, zinc, ruthenium, rhodium, palladium, silver, rhenium, osmium, iridium, platinum, gold, and any combination thereof and a catalyst support comprising a shaped porous carbon product comprising carbon black.

Other objects and features will be in part apparent and in part pointed out hereinafter.

BRIEF DESCRIPTION OF THE DRAWINGS

FIG. 15 presents the results of EDX analysis of the Ni—Re on carbon black extrudate catalyst shown in FIG. 14.

FIG. 17 presents the results of EDX analysis of the Ni—Re on carbon black extrudate catalyst shown in FIG. 16.

DETAILED DESCRIPTION

Figure 1:
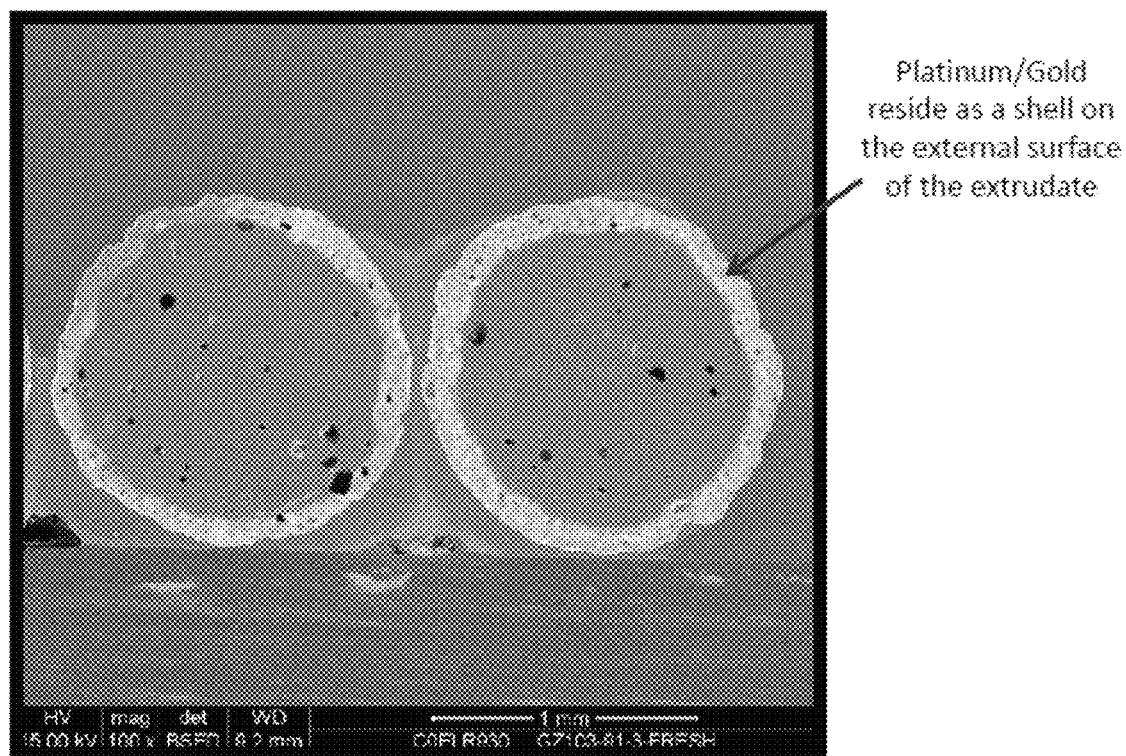
FIG. 1 provides a scanning electron microscopy image of the cross-section of a sample of the catalyst extrudate prepared with Monarch 700 carbon black.

The present invention generally relates to shaped porous carbon products and processes for preparing these products. The shaped porous carbon products can be used, for example, as catalyst supports, chromatographic support material, filtration media, adsorbents, and the like. The present invention also relates to catalyst compositions including these shaped porous carbon products, processes of preparing the catalyst compositions, and various processes of using the shaped porous carbon products and catalyst compositions.

The present invention provides shaped porous carbon products that exhibit high mechanical strength and are resistant to crushing and attrition during use. Further, the shaped porous carbon products possess excellent chemical stability to reactive solvents such as acids and other polar solvents even at elevated temperatures. The shaped porous carbon products are highly suited for liquid phase catalytic reactions because they provide for effective mass transfer of compounds having relatively large molecular volumes to and away the surface of the support.

The present invention also provides processes for preparing the shaped porous carbon products. The shaped porous carbon products can be prepared from inexpensive and readily available materials which advantageously improves process economics. Furthermore, the disclosed processes are suited for preparation of robust, mechanically strong, shaped porous carbon products through the use of water soluble organic binders. These processes avoid the use of organic solvents that require special handling and storage.

The present invention further provides catalyst compositions comprising the shaped porous carbon products as catalyst supports and processes for preparing these catalyst compositions. The shaped porous carbon products exhibit a high degree of retention of the catalytically active component(s) of the catalyst compositions, which beneficially avoids or reduces the amount of catalytically active material leached into a liquid phase reaction medium. Further, the catalyst compositions possess a high degree of stability which is necessary for commodity chemical production.

Further, the present invention provides processes utilizing shaped porous carbon products and catalyst compositions, such as for the conversion of biorenewably-derived molecules and intermediates for commodity applications (e.g., the selective oxidation of glucose to glucaric acid) or for applications requiring adsorption of compounds having relatively large molecular volumes. Surprisingly, it has been found that the shaped porous carbon products exhibit a superior mechanical strength (e.g., mechanical piece crush strength and/or radial piece crush strength), and the use of catalyst compositions comprising the shaped porous carbon products of the present invention provides unexpectedly higher productivity, selectivity and/or yield in certain reactions when compared to similar catalysts compositions with different catalyst support materials.

Shaped Porous Carbon Products and Methods of Preparation

The shaped porous carbon products of the present invention can be prepared with carbon black. Carbon black materials include various subtypes including acetylene black, conductive black, channel black, furnace black, lamp black and thermal black. The primary processes for manufacturing carbon black are the furnace and thermal processes. Generally, carbon black is produced through the deposition of solid carbon particles formed in the gas phase by combustion or thermal cracking of petroleum products. Carbon black materials are characterized by particles with diameters in the nanometer range, typically from about 5 to about 500 nm. These materials also have much lower surface areas, a higher concentration of mesopores, and lower ash and sulfur content when compared to activated carbons. Carbon black materials are deployed commercially for many applications such as fillers, pigments, reinforcement materials and viscosity modifiers. However, due to their very low surface areas, carbon black materials are not typically used as supports for chemical catalysis or adsorbents. Low surface area carbon black materials can be considered nonoptimal as support structures for catalytic applications because low surfaces areas are considered detrimental to effective dispersion of catalytically active components leading to poor catalytic activity.

As noted, activated carbons are thought to possess an optimum support structure for catalytic applications as they enable good dispersion of catalytically active components and effective adsorption and reaction of chemical reagents at the catalyst surface. In contrast, the use of carbon black as a catalyst support has been limited. In order to utilize carbon blacks as supports for chemical catalysis, several groups have reported methods to modify carbon black materials. Reported modifications are centered on methods to increase the surface area of the carbon black materials. U.S. Pat. No. 6,337,302 describes a process to render a "virtually useless" carbon black into an activated carbon for commodity applications. U.S. Pat. No. 3,329,626 describes a process to convert carbon black materials with surface areas from 40-150 $m^2/g$ by steam activation into activated carbons with surface areas up to around 1200 $m^2/g$.

Notwithstanding these teachings, it has been surprisingly discovered that certain carbon black materials exhibiting particular combinations of characteristics such as surface area, pore volume, and pore diameter are highly effective for use in shaped porous carbon catalyst supports for catalytic reactions including liquid and mixed phase reaction mediums. The shaped porous carbon products of the present invention can be shaped into mechanically strong, chemically stable robust forms that can reduce resistance to liquid and gas flows, withstand desired process conditions, and provide for long term, stable catalytic operation. These shaped porous carbon products provide high productivity and high selectivity during long term continuous flow operation under demanding reaction conditions including liquid phase reactions in which the catalyst composition is exposed to reactive solvents such as acids and water at elevated temperatures.

Carbon black may constitute a large portion of the shaped porous carbon product of the present invention. As such, the carbon black content of the shaped porous carbon product is at least about 35 wt. % or more such as at least about 40 wt. %, at least about 45 wt. %, at least about 50 wt. %, at least about 55 wt. %, at least about 60 wt. %, at least about 65 wt. %, or at least about 70 wt. %. In various embodiments, the carbon black content of the shaped porous carbon product is from about 35 wt. % to about 80 wt. %, from about 35 wt. % to about 75 wt. %, from about 40 wt. % to about 80 wt. %, or from about 40 wt. % to about 75 wt. %.

Typically, the carbon black materials used to prepare a shaped porous carbon product of the present invention have a BET specific surface area in the range of from about 20 $m^2/g$ to about 500 $m^2/g$. In various embodiments, the BET specific surface area of the carbon black is in the range of from about 20 $m^2/g$ to about 350 $m^2/g$, from about 20 $m^2/g$ to about 250 $m^2/g$, from about 20 $m^2/g$ to about 225 $m^2/g$, from about 20 $m^2/g$ to about 200 $m^2/g$, from about 20 $m^2/g$ to about 175 $m^2/g$, from about 20 $m^2/g$ to about 150 $m^2/g$, from about 20 $m^2/g$ to about 125 $m^2/g$, or from about 20 $m^2/g$ to about 100 $m^2/g$, from about 25 $m^2/g$ to about 500 $m^2/g$, from about 25 $m^2/g$ to about 350 $m^2/g$, from about 25 $m^2/g$ to about 250 $m^2/g$, from about 25 $m^2/g$ to about 225 $m^2/g$, from about 25 $m^2/g$ to about 200 $m^2/g$, from about 25 $m^2/g$ to about 175 $m^2/g$, from about 25 $m^2/g$ to about 150 $m^2/g$, from about 25 $m^2/g$ to about 125 $m^2/g$, from about 25 $m^2/g$ to about 100 $m^2/g$, from about 30 $m^2/g$ to about 500 $m^2/g$, from about 30 $m^2/g$ to about 350 $m^2/g$, from about 30 $m^2/g$ to about 250 $m^2/g$, from about 30 $m^2/g$ to about 225 $m^2/g$, from about 30 $m^2/g$ to about 200 $m^2/g$, from about 30 $m^2/g$ to about 175 $m^2/g$, from about 30 $m^2/g$ to about 150 $m^2/g$, from about 30 $m^2/g$ to about 125 $m^2/g$, or from about 30 $m^2/g$ to about 100 $m^2/g$. The specific surface area of carbon black materials is determined from nitrogen adsorption data using the Brunauer, Emmett and Teller (BET) Theory. See J. Am. Chem. Soc. 1938, 60, 309-331 and ASTM Test Methods ASTM 3663, D6556, or D4567 which are Standard Test Methods for Total and External Surface Area Measurements by Nitrogen Adsorption and are incorporated herein by reference.

The carbon black materials generally have a mean pore diameter greater than about 5 nm, greater than about 10 nm, greater than about 12 nm, or greater than about 14 nm. In some embodiments, the mean pore diameter of the carbon black materials used to prepare the shaped porous carbon product is in the range of from about 5 nm to about 100 nm, from about 5 nm to about 70 nm greater, from 5 nm to about 50 nm, from about 5 nm to about 25 nm, from about 10 nm to about 100 nm, from about 10 nm to about 70 nm greater, from 10 nm to about 50 nm, or from about 10 nm to about 25 nm. Such pore diameters enable effective transport of reactant molecules possessing large molecular volumes (such as biorenewably-derived molecules with 6-carbon atom frameworks) into and out of the pore structure of the catalytically active surface, thereby enabling enhanced activity.

The carbon black materials used to prepare the shaped porous carbon products of the present invention also generally have specific pore volumes greater than about 0.1 $cm^3/g$, greater than about 0.2 $cm^3/g$, or greater than about 0.3 $cm^3/g$. The specific pore volume of the carbon black materials can range from about 0.1 $cm^3/g$ to about 1 $cm^3/g$, from about 0.1 $cm^3/g$ to about 0.9 $cm^3/g$, from about 0.1 $cm^3/g$ to about 0.8 $cm^3/g$, from about 0.1 $cm^3/g$ to about 0.7 $cm^3/g$, from about 0.1 $cm^3/g$ to about 0.6 $cm^3/g$, from about 0.1 $cm^3/g$ to about 0.5 $cm^3/g$, from about 0.2 $cm^3/g$ to about 1 $cm^3/g$, from about 0.2 $cm^3/g$ to about 0.9 $cm^3/g$, from about 0.2 $cm^3/g$ to about 0.8 $cm^3/g$, from about 0.2 $cm^3/g$ to about 0.7 $cm^3/g$, from about 0.2 $cm^3/g$ to about 0.6 $cm^3/g$, from about 0.2 $cm^3/g$ to about 0.5 $cm^3/g$, from about 0.3 $cm^3/g$ to about 1 $cm^3/g$, from about 0.3 $cm^3/g$ to about 0.9 $cm^3/g$, from about 0.3 $cm^3/g$ to about 0.8 $cm^3/g$, from about 0.3 $cm^3/g$ to about 0.7 $cm^3/g$, from about 0.3 $cm^3/g$ to about 0.6 $cm^3/g$, or from about 0.3 $cm^3/g$ to about 0.5 $cm^3/g$. Carbon black materials with these specific pore volumes provide a volume sufficient to provide uniform wetting and good dispersion of the catalytically active components while enabling sufficient contact between the reactant molecules and the catalytically active surface. Mean pore diameters and pore volumes are determined in accordance with the procedures described in E. P. Barrett, L. G. Joyner, P. P. Halenda, J. Am. Chem. Soc. 1951, 73, 373-380 (BJH method), and ASTM D4222-03(2008) Standard Test Method for Determination of Nitrogen Adsorption and Desorption Isotherms of Catalysts and Catalyst Carriers by Static Volumetric Measurements, which are incorporated herein by reference.

Certain carbon black materials are known to be electrically conductive. Accordingly, in various embodiments, the shaped porous carbon product comprises conductive carbon black and in some embodiments, the shaped porous carbon product is electrically conductive. In other embodiments, the shaped porous carbon product comprises nonconductive carbon black. In further embodiments, the shaped porous carbon product comprises nonconductive carbon black wherein the shaped porous carbon product does not exhibit a conductivity that is suitable for a conductive electrode. In certain embodiments, the shaped porous carbon product comprises nonconductive carbon black and less than about 50%, less than about 40%, less than about 30%, less than about 20%, less than about 10%, less than about 5%, or less than about 1% conductive carbon black based on the total weight of the carbon black in the shaped porous carbon product and/or the total weight of the carbon black used to prepare the shaped porous carbon product. In some embodiments, the shaped porous carbon product comprises carbon black consisting of or consisting essentially of nonconductive carbon black. In some embodiments, the carbon black comprises a silica-bound or alumina-bound carbon black. In certain embodiments, the shaped porous carbon product can further include graphite and/or a metal oxide (e.g., alumina, silica, titania, and the like).

The shaped porous carbon product comprising carbon black may be prepared by various methods such as dry powder pressing, drip casting, injection molding, 3D-printing, extrusion and other pelletizing and granulating methods. For example, dry powder pressing involves compressing carbon black particles in a press such as a hot or cold isostatic press or a calandering press. Other pelletizing and granulating methods include tumbling carbon black particles and contacting the particles with a spray containing a binder.

Various methods of preparing the shaped porous carbon product comprise mixing water, carbon black, and a binder to form a carbon black mixture; forming the carbon black mixture to produce a shaped carbon black composite; heating the shaped carbon black composite to carbonize the binder to a water insoluble state and to produce a shaped porous carbon product. In various methods of preparing the shaped porous carbon products, a binder solution can be prepared by mixing water and the binder prior to mixing with carbon black. Typically, the binder solution and carbon black mixture are relatively concentrated in binder. For example, the water content of the carbon black mixture is typically no more than about 80% by weight, no more than about 55% by weight, no more than about 40% by weight, or no more than about 25% by weight. In various embodiments, the water content of the carbon black mixture can be from about 5 wt. % to about 70 wt. %, from about 5 wt. % to about 55 wt. %, from about 5 wt. % to about 40 wt. %, or from about 5 wt. % to about 25 wt. %. The viscosity of the binder solution can vary, for example, according to the binder content and can be readily adjusted to suit a particular shaping process by varying the relative quantities of solid and liquid components. For example, the viscosity of the aqueous solution can be varied by adjusting the amount of binder and type of binder utilized. Also in various methods, the water and binder can be mixed and heated to form the binder solution. In some instances, heating can enhance the amount of binder that can be incorporated into the binder solution and/or carbon black mixture (e.g., by increasing the solubility of the binder). For example, the water and binder can be heated to a temperature of at least about 50° C., at least about 60° C., or at least about 70° C. In various embodiments, the water and binder can be heated to a temperature of from about 50° C. to about 95° C., from about 50° C. to about 90° C., or from about 60° C. to about 85° C.

After mixing and heating to form the binder solution, the binder solution can be cooled as needed prior to mixing with carbon black or prior to forming the shaped carbon black composite.

One method of preparing the shaped porous carbon product of the present invention comprises mixing carbon black particles with a solution comprising a binder to produce a slurry; forming the slurry (e.g., by extrusion) to produce a shaped carbon black composite and heating or pyrolyzing the shaped carbon black composite to carbonize the binder to produce the shaped porous carbon product.

In various methods of preparing the shaped porous carbon product of the present invention as described herein, a binder solution or binder and water are thoroughly mixed and blended with the carbon black to prepare a carbon black mixture (e.g., a slurry or a paste). The weight ratio of binder to carbon black in the carbon black mixture is typically at least about 1:4, at least about 1:3, at least about 1:2, at least about 1:1, or at least 1.5:1. The weight ratio of binder to carbon black in the carbon black mixture can also be from about 1:4 to about 3:1, from about 1:4 to about 1:1, from about 1:3 to about 2:1, from about 1:3 to about 1:1, or about 1:1. Typically, the carbon black content of the carbon black mixture is at least about 35 wt. % or more such as at least about 40 wt. %, at least about 45 wt. %, as at least about 50 wt. %, as at least about 55 wt. %, at least about 60 wt. %, at least about 65 wt. %, or at least about 70 wt. % on a dry weight basis. In various embodiments, the carbon black content of the carbon black mixture is from about 35 wt. % to about 80 wt. %, from about 35 wt. % to about 75 wt. %, from about 40 wt. % to about 80 wt. %, or from about 40 wt. % to about 75 wt. % on a dry weight basis. Also, the binder content of the carbon black mixture is typically at least about 10 wt. %, at least about 20 wt. %, at least about 25 wt. %, at least about 30 wt. %, at least about 35 wt. %, at least about 40 wt. %, or at least 45 wt. % on a dry weight basis. In various methods for preparing the shaped porous carbon product of the present invention as described herein, the binder content of the carbon black mixture is from about 10 wt. % to about 50 wt. %, from about 10 wt. % to about 45 wt. %, from about 15 wt. % to about 50 wt. %, from about 20 wt. % to about 50 wt. %, or from about 20 wt. % to about 45 wt. % on a dry weight basis.

Various methods of preparing the shaped porous carbon products can further comprise pressing or kneading the carbon black mixture. Pressing or kneading the carbon black mixture compacts the mixture and can reduce the water content of the mixture. Pressing or kneading of the water, carbon black and binder (carbon black mixture) can be conducted simultaneously with the mixing of the water, carbon black and binder. For example, one method of mixing the water, carbon black, and binder and simultaneously pressing the resulting carbon black mixture can be conducted using a mixer muller.

After mixing of the carbon black and binder, the resulting carbon black mixture is formed into a shaped carbon black composite structure of the desired shape and dimensions by a forming technique such as extrusion, pelletizing, pilling, tableting, cold or hot isostatic pressing, calandering, injection molding, 3D printing, drip casting, or other methods known to produce shaped structures. Forming methods such as cold or hot isostatic pressing and 3D printing may or may not require a binder.

In general, the shaped porous carbon product can be shaped and sized for use in known industrial reactor formats such as batch slurry, continuous slurry-based stirred tank reactors, fixed beds, ebulated beds and other known industrial reactor formats. The shaped porous carbon product may be formed into various shapes including spheres, beads, cylinders, pellets, multi-lobed shapes, rings, stars, ripped cylinders, triholes, alphas, wheels, etc. Also, the shaped porous carbon product may be formed into amorphous, non-geometric, and random shapes as well as unsymmetrical shapes like hiflow rings and cones and alpha-rings. The mean diameter of the shaped porous carbon product is typically at least about 50 m (0.05 mm), at least about 500 μm (0.5 mm), at least about 1,000 μm (1 mm), at least about 10,000 μm (10 mm) or larger to accommodate process requirements.

For extrusion forming, a pressure of at least about 100 kPa (1 bar) or between about 100 kPa (1 bar) to about 10,000 kPa (100 bar), between 500 kPa (5 bar) and 5,000 kPa (50 bar), or between 1,000 kPa (10 bar) and 3,000 kPa (30 bar) is typically applied to the carbon black mixture.

In drip casting methods, the carbon black mixture comprising carbon black particles and the binder are dispensed as droplets into a casting bath to form the shaped carbon black composite, which is then separated from the casting bath. Carbon black mixture droplets of a tailored diameter may be dispensed through a sized nozzle and dropped into a bath to produce solidified, spherically-shaped carbon black composite of various diameters. In various embodiments of this method, the binder comprises an alginate (or alginate in combination with another carbohydrate binder as described herein) which can be dispensed into a bath containing a reagent to cause solidification such as an ionic salt (e.g., calcium salt) as described in U.S. Pat. No. 5,472,648, the entire contents of which are incorporated herein by reference. The droplets are subsequently allowed to remain substantially free in the ionic solution until the required degree of solidification and consolidation has been attained. Alternatively, the drip casting bath utilized may be, for example, an oil bath, or a bath to cause freeze drying. When an oil bath is used, the temperature of the oil is sufficiently high that the binder is thermally set (e.g., causes the binder to convert to a three-dimensional gel). When a freeze drying bath is used, the resultant beads are typically dried by vacuum treatment. The shaped carbon black composites resulting from such dip casting methods are subsequently pyrolyzed.

As described in further detail below, other components can be added to the carbon black mixture to assist with the shaping process (e.g., lubricants, compatibilizers, etc.) or to provide other benefits. In various embodiments, the carbon black mixture further comprises a forming adjuvant. For example, the forming adjuvant can comprise a lubricant. Suitable forming adjuvants include, for instance, lignin or lignin derivatives.

Further, porogens may be mixed with the carbon black and binder to modify and attain the desired pore characteristics in the shaped porous carbon product. Other methods of modifying the porosity of the shaped porous carbon product include mixing two or more different carbon black starting materials (e.g., carbon blacks having different shape and/or size that pack irregularly resulting in multimodal pore size distributions, or carbon blacks from different sources/suppliers, or mixing carbon black powders carbon. Other methods of modifying the porosity of the shaped porous carbon product include multiple thermal processing and/or multiple compounding (e.g., pyrolysis of a shaped carbon black composite of carbon powder and binder, then mixing with fresh carbon black powder and binder and pyrolyzing the resultant composite again).

In various methods of preparing the shaped porous carbon product, after processing the carbon black mixture (e.g., a slurry or a paste) into the shaped carbon black composite, the composite may be dried to dehydrate the composite. Drying may be achieved by heating the composite at atmospheric pressure and temperatures typically of from about room temperature (e.g., about 20° C.) to about 150° C., from about 40° C. to about 120° C., or from about 60° C. to about 120° C. Other methods of drying may be utilized including vacuum drying, freeze drying, and desiccation. When using certain preparation methods for forming (e.g., tableting, pressing), no drying step may be required.

In various methods of preparing the shaped porous carbon product, the shaped carbon black composite (e.g., resulting from extrusion, pelletizing, pilling, tableting, cold or hot isostatic pressing, calandering, injection molding, 3D printing, drip casting, and other forming methods) is heat treated in an inert (e.g., an inert nitrogen atmosphere), oxidative, or reductive atmosphere to carbonize at least a portion of the binder to a water insoluble state and produce a shaped porous carbon product. The heat treatment is typically conducted at a temperature of from about 250° C. to about 1,000° C., from about 300° C. to about 900° C., from about 300° C. to about 850° C., from about 300° C. to about 800° C., from about 350° C. to about 850° C., from about 350° C. to about 800° C., from about 350° C. to about 700° C., from about 400° C. to about 850° C. or from about 400° C. to about 800° C. In some instances and depending upon the binder employed, it has been determined that lower carbonization temperatures can lead to slow leaching of the remnants of the binder from the shaped porous carbon product which reduces mechanical strength over extended periods of use in catalytic reactions. Generally, to ensure longer term stability, the heat treatment is conducted at higher carbonization temperatures within the ranges specified above. In some instances, the resultant shaped porous carbon product may be washed after the heat treatment to remove impurities.

In accordance with various preparation methods, shaped porous carbon products of the present invention comprise a binder or carbonization product thereof in addition to carbon black. Various references, including U.S. Pat. No. 3,978,000, describe the use of acetone soluble organic polymers and thermosetting resin as binders for shaped carbon supports. However, the use of flammable organic solvents and expensive thermosetting resins is not desirable or economical for manufacturing large quantities of shaped porous carbon product.

Mechanically-strong, shaped porous carbon products of the invention can be prepared by the use of an effective binder. The use of an effective binder provides a robust shaped porous carbon product capable of withstanding the prevailing conditions within continuous liquid phase flow environments such as in conversions of biorenewably-derived molecules or intermediates in which the liquid phase may contain water or acidic media. In such instances the shaped porous carbon product is mechanically and chemically stable to enable long-term operation without significant loss in catalyst performance. Moreover, the use of an effective binder provides a robust shaped porous carbon product capable of withstanding elevated temperatures.

Applicants have found that readily available water soluble organic compounds are suitable binders for the preparation of mechanically strong shaped porous carbon products. As used in herein, a binder is deemed water soluble if the solubility at 50° C. is at least about 1 wt. %, preferably at least about 2 wt. %. Aqueous solutions of organic binders are highly amenable to commercial manufacturing methods. Organic binders that dissolve in aqueous solutions enable good mixing and dispersion when contacted with the carbon black materials. These binders also avoid safety and processing issues associated with large-scale use of organic solvents which may be flammable and require special storage and handling. Also, these binders are relatively inexpensive when compared to costly polymer-based binders. As such, in various embodiments, the carbon black mixtures do not contain water immiscible solvents.

In various embodiments, the water soluble organic binder comprises a carbohydrate or derivative thereof, which may be a monomeric or oligomeric or polymeric carbohydrate (also known as saccharides, oligosaccharide and polysaccharides). Derivatives of carbohydrates (in monomeric or oligomeric polymeric forms) are also included wherein a functional group or groups bound to the carbohydrate may be exchanged or derivatized. Such derivatives may be acidic or charged carbohydrates such as alginic acid or alginate salts, or pectin, or aldonic acids, aldaric acids, uronic acids, xylonic or xylaric acids (or oligomers, or polymers or salts thereof). Other derivatives include sugar alcohols and polymeric forms thereof (e.g., sorbitol, mannitol, xylitol or polyols derived from carbohydrates). The carbohydrate binder may be used in the form of syrups such as molasses or corn syrups or soluble starches or soluble gum or modified versions thereof.

In various embodiments, the water soluble organic binder comprises a saccharide selected from the group consisting of a monosaccharide, a disaccharide, an oligosaccharide, a derivative thereof, and any combination thereof. In these and other embodiments, the water soluble organic binder comprises: (i) a saccharide selected from the group consisting of a monosaccharide, a disaccharide, an oligosaccharide, a derivative thereof, and any combination thereof and (ii) a polymeric carbohydrate, a derivative of a polymeric carbohydrate, or a non-carbohydrate synthetic polymer, or any combination thereof. The weight ratio of (i) the saccharide to (ii) the polymeric carbohydrate, derivative of the polymeric carbohydrate, or the non-carbohydrate synthetic polymer, or combination thereof can be from about 5:1 to about 50:1, from about 10:1 to about 25:1, or from about 10:1 to about 20:1.

In various embodiments, the water soluble organic binder comprises a monosaccharide. For example, the monosaccharide can be selected from the group consisting of glucose, fructose, hydrates thereof, syrups thereof (e.g., corn syrups, molasses, and the like) and combinations thereof. In further embodiments, the water soluble organic binder comprises a disaccharide. Disaccharides include for example, maltose, sucrose, syrup thereof, and combinations thereof.

As noted, the binder can comprises a polymeric carbohydrate, derivative of a polymeric carbohydrate, or a non-carbohydrate synthetic polymer, or any combination thereof. In various embodiments, the binder comprises a polymeric carbohydrate, derivative of a polymeric carbohydrate, or any combination thereof. The polymeric carbohydrate or derivative of the polymeric carbohydrate can comprise a cellulosic compound. Cellulosic compounds include, for example, methylcellulose, ethylcellulose, ethylmethylcellulose, hydroxyethylcellulose, hydroxypropylcellulose, methylhydroxyethylcellulose, ethylhydroxyethylcellulose, hydroxypropylmethylcellulose, carboxymethylcellulose, and mixtures thereof.

Further, the polymeric carbohydrate or derivative of the polymeric carbohydrate derivative can be selected from the group consisting of alginic acid, pectin, aldonic acids, aldaric acids, uronic acids, sugar alcohols, and salts, oligomers, and polymers thereof. The polymeric carbohydrate or derivative of the polymeric carbohydrate can also comprise a starch or a soluble gum.

In various embodiments, the water soluble organic binder comprises a cellulosic compound. In another embodiment, the binder comprises an acidic polysaccharide such as alginic acid, pectin or a salt thereof. In other embodiments, the binder comprises a soluble cellulose such as an alkyl cellulose (e.g., hydroxyethylcellulose, hydroxypropylcellulose, hydroxyethylmethylcellulose, hydroxypropylmethylcellulose, and carboxymethylcellulose).

In various embodiments, the binder comprises a non-carbohydrate synthetic polymer. Water soluble polymers or copolymers may be used as binders. For example, polyacrylic acid, polyvinyl alcohols, polyvinylpyrrolidones, polyvinyl acetates, polyacrylates, polyethers (such as, for example, polyethyelene glycol and the like) and copolymers (which can be block copolymers comprising a water insoluble block monomers and water soluble block monomers) derived therefrom, and blends thereof. In some instances, the water soluble copolymer may be a block copolymer comprising a water soluble polymer block and a second polymer block which may be hydrophobic and amenable to carbonization (e.g., polystyrene). In another embodiment, polymer dispersions in water are used as binders, i.e., non-water soluble polymers dispersed in water (with the aid of surfactants) such as commercial polyvinyl alcohol, polyacrylonitrile, polyacrylonitrile-butadiene-styrene, phenolic polymer or lignin polymer dispersions. Also copolymers consisting of a water-soluble branch (e.g., polyacrylic acid) and a hydrophobic branch (e.g., polymaleic anhydride, polystyrene) enabling water solubility of the copolymer and enabling carbonization of the hydrophobic branch without depolymerisation upon pyrolysis. Carbohydrates or derivatives thereof, water soluble polymers and polymer dispersions in water may be used together in various combinations.

As described above, water soluble organic binders that may be used in combination with the saccharide binders include water soluble celluloses and starches (e.g., hydroxyethylcellulose, hydroxypropylcellulose, hydroxyethylmethylcellulose, hydroxylpropylmethylcellulose, carboxymethylcellulose), water soluble alcohols (e.g., sorbitol, xylitol, polyvinylalcohols), water soluble acetals (e.g., polyvinylbutyral), water soluble acids (e.g., stearic acid, citric acid, alginic acid, aldonic acids, aldaric acids, uronic acids, xylonic or xylaric acids (or oligomers, or polymers or salts or esters thereof) polyvinyl acrylic acids (or salts or esters thereof). In some embodiments, the combination of water soluble organic binders comprises a cellulosic compound and a monosaccharide. In certain embodiments, the cellulosic compound comprises hydroxyethylcellulose, or methylcellulose and the monosaccharide comprises a glucose, fructose or hydrate thereof (e.g., glucose). In particular, one combination comprises glucose and hydroxyethylcellulose, which provides shaped porous carbon products with enhanced mechanical strength, particularly when processed at high carbonization temperatures. In other embodiments the combination of water soluble organic binders comprises a monosaccharide and a water-soluble alcohol such as sorbitol, mannitol, xylitol or a polyvinyl alcohol. In other embodiments, the combination of water soluble organic binders comprises a monosaccharide, and a water-soluble acid such as stearic acid, pectin, alginic acid or polyacrylic acid (or salts thereof). In further embodiments, the combination of water soluble organic binders comprises a monosaccharide and a water-soluble ester such as a polyacrylate or polyacetate. In still other embodiments, the combination of water soluble organic binders comprises a monosaccharide and a water-soluble acetal such as a polyacetal (e.g., polyvinylbutyral).

Other water soluble compounds may be used in combination with a carbohydrate or polymeric binder. Combining a carbohydrate or other binder with selected other water soluble organic compounds can provide advantages in the preparation of and in the properties of the resultant shaped porous carbon product. For example, water soluble organic compounds such as stearic acid or stearates such as Zr or $NH_4$ stearate can provide lubrication during the forming process. Wetting agents may be added (e.g., GLYDOL series available commercially from Zschimmer and Schwarz).

Porogens may also be added in combination with the binder (or binders). Porogens are typically added to occupy a specific molecular volume within the formulation such that after the shaping and thermal processing the porogen will be pyrolyzed leaving pores of a certain volume and diameter within the shaped product. The presence of such pores can be beneficial to performance. For example, when used as a catalyst support the presence of such pores can lead to more efficient diffusion (of reactants and products) to and from the catalytically active surfaces. More efficient access and egress for the reactants and products can lead to improvements in catalyst productivity and selectivity. Porogens are typically oligomeric (e.g., dimer, trimers of higher order oligomers) or polymeric in nature. Water soluble organic compounds such as water soluble linear and branched polymers and cross-linked polymers are suitable for use as porogens. Polyacrylates (such as weakly cross-linked polyacrylates known as superabsorbers), polyvinyl alcohols, polyvinylacetates, polyesters, polyethers, or copolymers (which may be block copolymers) thereof may be used as porogens. In some instances, the water soluble copolymer may be a block copolymer comprising a water soluble polymer block and a second polymer block which may be hydrophobic and amenable to carbonization (e.g., polystyrene). In another embodiment, polymer dispersions in water are used as binders, i.e., non-water soluble polymers dispersed in water (with the aid of surfactants) such as commercial polyvinyl alcohol, polyacrylonitrile, polyacrylonitrile-butadiene-styrene, phenolic polymer dispersions. Also copolymers consisting of a water-soluble branch (e.g., polyacrylic acid) and a hydrophobic branch (e.g., polymaleic anhydride, polystyrene) enabling water solubility of the copolymer and enabling carbonization of the hydrophobic branch without depolymerisation upon pyrolysis. Carbohydrates or derivatives thereof, (disaccharides, oligosaccharides, polysaccharides such as sucrose, maltose, trihalose, starch, cellubiose, celluloses), water soluble polymers and polymer dispersions in water may be used together in any combination as a porogen to attain a shaped porous carbon black product having the desired pore size and volume characteristics described herein.

Porogens can also be added as gels (e.g., pre-gelated superabsorber) or water insoluble incompressible solids (e.g., polystyrene microbeads, lignins, phenolic polymers) or expandable porogens such as EXPANSEL microspheres available from Akzo Nobel Pulp and Performance (Sundsvall, Sweden). The molecular weight of the oligomer or polymer can be also chosen to design a desired pore sizes and volume characteristics of the shaped carbon product of the invention. For example the desired shaped carbon product may have a monomodal, bimodal or multimodal pore size distribution as a consequence of addition of a porogen. For illustration, a bimodal or multimodal pore size distribution may consist of a high percentage of pores between 10 and 100 nm and additionally the presence of pores >100 nm. Such a pore structure may provide performance advantages. For example, the presence of a such a pore size distribution can lead to more efficient diffusion (of reactants and products) through the larger pore (transport pores) to and from catalytically active surfaces which reside in the pores sized between 10 and 100 nm. More efficient access and egress for the reactants and products can lead to improvements in catalyst productivity, selectivity, and/or yield.

Following heat treatment of the shaped carbon black composite, the resulting shaped porous carbon product comprises carbon black and carbonized binder. More generally, the shaped porous carbon product can comprise a carbon agglomerate. Without being bound by any particular theory, it is believed that the carbon agglomerate comprises carbon aggregates or particles that are physically bound or entangled at least in part by the carbonized binder. Moreover, and without being bound by any particular theory, the resulting agglomerate may include chemical bonding of the carbonized binder with the carbon aggregates or particles.

The carbonized binder comprises a carbonization product of a water soluble organic binder as described herein. Carbonizing the binder during preparation of the shaped porous carbon product may reduce the weight of the shaped carbon black composite from which it is formed. Accordingly, in various embodiments, the carbonized binder content of the shaped porous carbon product is from about 10 wt. % to about 50 wt. %, from about 20 wt. % to about 50 wt. %, from about 25 wt. % to about 40 wt. %, or from about 25 wt. % to about 35 wt. % (e.g., 30 wt. %).

The specific surface area (BET surface area), mean pore diameter, and specific pore volume of the shaped porous carbon products are generally comparable to that exhibited by the carbon black material used to prepare the products. However, the preparation process can lead to a reduction or an increase in these characteristics of the products as compared to the carbon black material (e.g., about a 10-50% or 10-30% decrease or increase). In various embodiments, the shaped porous carbon product has a specific surface area from about 20 $m^2/g$ to about 500 $m^2/g$, from about 20 $m^2/g$ to about 350 $m^2/g$, from about 20 $m^2/g$ to about 250 $m^2/g$, from about 20 $m^2/g$ to about 225 $m^2/g$, from about 20 $m^2/g$ to about 200 $m^2/g$, from about 20 $m^2/g$ to about 175 $m^2/g$, from about 20 $m^2/g$ to about 150 $m^2/g$, from about 20 $m^2/g$ to about 125 $m^2/g$, or from about 20 $m^2/g$ to about 100 $m^2/g$, from about 25 $m^2/g$ to about 500 $m^2/g$, from about 25 $m^2/g$ to about 350 $m^2/g$, from about 25 $m^2/g$ to about 250 $m^2/g$, from about 25 $m^2/g$ to about 225 $m^2/g$, from about 25 $m^2/g$ to about 200 $m^2/g$, from about 25 $m^2/g$ to about 175 $m^2/g$, from about 25 $m^2/g$ to about 150 $m^2/g$, from about 25 $m^2/g$ to about 125 $m^2/g$, from about 25 $m^2/g$ to about 100 $m^2/g$, from about 30 $m^2/g$ to about 500 $m^2/g$, from about 30 $m^2/g$ to about 350 $m^2/g$, from about 30 $m^2/g$ to about 250 $m^2/g$, from about 30 $m^2/g$ to about 225 $m^2/g$, from about 30 $m^2/g$ to about 200 $m^2/g$, from about 30 $m^2/g$ to about 175 $m^2/g$, from about 30 $m^2/g$ to about 150 $m^2/g$, from about 30 $m^2/g$ to about 125 $m^2/g$, or from about 30 $m^2/g$ to about 100 $m^2/g$. The specific surface area of the shaped porous carbon product is determined from nitrogen adsorption data using the Brunauer, Emmett and Teller. See the methods described in J. Am. Chem. Soc. 1938, 60, 309-331 and ASTM Test Methods D3663, D6556 or D4567, which are Standard Test Methods for Surface Area Measurements by Nitrogen Adsorption.

The shaped porous carbon products typically have a mean pore diameter greater than about 5 nm, greater than about 10 nm, greater than about 12 nm, or greater than about 14 nm. In some embodiments, the mean pore diameter of the shaped porous carbon product is from about 5 nm to about 100 nm, from about 5 nm to about 70 nm, from 5 nm to about 50 nm, from about 5 nm to about 25 nm, from about 10 nm to about 100 nm, from about 10 nm to about 70 nm, from 10 nm to about 50 nm, or from about 10 nm to about 25 nm. Also, the shaped porous carbon products of the present invention have specific pore volumes of the pores having a diameter of 1.7 nm to 100 nm as measured by the BJH method that is generally greater than about 0.1 $cm^3/g$, greater than about 0.2 $cm^3/g$, or greater than about 0.3 $cm^3/g$. In various embodiments, the shaped porous carbon products have a specific pore volume of the pores having a diameter of 1.7 nm to 100 nm as measured by the BJH method that is from about 0.1 $cm^3/g$ to about 1.5 $cm^3/g$, from about 0.1 $cm^3/g$ to about 0.9 $cm^3/g$, from about 0.1 $cm^3/g$ to about 0.8 $cm^3/g$, from about 0.1 $cm^3/g$ to about 0.7 $cm^3/g$, from about 0.1 $cm^3/g$ to about 0.6 $cm^3/g$, from about 0.1 $cm^3/g$ to about 0.5 $cm^3/g$, from about 0.2 $cm^3/g$ to about 1 $cm^3/g$, from about 0.2 $cm^3/g$ to about 0.9 $cm^3/g$, from about 0.2 $cm^3/g$ to about 0.8 $cm^3/g$, from about 0.2 $cm^3/g$ to about 0.7 $cm^3/g$, from about 0.2 $cm^3/g$ to about 0.6 $cm^3/g$, from about 0.2 $cm^3/g$ to about 0.5 $cm^3/g$, from about 0.3 $cm^3/g$ to about 1 $cm^3/g$, from about 0.3 $cm^3/g$ to about 0.9 $cm^3/g$, from about 0.3 $cm^3/g$ to about 0.8 $cm^3/g$, from about 0.3 $cm^3/g$ to about 0.7 $cm^3/g$, from about 0.3 $cm^3/g$ to about 0.6 $cm^3/g$, or from about 0.3 $cm^3/g$ to about 0.5 $cm^3/g$. Mean pore diameters and specific pore volumes are determined in accordance with the procedures described in E. P. Barrett, L. G. Joyner, P. P. Halenda, J. Am. Chem. Soc. 1951, 73, 373-380 (BJH method), and ASTM D4222-03(2008) Standard Test Method for Determination of Nitrogen Adsorption and Desorption Isotherms of Catalysts and Catalyst Carriers by Static Volumetric Measurements, which are incorporated herein by reference.

It has been observed that the magnitude of the specific surface area is generally proportional to the concentration of micropores in the shaped porous carbon product structure. In particular, the shaped porous carbon products generally possess a low concentration of pores having a mean diameter less than 1.7 nm. Typically, pores having a mean diameter less than 1.7 nm constitute no more than about 10%, no more than about 5%, no more than about 4%, no more than about 3%, or no more than about 2.5% of the pore volume of the shaped porous carbon product. Similarly, in various embodiments, the pore size distribution of the shaped porous carbon products is such that peaks below about 10 nm or about 5 nm are not observed. For example, the shaped porous carbon products can have a pore size distribution such that the peak of the distribution is at a diameter greater than about 5 nm, greater than about 7.5 nm, greater than about 10 nm, greater than about 12.5 nm, greater than about 15 nm, or greater than about 20 nm. Also, the shaped porous carbon product can have a pore size distribution such that the peak of the distribution is at a diameter less than about 100 nm, less than about 90 nm, less than about 80 nm, or less than about 70 nm.

Moreover, the shaped porous carbon product advantageously exhibits a high concentration of mesopores between about 10 nm to about 100 nm, between about 20 nm to about 100 nm, or between about 10 nm to about 50 nm. Accordingly, in various embodiments, at least about 50%, at least about 60%, at least about 70%, at least about 80%, at least about 90%, at least about 95% of the pore volume of the shaped porous carbon product, as measured by the BJH method on the basis of pores having a diameter from 1.7 nm to 100 nm, is attributable to pores having a mean pore diameter of from about 10 nm to about 100 nm. For example, from about 50% to about 99%, from about 50% to about 95%, from about 50% to about 90%, from about 50% to about 80%, from about 60% to about 99%, from about 60% to about 95%, from about 60% to about 90%, from about 60% to about 80%, from about 70% to about 99%, from about 70% to about 95%, from about 70% to about 90%, from about 70% to about 80%, from about 80% to about 99%, from about 80% to about 95%, from about 80% to about 90%, or from about 90% to about 99% of the pore volume of the shaped porous carbon product, as measured by the BJH method on the basis of pores having a diameter from 1.7 nm to 100 nm, is attributable to pores having a mean pore diameter of from about 10 nm to about 100 nm. Also, in various embodiments, at least about 35%, at least about 40%, at least about 45%, or at least about 50% of the pore volume of the shaped porous carbon product, as measured by the BJH method on the basis of pores having a diameter from 1.7 nm to 100 nm, is attributable to pores having a mean pore diameter of from about 20 nm to about 90 nm or from about 10 nm to about 50 nm. For example, from about 35% to about 80%, from about 35% to about 75%, from about 35% to about 65%, from about 40% to about 80%, from about 40% to about 75%, or from about 40% to about 70% of the pore volume of the shaped porous carbon product, as measured by the BJH method on the basis of pores having a diameter from 1.7 nm to 100 nm, is attributable to pores having a mean pore diameter of from about 20 nm to about 90 nm or from about 10 nm to about 50 nm.

Typically, the shaped porous carbon product exhibits a relatively low concentration of pores less than 10 nm, less than 5 nm, or less than 3 nm. For example, no more than about 10%, no more than about 5%, or no more than about 1% of the pore volume of the shaped porous carbon product, as measured by the BJH method on the basis of pores having a diameter from 1.7 nm to 100 nm, is attributable to pores having a mean pore diameter less than 10 nm, less than 5 nm, or less than 3 nm. In various embodiments, from about 0.1% to about 10%, from about 0.1% to about 5%, from about 0.1% to about 1%, from about 1% to about 10%, or from about 1% to about 5% of the pore volume of the shaped porous carbon product, as measured by the BJH method on the basis of pores having a diameter from 1.7 nm to 100 nm, is attributable to pores having a mean pore diameter less than 10 nm, less than 5 nm, or less than 3 nm.

The shaped porous carbon products described herein are mechanically strong and stable. Crush strength represents the resistance of a solid to compression, and is an important property in the industrial use of the shaped porous carbon product as described herein. Instruments for measuring the piece crush strength of individual solid particles generally include a dynamometer that measures the force progressively applied to the solid during the advancement of a piston. The applied force increases until the solid breaks and collapses into small pieces and eventually powder. The corresponding value of the collapsing force is defined as piece crush strength and is typically averaged over multiple samples. Standard protocols for measuring crush strength are known in the art. For example, the mechanical strength of the shaped porous carbon product can be measured by piece crush strength test protocols described by ASTM D4179 or ASTM D6175, which are incorporated herein by reference. Some of these test methods are reportedly limited to particles of a defined dimensional range, geometry, or method of manufacture. However, crush strength of irregularly shaped particles and particles of varying dimension and manufacture may nevertheless be adequately measured by these and similar test methods.

In various embodiments, the shaped porous carbon product prepared in accordance with the present invention has a radial piece crush strength of greater than about 4.4 N/mm (1 lb/mm), greater than about 8.8 N/mm (2 lbs/mm), or greater than about 13.3 N/mm (3 lbs/mm). In certain embodiments, the radial piece crush strength of the shaped porous carbon product is from about 4.4 N/mm (1 lb/mm) to about 88 N/mm (20 lbs/mm), from about 4.4 N/mm (1 lb/mm) to about 66 N/mm (15 lbs/mm), or from about 8.8 N/mm (2 lb/mm) to about 44 N/mm (10 lbs/mm). In radial piece crush strength measurements, the measured force is relative to the dimension of the solid perpendicular to the applied load, which typically can range from about 0.5 mm to about 20 mm, from about 1 mm to about 10 mm, or from about 1.5 mm to 5 mm. For irregularly shaped porous carbon products, the radial piece crush strength is measured by applying the load perpendicular to the longest dimension of the solid.

Mechanical piece crush strength can also be reported on a basis that is unitless with respect to the dimension of the shaped porous carbon product (e.g., for generally spherically shaped solids or solids having approximately equal transverse dimensions). The shaped porous carbon product prepared in accordance with the present invention typically has a piece crush strength greater than about 22 N (5 lbs), greater than about 36 N (8 lbs), or greater than about 44 N (10 lbs). In various embodiments, shaped porous carbon product may have a piece crush strength from about 22 N (5 lbs) to about 88 N (20 lbs), from about 22 N (5 lbs) to about 66 N (15 lbs), or from about 33 N (7.5 lbs) to about 66 N (15 lbs).

In addition to crush strength, the shaped porous carbon products also exhibit desirable attrition and abrasion resistance characteristics. There are several test methods suitable for determining the attrition and abrasion resistance of the shaped porous carbon products and catalysts produced in accordance with the present disclosure. These methods are a measure of the propensity of the material to produce fines in the course of transportation, handling, and use on stream.

One such method is the attrition index as determined in accordance with ASTM D4058-96 (Standard Test Method for Attrition and Abrasion of Catalysts and Catalyst Carriers), which is a measurement of the resistance of a material (e.g., extrudate or catalyst particle) to attrition wear due to the repeated striking of the particle against hard surfaces within a specified rotating test drum and is incorporated herein by reference. This test method is generally applicable to tablets, extrudates, spheres, granules, pellets as well as irregularly shaped particles typically having at least one dimension larger than about 1/16 in. (1.6 mm) and smaller than about ¾ in. (19 mm), although attrition measurements can also be performed on larger size materials. Variable and constant rate rotating cylinder abrasimeters designed according to ASTM D4058-96 are readily available. Typically, the material to be tested is placed in drum of the rotating test cylinder and rolled at from about 55 to about 65 RPM for about 35 minutes. Afterwards, the material is removed from test cylinder and screened on a 20-mesh sieve. The percentage (by weight) of the original material sample that remains on the 20-mesh sieve is referred to as the "percent retained." The shaped porous carbon products (e.g., extrudates) and catalysts prepared therefrom typically exhibit a rotating drum attrition index as measured in accordance with ASTM D4058-96 or similar test method such that the percent retained is greater than about 85%, greater than about 90%, greater than about 92%, greater than about 95%, greater than about 97%, or greater than about 99% by weight. A percent retained result of greater than about 97% is indicative of materials with exceptional mechanical stability and robust structure particularly desirable for industrial applications.

Abrasion loss (ABL) is an alternate measurement of the resistance of the shaped porous carbon products (e.g., extrudates) and catalysts prepared therefrom. As with the attrition index, the results of this test method can be used as a measure of fines production during the handling, transportation, and use of the material. Abrasion loss is a measurement of the resistance of a material to attrition wear due to the intense horizontal agitation of the particles within the confines of a 30-mesh sieve. Typically, the material to be tested is first de-dusted on a 20-mesh sieve by gently moving the sieve side-to-side at least about 20 times. The de-dusted sample is weighed and then transferred to the inside of a clean, 30-mesh sieve stacked above a clean sieve pan for the collection of fines. The complete sieve stack is then assembled onto a sieve shaker (e.g., RO-Tap RX-29 sieve shaker from W. S. Tyler Industrial Group, Mentor, OH), covered securely and shaken for about 30 minutes. The collected fines generated are weighed and divided by the de-dusted sample weight to provide a sample abrasion loss in percent by weight. The shaped porous carbon products (e.g., extrudates) and catalysts prepared therefrom typically exhibit a horizontal agitation sieve abrasion loss of less than about 5%, less than about 3%, less than about 2%, less than about 1%, less than about 0.5%, less than about 0.2%, less than about 0.1%, less than about 0.05%, or less than about 0.03% by weight. An abrasion loss result of less than about 2% is particularly desired for industrial applications.

The shaped porous carbon products and methods for preparing the shaped porous carbon products of the present invention include various combinations of features described herein. For example, in various embodiments, the shaped porous carbon product comprises (a) carbon black and (b) a carbonized binder comprising a carbonization product of a water soluble organic binder, wherein the shaped porous carbon product has a BET specific surface area from about 20 $m^2/g$ to about 500 $m^2/g$ or from about 25 $m^2/g$ to about 250 $m^2/g$, a mean pore diameter greater than about 10 nm, a specific pore volume greater than about 0.1 $cm^3/g$, a radial piece crush strength greater than about 4.4 N/mm (1 lb/mm), and a carbon black content of at least about 35 wt. %. In other embodiments, the shaped porous carbon product comprises a carbon agglomerate, wherein the shaped porous carbon product has a mean diameter of at least about 50 μm, a BET specific surface area from about 20 $m^2/g$ to about 500 $m^2/g$ or from about 25 $m^2/g$ to about 250 $m^2/g$, a mean pore diameter greater than about 10 nm, a specific pore volume greater than about 0.1 $cm^3/g$, and a radial piece crush strength greater than about 4.4 N/mm (1 lb/mm).

The shaped porous carbon product of the present invention may also have a low sulfur content. For example, the sulfur content of the shaped porous carbon product may be no greater than about 1 wt. % or about 0.1 wt. %.

Features and characteristics including the type of carbon black, the binder, the specific surface area, the specific pore volume, the mean pore diameter, the crush strength, attrition and abrasion resistance and the carbon black content may be independently adjusted or modified within the ranges described herein. Also, shaped porous carbon products may be further defined according to characteristics described herein.

For instance, the shaped porous carbon product can comprises (a) carbon black and (b) a carbonized binder comprising a carbonization product of a water soluble organic binder and wherein the shaped porous carbon product has a BET specific surface area from about 20 $m^2/g$ to about 500 $m^2/g$, a mean pore diameter greater than about 5 nm, a specific pore volume greater than about 0.1 $cm^3/g$, a radial piece crush strength greater than about 4.4 N/mm (1 lb/mm), a carbon black content of at least about 35 wt. %, and a carbonized binder content from about 20 wt. % to about 50 wt. %.

In other embodiments, a shaped porous carbon product of the present invention comprises (a) carbon black and (b) a carbonized binder comprising a carbonization product of a water soluble organic binder, wherein the shaped porous carbon product has a BET specific surface area from about 20 $m^2/g$ to about 500 $m^2/g$ or from about 25 $m^2/g$ to about 250 $m^2/g$, a mean pore diameter greater than about 10 nm, a specific pore volume greater than about 0.1 $cm^3/g$, and a radial piece crush strength greater than about 4.4 N/mm (1 lb/mm), and a carbon black content of at least about 35 wt. %, and wherein the shaped porous carbon product has a pore volume measured on the basis of pores having a diameter from 1.7 nm to 100 nm and at least about 35% of the pore volume is attributable to pores having a mean pore diameter of from about 10 nm to about 50 nm.

Yet another shaped porous carbon product of the present invention comprises a carbon agglomerate, wherein the shaped porous carbon product has a mean diameter of at least about 50 μm, a BET specific surface area from about 20 $m^2/g$ to about 500 $m^2/g$ or from about 25 $m^2/g$ to about 250 $m^2/g$, a mean pore diameter greater than about 10 nm, a specific pore volume greater than about 0.1 $cm^3/g$, and a radial piece crush strength greater than about 4.4 N/mm (1 lb/mm), and wherein the shaped porous carbon product has a pore volume measured on the basis of pores having a diameter from 1.7 nm to 100 nm and at least about 35% of the pore volume is attributable to pores having a mean pore diameter of from about 10 nm to about 50 nm.

Methods of the present invention include various combinations of the features, characteristics, and method steps described herein. For example, various methods for preparing the shaped porous carbon product include mixing and heating water and a water soluble organic binder to form a binder solution, wherein the water and binder are heated to a temperature of at least about 50° C., and wherein the binder comprises: (i) a saccharide selected from the group consisting of a monosaccharide, a disaccharide, an oligosaccharide, a derivative thereof, and any combination thereof and (ii) a polymeric carbohydrate, a derivative of a polymeric carbohydrate, or a non-carbohydrate synthetic polymer, or any combination thereof, mixing carbon black particles with the binder solution to produce a carbon black mixture; forming the carbon black mixture to produce a shaped carbon black composite; and heating the shaped carbon black composite to carbonize the binder to a water insoluble state and to produce a shaped porous carbon product.

Other methods for preparing the shaped porous carbon product include mixing water, carbon black, and a water soluble organic binder to form a carbon black mixture, wherein the binder comprises: (i) a saccharide selected from the group consisting of a monosaccharide, a disaccharide, an oligosaccharide, a derivative thereof, and any combination thereof and (ii) a polymeric carbohydrate, a derivative of a polymeric carbohydrate, or a non-carbohydrate synthetic polymer, or any combination thereof, forming the carbon black mixture to produce a shaped carbon black composite; and heating the shaped carbon black composite to carbonize the binder to a water insoluble state and to produce a shaped porous carbon product.

Further methods include mixing water, carbon black, and a binder to form a carbon black mixture, wherein the binder comprises a saccharide selected from the group consisting of a monosaccharide, a disaccharide, an oligosaccharide, a derivative thereof, or any combination thereof and wherein the weight ratio of the binder to carbon black in the carbon black mixture is at least about 1:4, at least about 1:3, at least about 1:2, at least about 1:1, or at least 1.5:1; forming the carbon black mixture to produce a shaped carbon black composite; and heating the shaped carbon black composite to carbonize the binder to a water insoluble state and to produce a shaped porous carbon product.

Still other methods include mixing water, carbon black, and a binder to form a carbon black mixture, wherein the binder comprises a saccharide selected from the group consisting of a monosaccharide, a disaccharide, an oligosaccharide, a derivative thereof, or any combination thereof and wherein the water content of the carbon black mixture is no more than about 80% by weight, no more than about 55% by weight, no more than about 40% by weight, or no more than about 25% by weight; forming the carbon black mixture to produce a shaped carbon black composite; and heating the shaped carbon black composite to carbonize the binder to a water insoluble state and to produce a shaped porous carbon product.

Another method of preparing the shaped porous carbon product by extrusion preferably comprises mixing carbon black particles with an aqueous solution comprising a water soluble organic binder compound selected from the group consisting of a monosaccharide, a disaccharide, an oligosaccharide, a polysaccharide, and combinations thereof to produce a carbon black mixture, wherein the carbon black mixture comprises at least about 40 wt. % of the carbon black and at least about 40 wt. % of the binder on a dry basis; forming the carbon black mixture under a pressure of at least 500 kPa (5 bar) to produce a shaped carbon black composite; drying the shaped carbon black material at a temperature from about room temperature (e.g., about 20° C.) to about 150° C.; and heating the dried shaped carbon black composite to a temperature between about 250° C. and about 800° C. in an oxidative, inert, or reductive atmosphere (e.g., an inert $N_2$ atmosphere) to carbonize the binder to a water insoluble state and produce the shaped porous carbon product, wherein the shaped porous carbon product has a mean diameter of at least about 50 µm, a BET specific surface area from about 20 $m^2$/g to about 500 $m^2$/g or from about 25 $m^2$/g to about 250 $m^2$/g, a mean pore diameter greater than about 10 nm, a specific pore volume greater than about 0.1 $cm^3$/g, and a radial crush strength greater than about 4.4 N/mm (1 lb/mm). Typically, the water soluble organic binder compound is selected from the group consisting of a monosaccharide, an oligosaccharide, a polysaccharide, and combinations thereof. The carbon black content of the shape porous carbon product can be at least about 35 wt. % or as described herein. Also, in some embodiments, the shaped porous carbon product has a pore volume measured on the basis of pores having a diameter from 1.7 nm to 100 nm and at least about 35% of the pore volume is attributable to pores having a mean pore diameter of from about 10 nm to about 50 nm. The carbon black mixture may optionally be heated during the forming step (e.g., extrusion, pelletizing, pilling, tableting, cold or hot isostatic pressing, calandering, injection molding, 3D printing, drip casting, or other methods) to facilitate the forming of the carbon black mixture into the desired shape.

Additional shaped porous carbon products and methods of preparation of the present invention include any combinations of the features described herein and where features described above are independently substituted or added to the aforementioned embodiments.

The shaped porous carbon black products can also be wash-coated or dip-coated onto other materials to prepare structured composite materials. The shaped porous carbon black products (at least micron-sized) can be domains on heterogeneous, segregated composite materials (e.g., carbon —$ZrO_2$ composites or carbon domains hosted by large-pore (mm-sized) ceramic foams) as well as layered or structured materials (e.g., carbon black wash-coats onto inert supports such as steatite, plastic or glass balls).

The shaped porous carbon black product of the invention may be further treated thermally or chemically to alter the physical and chemical characteristics of the shaped porous carbon black product. For example chemical treatment such as an oxidation may a produce a more hydrophilic surface which may provide advantages for preparing a catalyst (improved wetting and dispersion). Oxidation methods are known in the art, see for example U.S. Pat. Nos. 7,922,805 and 6,471,763. In other embodiments, the shaped porous carbon black product has been surface treated using known methods for attaching a functional group to a carbon based substrate. See, e.g., WO2002/018929, WO97/47691, WO99/23174, WO99/31175, WO99/51690, WO2000/022051, and WO99/63007, all of which are incorporated herein by reference. The functional group may be an ionizable group such that when the shaped porous carbon black product is subjected to ionizing conditions, it comprises an anionic or cationic moiety. This embodiment is useful when the shaped porous carbon black product is used as a separation media in chromatography columns and other separation devices.

Catalyst Compositions and Methods of Preparation

Various aspects of the present invention are also directed to catalyst compositions comprising the shaped porous carbon product as a catalyst support and methods of preparing the catalyst compositions. The shaped porous carbon products of the present invention provide effective dispersion and anchoring of catalytically active components or precursors thereof to the surface of the carbon product. The catalyst compositions of the present invention are suitable for use in long term continuous flow operation phase reactions under demanding reaction conditions such as liquid phase reactions in which the shaped porous carbon product is exposed to reactive solvents such as acids and water at elevated temperatures. The catalyst compositions comprising the shaped porous carbon products of the present invention demonstrate operational stability necessary for commodity applications.

In general, the catalyst compositions of the present invention comprise the shaped porous carbon product as a catalyst support and a catalytically active component or precursor thereof at a surface of the support (external and/or internal surface). In various catalyst compositions of the present invention, the catalytically active component or precursor thereof comprises a metal at a surface of the shaped porous carbon product. In these and other embodiments, the metal comprises at least one metal selected from groups IV, V, VI, VII, VIII, IX, X, XI, XII, and XIII. Some preferred metals include cobalt, nickel, copper, zinc, iron, vanadium, molybdenum, manganese, barium, ruthenium, rhodium, rhenium, palladium, silver, osmium, iridium, platinum, gold, and combinations thereof. In various embodiments, the metal comprises at least one d-block metal. Some preferred d-block metals are selected from the group consisting of cobalt, nickel, copper, zinc, iron, ruthenium, rhodium, palladium, silver, osmium, iridium, platinum, gold and combinations thereof. Typically, the metal(s) at a surface of the catalyst support may constitute f from about 0.1% to about 50%, from about 0.1% to about 25%, from about 0.1% to about 10%, from about 0.1% to about 5%, from about 0.25% to about 50%, from about 0.25% to about 25%, from about 0.25% to about 10%, from about 0.25% to about 5%, from about 1% to about 50%, from about 1% to about 25%, from about 1% to about 10%, from about 1% to about 5%, from about 5% to about 50%, from about 5% to about 25%, or from about 5% to about 10% of the total weight of the catalyst.

In general, the metals may be present in various forms (e.g., elemental, metal oxide, metal hydroxides, metal ions, metalates, polyanions, oligomers or colloidal etc.). Typically, however, the metals are reduced to elemental form during preparation of the catalyst composition or in-situ in the reactor under reaction conditions.

The metal(s) may be deposited on a surface of the shaped porous carbon product according procedures known in the art including, but not limited to incipient wetness, ion-exchange, deposition-precipitation, coating and vacuum impregnation. When two or more metals are deposited on the same support, they may be deposited sequentially or simultaneously. Multiple impregnation steps are also possible (e.g., dual impregnation of the same metal under different conditions to increase overall metal loading or tune the metal distribution across the shell). In various embodiments, the metal(s) deposited on the shaped porous carbon product for the oxidation catalyst form a shell at least partially covering the surface of the carbon product. In other words, metal deposited on the shaped porous carbon product coats external surfaces of the carbon product. In various embodiments, the metal penetrates surficial pores of the shaped porous carbon product to form a shell layer ("egg shell") with a thickness of from about 10 μm to about 400 μm, or from about 50 μm to about 150 μm (e.g., about 100 m). In certain embodiments the shell may be produced sub-surface to produce a 10 μm to about 400 μm sub-surface band containing the catalytically active metals ("egg yolk"). Also structured shells featuring different metal distributions across the shell for the various metals are possible.

In other embodiments, the metal(s) may be deposited on the carbon black particles before forming the shaped porous carbon product. Accordingly, in these embodiments, the carbon black mixture may further comprise a metal, such as, for example, a d-block metal. Some preferred d-block metals are selected from the group consisting of cobalt, nickel, copper, zinc, iron, ruthenium, rhodium, palladium, silver, osmium, iridium, platinum, gold and combinations thereof. In various embodiments, the metal comprises at least one metal selected from groups IV, V, VI, VII, VIII, IX, X, XI, XII, and XIII. Preferred metals include cobalt, nickel, copper, zinc, iron, vanadium, molybdenum, manganese, barium, ruthenium, rhodium, rhenium, palladium, silver, osmium, iridium, platinum, gold, and combinations thereof. Typically, the metal(s) may constitute from about 0.1% to about 50%, from about 0.1% to about 25%, from about 0.1% to about 10%, from about 0.1% to about 5%, from about 0.25% to about 50%, from about 0.25% to about 25%, from about 0.25% to about 10%, from about 0.25% to about 5%, from about 1% to about 50%, from about 1% to about 25%, from about 1% to about 10%, from about 1% to about 5%, from about 5% to about 50%, from about 5% to about 25%, or from about 5% to about 10%. For example, when the metal used is a noble metal, the metal content can be from about 0.25% to about 10% of the total weight of the shaped porous carbon product. Alternatively, when the metal used is a non-noble metal, the metal content can be from about 0.1% to about 50% of the total weight of the shaped porous carbon product.

In various embodiments, following metal deposition, the catalyst composition is optionally dried, for example, at a temperature of at least about 50° C., more typically at least about 120° C. for a period of time of at least about 1 hour, more typically 3 hours or more. Alternatively, the drying may be conducted in a continuous or staged manner where independently controlled temperature zones (e.g., 60° C., 80° C., and 120° C.) are utilized. Typically, drying is initiated below the boiling point of the solvent, e.g., 60° C. and then increased. In these and other embodiments, the catalyst is dried under sub-atmospheric or atmospheric pressure conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of at least about 200° C. for a period of time (e.g., at least about 3 hours).

In some embodiments, the catalyst composition of the present invention is prepared by depositing the catalytically active component or precursor thereof subsequent to forming the shaped porous carbon product (i.e., depositing directly on a surface of the shaped porous carbon product). The catalyst composition of the present invention can be prepared by contacting the shaped porous carbon product with a solubilized metal complex or combination of solubilized metal complexes. The heterogeneous mixture of solid and liquids can then be stirred, mixed and/or shaken to enhance the uniformity of dispersion of the catalyst, which, in turn, enables the more uniform deposition of metal(s) on the surface of the support upon removal of the liquids. Following deposition, the metal complex(es) on the shaped porous carbon products are heated and reduced under a reducing agent such as a hydrogen containing gas (e.g., forming gas 5% $H_2$ and 95% $N_2$). The temperature at which the heating is conducted generally ranges from about 150° C. to about 600° C., from about 200° C. to about 500° C., or from about 100° C. to about 400° C. Heating is typically conducted for a period of time ranging from about 1 hour to about 5 hours or from about 2 hour to about 4 hours. Reduction may also be carried in the liquid phase. For example, catalyst compositions can be treated in a fixed bed with the liquid containing a reducing agent pumped through the static catalyst.

In other embodiments, the catalyst composition of the present invention is prepared by depositing the catalytically active component or precursor thereof on carbon black prior to forming the shaped porous carbon product. In one such method, a slurry of carbon black with solubilized metal complex(es) is prepared. Carbon black may be initially dispersed in a liquid such as water. Thereafter, the solubilized metal complex(es) may be added to the slurry containing the carbon black. The heterogeneous mixture of solid and liquids can then be stirred, mixed and/or shaken to enhance the uniformity of dispersion of the catalyst, which, in turn, enables the more uniform deposition of metal(s) on the surface of the carbon black upon removal of the liquids. Following deposition, the metal complex(es) on the carbon black are heated and reduced with a reducing agent as described above. The metal-loaded carbon black particles can then be formed according to the method described for the shaped porous carbon product. The slurry can also be wash-coated onto inert supports rather than shaped into bulk catalyst pellets.

The catalyst compositions comprising the shaped porous carbon product as a catalyst support can be deployed in various reactor formats, particularly those suited liquid phase medium such as batch slurry, continuous slurry-based stirred tank reactors, cascade of stirred tank reactors, bubble slurry reactor, fixed beds, ebulated beds and other known industrial reactor formats. Accordingly, in various aspects, the present invention is further directed to methods of preparing a reactor vessel for a liquid phase catalytic reaction. In other aspects, the present invention is further directed to methods of preparing a reactor vessel for a gaseous phase catalytic reaction. The method comprises charging the reactor vessel with a catalyst composition comprising the shaped porous carbon product as described herein as a catalyst support. In some embodiments, the reactor vessel is a fixed bed reactor.

Various methods for preparing a catalyst composition in accordance with the present invention include mixing and heating water and a water soluble organic binder to form a binder solution, wherein the water and binder are heated to a temperature of at least about 50° C., and wherein the binder comprises: (i) a saccharide selected from the group consisting of a monosaccharide, a disaccharide, an oligosaccharide, a derivative thereof, and any combination thereof and (ii) a polymeric carbohydrate, a derivative of a polymeric carbohydrate, or a non-carbohydrate synthetic polymer, or any combination thereof, mixing carbon black particles with the binder solution to produce a carbon black mixture; forming the carbon black mixture to produce a shaped carbon black composite; heating the shaped carbon black composite to carbonize the binder to a water insoluble state and to produce a shaped porous carbon product; and depositing a catalytically active component or precursor thereof on the shaped porous carbon product to produce the catalyst composition.

Other methods include mixing water, carbon black, and a water soluble organic binder to form a carbon black mixture, wherein the binder comprises: (i) a saccharide selected from the group consisting of a monosaccharide, a disaccharide, an oligosaccharide, a derivative thereof, and any combination thereof and (ii) a polymeric carbohydrate, a derivative of a polymeric carbohydrate, or a non-carbohydrate synthetic polymer, or any combination thereof, forming the carbon black mixture to produce a shaped carbon black composite; heating the shaped carbon black composite to carbonize the binder to a water insoluble state and to produce a shaped porous carbon product; and depositing a catalytically active component or precursor thereof on the shaped porous carbon product to produce the catalyst composition.

Further methods for preparing a catalyst composition in accordance with the present invention include mixing water, carbon black, and a binder to form a carbon black mixture, wherein the binder comprises a saccharide selected from the group consisting of a monosaccharide, a disaccharide, an oligosaccharide, a derivative thereof, or any combination thereof and wherein the weight ratio of the binder to carbon black in the carbon black mixture is at least about 1:4, at least about 1:3, at least about 1:2, at least about 1:1, or at least 1.5:1; forming the carbon black mixture to produce a shaped carbon black composite; heating the shaped carbon black composite to carbonize the binder to a water insoluble state and to produce a shaped porous carbon product; and depositing a catalytically active component or precursor thereof on the shaped porous carbon product to produce the catalyst composition.

Other methods include mixing water, carbon black, and a binder to form a carbon black mixture, wherein the binder comprises a saccharide selected from the group consisting of a monosaccharide, a disaccharide, an oligosaccharide, a derivative thereof, or any combination thereof and wherein the water content of the carbon black mixture is no more than about 80% by weight, no more than about 55% by weight, no more than about 40% by weight, or no more than about 25% by weight; forming the carbon black mixture to produce a shaped carbon black composite; heating the shaped carbon black composite to carbonize the binder to a water insoluble state and to produce a shaped porous carbon product; and depositing a catalytically active component or precursor thereof on the shaped porous carbon product to produce the catalyst composition.

Still further methods include depositing a catalytically active component or precursor thereof on a shaped porous carbon product to produce the catalyst composition, wherein the shaped porous carbon product comprises: (a) carbon black and (b) a carbonized binder comprising a carbonization product of a water soluble organic binder and wherein the shaped porous carbon product has a BET specific surface area from about 20 $m^2/g$ to about 500 $m^2/g$, a mean pore diameter greater than about 5 nm, a specific pore volume greater than about 0.1 $cm^3/g$, a radial piece crush strength greater than about 4.4 N/mm (1 lb/mm), a carbon black content of at least about 35 wt. %, and a carbonized binder content from about 20 wt. % to about 50 wt. %.

Catalytic Processes

The catalyst compositions comprising the shaped porous carbon product of the present invention are useful for various catalytic conversions including oxidations, reductions, dehydrations, hydrogenations and other known transformations using appropriate active metals formulations and which can be conducted in gaseous or liquid medium. Accordingly, in further aspects, the present invention is directed to processes for the catalytic conversion of a reactant.

Processes of the present invention comprise contacting a liquid medium comprising the reactant with a catalyst composition comprising the shaped porous carbon product as a catalyst support. In various embodiments, the shaped porous carbon product comprises (a) carbon black and (b) a carbonized binder comprising a carbonization product of a water soluble organic binder, wherein the shaped porous carbon product has a BET specific surface area from about 20 $m^2/g$ to about 500 $m^2/g$ or from about 25 $m^2/g$ to about 250 $m^2/g$, a mean pore diameter greater than about 10 nm, a specific pore volume greater than about 0.1 $cm^3/g$, a radial piece crush strength greater than about 4.4 N/mm (1 lb/mm), and a carbon black content of at least about 35 wt. %. In other embodiments, the shaped porous carbon product comprises a carbon agglomerate, wherein the shaped porous carbon product has a mean diameter of at least about 50 μm, a BET specific surface area from about 20 $m^2/g$ to about 500 $m^2/g$ or from about 25 $m^2/g$ to about 250 $m^2/g$, a mean pore diameter greater than about 10 nm, a specific pore volume greater than about 0.1 $cm^3/g$, and a radial piece crush strength greater than about 4.4 N/mm (1 lb/mm). Typically, the catalyst composition has superior mechanical strength (e.g., mechanical piece crush strength and/or radial piece crush strength) and is stable to the continuous flow of the liquid medium and reaction conditions for at least about 500 hours or about 1,000 hours without substantial loss in catalytic productivity, selectivity, and/or yield.

In addition, it has been surprisingly discovered that the catalyst compositions comprising the shaped porous carbon product of the present invention are highly productive and selective catalysts for a certain of chemical transformations such as the conversion of highly functionalized and/or non-volatile molecules including, but not limited to biorenewably-derived molecules and intermediates for commodity applications.

Catalytic Oxidation

One series of chemical transformations that the catalyst compositions of the present invention are suited for is the selective oxidation of a hydroxyl group to a carboxyl group in a liquid or gaseous reaction medium. For example, one series of chemical transformations that the catalyst compositions of the present invention are especially suited for is the selective oxidation an aldose to an aldaric acid. Accordingly, catalyst compositions of the present invention as described herein can be utilized as oxidation catalysts. Aldoses include, for example, pentoses and hexoses (i.e., C-5 and C-6 monosaccharides). Pentoses include ribose, arabinose, xylose, and lyxose, and hexoses include glucose, allose, altrose, mannose, gulose, idose, galactose, and talose. Accordingly, in various embodiments, the present invention is also directed to a process for the selective oxidation of an aldose to an aldaric acid comprising reacting the aldose with oxygen in the presence of a catalyst composition as described herein to form the aldaric acid. Typically, the catalyst composition comprises at least platinum as a catalytically active component.

The catalyst compositions of the present invention have been found to be especially selective for the oxidation of the glucose to glucaric acid. Accordingly, the present invention is directed to a process for the selective oxidation of glucose to glucaric acid comprising reacting the aldose with oxygen in the presence of a catalyst composition as described herein to form glucaric acid. U.S. Pat. No. 8,669,397, the entire contents of which are incorporated herein by reference, discloses various catalytic processes for the oxidation of glucose to glucaric acid. In general, glucose may be converted to glucaric acid in high yield by reacting glucose with oxygen (e.g., air, oxygen-enriched air, oxygen alone, or oxygen with other constituents substantially inert to the reaction) in the presence of an oxidation catalyst according to the following reaction:

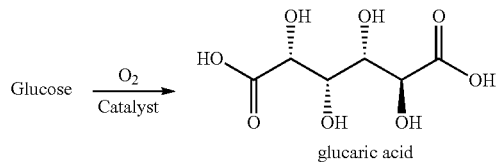 [SMILES: "O2" ; O=C(O)[C@@H](O)[C@@H](O)[C@H](O)[C@@H](O)C(=O)O]

glucaric acid

The oxidation can be conducted in the absence of added base (e.g., KOH) or where the initial pH of the reaction medium and/or the pH of reaction medium at any point in the reaction is no greater than about 7, no greater than 7.0, no greater than about 6.5, or no greater than about 6. The initial pH of the reaction mixture is the pH of the reaction mixture prior to contact with oxygen in the presence of an oxidation catalyst. In fact, catalytic selectivity can be maintained to attain glucaric acid yield in excess of about 30%, about 40%, about 50%, about 60% and, in some instances, attain yields in excess of 65% or higher. The absence of added base advantageously facilitates separation and isolation of the glucaric acid, thereby providing a process that is more amenable to industrial application, and improves overall process economics by eliminating a reaction constituent. The "absence of added base" as used herein means that base, if present (for example, as a constituent of a feedstock), is present in a concentration which has essentially no effect on the efficacy of the reaction; i.e., the oxidation reaction is being conducted essentially free of added base. The oxidation reaction can also be conducted in the presence of a weak carboxylic acid, such as acetic acid, in which glucose is soluble. The term "weak carboxylic acid" as used herein means any unsubstituted or substituted carboxylic acid having a pKa of at least about 3.5, more preferably at least about 4.5 and, more particularly, is selected from among unsubstituted acids such as acetic acid, propionic acid or butyric acid, or mixtures thereof.

The oxidation reaction may be conducted under increased oxygen partial pressures and/or higher oxidation reaction mixture temperatures, which tends to increase the yield of glucaric acid when the reaction is conducted in the absence of added base or at a pH below about 7. Typically, the partial pressure of oxygen is at least about 15 pounds per square inch absolute (psia) (104 kPa), at least about 25 psia (172 kPa), at least about 40 psia (276 kPa), or at least about 60 psia (414 kPa). In various embodiments, the partial pressure of oxygen is up to about 1,000 psia (6895 kPa), more typically in the range of from about 15 psia (104 kPa) to about 500 psia (3447 kPa), from about 75 psia (517 kPa) to about 500 psia (3447 kPa), from about 100 psia (689 kPa) to about 500 psia (3447 kPa), from about 150 psia (1034 kPa) to about 500 psia (3447 kPa). Generally, the temperature of the oxidation reaction mixture is at least about 40° C., at least about 60° C., at least about 70° C., at least about 80° C., at least about 90° C., at least about 100° C., or higher. In various embodiments, the temperature of the oxidation reaction mixture is from about 40° C. to about 200° C., from about 60° C. to about 200° C., from about 70° C. to about 200° C., from about 80° C. to about 200° C., from about 80° C. to about 180° C., from about 80° C. to about 150° C., from about 90° C. to about 180° C., or from about 90° C. to about 150° C. Surprisingly, the catalyst compositions comprising the shaped porous carbon product as a catalyst support permit glucose oxidation at elevated temperatures (e.g., from about 100° C. to about 160° C. or from about 125° C. to about 150° C.) without heat degradation of the catalyst. In particular, reactor formats such as a fixed bed reactor which can provide a relatively high liquid throughput in combination with the catalyst compositions comprising the shaped porous carbon product comprising carbon black have been found to permit oxidation at temperatures in excess of 140° C. (e.g., 1400 to about 150° C.).

Oxidation of glucose to glucaric acid can also be conducted in the absence of nitrogen as an active reaction constituent. Some processes employ nitrogen compounds such as nitric acid as an oxidant. The use of nitrogen in a form in which it is an active reaction constituent, such as nitrate or nitric acid, results in the need for $NO_x$ abatement technology and acid regeneration technology, both of which add significant cost to the production of glucaric acid from these known processes, as well as providing a corrosive environment which may deleteriously affect the equipment used to carry out the process. By contrast, for example, in the event air or oxygen-enriched air is used in the oxidation reaction of the present invention as the source of oxygen, the nitrogen is essentially an inactive or inert constituent. Thus, an oxidation reaction employing air or oxygen-enriched air is a reaction conducted essentially free of nitrogen in a form in which it would be an active reaction constituent.

In accordance with various embodiments, glucose is oxidized to glucaric acid in the presence of a catalyst composition comprising the shaped porous carbon product as a catalyst support described herein and a catalytically active component at a surface of the support. In certain embodiments the catalytically active component comprises platinum. In some embodiments, the catalytically active component comprises platinum and gold.

Applicants have discovered that oxidation catalyst compositions comprising the shaped porous carbon product of the present invention provide unexpectedly greater selectivity and yield for producing glucaric acid from glucose when compared to similar catalysts comprising similar support materials such as activated carbon. In particular, applicants have unexpectedly found that enhanced selectivity and yield for glucaric acid can be achieved by use of an oxidation catalyst composition comprising the shaped porous carbon product as a catalyst support and a catalytically active component comprising platinum and gold at a surface of the shaped porous carbon product (i.e., at a surface of the catalyst support).

The oxidation catalyst can include any of the shaped porous carbon products as described herein. For example, in various embodiments, the shaped porous carbon product comprises (a) carbon black and (b) a carbonized binder comprising a carbonization product of a water soluble organic binder, wherein the shaped porous carbon product has a BET specific surface area from about 20 $m^2/g$ to about 500 $m^2/g$ or from about 25 $m^2/g$ to about 250 $m^2/g$, a mean pore diameter greater than about 10 nm, a specific pore volume greater than about 0.1 $cm^3/g$, a radial piece crush strength greater than about 4.4 N/mm (1 lb/mm), and a carbon black content of at least about 35 wt. %. In other embodiments, the shaped porous carbon product comprises a carbon agglomerate, wherein the shaped porous carbon product has a mean diameter of at least about 50 μm, a BET specific surface area from about 20 $m^2/g$ to about 500 $m^2/g$ or from about 25 $m^2/g$ to about 250 $m^2/g$, a mean pore diameter greater than about 10 nm, a specific pore volume greater than about 0.1 $cm^3/g$, and a radial piece crush strength greater than about 4.4 N/mm (1 lb/mm). Another shaped porous carbon product in accordance with the present invention also has a pore volume measured on the basis of pores having a diameter from 1.7 nm to 100 nm and at least about 35% of the pore volume is attributable to pores having a mean pore diameter of from about 10 nm to about 50 nm.

The enhanced glucaric acid yield is typically at least about 30%, at least about 35%, at least about 40%, at least about, 45%, or at least about 50% (e.g., from about 35% to about 65%, from about 40% to about 65%, or from about 45% to about 65%). Further, the enhanced glucaric acid selectivity is typically at least about 70%, at least about 75%, or at least about 80%.

In various embodiments, the catalytically active components or precursors thereof comprising platinum and gold are in the form described in U.S. Patent Application Publication 2011/0306790, the entire contents of which are incorporated herein by reference. This publication describes various oxidation catalysts comprising a catalytically active component comprising platinum and gold, which are useful for the selective oxidation of compositions comprised of a primary alcohol group and at least one secondary alcohol group (e.g., glucose).

In various embodiments, an oxidation catalyst composition according the present invention comprises the shaped porous carbon product as described herein as a catalyst support comprising particles of gold in the form of a gold-containing alloy and particles consisting essentially of platinum (0) as the catalytically active components on a surface of the catalyst support. Typically, the total metal loading of the catalyst composition is about 10 wt. % or less, from about 1 wt. % to about 8 wt. %, from about 1 wt. % to about 5 wt. %, or from about 2 wt. % to about 4 wt. %.

In order to oxidize glucose to glucaric acid, a sufficient amount of the catalytically active component must be present relative to the amount of reactant (i.e., glucose). Accordingly, in a process of the present invention for the oxidation of glucose to glucaric acid as described herein where the catalytically active component comprises platinum, typically the mass ratio of glucose to platinum is from about 10:1 to about 1000:1, from about 10:1 to about 500:1, from about 10:1 to about 200:1, or from about 10:1 to about 100:1.

In various embodiments, the oxidation catalyst of the present invention may be prepared according to the following method. The gold component of the catalyst is typically added to the shaped porous carbon product as a solubilized constituent to enable the formation of a uniform suspension. A base is then added to the suspension in order to create an insoluble gold complex which can be more uniformly deposited onto the support. For example, the solubilized gold constituent is provided to the slurry as gold salt, such as HAuCl4. Upon creation of a well dispersed, heterogeneous mixture, a base is added to the slurry to form an insoluble gold complex which then deposits on the surface of the shaped porous carbon product. Although any base which can affect the formation of an insoluble gold complex is useable, bases such as KOH, NaOH are typically employed. It may be desirable, though not required, to collect the shaped porous carbon product on which has been deposited the insoluble gold complex prior to adding the platinum-containing constituent, which collection can readily be accomplished by any of a variety of means known in the art such as, for example, centrifugation. The collected solids may optionally be washed and then may be heated to dry. Heating may also be employed so as to reduce the gold complex on the support to gold (0). Heating may be conducted at temperatures ranging from about 60° C. (to dry) up to about 500° C. (at which temperature the gold can be effectively reduced). In various embodiments, the heating step may be conducted in the presence of a reducing or oxidizing atmosphere in order to promote the reduction of the complex to deposit the gold onto the support as gold (0). Heating times vary depending upon, for example, the objective of the heating step and the decomposition rate of the base added to form the insoluble complex, and the heating times can range from a few minutes to a few days. More typically, the heating time for the purpose of drying ranges from about 2 to about 24 hours and for reducing the gold complex is on the order of about 1 to about 4 hours.

In various embodiments, the concentration of the shaped porous carbon product in the slurry can be in the range of about 1 to about 100 g of solid/liter of slurry, and in other embodiments the concentration can be in the range of about 5 to about 25 g of solid/liter of slurry.

Mixing of the slurry containing the soluble gold-containing compound is continued for a time sufficient to form at least a reasonably uniform suspension. Appropriate times can range from minutes to a few hours. After addition of the base to convert the gold-containing compound to an insoluble gold-containing complex, the uniformity of the slurry should be maintained for a time sufficient to enable the insoluble complex to be formed and deposit on the shaped porous carbon product. In various embodiments, the time can range from a few minutes to several hours.

Platinum can be added to the shaped porous carbon product or slurry thereof after deposition of gold onto the shaped porous carbon product or after heat treatment to reduce the gold complex on the support to gold (0). Alternatively, the platinum may be added to the shaped porous carbon product or slurry thereof prior to the addition of the solubilized gold compound provided the platinum present on the support is in a form that will not be re-dissolved upon the addition of base used to promote the deposition of gold onto the support. The platinum is typically added as a solution of a soluble precursor or as a colloid. Platinum may be added as a compound selected form the group of platinum (II) nitrate, platinum(IV) nitrate, platinum oxynitrate, platinum (II) acetylacetonate (acac), tetraamineplatinum (II) nitrate, tetraamineplatinum (II) hydrogenphosphate, tetraamineplatinum (II) hydrogencarbonate, tetraamineplatinum (II) hydroxide, $H_2PtCl_6$, $PtCl_4$, $Na_2PtCl_4$, $K_2PtCl_4$, $(NH_4)_2PtCl_4$, $Pt(NH_3)_4C_2$, mixed $Pt(NH_3)_xCl_y$, $K_2Pt(OH)_6$, $Na_2Pt(OH)_6$, $(NMe_4)_2Pt(OH)_6$, and $(EA)_2Pt(OH)_6$ where EA=ethanolamine. More preferred compounds include platinum(II) nitrate, platinum(IV) nitrate, platinum(II) acetylacetonate (acac), tetraamine platinum(II) hydroxide, $K_2PtCl_4$, and $K_2Pt(OH)_6$.

Subsequent to the addition of the platinum compound, the support slurry and platinum-containing compound is dried. Drying may be conducted at room temperature or at a temperature up to about 120° C. More preferably, drying is conducted at a temperature in the range of about 40° C. to about 80° C. and more preferably still at about 60° C. The drying step may be conducted for a period of time ranging from about a few minutes to a few hours. Typically, the drying time is in the range of about 6 hours to about 24 hours. The drying can also be done with continuous or staged temperature increase from about 60° C. to 120° C. on a band calciner or belt dryer (which is preferred for commercial applications).

After drying the support having the platinum compound deposited thereon, it is subjected to at least one thermal treatment in order to reduce platinum deposited as platinum (II) or platinum (IV) to platinum (0). The thermal treatment(s) can be conducted in air or in any reducing or oxidizing atmosphere. In various embodiments the thermal treatment(s) is (are) conducted under a forming gas atmosphere. Alternatively, a liquid reducing agent may be employed to reduce the platinum; for example, hydrazine or formaldehyde or formic acid or salts thereof (e.g., sodium formate) or $NaH_2PO_2$ may be employed to effect the requisite reduction of the platinum. The atmosphere under which the thermal treatment is conducted is dependent upon the platinum compound employed, with the objective being substantially converting the platinum on the support to platinum (0).

The temperatures at which the thermal treatment(s) is (are) conducted generally range from about 150° C. to about 600° C. More typically, the temperatures of the thermal treatment(s) range from about 200° C. to about 500° C. and, preferably, the range is from about 200° C. to about 400° C. The thermal treatment is typically conducted for a period of time ranging from about 1 hour to about 8 hours or from about 1 hour to about 3 hours.

In various embodiments, the metal(s) deposited on the shaped porous carbon product for the oxidation catalyst form a shell at least partially covering the surface of the carbon product. In other words, metal deposited on the shaped porous carbon product coats external surfaces of the carbon product. In various embodiments, the metal penetrates surficial pores of the shaped porous carbon product to form a shell layer ("egg shell") with a thickness of from about 10 μm to about 400 μm, or from about 50 μm to about 150 μm (e.g., about 100 m). In certain embodiments the shell may be produced sub-surface to produce a 10 μm to about 400 μm sub-surface band containing the catalytically active metals ("egg yolk").

Catalytic Hydrodeoxygenation

One series of chemical transformations that the catalyst compositions of the present invention are suited for is the hydrodeoxygenation of carbon-hydroxyl groups to carbon-hydrogen groups in a liquid or gaseous reaction medium. For example, one series of chemical transformation that the catalyst compositions of the present invention are especially suited for is the selective halide-promoted hydrodeoxygenation of an aldaric acid or salt, ester, or lactone thereof to a dicarboxylic acid. Accordingly, catalyst compositions of the present invention as described herein can be utilized as hydrodeoxygenation catalysts. As such, the present invention is also directed to a process for the selective halide promoted hydrodeoxygenation of an aldaric acid comprising reacting the aldaric acid or salt, ester, or lactone thereof with hydrogen in the presence of a halogen-containing compound and a catalyst composition as described herein to form a dicarboxylic acid. Typically, the catalyst composition comprises at least one noble metal as a catalytically active component.

The catalyst compositions of the present invention have been found to be especially selective for halide-promoted hydrodeoxygenation of glucaric acid or salt, ester, or lactone thereof to adipic acid. U.S. Pat. No. 8,669,397, referenced above and incorporated herein by reference, describes the chemocatalytic processes for the hydrodeoxygenation of glucaric acid to adipic acid.

Adipic acid or salts and esters thereof may be prepared by reacting, in the presence of a hydrodeoxygenation catalyst and a halogen source, glucaric acid or salt, ester, or lactone thereof, and hydrogen, according to the following reaction:

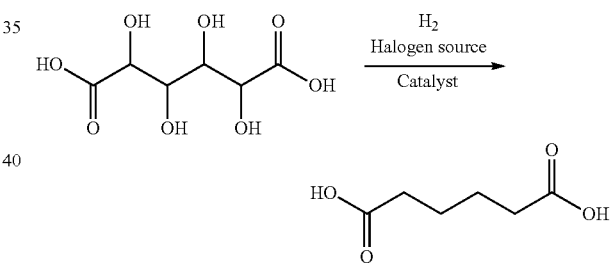

In the above reaction, glucaric acid or salt, ester, or lactone thereof is converted to an adipic acid product by catalytic hydrodeoxygenation in which carbon-hydroxyl groups are converted to carbon-hydrogen groups. In various embodiments, the catalytic hydrodeoxygenation is hydroxyl-selective wherein the reaction is completed without substantial conversion of the one or more other non-hydroxyl functional group of the substrate.

The halogen source may be in a form selected from the group consisting of ionic, molecular, and mixtures thereof. Halogen sources include hydrohalic acids (e.g., HCl, HBr, HI and mixtures thereof; preferably HBr and/or HI), halide salts, (substituted or unsubstituted) alkyl halides, or molecular (diatomic) halogens (e.g., chlorine, bromine, iodine or mixtures thereof, preferably bromine and/or iodine). In various embodiments the halogen source is in diatomic form, hydrohalic acid, or halide salt and, more preferably, diatomic form or hydrohalic acid. In certain embodiments, the halogen source is a hydrohalic acid, in particular hydrogen bromide.

Generally, the molar ratio of halogen to the glucaric acid or salt, ester, or lactone thereof is about equal to or less than about 1. In various embodiments, the mole ratio of halogen to the glucaric acid or salt, ester, or lactone thereof is typically from about 1:1 to about 0.1:1, more typically from about 0.7:1 to about 0.3:1, and still more typically about 0.5:1.

Generally, the reaction allows for recovery of the halogen source and catalytic quantities (where molar ratio of halogen to the glucaric acid or salt, ester, or lactone thereof is less than about 1) of halogen can be used, recovered and recycled for continued use as a halogen source.

Generally, the temperature of the hydrodeoxygenation reaction mixture is at least about 20° C., typically at least about 80° C., and more typically at least about 100° C. In various embodiments, the temperature of the hydrodeoxygenation reaction is conducted in the range of from about 20° C. to about 250° C., from about 80° C. to about 200° C., from about 120° C. to about 180° C., or from about 140° C. to 180° C. Typically, the partial pressure of hydrogen is at least about 25 psia (172 kPa), more typically at least about 200 psia (1379 kPa) or at least about 400 psia (2758 kPa). In various embodiments, the partial pressure of hydrogen is from about 25 psia (172 kPa) to about 2500 psia (17237 kPa), from about 200 psia (1379 kPa) to about 2000 psia (13790 kPa), or from about 400 psia (2758 kPa) to about 1500 psia (10343 kPa).

The hydrodeoxygenation reaction is may be conducted in the presence of a solvent. Solvents suitable for the selective hydrodeoxygenation reaction include water and carboxylic acids, amides, esters, lactones, sulfoxides, sulfones and mixtures thereof. Preferred solvents include water, mixtures of water and weak carboxylic acid, and weak carboxylic acid. A preferred weak carboxylic acid is acetic acid.

Applicants have discovered that hydrodeoxygenation catalyst compositions comprising the shaped porous carbon product of the present invention provide enhanced selectivity and yield for producing adipic acid. In particular, applicants have unexpectedly found that enhanced selectivity and yield for adipic acid can be achieved by use of a catalyst composition comprising the shaped porous carbon product of the present invention as a catalyst support and a catalytically active component at a surface of the shaped porous carbon product (i.e., at a surface of the catalyst support).

The catalyst can include any of the shaped porous carbon products as described herein. For example, in various embodiments, the shaped porous carbon product comprises (a) carbon black and (b) a carbonized binder comprising a carbonization product of a water soluble organic binder, wherein the shaped porous carbon product has a BET specific surface area from about 20 m²/g to about 500 m²/g or from about 25 m²/g to about 250 m²/g, a mean pore diameter greater than about 5 nm, a specific pore volume greater than about 0.1 cm³/g, a radial piece crush strength greater than about 4.4 N/mm (1 lb/mm), and a carbon black content of at least about 35 wt. %. In other embodiments, the shaped porous carbon product comprises a carbon agglomerate, wherein the shaped porous carbon product has a mean diameter of at least about 50 μm, a BET specific surface area from about 20 m²/g to about 500 m²/g or from about 25 m²/g to about 250 m²/g, a mean pore diameter greater than about 5 nm, a specific pore volume greater than about 0.1 cm³/g, and a radial piece crush strength greater than about 4.4 N/mm (1 lb/mm). Another shaped porous carbon product in accordance with the present invention also has a pore volume measured on the basis of pores having a diameter from 1.7 nm to 100 nm and at least about 35% of the pore volume is attributable to pores having a mean pore diameter of from about 10 nm to about 50 nm.

The catalytically active component or precursor thereof may include noble metals selected from the group consisting of ruthenium, rhodium, palladium, platinum, and combinations thereof. In various embodiments, the hydrodeoxygenation catalyst comprises two or more metals. For example, in some embodiments, the first metal is selected from the group consisting of cobalt, nickel, ruthenium, rhodium, palladium, osmium, iridium, and platinum (more particularly, ruthenium, rhodium, palladium, and platinum) and the second metal is selected from the group consisting of titanium, vanadium, chromium, manganese, iron, cobalt, nickel, copper, molybdenum, ruthenium, rhodium, palladium, silver, tungsten, iridium, platinum, and gold (more particularly, molybdenum, ruthenium, rhodium, palladium, iridium, platinum, and gold). In select embodiments, the first metal is selected from the group of platinum, rhodium and palladium, and the second metal is selected from the group consisting of ruthenium, rhodium, palladium, platinum, and gold. In certain embodiments, the first metal is platinum and the second metal is rhodium. In these and other embodiments, the platinum to rhodium molar ratio of the catalyst composition of the present invention is in the range of from about 3:1 to about 1:2 or from about 3:1 to about 1:1.

In various embodiments, the metal(s) deposited on the shaped porous carbon product for the hydrodeoxygenation catalyst form a shell at least partially covering the surface of the carbon product. In other words, metal deposited on the shaped porous carbon product coats external surfaces of the carbon product. In various embodiments, the metal penetrates surficial pores of the shaped porous carbon product to form a shell layer ("egg shell") with a thickness of from about 10 μm to about 400 μm, or from about 50 μm to about 150 μm (e.g., about 100 m). In certain embodiments the shell may be produced sub-surface to produce a 10 μm to about 400 μm sub-surface band containing the catalytically active metals ("egg yolk").

Hydrodeoxygenation of 1,2,6-Hexanetriol

Another chemical transformation that the catalyst compositions of the present invention is advantageous for is the selective hydrodeoxygenation of 1,2,6-hexanetriol to 1,6-hexanediol (HDO) and 1,2,5,6-hexanetetraol to 1,6-HDO). Accordingly, one process of the present invention is directed to the selective hydrodeoxygenation of 1,2,6-hexanetriol comprising reacting 1,2,6-hexanetriol with hydrogen in the presence of a catalyst composition as disclosed herein to form HDO. In embodiments of this process, the catalytically active component of the catalyst composition comprises platinum. In some embodiments, the catalytically active component of the catalyst composition comprises platinum and at least one metal (M2) selected from the group of molybdenum, lanthanum, samarium, yttrium, tungsten, and rhenium. In certain embodiments, the catalytically active component of the catalyst composition comprises platinum and tungsten.

Typically, the total weight of metal(s) is from about 0.1% to about 10%, or from 0.2% to 10%, or from about 0.2% to about 8%, or from about 0.2% to about 5%, of the total weight of the catalyst. In more preferred embodiments the total weight of metal of the catalyst is less than about 4%. The molar ratio of platinum to (M2) may vary, for example, from about 20:1 to about 1:10. In various embodiments, the M1:M2 molar ratio is in the range of from about 10:1 to about 1:5. In still more preferred embodiments, the ratio of M1:M2 is in the range of about 8:1 to about 1:2.

Typically, the conversion of 1,2,6-hexanetriol to HDO is conducted at a temperature in the range of about 60° C. to about 200° C. or about 120° C. to about 180° C. and a partial pressure of hydrogen in the range of about 200 psig to about 2000 psig or about 500 psig to about 2000 psig.

Catalytic Amination of 1,6-Hexanediol

Furthermore, the catalyst compositions of the present invention are also useful for the selective amination of 1,6-hexanediol (HDO) to 1,6-hexamethylenediamine (HMDA). Accordingly, another process of the present invention is directed to the selective amination of 1,6-hexanediol to 1,6-hexamethylenediamine comprising reacting the HDO with an amine in the presence of a catalyst composition as disclosed herein. In various embodiments of this process, the catalytically active component of the catalyst composition comprises ruthenium.

In some embodiments of this process, the catalytically active component of the catalyst composition comprises ruthenium and optionally a second metal such as rhenium or nickel. One or more other d-block metals, one or more rare earth metals (e.g., lanthanides), and/or one or more main group metals (e.g., Al) may also be present in combination with ruthenium and with ruthenium and rhenium combinations. In select embodiments, the catalytically active phase consists essentially of ruthenium and rhenium. Typically, the total weight of metal(s) is from about 0.1% to about 10%, from about 1% to about 6%, or from about 1% to about 5% of the total weight of the catalyst composition.

When the catalysts of the present invention comprise ruthenium and rhenium in combination, the molar ratio of ruthenium to rhenium is important. A by-product of processes for converting HDO to HMDA is pentylamine. Pentylamine is an off path by-product of the conversion of HDO to HMDA that cannot be converted to HMDA or to an intermediate which can, on further reaction in the presence of the catalysts of the present invention, be converted to HMDA. However, the presence of too much rhenium can have an adverse effect on the yield of HMDA per unit area time (commonly known as space time yield, or STY). Therefore, the molar ratio of ruthenium:rhenium should be maintained in the range of from about 20:1 to about 4:1. In various embodiments, the ruthenium:rhenium molar ratio is in the range of from about 10:1 to about 4:1 or from about 8:1 to about 4:1. In some embodiments, the ruthenium:rhenium molar ratio of from about 8:1 to about 4:1 produces HMDA in at least 25% yield with an HMDA/pentylamine ratio of at least 20:1, at least 25:1, or at least 30:1.

In accordance with the present invention, HDO is converted to HMDA by reacting HDO with an amine, e.g., ammonia, in the presence of the catalysts of the present invention. Generally, in some embodiments, the amine may be added to the reaction in the form of a gas or liquid. Typically, the molar ratio of ammonia to HDO is at least about 40:1, at least about 30:1, or at least about 20:1. In various embodiments, it is in the range of from about 40:1 to about 5:1, from about 30:1 to about 10:1. The reaction of HDO with amine in the presence of the catalyst composition of the present invention is carried out at a temperature less than or equal to about 200° C. In various embodiments, the catalyst composition is contacted with HDO and amine at a temperature less than or equal to about 100° C. In some embodiments, the catalyst is contacted with HDO and amine at a temperature in the range of about 100° C. to about 180° C. or about 140° C. to about 180° C.

Generally, in accordance with the present invention, the reaction is conducted at a pressure not exceeding about 1500 psig. In various embodiments, the reaction pressure is in the range of about 200 psig to about 1500 psig. In other embodiments, and a pressure in the range of about 400 psig to about 1200 psig. In certain preferred embodiments, the pressure in the range of about 400 psig to about 1000 psig. In some embodiments, the disclosed pressure ranges includes the pressure of $NH_3$ gas and an inert gas, such as $N_2$. In some embodiments, the pressure of $NH_3$ gas is in the range of about 50-150 psig and an inert gas, such as $N_2$ is in the range of about 700 psig to about 1450 psig.

In some embodiments, the catalyst is contacted with HDO and ammonia at a temperature in the range of about 100° C. to about 180° C. and a pressure in the range of about 200 psig to about 1500 psig. In other embodiments, the catalyst is contacted with HDO and ammonia at a temperature in the range of about 140° C. to about 180° C. and a pressure in the range of about 400 psig to about 1200 psig. In some embodiments, the disclosed pressure ranges includes the pressure of $NH_3$ gas and an inert gas, such as $N_2$. In some embodiments, the pressure of $NH_3$ gas is in the range of about 50-150 psig and an inert gas, such as $N_2$ is in the range of about 500 psig to about 1450 psig.

The process of the present invention may be carried out in the presence of hydrogen. Typically, in those embodiments in which the HDO and amine are reacted in the presence of hydrogen and the catalyst of the present invention, the hydrogen partial pressure is equal to or less than about 100 psig.

The conversion of HDO to HMDA can also be conducted in the presence of a solvent. Solvents suitable for use in conjunction with the conversion of HDO to HMDA in the presence of the catalysts of the present invention may include, for example, water, alcohols, esters, ethers, ketones, or mixtures thereof. In various embodiments, the preferred solvent is water.

The chemocatalytic conversion of HDO to HMDA is likely to produce one or more by-products such as, for example, pentylamine and hexylamine. By-products which are subsequently convertible to HMDA by further reaction in the presence of catalysts of the present invention are considered on-path by-products. Other by-products such as, for example, pentylamine and hexylamine are considered off path by-products for the reasons above discussed. In accordance with the present invention, at least 20%, at least 30%, at least 40%, at least 50%, at least 60%, or at least 70% of the product mixture resulting from a single pass reaction of HDO with amine (e.g., ammonia) in the presence of the catalysts of the present invention is HMDA.

The product mixture may be separated into one or more products by any suitable methods known in the art. In some embodiments, the product mixture can be separated by fractional distillation under subatmospheric pressures. For example, in some embodiments, HMDA can be separated from the product mixture at a temperature between about 180° C. and about 220° C. The HDO may be recovered from any remaining other products of the reaction mixture by one or more conventional methods known in the art including, for example, solvent extraction, crystallization or evaporative processes. The on-path by-products can be recycled to the reactor employed to produce the product mixture or, for example, supplied to a second reactor in which the on path by-products are further reacted with ammonia in the presence of the catalysts of the present invention to produce additional HMDA.

Glycerol Hydrogenolysis

Another chemical transformation that the catalyst supports and catalyst compositions of the present invention are advantageous for is the hydrogenolysis of glycerol to various diols, particularly propylene glycol (1,2-propanediol) and/or ethylene glycol (1,2-ethanediol). For example, processes for the hydrogenolysis of glycerol are described in U.S. Pat. Nos. 6,479,713 and 7,928,148 as well as U.S. Patent Application Publication No. 2018/0201559, the contents of which are hereby incorporated herein by reference. Accordingly, in various embodiments, processes for the hydrogenolysis of glycerol comprise feeding a feed composition comprising glycerol to a reaction zone and reacting the glycerol with hydrogen in the presence of a catalyst composition as described herein in the reaction zone to form a reaction product comprising propylene glycol and/or ethylene glycol.

In some embodiments, processes for the hydrogenolysis of glycerol comprise feeding a feed composition comprising glycerol to a reaction zone and reacting the glycerol with hydrogen in the presence of a catalyst composition in the reaction zone to form a reaction product comprising propylene glycol and/or ethylene glycol, wherein the catalyst composition comprises a catalytically active component comprising a metal selected from the group consisting of chromium, cobalt, nickel, copper, zinc, ruthenium, rhodium, palladium, silver, rhenium, osmium, iridium, platinum, gold, and any combination thereof and a catalyst support comprising a shaped porous carbon product comprising carbon black. The shaped porous carbon product can include one or more features as described herein (e.g., specific surface area, mean pore diameter, specific pore volume, mesoporosity, pore size distribution, radial and mechanical piece crush strength, mean diameter, attrition index, abrasion loss, and so on). The shaped porous carbon product can also include a carbonization product of a binder as described herein (e.g., carbonized saccharide, cellulosic compound, etc.)

For example, a catalyst comprising a shaped porous carbon product as the catalyst support, which exhibits a high level of mesoporosity, has been found to be an especially effective catalyst for this reaction. The shaped porous carbon product advantageously exhibits a high concentration of mesopores between about 10 nm to about 100 nm, between about 20 nm to about 100 nm, or between about 10 nm to about 50 nm. Accordingly, in various embodiments, at least about 50%, at least about 60%, at least about 70%, at least about 80%, at least about 90%, at least about 95% of the pore volume of the shaped porous carbon product, as measured by the BJH method on the basis of pores having a diameter from 1.7 nm to 100 nm, is attributable to pores having a mean pore diameter of from about 10 nm to about 100 nm. For example, from about 50% to about 99%, from about 50% to about 95%, from about 50% to about 90%, from about 50% to about 80%, from about 60% to about 99%, from about 60% to about 95%, from about 60% to about 90%, from about 60% to about 80%, from about 70% to about 99%, from about 70% to about 95%, from about 70% to about 90%, from about 70% to about 80%, from about 80% to about 99%, from about 80% to about 95%, from about 80% to about 90%, or from about 90% to about 99% of the pore volume of the shaped porous carbon product, as measured by the BJH method on the basis of pores having a diameter from 1.7 nm to 100 nm, is attributable to pores having a mean pore diameter of from about 10 nm to about 100 nm. Also, in various embodiments, at least about 35%, at least about 40%, at least about 45%, or at least about 50% of the pore volume of the shaped porous carbon product, as measured by the BJH method on the basis of pores having a diameter from 1.7 nm to 100 nm, is attributable to pores having a mean pore diameter of from about 20 nm to about 90 nm or from about 10 nm to about 50 nm. For example, from about 35% to about 80%, from about 35% to about 75%, from about 35% to about 65%, from about 40% to about 80%, from about 40% to about 75%, or from about 40% to about 70% of the pore volume of the shaped porous carbon product, as measured by the BJH method on the basis of pores having a diameter from 1.7 nm to 100 nm, is attributable to pores having a mean pore diameter of from about 20 nm to about 90 nm or from about 10 nm to about 50 nm.

Also, in various embodiments, the shaped porous carbon product has a relatively low concentration of macropores. For example, in some embodiments, about 10% or less, at least about 5% or less, or about 3% or less of the pore volume of the shaped porous carbon product as measured by mercury porosimetry is attributable to pores having a mean pore diameter of about 100 nm or greater. In certain embodiments, from about 0.1% to about 10%, from about 0.1% to about 5%, from about 0.1% to about 3%, from about 1% to about 10%, from about 1% to about 5%, or from about 1% to about 3% of the pore volume of the shaped porous carbon product as measured by mercury porosimetry is attributable to pores having a mean pore diameter of about 100 nm or greater. Further details regarding mercury porosimetry analysis are provided in the Examples.

Processes of the present invention for the hydrogenolysis of glycerol have been found to advantageously provide for high yields of propylene glycol. For example, various processes provide for a yield of propylene glycol that is at least about 50%, at least about 60%, at least about 65%, at least about 70%, at least about 75%, or at least about 80%.

As noted, in these hydrogenolysis processes, glycerol is reacted with hydrogen. In various embodiments, the partial pressure of hydrogen in the reaction zone is at least about 2.1 MPa (300 psi), at least about 6.9 MPa (1000 psi), at least about 12.4 MPa (1800 psi), or at least about 13.8 MPa (2000 psi). In some embodiments, the partial pressure of hydrogen in reaction zone is from about 2.1 MPa (300 psi) to about 13.8 MPa (2000 psi), from about 6.9 MPa (1000 psi) to about 13.8 MPa (2000 psi), or from about 12.4 MPa (1800 psi) to about 13.8 MPa (2000 psi). In some instances, it has been found that increasing the flow of hydrogen relative to the flow of glycerol in the reaction zone increases the yield of propylene glycol.

As noted, the catalyst composition typically comprises at least one catalytically active component comprising a metal selected from the group consisting of chromium, cobalt, nickel, copper, zinc, ruthenium, rhodium, palladium, silver, rhenium, osmium, iridium, platinum, gold, and any combination thereof. In some embodiments, the catalytically active component comprises rhenium. In various embodiments, the catalytically active component comprises nickel. In further embodiments, the catalytically active component comprises copper. In various embodiments, the catalytically active component comprises a combination of metals. For example, the combination of metals can be selected from the group consisting of nickel and rhenium, copper and rhenium, and cobalt and rhenium. In certain embodiments, the catalyst composition further comprises manganese, molybdenum, and/or zinc.

The catalyst composition can have a loading of the catalytically active component as described herein. In some embodiments, the catalyst composition has a loading of the catalytically active component of about 0.1 wt. % or greater, about 1 wt. % or greater, about 2 wt. % or greater, about 3 wt. % or greater, about 4 wt. % or greater, or about 5 wt. % or greater. In various embodiments, the catalyst composition has a loading of the catalytically active component of from about 0.1 wt. % to about 10 wt. %, from about 0.1 wt. % to about 7.5 wt. %, from about 0.1 wt. % to about 5 wt. %, about 0.5 wt. % to about 10 wt. %, from about 0.5 wt. % to about 7.5 wt. %, from about 0.5 wt. % to about 5 wt. %, from about 1 wt. % to about 10 wt. %, from about 1 wt. % to about 7.5 wt. %, or from about 1 wt. % to about 5 wt. %.

The catalyst composition for glycerol hydrogenolysis can have a catalyst structure as described herein. For example, the catalytically active component can form a shell layer at least partially covering the surface of the shaped porous carbon product. In some embodiments, the catalytically active component is primarily present on surficial pores of the shaped porous carbon product to form a shell layer with a thickness of from about 10 m to about 400 μm, or from about 50 μm to about 150 μm. In these and other embodiments, the catalyst composition comprises an inner region (e.g., core) and outer region (e.g., shell) and the outer region has a greater concentration of the catalytically active component than the inner region. For example, see FIGS. 14 and 16. In some embodiments, the outer region concentration of the catalytically active component is at least 2, 5, 10, or 100 times greater than the inner region concentration of the catalytically active component. In further embodiments, the catalyst composition has an average diameter and the outer region constitutes at least about 5%, at least about 10%, at least about 20%, from about 5% to about 50%, or from about 10% to about 40% of the average diameter. Also, in some embodiments, the inner region constitutes at least about 20%, at least about 30%, at least about 40%, from about 20% to about 80%, or from about 20% to about 70% of the average diameter.

The hydrogenolysis processes described herein can also be conducted in the presence of a co-catalyst. One example of a co-catalyst is a base. Therefore, in some embodiments, the reaction zone can further comprise a co-catalyst comprising a base. In various embodiments, the base comprises sodium hydroxide. Also, the base (e.g., sodium hydroxide) can be co-fed to the reaction zone with the feed composition comprising glycerol, or can be supplied at the inlet as well as one or more additional points along the length of a continuous flow, tubular reactor or at the start and at one or more later times in a batchwise process as described in U.S. Pat. No. 9,938,215.

The hydrogenolysis processes described herein can be conducted under neutral or basic conditions (e.g., slightly basic to basic). For example, the reaction can be conducted at a pH of from about 7 to about 11, from about 7.5 to about 10, from about 8 to about 14, or from about 10 to about 13.

The hydrogenolysis processes described herein can be conducted at a temperature of from about 150° C. to about 300° C., from about 175° C. to about 250° C., from about 190° C. to about 250° C., or from about 190° C. to about 225° C.

Further, the feed composition can comprise an aqueous glycerol solution. In some embodiments, the feed composition has a glycerol concentration of about 10 wt % or more, about 20 wt % or greater, about 30 wt % or greater, about 40 wt % or greater, from about 10 wt. % to about 50 wt. %, or from about 20 wt. % to about 40 wt. %. In certain embodiments, the feed composition further comprises at least one other polyol selected from the group consisting of five- and six-carbon sugars and sugar alcohols.

EMBODIMENTS

For further illustration, additional non-limiting embodiments of the shaped porous carbon products of the present disclosure, and of various methods of making and methods of using the same are set forth below.

Embodiment A1 is a shaped porous carbon product comprising:
carbon black and
a carbonized binder comprising a carbonization product of a water soluble organic binder, wherein the shaped porous carbon product has a BET specific surface area from about 20 $m^2/g$ to about 500 $m^2/g$ or from about 25 $m^2/g$ to about 250 $m^2/g$, a mean pore diameter greater than about 10 nm, a specific pore volume greater than about 0.1 $cm^3/g$, and a radial piece crush strength greater than about 4.4 N/mm (1 lb/mm).

Embodiment A2 is the shaped porous carbon product of embodiment A1, wherein the shaped porous carbon product has a BET specific surface area from about 25 $m^2/g$ to about 225 $m^2/g$, from about 25 $m^2/g$ to about 200 $m^2/g$, from about 25 $m^2/g$ to about 175 $m^2/g$, from about 25 $m^2/g$ to about 150 $m^2/g$, from about 25 $m^2/g$ to about 125 $m^2/g$, or from about 25 $m^2/g$ to about 100 $m^2/g$.

Embodiment A3 is the shaped porous carbon product of embodiment A1, wherein the shaped porous carbon product has a BET specific surface area from about 30 $m^2/g$ to about 225 $m^2/g$, from about 30 $m^2/g$ to about 200 $m^2/g$, from about 30 $m^2/g$ to about 175 $m^2/g$, from about 30 $m^2/g$ to about 150 $m^2/g$, from about 30 $m^2/g$ to about 125 $m^2/g$, or from about 30 $m^2/g$ to about 100 $m^2/g$.

Embodiment A4 is the shaped porous carbon product of any one of embodiments A1 to A3, wherein the shaped porous carbon product has a mean pore diameter greater than about 12 nm or greater than about 14 nm.

Embodiment A5 is the shaped porous carbon product of any one of embodiments A1 to A3, wherein the shaped porous carbon product has a mean pore diameter from about 10 nm to about 100 nm, from about 10 nm to about 70 nm, from 10 nm to about 50 nm, or from about 10 nm to about 25 nm.

Embodiment A6 is the shaped porous carbon product of any one of embodiments A1 to A5, wherein the shaped porous carbon product has a specific pore volume greater than about 0.2 $cm^3/g$ or greater than about 0.3 $cm^3/g$.

Embodiment A7 is the shaped porous carbon product of any one of embodiments A1 to A5, wherein the shaped porous carbon product has a specific pore volume of from about 0.1 $cm^3/g$ to about 1.5 $cm^3/g$, from about 0.1 $cm^3/g$ to about 0.9 $cm^3/g$, from about 0.1 $cm^3/g$ to about 0.8 $cm^3/g$, from about 0.1 $cm^3/g$ to about 0.7 $cm^3/g$, from about 0.1 $cm^3/g$ to about 0.6 $cm^3/g$, from about 0.1 $cm^3/g$ to about 0.5 $cm^3/g$, from about 0.2 $cm^3/g$ to about 1 $cm^3/g$, from about 0.2 $cm^3/g$ to about 0.9 $cm^3/g$, from about 0.2 $cm^3/g$ to about 0.8 $cm^3/g$, from about 0.2 $cm^3/g$ to about 0.7 $cm^3/g$, from about 0.2 $cm^3/g$ to about 0.6 $cm^3/g$, from about 0.2 $cm^3/g$ to about 0.5 $cm^3/g$, from about 0.3 $cm^3/g$ to about 1 $cm^3/g$, from about 0.3 $cm^3/g$ to about 0.9 $cm^3/g$, from about 0.3 $cm^3/g$ to about 0.8 $cm^3/g$, from about 0.3 $cm^3/g$ to about 0.7 $cm^3/g$, from about 0.3 $cm^3/g$ to about 0.6 $cm^3/g$, or from about 0.3 $cm^3/g$ to about 0.5 $cm^3/g$.

Embodiment A8 is the shaped porous carbon product of any one of embodiments A1 to A7, wherein the shaped porous carbon product has a pore volume measured on the basis of pores having a diameter from 1.7 nm to 100 nm and at least about 35%, at least about 40%, at least about 45%, or at least about 50% of the pore volume is attributable to pores having a mean pore diameter of from about 10 nm to about 50 nm.

Embodiment A9 is the shaped porous carbon product of any one of embodiments A1 to A7, wherein the shaped porous carbon product has a pore volume measured on the basis of pores having a diameter from 1.7 nm to 100 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment A10 is the shaped porous carbon product of any one of embodiments A1 to A9, wherein the shaped porous carbon product has a pore volume measured on the basis of pores having a diameter from 1.7 nm to 150 nm and at least about 35%, at least about 40%, at least about 45%, or at least about 50% of the pore volume is attributable to pores having a mean pore diameter of from about 10 nm to about 50 nm.

Embodiment A11 is the shaped porous carbon product of any one of embodiments A1 to A9, wherein the shaped porous carbon product has a pore volume measured on the basis of pores having a diameter from 1.7 nm to 150 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment A12 is the shaped porous carbon product of any one of embodiments A1 to A11, wherein the shaped porous carbon product has a pore volume measured on the basis of pores having a diameter from 1.7 nm to 200 nm and at least about 35%, at least about 40%, at least about 45%, or at least about 50% of the pore volume is attributable to pores having a mean pore diameter of from about 10 nm to about 50 nm.

Embodiment A13 is the shaped porous carbon product of any one of embodiments A1 to A11, wherein the shaped porous carbon product has a pore volume measured on the basis of pores having a diameter from 1.7 nm to 200 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment A14 is the shaped porous carbon product of any one of embodiments A1 to A13, wherein the shaped porous carbon product has a pore volume measured on the basis of pores having a diameter from 1.7 nm to 250 nm and at least about 35%, at least about 40%, at least about 45%, or at least about 50% of the pore volume is attributable to pores having a mean pore diameter of from about 10 nm to about 50 nm.

Embodiment A15 is the shaped porous carbon product of any one of embodiments A1 to A13, wherein the shaped porous carbon product has a pore volume measured on the basis of pores having a diameter from 1.7 nm to 250 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment A16 is the shaped porous carbon product of any one of embodiments A1 to A15, wherein the shaped porous carbon product has a pore volume measured on the basis of pores having a diameter from 1.7 nm to 300 nm and at least about 35%, at least about 40%, at least about 45%, or at least about 50% of the pore volume is attributable to pores having a mean pore diameter of from about 10 nm to about 50 nm.

Embodiment A17 is the shaped porous carbon product of any one of embodiments A1 to A15, wherein the shaped porous carbon product has a pore volume measured on the basis of pores having a diameter from 1.7 nm to 300 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment A18 is the shaped porous carbon product of any one of embodiments A1 to A17, wherein the shaped porous carbon product has a pore size distribution such that peaks below about 10 nm or about 5 nm are not observed.

Embodiment A19 is the shaped porous carbon product of any one of embodiments A1 to A18, wherein the shaped porous carbon product has a radial piece crush strength greater than about 8.8 N/mm (2 lbs/mm) or greater than about 13.3 N/mm (3 lbs/mm).

Embodiment A20 is the shaped porous carbon product of any one of embodiments A1 to A18, wherein the shaped porous carbon product has a radial piece crush strength from about 4.4 N/mm (1 lb/mm) to about 88 N/mm (20 lbs/mm), from about 4.4 N/mm (1 lb/mm) to about 66 N/mm (15 lbs/mm), or from about 8.8 N/mm (2 lb/mm) to about 44 N/mm (10 lbs/mm).

Embodiment A21 is the shaped porous carbon product of any one of embodiments A1 to A20, wherein the shaped porous carbon product has a mechanical piece crush strength greater than about 22 N (5 lbs), greater than about 36 N (8 lbs), or greater than about 44 N (10 lbs).

Embodiment A22 is the shaped porous carbon product of any one of embodiments A1 to A20, wherein the shaped porous carbon product has a mechanical piece crush strength from about 22 N (5 lbs) to about 88 N (20 lbs), from about 22 N (5 lbs) to about 66 N (15 lbs), or from about 33 N (7.5 lbs) to about 66 N (15 lbs).

Embodiment A23 is the shaped porous carbon product of any one of embodiments A1 to A22, wherein the shaped porous carbon product has a mean diameter of at least about 50 μm, at least about 500 μm, at least about 1,000 μm, or at least about 10,000 m.

Embodiment A24 is the shaped porous carbon product of any one of embodiments A1 to A23, wherein the carbon black content of the shaped porous carbon product is at least about 35 wt. %, at least about 40 wt. %, at least about 45 wt. %, at least about 50 wt. %, at least about 55 wt. %, at least about 60 wt. %, at least about 65 wt. %, or at least about 70 wt. %.

Embodiment A25 is the shaped porous carbon product of any one of embodiments A1 to A23, wherein the carbon black content of the shaped porous carbon product is from about 35 wt. % to about 80 wt. %, from about 35 wt. % to about 75 wt. %, from about 40 wt. % to about 80 wt. %, or from about 40 wt. % to about 75 wt. %.

Embodiment A26 is the shaped porous carbon product of any one of embodiments A1 to A25, wherein the carbon black comprises conductive carbon black.

Embodiment A27 is the shaped porous carbon product of any one of embodiments A1 to A26, wherein the carbon black comprises nonconductive carbon black.

Embodiment A28 is the shaped porous carbon product of embodiment A27, wherein the shaped porous carbon product does not exhibit a conductivity that is suitable for a conductive electrode.

Embodiment A29 is the shaped porous carbon product of embodiment A27 or A28, wherein the shaped porous carbon product comprises nonconductive carbon black and less than about 50%, less than about 40%, less than about 30%, less than about 20%, less than about 10%, less than about 5%, or less than about 1% conductive carbon black based on the total weight of the carbon black in the shaped porous carbon product.

Embodiment A30 is the shaped porous carbon product of any one of embodiments A1 to A25, wherein the shaped porous carbon product comprises carbon black consisting essentially of nonconductive carbon black.

Embodiment A31 is the shaped porous carbon product of any one of embodiments A1 to A25, wherein the shaped porous carbon product comprises carbon black consisting of nonconductive carbon black.

Embodiment A32 is the shaped porous carbon product of any one of embodiments A1 to A31, wherein the shaped porous carbon product has a carbonized binder content from about 10 wt. % to about 50 wt. %, from about 20 wt. % to about 50 wt. %, from about 25 wt. % to about 40 wt. %, or from about 25 wt. % to about 35 wt. %.

Embodiment A33 is the shaped porous carbon product of any one of embodiments A1 to A32, wherein the water soluble organic binder comprises a carbohydrate or derivative thereof.

Embodiment A34 is the shaped porous carbon product of embodiment A33, wherein derivatives of carbohydrates are selected from the group consisting of alginic acid, pectin, aldonic acids, aldaric acids, uronic acids, sugar alcohols, and salts, oligomers, and polymers thereof.

Embodiment A35 is the shaped porous carbon product of any one of embodiments A1 to A34, wherein the water soluble organic binder comprises a monosaccharide selected from the group consisting of a glucose, a fructose, hydrate thereof, syrup thereof, and combinations thereof.

Embodiment A36 is the shaped porous carbon product of any one of embodiments A1 to A35, wherein the water soluble organic binder comprises a saccharide selected from the group consisting of maltose, sucrose, syrups thereof, soluble starches, soluble gums, and combinations thereof.

Embodiment A37 is the shaped porous carbon product of any one of embodiments A1 to A36, wherein the water soluble organic binder comprises a cellulosic compound.

Embodiment A38 is the shaped porous carbon product of embodiment A37, wherein the cellulosic compound comprises hydroxyethylcellulose, hydroxypropylcellulose, hydroxyethylmethylcellulose, hydroxypropylmethylcellulose, or carboxymethylcellulose.

Embodiment A39 is the shaped porous carbon product of embodiment A37 or A38, wherein the cellulosic compound comprises alginic acid, pectin, or a salt thereof.

Embodiment A40 is the shaped porous carbon product of any one of embodiments A1 to A39, wherein the water soluble organic binder comprises a water soluble polymer or copolymer.

Embodiment A41 is the shaped porous carbon product of embodiment A40, wherein the water soluble polymer or copolymer is selected from the group consisting of polyacrylic acid, polyvinyl alcohols, polyvinyl acetates, polyacrylates and copolymers derived therefrom.

Embodiment A42 is the shaped porous carbon product of any one of embodiments A1 to A41, wherein the water soluble organic binder is selected from the group consisting of water soluble celluloses; water soluble alcohols; water soluble acetals; water soluble acids; polyvinyl acrylic acids; and salts, esters, oligomers, or polymers of any of these.

Embodiment A43 is the shaped porous carbon product of any one of embodiments A1 to A42, wherein the water soluble organic binder comprises a saccharide in combination with one or more water soluble celluloses; water soluble alcohols; water soluble acetals; water soluble acids; polyvinyl acrylic acids; or salts, esters, oligomers, or polymers of any of these.

Embodiment A44 is the shaped porous carbon product of embodiment A43, wherein the saccharide comprises a monosaccharide.

Embodiment A45 is the shaped porous carbon product of embodiment A44, wherein the water soluble cellulose comprises hydroxyethylcellulose or methylcellulose and the monosaccharide comprises a glucose, fructose or hydrate thereof.

Embodiment A46 is the shaped porous carbon product of embodiment A45, wherein the water soluble cellulose comprises hydroxyethylcellulose and the monosaccharide comprises a glucose or hydrate thereof.

Embodiment A47 is the shaped porous carbon product of any of embodiments A42 to A46, wherein the water soluble alcohol is selected from the group consisting of sorbitol, mannitol, xylitol and a polyvinyl alcohol.

Embodiment A48 is the shaped porous carbon product of any of embodiments A42 to A46, wherein the water soluble acid is selected from the group consisting of stearic acid, pectin, alginic acid, polyacrylic acid, and salts thereof.

Embodiment A49 is the shaped porous carbon product of any of embodiments A1 to A48, wherein the sulfur content of the shaped porous carbon product is no greater than about 1 wt. % or no greater than about 0.1 wt. %.

Embodiment B1 is a shaped porous carbon product comprising a carbon agglomerate, wherein the shaped porous carbon product has a mean diameter of at least about 50 μm, a BET specific surface area from about 20 m$^2$/g to about 500 m$^2$/g, a mean pore diameter greater than about 10 nm, a specific pore volume greater than about 0.1 cm$^3$/g, and a radial piece crush strength greater than about 4.4 N/mm (1 lb/mm).

Embodiment B2 is the shaped porous carbon product of embodiment B1, wherein the shaped porous carbon product has a BET specific surface area from about 25 m$^2$/g to about 250 m$^2$/g, from about 25 m$^2$/g to about 225 m$^2$/g, from about 25 m$^2$/g to about 200 m$^2$/g, from about 25 m$^2$/g to about 175 m$^2$/g, from about 25 m$^2$/g to about 150 m$^2$/g, from about 25 m$^2$/g to about 125 m$^2$/g, or from about 25 m$^2$/g to about 100 m$^2$/g.

Embodiment B3 is the shaped porous carbon product of embodiment B1, wherein the shaped porous carbon product has a BET specific surface area from about 30 m$^2$/g to about 225 m$^2$/g, from about 30 m$^2$/g to about 200 m$^2$/g, from about 30 m$^2$/g to about 175 m$^2$/g, from about 30 m$^2$/g to about 150 m$^2$/g, from about 30 m$^2$/g to about 125 m$^2$/g, or from about 30 m$^2$/g to about 100 m$^2$/g.

Embodiment B4 is the shaped porous carbon product of any one of embodiments B1 to B3, wherein the shaped porous carbon product has a mean pore diameter greater than about 12 nm or greater than about 14 nm.

Embodiment B5 is the shaped porous carbon product of any one of embodiments B1 to B3, wherein the shaped porous carbon product has a mean pore diameter from about 10 nm to about 100 nm, from about 10 nm to about 70 nm, from 10 nm to about 50 nm, or from about 10 nm to about 25 nm.

Embodiment B6 is the shaped porous carbon product of any one of embodiments B1 to B5, wherein the shaped porous carbon product has a specific pore volume greater than about 0.2 cm$^3$/g or greater than about 0.3 cm$^3$/g.

Embodiment B7 is the shaped porous carbon product of any one of embodiments B1 to B5, wherein the shaped porous carbon product has a specific pore volume of from about 0.1 cm$^3$/g to about 1.5 cm$^3$/g, from about 0.1 cm$^3$/g to about 0.9 cm$^3$/g, from about 0.1 cm$^3$/g to about 0.8 cm$^3$/g, from about 0.1 cm$^3$/g to about 0.7 cm$^3$/g, from about 0.1 cm$^3$/g to about 0.6 cm$^3$/g, from about 0.1 cm$^3$/g to about 0.5 cm$^3$/g, from about 0.2 cm$^3$/g to about 1 cm$^3$/g, from about 0.2 cm$^3$/g to about 0.9 cm$^3$/g, from about 0.2 cm$^3$/g to about 0.8 cm$^3$/g, from about 0.2 cm$^3$/g to about 0.7 cm$^3$/g, from about 0.2 cm$^3$/g to about 0.6 cm$^3$/g, from about 0.2 cm$^3$/g to about 0.5 cm$^3$/g, from about 0.3 cm$^3$/g to about 1 cm$^3$/g, from about 0.3 cm$^3$/g to about 0.9 cm$^3$/g, from about 0.3 cm$^3$/g to about 0.8 cm$^3$/g, from about 0.3 cm$^3$/g to about 0.7 cm$^3$/g, from about 0.3 cm$^3$/g to about 0.6 cm$^3$/g, or from about 0.3 cm$^3$/g to about 0.5 cm$^3$/g.

Embodiment B8 is the shaped porous carbon product of any one of embodiments B1 to B7, wherein the shaped porous carbon product has a pore volume measured on the basis of pores having a diameter from 1.7 nm to 100 nm and at least about 35%, at least about 40%, at least about 45%, or at least about 50% of the pore volume is attributable to pores having a mean pore diameter of from about 10 nm to about 50 nm.

Embodiment B9 is the shaped porous carbon product of any one of embodiments B1 to B7, wherein the shaped porous carbon product has a pore volume measured on the basis of pores having a diameter from 1.7 nm to 100 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment B10 is the shaped porous carbon product of any one of embodiments B1 to B9, wherein the shaped porous carbon product has a pore volume measured on the basis of pores having a diameter from 1.7 nm to 150 nm and at least about 35%, at least about 40%, at least about 45%, or at least about 50% of the pore volume is attributable to pores having a mean pore diameter of from about 10 nm to about 50 nm.

Embodiment B11 is the shaped porous carbon product of any one of embodiments B1 to B9, wherein the shaped porous carbon product has a pore volume measured on the basis of pores having a diameter from 1.7 nm to 150 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment B12 is the shaped porous carbon product of any one of embodiments B1 to B11, wherein the shaped porous carbon product has a pore volume measured on the basis of pores having a diameter from 1.7 nm to 200 nm and at least about 35%, at least about 40%, at least about 45%, or at least about 50% of the pore volume is attributable to pores having a mean pore diameter of from about 10 nm to about 50 nm.

Embodiment B13 is the shaped porous carbon product of any one of embodiments B1 to B11, wherein the shaped porous carbon product has a pore volume measured on the basis of pores having a diameter from 1.7 nm to 200 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment B14 is the shaped porous carbon product of any one of embodiments B1 to B13, wherein the shaped porous carbon product has a pore volume measured on the basis of pores having a diameter from 1.7 nm to 250 nm and at least about 35%, at least about 40%, at least about 45%, or at least about 50% of the pore volume is attributable to pores having a mean pore diameter of from about 10 nm to about 50 nm.

Embodiment B15 is the shaped porous carbon product of any one of embodiments B1 to B13, wherein the shaped porous carbon product has a pore volume measured on the basis of pores having a diameter from 1.7 nm to 250 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment B16 is the shaped porous carbon product of any one of embodiments B1 to B15, wherein the shaped porous carbon product has a pore volume measured on the basis of pores having a diameter from 1.7 nm to 300 nm and at least about 35%, at least about 40%, at least about 45%, or at least about 50% of the pore volume is attributable to pores having a mean pore diameter of from about 10 nm to about 50 nm.

Embodiment B17 is the shaped porous carbon product of any one of embodiments B1 to B15, wherein the shaped porous carbon product has a pore volume measured on the basis of pores having a diameter from 1.7 nm to 300 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment B18 is the shaped porous carbon product of any one of embodiments B1 to B17, wherein the shaped porous carbon product has a pore size distribution such that peaks below about 10 nm or about 5 nm are not observed.

Embodiment B19 is the shaped porous carbon product of any one of embodiments B1 to B18, wherein the shaped porous carbon product has a radial piece crush strength greater than about 8.8 N/mm (2 lbs/mm) or greater than about 13.3 N/mm (3 lbs/mm).

Embodiment B20 is the shaped porous carbon product of any one of embodiments B1 to B18, wherein the shaped porous carbon product has a radial piece crush strength from about 4.4 N/mm (1 lb/mm) to about 88 N/mm (20 lbs/mm), from about 4.4 N/mm (1 lb/mm) to about 66 N/mm (15 lbs/mm), or from about 8.8 N/mm (2 lb/mm) to about 44 N/mm (10 lbs/mm).

Embodiment B21 is the shaped porous carbon product of any one of embodiments B1 to B20, wherein the shaped porous carbon product has a mechanical piece crush strength greater than about 22 N (5 lbs), greater than about 36 N (8 lbs), or greater than about 44 N (10 lbs).

Embodiment B22 is the shaped porous carbon product of any one of embodiments B1 to B20, wherein the shaped porous carbon product has a mechanical piece crush strength from about 22 N (5 lbs) to about 88 N (20 lbs), from about 22 N (5 lbs) to about 66 N (15 lbs), or from about 33 N (7.5 lbs) to about 66 N (15 lbs).

Embodiment B23 is the shaped porous carbon product of any one of embodiments B1 to B22, wherein the shaped porous carbon product has a mean diameter of at least about 500 µm, at least about 1,000 µm, or at least about 10,000 µm.

Embodiment B24 is the shaped porous carbon product of any one of embodiments B1 to B23, wherein the carbon agglomerate comprises carbon black.

Embodiment B25 is the shaped porous carbon product of embodiment B24, wherein the carbon black content of the shaped porous carbon product is at least about 35 wt. %, at least about 40 wt. %, at least about 45 wt. %, at least about 50 wt. %, at least about 55 wt. %, at least about 60 wt. %, at least about 65 wt. %, or at least about 70 wt. %.

Embodiment B26 is the shaped porous carbon product of embodiment B25, wherein the carbon black content of the shaped porous carbon product is from about 35 wt. % to about 80 wt. %, from about 35 wt. % to about 75 wt. %, from about 40 wt. % to about 80 wt. %, or from about 40 wt. % to about 75 wt. %.

Embodiment B27 is the shaped porous carbon product of any one of embodiments B24 to B26, wherein the carbon black comprises conductive carbon black.

Embodiment B28 is the shaped porous carbon product of any one of embodiments B24 to B27, wherein the carbon black comprises nonconductive carbon black.

Embodiment B29 is the shaped porous carbon product of embodiment B28, wherein the shaped porous carbon product does not exhibit a conductivity that is suitable for a conductive electrode.

Embodiment B30 is the shaped porous carbon product of embodiment B28 or B29, wherein the shaped porous carbon product comprises nonconductive carbon black and less than about 50%, less than about 40%, less than about 30%, less than about 20%, less than about 10%, less than about 5%, or less than about 1% conductive carbon black based on the total weight of the carbon black in shaped porous carbon product.

Embodiment B31 is the shaped porous carbon product of any one of embodiments B24 to B26, wherein the shaped porous carbon product comprises carbon black consisting essentially of nonconductive carbon black.

Embodiment B32 is the shaped porous carbon product of any one of embodiments B24 to B26, wherein the shaped porous carbon product comprises carbon black consisting of nonconductive carbon black.

Embodiment B33 is the shaped porous carbon product of any of embodiments B1 to B32, wherein the sulfur content of the shaped porous carbon product is no greater than about 1 wt. % or no greater than about 0.1 wt. %.

Embodiment C1 is a catalyst composition comprising the shaped porous carbon product of any one of embodiments A1 to A49 or B1 to B33 as a catalyst support and a catalytically active component at a surface of the support.

Embodiment C2 is the catalyst composition of embodiment C1, wherein the catalytically active component comprises a metal.

Embodiment C3 is the catalyst composition of embodiment C2, wherein the metal comprises at least one d-block metal.

Embodiment C4 is the catalyst composition of embodiment C2 or C3, wherein the metal comprises at least one metal selected from groups V, VI, VII, VIII, IX, X, XI, XII, and XIII.

Embodiment C5 is the catalyst composition of any one of embodiments C2 to C4, wherein the metal is selected from the group consisting of cobalt, nickel, copper, zinc, iron, ruthenium, rhodium, rhenium, palladium, silver, osmium, iridium, platinum, gold, and combinations thereof.

Embodiment D1 is a catalyst composition comprising a shaped porous carbon support and a catalytically active component comprising platinum and gold at a surface of the support.

Embodiment D2 is the catalyst composition of embodiment D1, wherein the shaped porous carbon support comprises the shaped porous carbon product of any one of embodiments A1 to A49 or B1 to B33.

Embodiment D3 is the catalyst composition of embodiment D1 of D2, wherein the total metal loading of the catalyst composition is about 10 wt. % or less, from about 1 wt. % to about 8 wt. %, from about 1 wt. % to about 5 wt. %, or from about 2 wt. % to about 4 wt. %.

Embodiment D4 is the catalyst composition of any one of embodiments D1 to D3, wherein the catalytically active component is present in a shell layer at external surfaces of the shaped porous carbon support.

Embodiment D5 is the catalyst composition of any one of embodiments D1 to D4, wherein the shell thickness is from about 10 µm to about 400 µm, or from about 50 µm to about 150 µm.

Embodiment D6 is the catalyst composition of any one of embodiments D1 to D5, wherein the molar ratio of platinum to gold is from about 100:1 to about 1:4, from about 10:1 to about 1:2, from about 3:1 to about 1:2, from about 3:1 to about 1:2, or from about 2:1 to about 1:2.

Embodiment D7 is the catalyst composition of any one of embodiments D1 to D6, wherein the catalytically active component comprises particles comprising platinum having a particle size in the range of from about 1 nm to about 50 nm, from about 1 nm to about 20 nm, or from about 1 nm to about 10 nm.

Embodiment D8 is the catalyst composition of any one of embodiments D1 to D7, wherein the catalytically active component comprises particles comprising gold having a particle size in the range of about 1 to about 20 nanometers or about 1 nm to about 10 nm.

Embodiment D9 is the catalyst composition of any one of embodiments D1 to D8, wherein the catalytically active component comprises particles comprising gold-platinum alloy.

Embodiment D10 is the catalyst composition of any one of embodiments D1 to D9, wherein at least about 1 wt. %, at least about 5 wt. %, at least about 10 wt. %, at least about 15 wt. %, or at least about 20 wt. % of the total platinum content of the catalyst composition is present as particles consisting essentially of platinum (0).

Embodiment E1 is a catalyst composition comprising a shaped porous carbon support and a catalytically active component comprising platinum and rhodium at a surface of the support.

Embodiment E2 is the catalyst composition of embodiment E1, wherein the shaped porous carbon support comprises the shaped porous carbon product of any one of embodiments A1 to A49 or B1 to B33.

Embodiment E3 is the catalyst composition of embodiment E1 or E2, wherein the total metal loading of the catalyst composition is from about 0.1% to about 10%, or from 0.2% to about 10%, from about 0.2% to about 8%, from about 0.2% to about 5%, or less than about 4% of the total weight of the catalyst.

Embodiment E4 is the catalyst composition of any one of embodiments E1 to E3, wherein the catalytically active component is present in a shell layer at external surfaces of the shaped porous carbon support.

Embodiment E5 is the catalyst composition of any one of embodiments E1 to E4, wherein the shell thickness is from about 10 µm to about 400 µm, or from about 50 µm to about 150 µm.

Embodiment E6 is the catalyst composition of any one of embodiments E1 to E5, wherein the molar ratio of platinum to rhodium of the catalyst composition is in the range of from about 3:1 to about 1:2 or from about 3:1 to about 1:1.

Embodiment F1 is a method of preparing a catalyst composition as defined in any one of embodiments C1 to C5, D1 to D10, or E1 to E6 comprising depositing a catalytically active component on the shaped porous carbon product of any one of embodiments A1 to A49 or B1 to B33.

Embodiment G1 is a process for the catalytic conversion of a reactant comprising contacting a liquid medium comprising the reactant with a catalyst composition of any one of embodiments C1 to C5, D1 to D10, or E1 to E6.

Embodiment G2 is the process of embodiment G1, wherein the catalyst composition is stable to the continuous flow of the liquid medium and reaction conditions for at least about 500 hours without substantial loss in activity.

Embodiment H1 is a process for the selective oxidation of an aldose to an aldaric acid comprising reacting the aldose with oxygen in the presence of a catalyst composition of any one of embodiments C1 to C5 or D1 to D10 to form the aldaric acid.

Embodiment H2 is the process of embodiment H1, wherein the aldose is selected from the group consisting of pentoses and hexoses.

Embodiment H3 is the process of embodiment H1 or H2, wherein the aldaric acid is selected from the group consisting of xylaric acid and glucaric acid.

Embodiment H4 is the process of any one of embodiments H1 to H3, wherein the catalytically active component of the catalyst composition comprises at least platinum.

Embodiment H5 is the process of any one of embodiments H1 to H4, wherein the catalytically active component of the catalyst composition comprises platinum and gold.

Embodiment H6 is the process of any one of embodiments H1 to H5, wherein the aldaric acid comprises glucaric acid and the glucaric acid yield is at least about 30%, at least about 35%, at least about 40%, at least about, 45%, or at least about 50%.

Embodiment H7 is the process of any one of embodiments H1 to H5, wherein the aldaric acid comprises glucaric acid and the glucaric acid yield is from about 35% to about 65%, from about 40% to about 65%, or from about 45% to about 65%.

Embodiment H8 is the process of any one of embodiments H1 to H7, wherein the aldaric acid comprises glucaric acid and the glucaric acid selectivity is at least about 70%, at least about 75%, or at least about 80%.

Embodiment H9 is the process of any one of embodiments H1 to H8, wherein the aldose comprises glucose and the catalytically active component comprises platinum and the mass ratio of glucose to platinum is from about 10:1 to about 1000:1, from about 10:1 to about 500:1, from about 10:1 to about 200:1, or from about 10:1 to about 100:1.

Embodiment I1 is a process for the selective hydrodeoxygenation of aldaric acid or salt, ester, or lactone thereof to a dicarboxylic acid comprising:
reacting the aldaric acid or salt, ester, or lactone thereof with hydrogen in the presence of a halogen-containing compound and a catalyst composition of any one of embodiments C1 to C5 or E1 to E6 to form the dicarboxylic acid.

Embodiment 2 is the process of embodiment I1, wherein the aldaric acid or salt, ester, or lactone thereof comprises glucaric acid or salt, ester, or lactone thereof.

Embodiment 3 is the process of embodiment I1 or 12, wherein the dicarboxylic acid comprises adipic acid.

Embodiment 4 is the process of any one of embodiments I1 to 13, wherein the catalytically active component of the catalyst composition comprises at least one noble metal.

Embodiment K1 is a method of preparing a reactor vessel for a liquid phase catalytic reaction comprising charging the reactor vessel with a catalyst composition of any one of embodiments C1 to C5, D1 to D10, or E1 to E6.

Embodiment L1 is a method of preparing a shaped porous carbon product comprising:
mixing carbon black particles with a solution comprising a water soluble organic binder compound to produce a slurry;
forming the slurry to produce a shaped carbon black composite; and
heating the shaped carbon black composite to carbonize the binder to a water insoluble state to produce the shaped porous carbon product.

Embodiment L2 is the method of embodiment L1, wherein the weight ratio of binder to carbon black in the slurry is at least about 1:4, at least about 1:3, at least about 1:2, or at least about 1:1.

Embodiment L3 is the method of embodiment L1, wherein the weight ratio of binder to carbon black in the slurry is from about 1:4 to about 3:1, from about 1:4 to about 1:1, from about 1:3 to about 2:1, from about 1:3 to about 1:1, or about 1:1.

Embodiment L4 is the method of any one of embodiments L1 to L3, wherein the carbon black content of the slurry is at least about 35 wt. %, at least about 40 wt. %, at least about 45 wt. %, at least about 50 wt. %, at least about 55 wt. %, at least about 60 wt. %, at least about 65 wt. %, or at least about 70 wt. % on a dry weight basis.

Embodiment L5 is the method of any one of embodiments L1 to L3, wherein the carbon black content of the slurry is from about 35 wt. % to about 80 wt. %, from about 35 wt. % to about 75 wt. %, from about 40 wt. % to about 80 wt. %, or from about 40 wt. % to about 75 wt. % on a dry weight basis.

Embodiment L6 is the method of any one of embodiments L1 to L5, wherein the binder content of the slurry is at least about 10 wt. %, at least about 20 wt. %, at least about 25 wt. %, at least about 30 wt. %, at least about 35 wt. %, at least about 40 wt. %, or at least 45 wt. % binder on a dry weight basis.

Embodiment L7 is the method of any one of embodiments L1 to L5, wherein the binder content of the slurry is from about 10 wt. % to about 50 wt. %, from about 10 wt. % to about 45 wt. %, from about 15 wt. % to about 50 wt. %, from about 20 wt. % to about 50 wt. %, or from about 20 wt. % to about 45 wt. % on a dry weight basis.

Embodiment L8 is the method of any one of embodiments L1 to L7, wherein heating the carbon black composite to carbonize the binder is conducted in an inert, oxidative, or reductive atmosphere.

Embodiment L9 is the method of embodiment L8, wherein the atmosphere is an inert nitrogen atmosphere.

Embodiment L10 is the method of any one of embodiments L1 to L9, wherein heating the carbon black composite to carbonize the binder is conducted at a temperature of from about 250° C. to about 1,000° C., from about 300° C. to about 900° C., from about 300° C. to about 800° C., from about 350° C. to about 800° C., from about 350° C. to about 700° C., or from about 400° C. to about 800° C.

Embodiment L11 is the method of any one of embodiments L1 to L10, further comprising mixing a porogen with the carbon black and binder.

Embodiment L12 is the method of any one of embodiments L1 to L11, further comprising drying the shaped carbon black composite after forming.

Embodiment L13 is the method of embodiment L12, wherein drying the shaped carbon black composite comprises heating at a temperature of from about 20° C. to about 150° C., from about 40° C. to about 120° C., or from about 60° C. to about 120° C.

Embodiment L14 is the method of embodiment L12, wherein drying the shaped carbon black composite comprises a method selected from the group consisting of vacuum drying, freeze drying, and desiccation.

Embodiment L15 is the method of any one of embodiments L1 to L14, further comprising washing the shaped porous carbon product.

Embodiment L16 is the method of any one of embodiments L1 to L15, wherein the shaped carbon black composite is formed by extruding the slurry.

Embodiment L17 is the method of any one of embodiments L1 to L16, wherein the slurry is formed under a pressure of at least about 100 kPa (1 bar), or between about 100 kPa (1 bar) to about 10,000 kPa (100 bar), between 500 kPa (5 bar) and 5,000 kPa (50 bar), or between 1,000 kPa (10 bar) and 3,000 kPa (30 bar).

Embodiment L18 is the method of any one of embodiments L1 to L15, wherein the shaped carbon black composite is formed by drip casting the slurry.

Embodiment L19 is the method of embodiment L18, wherein drip casting comprises:
dispensing droplets of the slurry into a casting bath to form the shaped carbon black composite; and
separating the shaped carbon black composite from the casting bath.

Embodiment L20 is the method of embodiment L19, wherein the casting bath comprises an ionic salt.

Embodiment L21 is the method of embodiment L20, wherein the ionic salt is a calcium salt.

Embodiment L22 is the method of embodiment L21, wherein the binder comprises an alginate.

Embodiment L23 is the method of embodiment L19, wherein the casting bath comprises an oil.

Embodiment L24 is the method of embodiment L19, wherein the casting bath is a freeze drying bath.

Embodiment L25 is the method of any one of embodiments L1 to L24, wherein the shaped porous carbon product has a BET specific surface area from about 20 m$^2$/g to about 500 m$^2$/g or from about 25 m$^2$/g to about 250 m$^2$/g, from about 25 m$^2$/g to about 250 m$^2$/g, from about 25 m$^2$/g to about 225 m$^2$/g, from about 25 m$^2$/g to about 200 m$^2$/g, from about 25 m$^2$/g to about 175 m$^2$/g, from about 25 m$^2$/g to about 150 m$^2$/g, from about 25 m$^2$/g to about 125 m$^2$/g, or from about 25 m$^2$/g to about 100 m$^2$/g.

Embodiment L26 is the method of any one of embodiments L1 to L24, wherein the shaped porous carbon product has a BET specific surface area from about 30 m$^2$/g to about 225 m$^2$/g, from about 30 m$^2$/g to about 200 m$^2$/g, from about 30 m$^2$/g to about 175 m$^2$/g, from about 30 m$^2$/g to about 150 m$^2$/g, from about 30 m$^2$/g to about 125 m$^2$/g, or from about 30 m$^2$/g to about 100 m$^2$/g.

Embodiment L27 is the method of any one of embodiments L1 to L26, wherein the shaped porous carbon product has a mean pore diameter greater than about 10 nm, greater than about 12 nm, or greater than about 14 nm.

Embodiment L28 is the method of any one of embodiments L1 to L26, wherein the shaped porous carbon product has a mean pore diameter from about 10 nm to about 100 nm, from about 10 nm to about 70 nm, from 10 nm to about 50 nm, or from about 10 nm to about 25 nm.

Embodiment L29 is the method of any one of embodiments L1 to L28, wherein the shaped porous carbon product has a specific pore volume greater than about 0.1 cm$^3$/g, greater than about 0.2 cm$^3$/g, or greater than about 0.3 cm$^3$/g.

Embodiment L30 is the method of any one of embodiments L1 to L28, wherein the shaped porous carbon product has a specific pore volume of from about 0.1 cm$^3$/g to about 1.5 cm$^3$/g, from about 0.1 cm$^3$/g to about 0.9 cm$^3$/g, from about 0.1 cm$^3$/g to about 0.8 cm$^3$/g, from about 0.1 cm$^3$/g to about 0.7 cm$^3$/g, from about 0.1 cm$^3$/g to about 0.6 cm$^3$/g, from about 0.1 cm$^3$/g to about 0.5 cm$^3$/g, from about 0.2 cm$^3$/g to about 1 cm$^3$/g, from about 0.2 cm$^3$/g to about 0.9 cm$^3$/g, from about 0.2 cm$^3$/g to about 0.8 cm$^3$/g, from about 0.2 cm$^3$/g to about 0.7 cm$^3$/g, from about 0.2 cm$^3$/g to about 0.6 cm$^3$/g, from about 0.2 cm$^3$/g to about 0.5 cm$^3$/g, from about 0.3 cm$^3$/g to about 1 cm$^3$/g, from about 0.3 cm$^3$/g to about 0.9 cm$^3$/g, from about 0.3 cm$^3$/g to about 0.8 cm$^3$/g, from about 0.3 cm$^3$/g to about 0.7 cm$^3$/g, from about 0.3 cm$^3$/g to about 0.6 cm$^3$/g, or from about 0.3 cm$^3$/g to about 0.5 cm$^3$/g.

Embodiment L31 is the method of any one of embodiments L1 to L30, wherein the shaped porous carbon product has a pore volume measured on the basis of pores having a diameter from 1.7 nm to 100 nm and at least about 35%, at least about 40%, at least about 45%, or at least about 50% of the pore volume is attributable to pores having a mean pore diameter of from about 10 nm to about 50 nm.

Embodiment L32 is the method of any one of embodiments L1 to L30, wherein the shaped porous carbon product has a pore volume measured on the basis of pores having a diameter from 1.7 nm to 100 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment L33 is the method of any one of embodiments L1 to L32, wherein the shaped porous carbon product has a pore volume measured on the basis of pores having a diameter from 1.7 nm to 150 nm and at least about 35%, at least about 40%, at least about 45%, or at least about 50% of the pore volume is attributable to pores having a mean pore diameter of from about 10 nm to about 50 nm.

Embodiment L34 is the method of any one of embodiments L1 to L32, wherein the shaped porous carbon product has a pore volume measured on the basis of pores having a diameter from 1.7 nm to 150 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment L35 is the method of any one of embodiments L1 to L34, wherein the shaped porous carbon product has a pore volume measured on the basis of pores having a diameter from 1.7 nm to 200 nm and at least about 35%, at least about 40%, at least about 45%, or at least about 50% of the pore volume is attributable to pores having a mean pore diameter of from about 10 nm to about 50 nm.

Embodiment L36 is the method of any one of embodiments L1 to L34, wherein the shaped porous carbon product has a pore volume measured on the basis of pores having a diameter from 1.7 nm to 200 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment L37 is the method of any one of embodiments L1 to L36, wherein the shaped porous carbon product has a pore volume measured on the basis of pores having a diameter from 1.7 nm to 250 nm and at least about 35%, at least about 40%, at least about 45%, or at least about 50% of the pore volume is attributable to pores having a mean pore diameter of from about 10 nm to about 50 nm.

Embodiment L38 is the method of any one of embodiments L1 to L36, wherein the shaped porous carbon product has a pore volume measured on the basis of pores having a diameter from 1.7 nm to 250 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment L39 is the method of any one of embodiments L1 to L38, wherein the shaped porous carbon product has a pore volume measured on the basis of pores having a diameter from 1.7 nm to 300 nm and at least about 35%, at least about 40%, at least about 45%, or at least about 50% of the pore volume is attributable to pores having a mean pore diameter of from about 10 nm to about 50 nm.

Embodiment L40 is the method of any one of embodiments L1 to L38, wherein the shaped porous carbon product has a pore volume measured on the basis of pores having a diameter from 1.7 nm to 300 nm and from about 35% to about 80%, from about 35% to about 75%, from about 35% to about 65%, from about 40% to about 80%, from about 40% to about 75%, from about 40% to about 70% of the pore volume is attributable to pores having a mean pore diameter of from about 10 nm to about 50 nm.

Embodiment L41 is the method of any one of embodiments L1 to L40, wherein the shaped porous carbon product has a pore size distribution such that peaks below about 10 nm or about 5 nm are not observed.

Embodiment L42 is the method of any one of embodiments L1 to L41, wherein the shaped porous carbon product has a radial piece crush strength greater than about 4.4 N/mm (1 lb/mm), greater than about 8.8 N/mm (2 lbs/mm), or greater than about 13.3 N/mm (3 lbs/mm).

Embodiment L43 is the method of any one of embodiments L1 to L41, wherein the shaped porous carbon product has a radial piece crush strength from about 4.4 N/mm (1 lb/mm) to about 88 N/mm (20 lbs/mm), from about 4.4 N/mm (1 lb/mm) to about 66 N/mm (15 lbs/mm), or from about 8.8 N/mm (2 lb/mm) to about 44 N/mm (10 lbs/mm).

Embodiment L44 is the method of any one of embodiments L1 to L43, wherein the shaped porous carbon product has a mechanical piece crush strength greater than about 22 N (5 lbs), greater than about 36 N (8 lbs), or greater than about 44 N (10 lbs).

Embodiment L45 is the method of any one of embodiments L1 to L43, wherein the shaped porous carbon product has a mechanical piece crush strength from about 22 N (5 lbs) to about 88 N (20 lbs), from about 22 N (5 lbs) to about 66 N (15 lbs), or from about 33 N (7.5 lbs) to about 66 N (15 lbs).

Embodiment L46 is the method of any one of embodiments L1 to L45, wherein the shaped porous carbon product has a mean diameter of at least about 50 μm, at least about 500 μm, at least about 1,000 μm, or at least about 10,000 μm.

Embodiment L47 is the method of any one of embodiments L1 to L46, wherein the shaped porous carbon product has the carbon black content of at least about 35 wt. %, at least about 40 wt. %, at least about 45 wt. %, at least about 50 wt. %, at least about 55 wt. %, at least about 60 wt. %, at least about 65 wt. %, or at least about 70 wt. %.

Embodiment L48 is the method of any one of embodiments L1 to L46, wherein the shaped porous carbon product has the carbon black content from about 35 wt. % to about 80 wt. %, from about 35 wt. % to about 75 wt. %, from about 40 wt. % to about 80 wt. %, or from about 40 wt. % to about 75 wt. %.

Embodiment L49 is the method of any one of embodiments L1 to L48, wherein the carbon black comprises conductive carbon black.

Embodiment L50 is the method of any one of embodiments L1 to L49, wherein the carbon black comprises nonconductive carbon black.

Embodiment L51 is the method of embodiment L50, wherein the shaped porous carbon product does not exhibit a conductivity that is suitable for a conductive electrode.

Embodiment L52 is the method of embodiment L50 or L51, wherein the shaped porous carbon product comprises nonconductive carbon black and less than about 50%, less than about 40%, less than about 30%, less than about 20%, less than about 10%, less than about 5%, or less than about 1% conductive carbon black based on the total weight of the carbon black in shaped porous carbon product.

Embodiment L53 is the method of any one of embodiments L1 to L48, wherein the shaped porous carbon product comprises carbon black consisting essentially of nonconductive carbon black.

Embodiment L54 is the method of any one of embodiments L1 to L48, wherein the shaped porous carbon product comprises carbon black consisting of nonconductive carbon black.

Embodiment L55 is the method of any one of embodiments L1 to L54, wherein the water soluble organic binder comprises a carbohydrate or derivative thereof.

Embodiment L56 is the method of embodiment L55, wherein derivatives of carbohydrates are selected from the group consisting of alginic acid, pectin, aldonic acids, aldaric acids, uronic acids, sugar alcohols, and salts, oligomers, and polymers thereof.

Embodiment L57 is the method of any one of embodiments L1 to L56, wherein the water soluble organic binder comprises a monosaccharide selected from the group consisting of a glucose, a fructose, hydrate thereof, syrup thereof, and combinations thereof.

Embodiment L58 is the method of any one of embodiments L1 to L57, wherein the water soluble organic binder comprises a saccharide selected from the group consisting of maltose, sucrose, syrups thereof, soluble starches, soluble gums, and combinations thereof.

Embodiment L59 is the method of any one of embodiments L1 to L58, wherein the water soluble organic binder comprises a cellulosic compound.

Embodiment L60 is the method of embodiment L59, wherein the cellulosic compound comprises hydroxyethylcellulose, hydroxypropylcellulose, hydroxyethylmethylcellulose, hydroxypropylmethylcellulose, or carboxymethylcellulose.

Embodiment L61 is the method of any one of embodiments L59 or L60, wherein the cellulosic compound comprises alginic acid, pectin, or a salt thereof.

Embodiment L62 is the method of any one of embodiments L1 to L61, wherein the water soluble organic binder comprises a water soluble polymer or copolymer.

Embodiment L63 is the method of embodiment L62, wherein the water soluble polymer or copolymer is selected from the group consisting of polyacrylic acid, polyvinyl alcohols, polyvinyl acetates, polyacrylates and copolymers derived therefrom.

Embodiment L64 is the method of any one of embodiments L1 to L63, wherein the water soluble organic binder is selected from the group consisting of water soluble celluloses; water soluble alcohols; water soluble acetals; water soluble acids; polyvinyl acrylic acids; and salts, esters, oligomers, or polymers of any of these.

Embodiment L65 is the method of any one of embodiments L1 to L64, wherein the water soluble organic binder comprises a saccharide in combination with one or more water soluble celluloses; water soluble alcohols; water soluble acetals; water soluble acids; polyvinyl acrylic acids; or salts, esters, oligomers, or polymers of any of these.

Embodiment L66. The method of embodiment L65, wherein the saccharide comprises a monosaccharide.

Embodiment L67 is the method of embodiment L66, wherein the water soluble cellulose comprises hydroxyethylcellulose or methylcellulose and the monosaccharide comprises a glucose, fructose or hydrate thereof.

Embodiment L68 is the method of embodiment L67, wherein the water soluble cellulose comprises hydroxyethylcellulose and the monosaccharide comprises a glucose or hydrate thereof.

Embodiment L69 is the method of any one of embodiments L64 to L68, wherein the water soluble alcohol is selected from the group consisting of sorbitol, mannitol, xylitol and a polyvinyl alcohol.

Embodiment L70. The method of any one of embodiments L64 to L69, wherein the water soluble acid is selected from the group consisting of stearic acid, pectin, alginic acid, polyacrylic acid, and salts thereof.

Embodiment L71 is the method of any one of embodiments L1 to L70, wherein the shape of the shaped carbon black product is selected from the group consisting of spheres, beads, cylinders, pellets, multi-lobed shapes, rings, stars, ripped cylinders, triholes, alphas, and wheels.

Embodiment L72 is the method of any one of embodiments L1 to L71, wherein the sulfur content of the shaped porous carbon product is no greater than about 1 wt. % or no greater than about 0.1 wt. %.

Embodiment L73 is the method of any one of embodiments L1 to L72, wherein the carbon black has a BET specific surface area from about 20 $m^2/g$ to about 500 $m^2/g$ or from about 25 $m^2/g$ to about 250 $m^2/g$, from about 25 $m^2/g$ to about 250 $m^2/g$, from about 25 $m^2/g$ to about 225 $m^2/g$, from about 25 $m^2/g$ to about 200 $m^2/g$, from about 25 $m^2/g$ to about 175 $m^2/g$, from about 25 $m^2/g$ to about 150 $m^2/g$, from about 25 $m^2/g$ to about 125 $m^2/g$, or from about 25 $m^2/g$ to about 100 $m^2/g$.

Embodiment L74 is the method of any one of embodiments L1 to L72, wherein the carbon black has a BET specific surface area from about 30 $m^2/g$ to about 250 $m^2/g$, 30 $m^2/g$ to about 225 $m^2/g$, from about 30 $m^2/g$ to about 200 $m^2/g$, from about 30 $m^2/g$ to about 175 $m^2/g$, from about 30 $m^2/g$ to about 150 $m^2/g$, from about 30 $m^2/g$ to about 125 $m^2/g$, or from about 30 $m^2/g$ to about 100 $m^2/g$.

Embodiment L75 is the method of any one of embodiments L1 to L74, wherein the carbon black has a mean pore diameter greater than about 10 nm, greater than about 12 nm, or greater than about 14 nm.

Embodiment L76 is the method of any one of embodiments L1 to L74, wherein the carbon black has a mean pore diameter from about 10 nm to about 100 nm, from about 10 nm to about 70 nm, from 10 nm to about 50 nm, or from about 10 nm to about 25 nm.

Embodiment L77 is the method of any one of embodiments L1 to L76, wherein the carbon black has a specific pore volume greater than about 0.1 $cm^3/g$, greater than about 0.2 $cm^3/g$, or greater than about 0.3 $cm^3/g$.

Embodiment L78 is the method of any one of embodiments L1 to L76, wherein the carbon black has a specific pore volume of from about 0.1 $cm^3/g$ to about 1.5 $cm^3/g$, from about 0.1 $cm^3/g$ to about 0.9 $cm^3/g$, from about 0.1 $cm^3/g$ to about 0.8 $cm^3/g$, from about 0.1 $cm^3/g$ to about 0.7 $cm^3/g$, from about 0.1 $cm^3/g$ to about 0.6 $cm^3/g$, from about 0.1 $cm^3/g$ to about 0.5 $cm^3/g$, from about 0.2 $cm^3/g$ to about 1 $cm^3/g$, from about 0.2 $cm^3/g$ to about 0.9 $cm^3/g$, from about 0.2 $cm^3/g$ to about 0.8 $cm^3/g$, from about 0.2 $cm^3/g$ to about 0.7 $cm^3/g$, from about 0.2 $cm^3/g$ to about 0.6 $cm^3/g$, from about 0.2 $cm^3/g$ to about 0.5 $cm^3/g$, from about 0.3 $cm^3/g$ to about 1 $cm^3/g$, from about 0.3 $cm^3/g$ to about 0.9 $cm^3/g$, from about 0.3 $cm^3/g$ to about 0.8 $cm^3/g$, from about 0.3 $cm^3/g$ to about 0.7 $cm^3/g$, from about 0.3 $cm^3/g$ to about 0.6 $cm^3/g$, or from about 0.3 $cm^3/g$ to about 0.5 $cm^3/g$.

Embodiment M1 is a catalyst composition comprising a shaped porous carbon support and a catalytically active component comprising platinum and at least one metal (M2) selected from the group consisting of molybdenum, lanthanum, samarium, yttrium, tungsten, and rhenium at a surface of the support.

Embodiment M2 is the catalyst composition of embodiment M1, wherein the shaped porous carbon support comprises the shaped porous carbon product of any one of embodiments A1 to A49 or B1 to B33.

Embodiment M3 is the catalyst composition of embodiment M1 or M2, wherein the catalytically active component of the catalyst composition comprises platinum and tungsten.

Embodiment M4 is the catalyst composition of any one of embodiments M1 to M3, wherein the total metal loading of the catalyst composition is from about 0.1% to about 10%, or from 0.2% to 10%, or from about 0.2% to about 8%, or from about 0.2% to about 5%, of the total weight of the catalyst.

Embodiment M5 is the catalyst composition of any one of embodiments M1 to M4, wherein the molar ratio of platinum to M2 metal is from about 20:1 to about 1:10, from about 10:1 to about 1:5, or from about 8:1 to about 1:2.

Embodiment N1 is a process for the selective hydrodeoxygenation of 1,2,6-hexanetriol to 1,6-hexanediol comprising:
reacting the 1,2,6-hexanetriol with hydrogen in the presence of a catalyst composition of any one of embodiments M1 to M5 to form 1,6-hexanediol.

Embodiment N2 is the process of embodiment N1, wherein the reaction of 1,2,6-hexanetriol to 1,6-hexanediol is conducted at a temperature in the range of about 60° C. to about 200° C. or about 120° C. to about 180° C. and a partial pressure of hydrogen in the range of about 200 psig to about 2000 psig or about 500 psig to about 2000 psig.

Embodiment P1 is a catalyst composition comprising a shaped porous carbon support and a catalytically active component comprising ruthenium.

Embodiment P2 is the catalyst composition of embodiment P1, wherein the shaped porous carbon support comprises the shaped porous carbon product of any one of embodiments A1 to A49 or B1 to B33.

Embodiment P3 is the catalyst composition of embodiment P1 or P2, wherein the catalytically active component of the catalyst composition further comprises rhenium.

Embodiment P4 is the catalyst composition of any one of embodiments P1 to P3, wherein the total metal loading of the catalyst composition is from about 0.1% to about 10%, from about 1% to about 6%, or from about 1% to about 5% of the total weight of the catalyst.

Embodiment P5 is the catalyst composition of any one of embodiments P1 to P4, wherein the catalytically active component of the catalyst composition further comprises rhenium and the molar ratio of ruthenium:rhenium is from about 20:1 to about 4:1, from about 10:1 to about 4:1, or from about 8:1 to about 4:1.

Embodiment P6 is the catalyst composition of any one of embodiments P1 to P5, wherein the catalytically active component of the catalyst composition further comprises nickel.

Embodiment Q1 is a process for the selective amination of 1,6-hexanediol to 1,6-hexamethylenediamine comprising reacting the 1,6-hexanediol with an amine in the presence of a catalyst composition of any one of embodiments P1 to P6 to form 1,6-hexamethylenediamine.

Embodiment Q2 is the process of embodiment Q1, wherein the amine comprises ammonia.

Embodiment Q3 is the process of embodiment Q2, wherein the molar ratio of ammonia to 1,6-hexanediol is at least about 40:1, at least about 30:1, at least about 20:1, or in the range of from about 40:1 to about 5:1, or from about 30:1 to about 10:1.

Embodiment Q4 is the process of any one of embodiments Q1 to Q3, wherein the reaction of 1,6-hexanediol with amine in the presence of the catalyst composition is carried out at a temperature less than or equal to about 200° C., less than or equal to about 100° C., or in the range of about 100° C. to about 180° C., or about 140° C. to about 180° C.

Embodiment Q5 is the process of any one of embodiments Q1 to Q4, wherein the reaction of 1,6-hexanediol with amine in the presence of the catalyst composition is conducted at a pressure not exceeding about 1500 psig, in the range of about 200 psig to about 1500 psig, of about 400 psig to about 1200 psig, of about 400 psig to about 1000 psig.

Embodiment Q6 is the process of any one of embodiments Q1 to Q5, wherein the reaction of 1,6-hexanediol with amine in the presence of the catalyst composition is conducted with 1,6-hexanediol and ammonia at a temperature in the range of about 100° C. to about 180° C. and a pressure in the range of about 200 psig to about 1500 psig.

Embodiment Q7 is the process of any one of embodiments Q1 to Q6, wherein the 1,6-hexanediol and amine are reacted in the presence of hydrogen and the catalyst composition, and the hydrogen partial pressure is equal to or less than about 100 psig.

Embodiment Q8 is the process of any one of embodiments Q1 to Q7, wherein at least 20%, at least 30%, at least 40%, at least 50%, at least 60%, or at least 70% of the product mixture resulting from a single pass reaction of 1,6-hexanediol with amine (e.g., ammonia) in the presence of the catalyst composition is 1,6-hexamethylenediamine.

Embodiment AA1 is a shaped porous carbon product:
(a) carbon black and
(b) a carbonized binder comprising a carbonization product of a water soluble organic binder and wherein the shaped porous carbon product has a BET specific surface area from about 20 m$^2$/g to about 500 m$^2$/g, a mean pore diameter greater than about 5 nm, a specific pore volume greater than about 0.1 cm$^3$/g, a carbon black content of at least about 35 wt. %, and a carbonized binder content from about 20 wt. % to about 50 wt. %, and wherein the shaped porous carbon product has a radial piece crush strength greater than about 4.4 N/mm (1 lb/mm) and/or a mechanical piece crush strength greater than about 22 N (5 lbs).

Embodiment AA2 is the shaped porous carbon product of embodiment AA1, wherein the shaped porous carbon product has a BET specific surface area from about 20 m$^2$/g to about 350 m$^2$/g, from about 20 m$^2$/g to about 250 m$^2$/g, from about 20 m$^2$/g to about 225 m$^2$/g, from about 20 m$^2$/g to about 200 m$^2$/g, from about 20 m$^2$/g to about 175 m$^2$/g, from about 20 m$^2$/g to about 150 m$^2$/g, from about 20 m$^2$/g to about 125 m$^2$/g, or from about 20 m$^2$/g to about 100 m$^2$/g, from about 25 m$^2$/g to about 500 m$^2$/g, from about 25 m$^2$/g to about 350 m$^2$/g, from about 25 m$^2$/g to about 250 m$^2$/g, from about 25 m$^2$/g to about 225 m$^2$/g, from about 25 m$^2$/g to about 200 m$^2$/g, from about 25 m$^2$/g to about 175 m$^2$/g, from about 25 m$^2$/g to about 150 m$^2$/g, from about 25 m$^2$/g to about 125 m$^2$/g, or from about 25 m$^2$/g to about 100 m$^2$/g.

Embodiment AA3 is the shaped porous carbon product of embodiment AA1, wherein the shaped porous carbon product has a BET specific surface area from about 30 m$^2$/g to about 500 m$^2$/g, from about 30 m$^2$/g to about 350 m$^2$/g, from about 30 m$^2$/g to about 250 m$^2$/g, from about 30 m$^2$/g to about 225 m$^2$/g, from about 30 m$^2$/g to about 200 m$^2$/g, from about 30 m$^2$/g to about 175 m$^2$/g, from about 30 m$^2$/g to about 150 m$^2$/g, from about 30 m$^2$/g to about 125 m$^2$/g, or from about 30 m$^2$/g to about 100 m$^2$/g.

Embodiment AA3 is the shaped porous carbon product of any one of embodiments 90 to 92, wherein the shaped porous carbon product has a mean pore diameter greater than about 10 nm, greater than about 12 nm, or greater than about 14 nm.

Embodiment AA4 is the shaped porous carbon product of any one of embodiments AA1 to 92, wherein the shaped porous carbon product has a mean pore diameter from about 5 nm to about 100 nm, from about 5 nm to about 70 nm, from 5 nm to about 50 nm, from about 5 nm to about 25 nm, from about 10 nm to about 100 nm, from about 10 nm to about 70 nm, from 10 nm to about 50 nm, or from about 10 nm to about 25 nm.

Embodiment AA5 is the shaped porous carbon product of any one of embodiments AA1 to AA4, wherein the shaped porous carbon product has a specific pore volume of the pores having a diameter of 1.7 nm to 100 nm as measured by the BJH method that is greater than about 0.2 cm$^3$/g or greater than about 0.3 cm$^3$/g.

Embodiment AA6 is the shaped porous carbon product of any one of embodiments AA1 to AA4, wherein the shaped porous carbon product has a specific pore volume of the pores having a diameter of 1.7 nm to 100 nm as measured by the BJH method that is from about 0.1 cm$^3$/g to about 1.5 cm$^3$/g, from about 0.1 cm$^3$/g to about 0.9 cm$^3$/g, from about 0.1 cm$^3$/g to about 0.8 cm$^3$/g, from about 0.1 cm$^3$/g to about 0.7 cm$^3$/g, from about 0.1 cm$^3$/g to about 0.6 cm$^3$/g, from about 0.1 cm$^3$/g to about 0.5 cm$^3$/g, from about 0.2 cm$^3$/g to about 1 cm³/g, from about 0.2 cm³/g to about 0.9 cm³/g, from about 0.2 cm³/g to about 0.8 cm³/g, from about 0.2 cm³/g to about 0.7 cm³/g, from about 0.2 cm³/g to about 0.6 cm³/g, from about 0.2 cm³/g to about 0.5 cm³/g, from about 0.3 cm³/g to about 1 cm³/g, from about 0.3 cm³/g to about 0.9 cm³/g, from about 0.3 cm³/g to about 0.8 cm³/g, from about 0.3 cm³/g to about 0.7 cm³/g, from about 0.3 cm³/g to about 0.6 cm³/g, or from about 0.3 cm³/g to about 0.5 cm³/g.

Embodiment AA7 is the shaped porous carbon product of any one of embodiments AA1 to AA6, wherein at least about 35%, at least about 40%, at least about 45%, or at least about 50% of the pore volume of the shaped porous carbon product, as measured by the BJH method on the basis of pores having a diameter from 1.7 nm to 100 nm, is attributable to pores having a mean pore diameter of from about 10 nm to about 50 nm.

Embodiment AA8 is the shaped porous carbon product of any one of embodiments AA1 to AA6, wherein from about 35% to about 80%, from about 35% to about 75%, from about 35% to about 65%, from about 40% to about 80%, from about 40% to about 75%, or from about 40% to about 70% of the pore volume of the shaped porous carbon product, as measured by the BJH method on the basis of pores having a diameter from 1.7 nm to 100 nm, is attributable to pores having a mean pore diameter of from about 10 nm to about 50 nm.

Embodiment AA9 is the shaped porous carbon product of any one of embodiments AA1 to AA8, wherein at least about 50%, at least about 60%, at least about 70%, at least about 80%, or at least about 90% of the pore volume of the shaped porous carbon product, as measured by the BJH method on the basis of pores having a diameter from 1.7 nm to 100 nm, is attributable to pores having a mean pore diameter of from about 10 nm to about 100 nm.

Embodiment AA10 is the shaped porous carbon product of any one of embodiments AA1 to AA8, wherein from about 50% to about 95%, from about 50% to about 90%, from about 50% to about 80%, from about 60% to about 95%, from about 60% to about 90%, from about 60% to about 80%, from about 70% to about 95%, from about 70% to about 90%, from about 70% to about 80%, from about 80% to about 95%, or from about 80% to about 90% of the pore volume of the shaped porous carbon product, as measured by the BJH method on the basis of pores having a diameter from 1.7 nm to 100 nm, is attributable to pores having a mean pore diameter of from about 10 nm to about 100 nm.

Embodiment AA11 is the shaped porous carbon product of any one of embodiments AA1 to AA10, wherein no more than about 10%, no more than about 5%, or no more than about 1% of the pore volume of the shaped porous carbon product, as measured by the BJH method on the basis of pores having a diameter from 1.7 nm to 100 nm, is attributable to pores having a mean pore diameter less than 10 nm, less than 5 nm, or less than 3 nm.

Embodiment AA12 is the shaped porous carbon product of any one of embodiments AA1 to AA10, wherein from about 0.1% to about 10%, from about 0.1% to about 5%, from about 0.1% to about 1%, from about 1% to about 10%, or from about 1% to about 5% of the pore volume of the shaped porous carbon product, as measured by the BJH method on the basis of pores having a diameter from 1.7 nm to 100 nm, is attributable to pores having a mean pore diameter less than 10 nm, less than 5 nm, or less than 3 nm.

Embodiment AA13 is the shaped porous carbon product of any one of embodiments AA1 to AA12, wherein the shaped porous carbon product has a pore size distribution such that the peak of the distribution is at a diameter greater than about 5 nm, greater than about 7.5 nm, greater than about 10 nm, greater than about 12.5 nm, greater than about 15 nm, or greater than about 20 nm.

Embodiment AA14 is the shaped porous carbon product of any one of embodiments AA1 to AA13, wherein the shaped porous carbon product has a pore size distribution such that the peak of the distribution is at a diameter less than about 100 nm, less than about 90 nm, less than about 80 nm, or less than about 70 nm.

Embodiment AA15 is the shaped porous carbon product of any one of embodiments AA1 to AA14, wherein the shaped porous carbon product has a radial piece crush strength greater than about 8.8 N/mm (2 lbs/mm) or greater than about 13.3 N/mm (3 lbs/mm).

Embodiment AA16 is the shaped porous carbon product of any one of embodiments AA1 to AA14, wherein the shaped porous carbon product has a radial piece crush strength from about 4.4 N/mm (1 lb/mm) to about 88 N/mm (20 lbs/mm), from about 4.4 N/mm (1 lb/mm) to about 66 N/mm (15 lbs/mm), or from about 8.8 N/mm (2 lbs/mm) to about 44 N/mm (10 lbs/mm).

Embodiment AA17 is the shaped porous carbon product of any one of embodiments AA1 to AA16, wherein the shaped porous carbon product has a mechanical piece crush strength greater than about 22 N (5 lbs), greater than about 36 N (8 lbs), or greater than about 44 N (10 lbs).

Embodiment AA18 is the shaped porous carbon product of any one of embodiments AA1 to AA16, wherein the shaped porous carbon product has a mechanical piece crush strength from about 22 N (5 lbs) to about 88 N (20 lbs), from about 22 N (5 lbs) to about 66 N (15 lbs), or from about 33 N (7.5 lbs) to about 66 N (15 lbs).

Embodiment AA19 is the shaped porous carbon product of any one of embodiments AA1 to AA18, wherein the shaped porous carbon product has a mean diameter of at least about 50 µm, at least about 500 µm, at least about 1,000 µm, or at least about 10,000 am.

Embodiment AA20 is the shaped porous carbon product of any one of embodiments AA1 to AA19, wherein the carbon black content of the shaped porous carbon product is at least about 40 wt. %, at least about 45 wt. %, at least about 50 wt. %, at least about 55 wt. %, at least about 60 wt. %, at least about 65 wt. %, or at least about 70 wt. %.

Embodiment AA21 is the shaped porous carbon product of any one of embodiments AA1 to AA19, wherein the carbon black content of the shaped porous carbon product is from about 35 wt. % to about 80 wt. %, from about 35 wt. % to about 75 wt. %, from about 40 wt. % to about 80 wt. %, or from about 40 wt. % to about 75 wt. %.

Embodiment AA22 is the shaped porous carbon product of any one of embodiments AA1 to AA20, wherein the shaped porous carbon product has a carbonized binder content from about 10 wt. % to about 50 wt. %, from about 20 wt. % to about 50 wt. %, from about 25 wt. % to about 40 wt. %, or from about 25 wt. % to about 35 wt. %.

Embodiment AA23 is the shaped porous carbon product of any one of embodiments AA1 to AA22, wherein the composition exhibits a rotating drum attrition index as measured in accordance with ASTM D4058-96 such that the percent retained is greater than about 85%, greater than about 90%, greater than about 92%, or greater than about 95%.

Embodiment AA24 is the shaped porous carbon product of embodiment AA23, wherein the composition exhibits a rotating drum attrition index as measured in accordance with ASTM D4058-96 such that the percent retained is greater than about 97%, or greater than about 99% by weight.

Embodiment AA25 is the shaped porous carbon product of any one of embodiments AA1 to AA24, wherein the composition exhibits a horizontal agitation sieve abrasion loss of less than about 5%, or less than about 3%.

Embodiment AA26 is the shaped porous carbon product of embodiment AA25, wherein the composition exhibits a horizontal agitation sieve abrasion loss of less than about 2%, less than about 1%, less than about 0.5%, less than about 0.2%, less than about 0.1%, less than about 0.05%, or less than about 0.03% by weight.

Embodiment AA27 is the shaped porous carbon product of any one of embodiments AA1 to AA26, wherein the binder comprises a saccharide selected from the group consisting of a monosaccharide, a disaccharide, an oligosaccharide, or any combination thereof.

Embodiment AA28 is the shaped porous carbon product of any one of embodiments AA1 to AA27, wherein the binder comprises a monosaccharide.

Embodiment AA29 is the shaped porous carbon product of embodiment AA35 or AA28, wherein the monosaccharide is selected from the group consisting of glucose, fructose, hydrate thereof, syrup thereof, and combinations thereof.

Embodiment AA30 is the shaped porous carbon product of any one of embodiments AA1 to AA29, wherein the binder comprises a disaccharide.

Embodiment AA31 is the shaped porous carbon product of any one of embodiments AA35 to AA30, wherein the disaccharide is selected from the group consisting of maltose, sucrose, syrup thereof, and combinations thereof.

Embodiment AA32 is the shaped porous carbon product of embodiment AA1 to AA31, wherein the binder comprises a polymeric carbohydrate, derivative of a polymeric carbohydrate, or a non-carbohydrate synthetic polymer, or any combination thereof.

Embodiment AA33 is the shaped porous carbon product of any one of embodiments AA1 to AA32, wherein the binder comprises a polymeric carbohydrate, derivative of a polymeric carbohydrate, or any combination thereof.

Embodiment AA34 is the shaped porous carbon product of any one of embodiments AA40 or AA33, wherein the polymeric carbohydrate or derivative of the polymeric carbohydrate comprises a cellulosic compound.

Embodiment AA35 is the shaped porous carbon product of embodiment AA34, wherein the cellulosic compound is selected from the group consisting of methylcellulose, ethylcellulose, ethylmethylcellulose, hydroxyethylcellulose, hydroxypropylcellulose, methylhydroxyethylcellulose, ethylhydroxyethylcellulose, hydroxypropylmethylcellulose, carboxymethylcellulose, and mixtures thereof.

Embodiment AA36 is the shaped porous carbon product of any one of embodiments AA40 to AA35, wherein the polymeric carbohydrate or derivative of the polymeric carbohydrate derivative is selected from the group consisting of alginic acid, pectin, aldonic acids, aldaric acids, uronic acids, sugar alcohols, and salts, oligomers, and polymers thereof.

Embodiment AA37 is the shaped porous carbon product of any one of embodiments AA40 to AA36, wherein the polymeric carbohydrate or derivative of the polymeric carbohydrate comprises a starch.

Embodiment AA38 is the shaped porous carbon product of any one of embodiments AA40 to AA37, wherein the polymeric carbohydrate or derivative of the polymeric carbohydrate comprises a soluble gum.

Embodiment AA39 is the shaped porous carbon product of any one of embodiments AA1 to AA38, wherein the binder comprises a non-carbohydrate synthetic polymer.

Embodiment AA40 is the shaped porous carbon product of any one of embodiments AA39, wherein the non-carbohydrate synthetic polymer is selected from the group consisting of polyacrylic acid, polyvinyl alcohols, polyvinylpyrrolidones, polyvinyl acetates, polyacrylates, polyethers, and copolymers derived therefrom.

Embodiment AA41 is the shaped porous carbon product of any one of embodiments AA1 to AA40, wherein the binder comprises one or more components selected from the group consisting of water soluble celluloses; water soluble alcohols; water soluble acetals; water soluble acids; polyvinyl acrylic acids; polyethers; and salts, esters, oligomers, or polymers of any of these.

Embodiment AA42 is the shaped porous carbon product of any one of embodiments AA1 to AA41, wherein the binder comprises a saccharide selected from the group consisting of glucose, fructose or hydrate thereof and a polymeric carbohydrate or derivative of the polymeric carbohydrate selected from the group consisting of hydroxyethylcellulose, methylcellulose, and starch.

Embodiment AA43 is the shaped porous carbon product of any one of embodiments AA1 to AA42, wherein the weight ratio of (i) the saccharide to (ii) the polymeric carbohydrate, derivative of the polymeric carbohydrate, or the non-carbohydrate synthetic polymer, or combination thereof is from about 5:1 to about 50:1, from about 10:1 to about 25:1, or from about 10:1 to about 20:1.

Embodiment BB1 is a catalyst composition comprising the shaped porous carbon product of any one of embodiments AA1 to AA51 as a catalyst support and a catalytically active component or precursor thereof at a surface of the support.

Embodiment BB2 is the catalyst composition of embodiment BB1, wherein the catalytically active component or precursor thereof comprises a metal.

Embodiment BB3 is the catalyst composition of embodiment BB2, wherein the metal comprises at least one d-block metal.

Embodiment BB4 is the catalyst composition of embodiment BB2, wherein the metal comprises at least one metal selected from groups VI, V, VI, VII, VIII, IX, X, XI, XII, and XIII.

Embodiment BB5 is the catalyst composition of embodiment BB2, wherein the metal is selected from the group consisting of cobalt, nickel, copper, zinc, iron, vanadium, molybdenum, manganese, barium, ruthenium, rhodium, rhenium, palladium, silver, osmium, iridium, platinum, gold, and combinations thereof.

Embodiment BB6 is the catalyst composition of embodiment BB2, wherein the metal comprises nickel.

Embodiment CC1 is a method of preparing a catalyst composition, the method comprising depositing a catalytically active component or precursor thereof at a surface of the shaped porous carbon product of any one of embodiments AA1 to AA51.

Embodiment CC2 is the catalyst composition of embodiment CC1, wherein the catalytically active component or precursor thereof comprises a metal.

Embodiment CC3 is the catalyst composition of embodiment CC2, wherein the metal comprises at least one d-block metal.

Embodiment CC4 is the catalyst composition of embodiment CC2, wherein the metal comprises at least one metal selected from groups VI, V, VI, VII, VIII, IX, X, XI, XII, and XIII.

Embodiment CC5 is the catalyst composition of embodiment CC2, wherein the metal is selected from the group consisting of cobalt, nickel, copper, zinc, iron, vanadium, molybdenum, manganese, barium, ruthenium, rhodium, rhenium, palladium, silver, osmium, iridium, platinum, gold, and combinations thereof.

Embodiment DD1 is a method of preparing a shaped porous carbon product, the method comprising:

mixing and heating water and a water soluble organic binder to form a binder solution, wherein the water and binder are heated to a temperature of at least about 50° C., and wherein the binder comprises: (i) a saccharide selected from the group consisting of a monosaccharide, a disaccharide, an oligosaccharide, a derivative thereof, and any combination thereof and (ii) a polymeric carbohydrate, a derivative of a polymeric carbohydrate, or a non-carbohydrate synthetic polymer, or any combination thereof, mixing carbon black with the binder solution to produce a carbon black mixture;

forming the carbon black mixture to produce a shaped carbon black composite; and heating the shaped carbon black composite to carbonize the binder to a water insoluble state and to produce the shaped porous carbon product.

Embodiment DD2 is a method of preparing a shaped porous carbon product, the method comprising:

mixing water, carbon black, and a water soluble organic binder to form a carbon black mixture, wherein the binder comprises: (i) a saccharide selected from the group consisting of a monosaccharide, a disaccharide, an oligosaccharide, a derivative thereof, and any combination thereof and (ii) a polymeric carbohydrate, a derivative of a polymeric carbohydrate, or a non-carbohydrate synthetic polymer, or any combination thereof, forming the carbon black mixture to produce a shaped carbon black composite; and heating the shaped carbon black composite to carbonize the binder to a water insoluble state and to produce the shaped porous carbon product.

Embodiment DD3 is a method of preparing a shaped porous carbon product, the method comprising:

mixing water, carbon black, and a binder to form a carbon black mixture, wherein the binder comprises a saccharide selected from the group consisting of a monosaccharide, a disaccharide, an oligosaccharide, a derivative thereof, or any combination thereof and wherein the weight ratio of the binder to carbon black in the carbon black mixture is at least about 1:4, at least about 1:3, at least about 1:2, at least about 1:1, or at least 1.5:1;

forming the carbon black mixture to produce a shaped carbon black composite; and heating the shaped carbon black composite to carbonize the binder to a water insoluble state and to produce the shaped porous carbon product.

Embodiment DD4 is a method of preparing a shaped porous carbon product, the method comprising:

mixing water, carbon black, and a binder to form a carbon black mixture, wherein the binder comprises a saccharide selected from the group consisting of a monosaccharide, a disaccharide, an oligosaccharide, a derivative thereof, or any combination thereof and wherein the water content of the carbon black mixture is no more than about 80% by weight, no more than about 55% by weight, no more than about 40% by weight, or no more than about 25% by weight;

forming the carbon black mixture to produce the shaped carbon black composite; and heating the shaped carbon black composite to carbonize the binder to a water insoluble state and to produce a shaped porous carbon product.

Embodiment DD5 is the method of any one of embodiments DD1 to DD4, wherein the water and water soluble organic binder are mixed and heated to form a binder solution prior to mixing with carbon black.

Embodiment DD6 is the method of embodiment DD9, wherein the water and binder are heated to a temperature of at least about 50° C., at least about 60° C., or at least about 70° C.

Embodiment DD7 is the method of embodiment DD1 or DD6, wherein the water and binder are heated to a temperature of from about 50° C. to about 95° C., from about 50° C. to about 90° C., or from about 60° C. to about 85° C.

Embodiment DD8 is the method of any one of embodiments DD1 or DD5 to DD7, further comprising cooling the binder solution prior to mixing with carbon black or prior to forming the shaped carbon black composite.

Embodiment DD9 is the method of any of embodiments DD1 or DD5 to DD8, wherein the water content of the carbon black mixture is no more than about 80% by weight, no more than about 55% by weight, no more than about 40% by weight, or no more than about 25% by weight.

Embodiment DD10 is the method of any of embodiments DD1 or DD5 to DD8, wherein the water content of the carbon black mixture is from about 5 wt. % to about 70 wt. % or from about 5 wt. % to about 55 wt. %.

Embodiment DD11 is the method of any of embodiments DD1 or DD5 to DD10, wherein the water content of the carbon black mixture is from about 5 wt. % to about 40 wt. % or from about 5 wt. % to about 25 wt. %.

Embodiment DD12 is the method of any one of embodiments DD1 to DD11 further comprising pressing or kneading the carbon black mixture.

Embodiment DD13 is the method of embodiment DD12, wherein mixing of the water, carbon black, and binder and pressing of the resulting carbon black mixture is conducted simultaneously.

Embodiment DD14 is the method of embodiment DD13, wherein mixing of the water, carbon black, and binder and pressing of the resulting carbon black mixture is conducted using a mixer muller.

Embodiment DD15 is the method of any one of embodiments DD1 to DD14, wherein the carbon black mixture further comprises a forming adjuvant.

Embodiment DD16 is the method of embodiment DD15, wherein the forming adjuvant comprises a lubricant.

Embodiment DD17 is the method of embodiment DD15, wherein the forming adjuvant comprises lignin or derivative thereof.

Embodiment DD18 is the method of any one of embodiments DD1 to DD17, wherein the shaped carbon black composite is heated in an inert or oxidative atmosphere.

Embodiment DD19 is the method of embodiment DD18, wherein the atmosphere is an inert atmosphere.

Embodiment DD20 is the method of any one of embodiments DD1 to DD19, wherein the shaped carbon black composite is heated at a temperature of from about 250° C. to about 1,000° C., from about 300° C. to about 900° C., from about 300° C. to about 850° C., from about 300° C. to about 800° C., from about 350° C. to about 850° C., from about 350° C. to about 800° C., from about 350° C. to about 700° C., from about 400° C. to about 850° C. or from about 400° C. to about 800° C.

Embodiment DD21 is the method of any one of embodiments DD1 to DD20, wherein the shaped carbon black composite is formed by extruding the carbon black mixture.

Embodiment DD22 is the method of any one of embodiments DD1 to DD21, wherein the carbon black mixture is formed under a pressure of at least about 100 kPa (1 bar), or from about 100 kPa (1 bar) to about 10,000 kPa (100 bar), from about 500 kPa (5 bar) to 5,000 kPa (50 bar), or from about 1,000 kPa (10 bar) to about 3,000 kPa (30 bar).

Embodiment DD23 is the method of any one of embodiments DD1 to DD22, further comprising drying the shaped carbon black composite after forming.

Embodiment DD24 is the method of embodiment DD23, wherein drying the shaped carbon black composite comprises heating at a temperature of from about 20° C. to about 150° C., from about 40° C. to about 120° C., or from about 60° C. to about 120° C.

Embodiment DD25 is the method of any one of embodiments DD1 to DD24, wherein the weight ratio of the binder to carbon black in the carbon black mixture is at least about 1:4, at least about 1:3, at least about 1:2, at least about 1:1, or at least 1.5:1.

Embodiment DD26 is the method of any one of embodiments DD1 to DD24, wherein the weight ratio of binder to carbon black in the carbon black mixture is from about 1:4 to about 3:1, from about 1:4 to about 1:1, from about 1:3 to about 2:1, from about 1:3 to about 1:1, or about 1:1.

Embodiment DD27 is the method of any one of embodiments DD1 to DD26, wherein the carbon black content of the carbon black mixture is at least about 35 wt. %, at least about 40 wt. %, at least about 45 wt. %, at least about 50 wt. %, at least about 55 wt. %, at least about 60 wt. %, at least about 65 wt. %, or at least about 70 wt. % on a dry weight basis.

Embodiment DD28 is the method of any one of embodiments DD1 to DD26, wherein the carbon black content of the carbon black mixture is from about 35 wt. % to about 80 wt. %, from about 35 wt. % to about 75 wt. %, from about 40 wt. % to about 80 wt. %, or from about 40 wt. % to about 75 wt. % on a dry weight basis.

Embodiment DD29 is the method of any one of embodiments DD1 to DD28, wherein the concentration of the binder in the carbon black mixture is at least about 10 wt. %, at least about 20 wt. %, at least about 25 wt. %, at least about 30 wt. %, at least about 35 wt. %, at least about 40 wt. %, or at least 45 wt. % binder on a dry weight basis.

Embodiment DD30 is the method of any one of embodiments DD1 to DD28, wherein the concentration of the binder in the carbon black mixture is from about 10 wt. % to about 50 wt. %, from about 10 wt. % to about 45 wt. %, from about 15 wt. % to about 50 wt. %, from about 20 wt. % to about 50 wt. %, or from about 20 wt. % to about 45 wt. % on a dry weight basis.

Embodiment DD31 is the method of any one of embodiments DD1 to DD30, wherein the binder comprises a saccharide selected from the group consisting of a monosaccharide, an oligosaccharide, or any combination thereof.

Embodiment DD32 is the method of any one of embodiments DD1 to DD31, wherein the binder comprises a monosaccharide.

Embodiment DD33 is the method of any one of embodiments DD1 to DD32, wherein the monosaccharide is selected from the group consisting of glucose, fructose, hydrate thereof, syrup thereof, and combinations thereof.

Embodiment DD34 is the method of any one of embodiments DD1 to DD33, wherein the binder comprises a disaccharide.

Embodiment DD35 is the method of any one of embodiments DD1 to DD34, wherein the disaccharide is selected from the group consisting of maltose, sucrose, syrup thereof, and combinations thereof.

Embodiment DD36 is the method of any one of embodiments DD1 to DD35, wherein the binder comprises a polymeric carbohydrate.

Embodiment DD37 is the method of any one of embodiments DD1 to DD36, wherein the binder comprises a polymeric carbohydrate, derivative of a polymeric carbohydrate, or any combination thereof.

Embodiment DD38 is the method of any one of embodiments DD1 to DD37, wherein the polymeric carbohydrate or derivative of the polymeric carbohydrate comprises a cellulosic compound.

Embodiment DD39 is the method of embodiment DD38, wherein the cellulosic compound is selected from the group consisting of methylcellulose, ethylcellulose, ethylmethylcellulose, hydroxyethylcellulose, hydroxypropylcellulose, methylhydroxyethylcellulose, ethylhydroxyethylcellulose, hydroxypropylmethylcellulose, carboxymethylcellulose, and mixtures thereof.

Embodiment DD40 is the method of any one of embodiments DD1 to DD39, wherein the polymeric carbohydrate or derivative of the polymeric carbohydrate derivative is selected from the group consisting of alginic acid, pectin, aldonic acids, aldaric acids, uronic acids, sugar alcohols, and salts, oligomers, and polymers thereof.

Embodiment DD41 is the method of any one of embodiments DD1 to DD40, wherein the polymeric carbohydrate or derivative of the polymeric carbohydrate comprises a starch.

Embodiment DD42 is the method of any one of embodiments DD1 to DD41, wherein the polymeric carbohydrate or derivative of the polymeric carbohydrate comprises a soluble gum.

Embodiment DD43 is the method of any one of embodiments DD1 to DD42, wherein the binder comprises a non-carbohydrate synthetic polymer.

Embodiment DD44 is the method of any one of embodiments DD1 to DD43, wherein the non-carbohydrate synthetic polymer is selected from the group consisting of polyacrylic acid, polyvinyl alcohols, polyvinylpyrrolidones, polyvinyl acetates, polyacrylates, polyethers, and copolymers derived therefrom.

Embodiment DD45 is the method of any one of embodiments DD1 to DD44, wherein the binder comprises one or more components selected from the group consisting of water soluble celluloses; water soluble alcohols; water soluble acetals; water soluble acids; polyvinyl acrylic acids; polyethers; and salts, esters, oligomers, or polymers of any of these.

Embodiment DD46 is the method of any one of embodiments DD1 to DD45, wherein the binder comprises a saccharide selected from the group consisting of glucose, fructose or hydrate thereof and a polymeric carbohydrate or derivative of the polymeric carbohydrate selected from the group consisting of hydroxyethylcellulose, methylcellulose, and starch.

Embodiment DD47 is the method of any one of embodiments DD1 to DD46, wherein the weight ratio of (i) the saccharide to (ii) the polymeric carbohydrate, derivative of the polymeric carbohydrate, or the non-carbohydrate synthetic polymer, or combination thereof is from about 5:1 to about 50:1, from about 10:1 to about 25:1, or from about 10:1 to about 20:1.

Embodiment DD48 is the method of any one of embodiments DD1 to DD47, wherein the carbon black mixture further comprises a porogen.

Embodiment DD49 is the method of embodiment DD48, wherein the porogen comprises a water soluble linear, branched, or cross-linked polymer.

Embodiment DD50 is the method any one of embodiments DD1 to DD49, wherein the water content of the carbon black mixture no more than about 80% by weight, no more than about 55% by weight, no more than about 40% by weight, or no more than about 25% by weight.

Embodiment DD51 is the method any one of embodiments DD1 to DD49, wherein the water content of the carbon black mixture is from about 5 wt. % to about 70 wt. %, from about 5 wt. % to about 55 wt. %, from about 5 wt. % to about 40 wt. %, or from about 5 wt. % to about 25 wt. %.

Embodiment DD52 is the method of any one of embodiments DD1 to DD51, wherein the shaped porous carbon product has a BET specific surface area from about 20 $m^2/g$ to about 500 $m^2/g$, from about 20 $m^2/g$ to about 350 $m^2/g$, from about 20 $m^2/g$ to about 250 $m^2/g$, from about 20 $m^2/g$ to about 225 $m^2/g$, from about 20 $m^2/g$ to about 200 $m^2/g$, from about 20 $m^2/g$ to about 175 $m^2/g$, from about 20 $m^2/g$ to about 150 $m^2/g$, from about 20 $m^2/g$ to about 125 $m^2/g$, or from about 20 $m^2/g$ to about 100 $m^2/g$, from about 25 $m^2/g$ to about 500 $m^2/g$, from about 25 $m^2/g$ to about 350 $m^2/g$, from about 25 $m^2/g$ to about 250 $m^2/g$, from about 25 $m^2/g$ to about 225 $m^2/g$, from about 25 $m^2/g$ to about 200 $m^2/g$, from about 25 $m^2/g$ to about 175 $m^2/g$, from about 25 $m^2/g$ to about 150 $m^2/g$, from about 25 $m^2/g$ to about 125 $m^2/g$, or from about 25 $m^2/g$ to about 100 $m^2/g$.

Embodiment DD53 is the method of any one of embodiments DD1 to DD52, wherein the shaped porous carbon product has a BET specific surface area from about 30 $m^2/g$ to about 500 $m^2/g$, from about 30 $m^2/g$ to about 350 $m^2/g$, from about 30 $m^2/g$ to about 250 $m^2/g$, from about 30 $m^2/g$ to about 225 $m^2/g$, from about 30 $m^2/g$ to about 200 $m^2/g$, from about 30 $m^2/g$ to about 175 $m^2/g$, from about 30 $m^2/g$ to about 150 $m^2/g$, from about 30 $m^2/g$ to about 125 $m^2/g$, or from about 30 $m^2/g$ to about 100 $m^2/g$.

Embodiment DD54 is the method of any one of embodiments DD1 to DD53, wherein the shaped porous carbon product has a mean pore diameter greater than about 5 nm, greater than about 10 nm, greater than about 12 nm, or greater than about 14 nm.

Embodiment DD55 is the method of any one of embodiments DD1 to DD54, wherein the shaped porous carbon product has a mean pore diameter from about 5 nm to about 100 nm, from about 5 nm to about 70 nm, from 5 nm to about 50 nm, from about 5 nm to about 25 nm, from about 10 nm to about 100 nm, from about 10 nm to about 70 nm, from 10 nm to about 50 nm, or from about 10 nm to about 25 nm.

Embodiment DD56 is the method of any one of embodiments DD1 to DD55, wherein the shaped porous carbon product has a specific pore volume of the pores having a diameter of 1.7 nm to 100 nm as measured by the BJH method that is greater than about 0.1 $cm^3/g$, greater than about 0.2 $cm^3/g$, or greater than about 0.3 $cm^3/g$.

Embodiment DD57 is the method of any one of embodiments DD1 to DD55, wherein the shaped porous carbon product has a specific pore volume of the pores having a diameter of 1.7 nm to 100 nm as measured by the BJH method that is from about 0.1 $cm^3/g$ to about 1.5 $cm^3/g$, from about 0.1 $cm^3/g$ to about 0.9 $cm^3/g$, from about 0.1 $cm^3/g$ to about 0.8 $cm^3/g$, from about 0.1 $cm^3/g$ to about 0.7 $cm^3/g$, from about 0.1 $cm^3/g$ to about 0.6 $cm^3/g$, from about 0.1 $cm^3/g$ to about 0.5 $cm^3/g$, from about 0.2 $cm^3/g$ to about 1 $cm^3/g$, from about 0.2 $cm^3/g$ to about 0.9 $cm^3/g$, from about 0.2 $cm^3/g$ to about 0.8 $cm^3/g$, from about 0.2 $cm^3/g$ to about 0.7 $cm^3/g$, from about 0.2 $cm^3/g$ to about 0.6 $cm^3/g$, from about 0.2 $cm^3/g$ to about 0.5 $cm^3/g$, from about 0.3 $cm^3/g$ to about 1 $cm^3/g$, from about 0.3 $cm^3/g$ to about 0.9 $cm^3/g$, from about 0.3 $cm^3/g$ to about 0.8 $cm^3/g$, from about 0.3 $cm^3/g$ to about 0.7 $cm^3/g$, from about 0.3 $cm^3/g$ to about 0.6 $cm^3/g$, or from about 0.3 $cm^3/g$ to about 0.5 $cm^3/g$.

Embodiment DD58 is the method of any one of embodiments DD1 to DD57, wherein at least about 35%, at least about 40%, at least about 45%, or at least about 50% of the pore volume of the shaped porous carbon product, as measured by the BJH method on the basis of pores having a diameter from 1.7 nm to 100 nm, is attributable to pores having a mean pore diameter of from about 10 nm to about 50 nm.

Embodiment DD59 is the method of any one of embodiments DD1 to DD57, wherein from about 35% to about 80%, from about 35% to about 75%, from about 35% to about 65%, from about 40% to about 80%, from about 40% to about 75%, or from about 40% to about 70% of the pore volume of the shaped porous carbon product, as measured by the BJH method on the basis of pores having a diameter from 1.7 nm to 100 nm, is attributable to pores having a mean pore diameter of from about 10 nm to about 50 nm.

Embodiment DD60 is the method of any one of embodiments DD1 to DD59, wherein at least about 50%, at least about 60%, at least about 70%, at least about 80%, or at least about 90% of the pore volume of the shaped porous carbon product, as measured by the BJH method on the basis of pores having a diameter from 1.7 nm to 100 nm, is attributable to pores having a mean pore diameter of from about 10 nm to about 100 nm.

Embodiment DD61 is the method of any one of embodiments DD1 to DD59, wherein from about 50% to about 95%, from about 50% to about 90%, from about 50% to about 80%, from about 60% to about 95%, from about 60% to about 90%, from about 60% to about 80%, from about 70% to about 95%, from about 70% to about 90%, from about 70% to about 80%, from about 80% to about 95%, or from about 80% to about 90% of the pore volume of the shaped porous carbon product, as measured by the BJH method on the basis of pores having a diameter from 1.7 nm to 100 nm, is attributable to pores having a mean pore diameter of from about 10 nm to about 100 nm.

Embodiment DD62 is the method of any one of embodiments DD1 to DD61, wherein no more than about 10%, no more than about 5%, or no more than about 1% of the pore volume of the shaped porous carbon product, as measured by the BJH method on the basis of pores having a diameter from 1.7 nm to 100 nm, is attributable to pores having a mean pore diameter less than 10 nm, less than 5 nm, or less than 3 nm.

Embodiment DD63 is the method of any one of embodiments DD1 to DD61, wherein from about 0.1% to about 10%, from about 0.1% to about 5%, from about 0.1% to about 1%, from about 1% to about 10%, or from about 1% to about 5% of the pore volume of the shaped porous carbon product, as measured by the BJH method on the basis of pores having a diameter from 1.7 nm to 100 nm, is attributable to pores having a mean pore less than 10 nm, less than 5 nm, or less than 3 nm.

Embodiment DD64 is the method of any one of embodiments DD1 to DD63, wherein the shaped porous carbon product has a pore size distribution such that the peak of the distribution is at a diameter greater than about 5 nm, greater than about 7.5 nm, greater than about 10 nm, greater than about 12.5 nm, greater than about 15 nm, or greater than about 20 nm.

Embodiment DD65 is the method of any one of embodiments DD1 to DD64, wherein the shaped porous carbon product has a pore size distribution such that the peak of the distribution is at a diameter less than about 100 nm, less than about 90 nm, less than about 80 nm, or less than about 70 nm.

Embodiment DD66 is the method of any one of embodiments DD1 to DD65, wherein the shaped porous carbon product has a radial piece crush strength greater than about 4.4 N/mm (1 lb/mm), greater than about 8.8 N/mm (2 lbs/mm), or greater than about 13.3 N/mm (3 lbs/mm).

Embodiment DD67 is the method of any one of embodiments DD1 to DD65, wherein the shaped porous carbon product has a radial piece crush strength from about 4.4 N/mm (1 lb/mm) to about 88 N/mm (20 lbs/mm), from about 4.4 N/mm (1 lb/mm) to about 66 N/mm (15 lbs/mm), or from about 8.8 N/mm (2 lb/mm) to about 44 N/mm (10 lbs/mm).

Embodiment DD68 is the method of any one of embodiments DD1 to DD67, wherein the shaped porous carbon product has a mechanical piece crush strength greater than about 22 N (5 lbs), greater than about 36 N (8 lbs), or greater than about 44 N (10 lbs).

Embodiment DD69 is the method of any one of embodiments DD1 to DD67, wherein the shaped porous carbon product has a mechanical piece crush strength from about 22 N (5 lbs) to about 88 N (20 lbs), from about 22 N (5 lbs) to about 66 N (15 lbs), or from about 33 N (7.5 lbs) to about 66 N (15 lbs).

Embodiment DD70 is the method of any one of embodiments DD1 to DD69, wherein the shaped porous carbon product has a mean diameter of at least about 50 μm, at least about 500 μm, at least about 1,000 μm, or at least about 10,000 μm.

Embodiment DD71 is the method of any one of embodiments DD1 to DD70, wherein the shaped porous carbon product has the carbon black content of at least about 35 wt. %, at least about 40 wt. %, at least about 45 wt. %, at least about 50 wt. %, at least about 55 wt. %, at least about 60 wt. %, at least about 65 wt. %, or at least about 70 wt. %.

Embodiment DD72 is the method of any one of embodiments DD1 to DD70, wherein the shaped porous carbon product has the carbon black content from about 35 wt. % to about 80 wt. %, from about 35 wt. % to about 75 wt. %, from about 40 wt. % to about 80 wt. %, or from about 40 wt. % to about 75 wt. %.

Embodiment DD73 is the method of any one of embodiments DD1 to DD72, wherein the shaped porous carbon product has a carbonized binder content from about 10 wt. % to about 50 wt. %, from about 20 wt. % to about 50 wt. %, from about 25 wt. % to about 40 wt. %, or from about 25 wt. % to about 35 wt. %.

Embodiment DD74 is the method of any one of embodiments DD1 to DD73, wherein the catalyst composition exhibits a rotating drum attrition index as measured in accordance with ASTM D4058-96 such that the percent retained is greater than about 85%, greater than about 90%, greater than about 92%, or greater than about 95%.

Embodiment DD75 is the method of any one of embodiments DD1 to DD73, wherein the catalyst composition exhibits a rotating drum attrition index as measured in accordance with ASTM D4058-96 such that the percent retained is greater than about 97%, or greater than about 99% by weight.

Embodiment DD76 is the method of any one of embodiments DD1 to DD75, wherein the catalyst composition exhibits a horizontal agitation sieve abrasion loss of less than about 5%, or less than about 3%.

Embodiment DD77 is the method of any one of embodiments DD1 to DD75, wherein the catalyst composition exhibits a horizontal agitation sieve abrasion loss of less than about 2%, less than about 1%, less than about 0.5%, less than about 0.2%, less than about 0.1%, less than about 0.05%, or less than about 0.03% by weight.

Embodiment EE1 is a method of preparing a catalyst composition, the method comprising depositing a catalytically active component or precursor thereof at a surface of the shaped porous carbon product of any one of embodiments AA1 to AA51 as a catalyst support.

Embodiment EE2 is the method of embodiment EE1, wherein the catalytically active component or precursor thereof comprises a metal.

Embodiment EE3 is the method of embodiment EE2, wherein the metal comprises at least one d-block metal.

Embodiment EE4 is the method of embodiment EE2, wherein the metal comprises at least one metal selected from groups VI, V, VI, VII, VIII, IX, X, XI, XII, and XIII.

Embodiment EE5 is the method of embodiment EE2, wherein the metal is selected from the group consisting of cobalt, nickel, copper, zinc, iron, vanadium, molybdenum, manganese, barium, ruthenium, rhodium, rhenium, palladium, silver, osmium, iridium, platinum, gold, and combinations thereof.

Embodiment FF1 is a process for the selective oxidation of an aldose to an aldaric acid comprising reacting the aldose with oxygen in the presence of a catalyst composition prepared according to any one of embodiments EE1 to EE5 to form the aldaric acid.

Embodiment FF2 is the process of embodiment FF1, wherein the aldose is selected from the group consisting of pentoses and hexoses.

Embodiment FF3 is the process of embodiment FF1 or FF2, wherein the aldaric acid is selected from the group consisting of xylaric acid and glucaric acid.

Embodiment FF4 is the process of any one of embodiments FF1 to FF3, wherein the catalytically active component of the catalyst composition comprises at least platinum.

Embodiment FF5 is the process of any one of embodiments FF1 to FF4, wherein the catalytically active component of the catalyst composition comprises platinum and gold.

Embodiment FF6 is the process of any one of embodiments FF1 to FF5, wherein the aldaric acid comprises glucaric acid and the glucaric acid yield is at least about 30%, at least about 35%, at least about 40%, at least about, 45%, or at least about 50%.

Embodiment FF7 is the process of any one of embodiments FF1 to FF5, wherein the aldaric acid comprises glucaric acid and the glucaric acid yield is from about 35% to about 65%, from about 40% to about 65%, or from about 45% to about 65%.

Embodiment FF8 is the process of any one of embodiments FF1 to FF7, wherein the aldaric acid comprises glucaric acid and the glucaric acid selectivity is at least about 70%, at least about 75%, or at least about 80%.

Embodiment FF9 is the process of any one of embodiments FF1 to FF8, wherein the aldose comprises glucose and the catalytically active component comprises platinum and the mass ratio of glucose to platinum is from about 10:1 to about 1000:1, from about 10:1 to about 500:1, from about 10:1 to about 200:1, or from about 10:1 to about 100:1.

Embodiment GG1 is a process for the selective hydrodeoxygenation of aldaric acid or salt, ester, or lactone thereof to a dicarboxylic acid comprising reacting the aldaric acid or salt, ester, or lactone thereof with hydrogen in the presence of a halogen-containing compound and a catalyst composition prepared according to of any one of embodiments EE1 to EE5 to form the dicarboxylic acid.

Embodiment GG2 is the process of embodiment GG1, wherein the aldaric acid or salt, ester, or lactone thereof comprises glucaric acid or salt, ester, or lactone thereof.

Embodiment GG3 is the process of embodiment GG1 or GG2, wherein the dicarboxylic acid comprises adipic acid.

Embodiment GG4 is the process of any one of embodiments GG1 to GG3, wherein the catalytically active component of the catalyst composition comprises at least one noble metal.

Embodiment HH1 is a process for the selective hydrodeoxygenation of 1,2,6-hexanetriol to 1,6-hexanediol comprising reacting the 1,2,6-hexanetriol with hydrogen in the presence of a catalyst composition prepared according to of any one of embodiments EE1 to EE5 to form 1,6-hexanediol.

Embodiment HH2 is the process of embodiment HH1, wherein the catalytically active component comprises platinum and at least one metal selected from the group consisting of molybdenum, lanthanum, samarium, yttrium, tungsten, and rhenium at a surface of the support.

Embodiment HH3 is the process of embodiment HH1 or HH2, wherein the catalytically active component of the catalyst composition comprises platinum and tungsten.

Embodiment HH4 is the process of any one of embodiments HH1 to HH3, wherein the total metal loading of the catalyst composition is from about 0.1% to about 10%, or from 0.2% to 10%, or from about 0.2% to about 8%, or from about 0.2% to about 5%, of the total weight of the catalyst.

Embodiment HH5 is the process of any one of embodiments HH1 to HH4, wherein the molar ratio of platinum to M2 metal is from about 20:1 to about 1:10, from about 10:1 to about 1:5, or from about 8:1 to about 1:2.

Embodiment HH6 is the process of any one of embodiments HH1 to HH4, wherein the reaction of 1,2,6-hexanetriol to 1,6-hexanediol is conducted at a temperature in the range of about 60° C. to about 200° C. or about 120° C. to about 180° C. and a partial pressure of hydrogen in the range of about 200 psig to about 2000 psig or about 500 psig to about 2000 psig.

Embodiment II1 is a process for the selective amination of 1,6-hexanediol to 1,6-hexamethylenediamine comprising reacting the 1,6-hexanediol with an amine in the presence of a catalyst composition prepared according to of any one of embodiments EE1 to EE5 to form 1,6-hexamethylenediamine.

Embodiment II2 is the process of embodiment II1, wherein the amine comprises ammonia.

Embodiment II3 is the process of embodiment II2, wherein the molar ratio of ammonia to 1,6-hexanediol is at least about 40:1, at least about 30:1, at least about 20:1, or in the range of from about 40:1 to about 5:1, or from about 30:1 to about 10:1.

Embodiment II4 is the process of any one of embodiments II1 to II3, wherein the reaction of 1,6-hexanediol with amine in the presence of the catalyst composition is carried out at a temperature less than or equal to about 200° C., less than or equal to about 100° C., or in the range of about 100° C. to about 180° C., or about 140° C. to about 180° C.

Embodiment II5 is the process of any one of embodiments II1 to 114, wherein the reaction of 1,6-hexanediol with amine in the presence of the catalyst composition is conducted at a pressure not exceeding about 1500 psig, in the range of about 200 psig to about 1500 psig, of about 400 psig to about 1200 psig, of about 400 psig to about 1000 psig.

Embodiment II6 is the process of any one of embodiments II1 to 115, wherein the reaction of 1,6-hexanediol with amine in the presence of the catalyst composition is conducted with 1,6-hexanediol and ammonia at a temperature in the range of about 100° C. to about 180° C. and a pressure in the range of about 200 psig to about 1500 psig.

Embodiment II7 is the process of any one of embodiments II1 to 116, wherein the 1,6-hexanediol and amine are reacted in the presence of hydrogen and the catalyst composition, and the hydrogen partial pressure is equal to or less than about 100 psig.

Embodiment II8 is the process of any one of embodiments II1 to 117, wherein at least 20%, at least 30%, at least 40%, at least 50%, at least 60%, or at least 70% of the product mixture resulting from a single pass reaction of 1,6-hexanediol with amine (e.g., ammonia) in the presence of the catalyst composition is 1,6-hexamethylenediamine.

Embodiment II9 is the process of any one of embodiments II1 to 118 wherein the catalytically active component comprises ruthenium.

Embodiment II10 is the process of any one of embodiments II1 to 119 wherein the catalytically active component comprises rhenium.

Embodiment II11 is the process of any one of embodiments II1 to II10, wherein the total metal loading of the catalyst composition is from about 0.1% to about 10%, from about 1% to about 6%, or from about 1% to about 5% of the total weight of the catalyst.

Embodiment II12 is the process of any one of embodiments II1 to II11, wherein the catalytically active component of the catalyst composition further comprises rhenium and the molar ratio of ruthenium:rhenium is from about 20:1 to about 4:1, from about 10:1 to about 4:1, or from about 8:1 to about 4:1.

Embodiment II13 is the process of any one of embodiments II1 to II12, wherein the catalytically active component of the catalyst composition comprises nickel.

For further illustration, additional non-limiting embodiments of the present disclosure are set forth below.

The following non-limiting examples are provided to further illustrate the present invention.

EXAMPLES

Surface areas were determined from nitrogen adsorption data using the BET method as described in S. Brunauer, P. H. Emmett, E. Teller, J. Am. Chem. Soc. 1938, 60, 309-331, and ASTM D3663-03(2008) Standard Test Method for Surface Area of Catalysts and Catalyst Carriers. Mean pore diameters and pore volumes were determined in accordance with the procedures described in E. P. Barrett, L. G. Joyner, P. P. Halenda, J. Am. Chem. Soc. 1951, 73, 373-380, and ASTM D4222-03(2008) Standard Test Method for Determination of Nitrogen Adsorption and Desorption Isotherms of Catalysts and Catalyst Carriers by Static Volumetric Measurements.

Mercury Porosimetry measurements were conducted using an AutoPore V Mercury Porosimeter from Micromeritics Instrument Corporation. A suitable amount of carbon extrudates were loaded into an appropriate penetrometer and mercury intrusion was measured in two sequential stages: low pressure analysis (0 to 50 psia) followed by high pressure analysis (50 to 33,000 psia). A total of 712 data points were collected across the whole range of pressure with a contact angle of 154.0°.

Radial piece crush strength measurements were conducted according to ASTM D6175-03(2013) Standard Test Method for Radial Crush Strength of Extruded Catalyst and Catalyst Carrier Particles using a press apparatus equipped with a Dillon GS100 Digital Force Gauge. Mean radial piece crush strength is the average value of independent measurements of at least 10 different extrudate pellets.

Single piece crush strength were conducted according to ASTM D4179-03(2013) Standard Test Method for Single Pellet Crush Strength of Formed Catalysts and Catalyst Carriers using a press apparatus equipped with a Dillon GS100 Digital Force Gauge. Single piece crush strength is the average value of independent measurements of at least 10 different extrudate pellets.

Example 1. Preparation of Carbon Black Extrudates 36.4 g of carbon black powder (Cabot Vulcan XC72, 224 m2/g) was added in multiple portions to a heated (overnight at 80° C.) aqueous solution (136.5 g) containing 24.3 wt. % Cerelose Dextrose from Ingredion and 4.7 wt. % hydroxyethylcellulose from Sigma-Aldrich (SKU 54290, viscosity 80-125 cP, 2% in H2O (20° C.)). The mixture was stirred well using a spatula to produce a paste. This paste was loaded into a syringe and the material was extruded into spaghetti-like strings with about 1.5 mm diameter. After drying in a 70° C. oven for 5 hours under a dry air purge, these strings were cut into small pieces about 1.0 cm long. Then they were treated at 350° C. for 2 hours with 10° C./min temperature ramp rate under continuous $N_2$ flow to carbonize the binder and produce a carbon black extrudate.

The properties of the resultant extrudate are show in Table 1.

TABLE 1

|  | BET Surface Area (m$^2$/g) | Mean Pore Diameter (Å) | Pore Volume (cm$^3$/g) |
| --- | --- | --- | --- |
| Extrudate of Cabot Vulcan XC72 | 110 | 110 | 0.15 |

Example 2. Characterization of Component Carbon Black Powder

The properties of various carbon black powders utilized in the shaped porous carbon black products were characterized.

A. Physical Properties of Carbon Black Powders

The BET specific surface area, specific mean pore diameter and specific pore volume of these carbon black powder starting materials were determined using the methods described above, and are provided in Table 2.

TABLE 2

| Carbon Black | BET Surface Area (m$^2$/g) | Mean Pore Diameter (Å) | Pore Volume (cm$^3$/g) |
| --- | --- | --- | --- |
| Asbury 5365R | 34 | 143 | 0.11 |
| Asbury 5353R | 35 | 186 | 0.14 |

TABLE 2-continued

| Carbon Black | BET Surface Area (m$^2$/g) | Mean Pore Diameter (Å) | Pore Volume (cm$^3$/g) |
| --- | --- | --- | --- |
| Asbury 5345R | 35 | 207 | 0.11 |
| Timcal Ensaco 250G | 64 | 140 | 0.24 |
| Asbury 5348R | 65 | 220 | 0.31 |
| Asbury 5358R | 67 | 213 | 0.34 |
| Asbury 5346R | 80 | 145 | 0.28 |
| Cabot Monarch 570 | 102 | 138 | 0.30 |
| Orion HP 160 | 158 | 208 | 0.87 |
| Cabot Monarch 700 | 181 | 121 | 0.38 |
| Cabot Vulcan XC72 | 224 | 161 | 0.43 |

B. Catalytic Performance

The carbon black powders were evaluated as catalyst support material in an oxidation reaction for converting glucose to glucaric acid as described below.

(i) Oxidation of Glucose to Glucaric Acid (Protocol 1)

Suitably concentrated aqueous solutions of $Me_4NAuO_2$ and $PtO(NO_3)$ were added together to carbon black powders by incipient wetness impregnation and agitated to impregnate the supports. The samples were dried in an oven at 70° C. overnight, and reduced at 350° C. under a forming gas (5% $H_2$ and 95% $N_2$) atmosphere for 4 hours with 2° C./min temperature ramp rate to produce catalysts with a composition of 2.0 wt % Au and 2.0 wt % Pt. By using other carbon black supports, Au and Pt precursors, and adjusting amount of Au and Pt in solution, different catalysts with various Au and Pt loadings on a variety of commercial carbon black powders or particles from extrudates were prepared in a similar manner.

These catalysts were tested for glucose oxidation using the following testing protocol. Catalyst (8 mg) was weighed into a glass vial insert followed by addition of an aqueous glucose solution (250 µl of 0.55 M). The glass vial insert was loaded into a reactor and the reactor was closed. The atmosphere in the reactor was replaced with oxygen and pressurized to 75 psig at room temperature. Reactor was heated to 110° C. and maintained at the respective temperature for 2 hours while vials were shaken. After that, shaking was stopped and reactor was cooled to 40° C. Pressure in the reactor was then slowly released. The glass vial insert was removed from the reactor and centrifuged. The solution was diluted with deionized water and analyzed by ion chromatography to determine the yield of glucaric acid. Selectivity is defined as 100%×(glucaric acid)/(sum of glucaric acid and all off-pathway species). Off-pathway species that cannot be converted to glucaric acid include 2-ketogluconic acid, 3-ketogluconic acid, 4-ketogluconic acid, 5-ketogluconic acid, trihydroxyglutaric acid, tartaric acid, tartronic acid and oxalic acid. On-pathway species include glucose, gluconic acid, guluronic acid and glucuronic acid. On-pathway species are not used in the selectivity calculation because these intermediates can be partially converted to glucaric acid and are not considered off-pathway. Results are presented in Table 3.

TABLE 3

| Support | Surface Area (m$^2$/g) | Mean Pore Diameter (Å) | Pore Volume (cm$^3$/g) | Glucaric Acid Yield (%) | Selectivity (%) |
| --- | --- | --- | --- | --- | --- |
| Asbury 5302 | 211 | 99 | 0.29 | 33 | 76 |
| Asbury 5303 | 219 | 79 | 0.23 | 38 | 77 |
| Asbury 5368 | 303 | 102 | 0.54 | 34 | 78 |
| Asbury 5379 | 271 | 163 | 0.83 | 33 | 75 |

(ii) Oxidation of Glucose to Glucaric Acid (Protocol 2)

Suitably concentrated aqueous solutions of $K_2Pt(OH)_6$ and $CsAuO_2$ were added together to carbon black powders by incipient wetness impregnation and agitated to impregnate the supports. The samples were dried in an oven at 40° C. overnight, and reduced at 250° C. under a forming gas (5% $H_2$ and 95% $N_2$) atmosphere for 3 hours with 5° C./min temperature ramp rate. The final catalysts were washed with deionized water and finally dried at 40° C. to produce catalysts with a composition of 2.44 wt. % Pt and 2.38 wt. % Au. By using other carbon black supports, Au and Pt precursors, and adjusting amount of Au and Pt in solution, different catalysts with various Au and Pt loadings on a variety of commercial carbon black powders or particles from extrudates were prepared in a similar manner.

These catalysts were tested for glucose oxidation using the following testing protocol. Catalyst (10 mg) was weighed into a glass vial insert followed by addition of an aqueous glucose solution (250 μl of 0.55 M). The glass vial insert was loaded into a reactor and the reactor was closed. The atmosphere in the reactor was replaced with oxygen and pressurized to 75 psig at room temperature. Reactor was heated to 90° C. and maintained at the respective temperature for 5 hours while vials were shaken. After that, shaking was stopped and reactor was cooled to 40° C. Pressure in the reactor was then slowly released. The glass vial insert was removed from the reactor and centrifuged. The solution was diluted with deionized water and analyzed by ion chromatography to determine the yield of glucaric acid and the selectivity as defined herein. Results are presented in Table 4.

TABLE 4

| Support | Surface Area ($m^2/g$) | Mean Pore Diameter (Å) | Pore Volume ($cm^3/g$) | Glucaric Acid Yield (%) | Selectivity (%) |
|---|---|---|---|---|---|
| Asbury 5365R | 34 | 143 | 0.11 | 42 | 78 |
| Asbury 5353R | 35 | 186 | 0.14 | 38 | 82 |
| Asbury 5345R | 35 | 207 | 0.11 | 44 | 76 |
| Timcal Ensaco 250G | 64 | 140 | 0.24 | 60 | 83 |
| Asbury 5348R | 65 | 220 | 0.31 | 54 | 78 |
| Asbury 5358R | 67 | 213 | 0.34 | 52 | 77 |
| Asbury 5346R | 80 | 145 | 0.28 | 48 | 75 |
| Cabot Monarch 570 | 102 | 138 | 0.3 | 37 | 75 |
| Orion HP 160 | 158 | 208 | 0.87 | 35 | 77 |
| Cabot Monarch 700 | 181 | 121 | 0.38 | 42 | 77 |
| Cabot Vulcan XC72 | 224 | 161 | 0.43 | 46 | 77 |

Example 3. Preparation of Shaped Porous Carbon Black Product Using a Variety of Carbon Black Powders and Binders By using other carbon black powders and carbohydrate binders, different carbon black extrudates were prepared as described in Example 1. Other carbon black powders included, but were not limited to, Orion carbon HI-BLACK 40B2, Orion HI-BLACK 50LB, Orion Hi-Black 50L, Orion HP-160, Orion Carbon HI-BLACK N330, Timcal Ensaco 150 G, Timcal Ensaco 250 G, Timcal Ensaco 260G, Timcal Ensaco 250P, Cabot Vulcan XC72R, Cabot Monarch 120, Cabot Monarch 280, Cabot Monarch 570, Cabot Monarch 700, Asbury 5365R, Asbury 5353R, Asbury 5345R, Asbury 5352, Asbury 5374, Asbury 5348R, Asbury 5358R, Sid Richardson SC159, Sid Richardson SR155. Other carbohydrate binders included, but were not limited to, Cargill Clearbrew 60/44 IX (80% Carbohydrate), Casco Lab Fructose 90 (70% Carbohydrate) and Molasses (80% Carbohydrate). Formulations with these variations yielded illustrative examples of the shaped carbon product of the present invention. The properties of some of these embodiments are described in more detail below.

Example 4. Crush Testing of Carbon Black Extrudates

Extrudate pellets (Nos. 1-8 below), having an approximately 1.5 mm diameter, were prepared according to the method described in Example 1 except that the final pyrolysis times and temperatures were varied as listed in Table 5 in the extrudate description column. After the pyrolysis step the extrudates were cut to the sizes ranging from 2-6 mm in length. The percentage of carbonized binder (after pyrolysis) present in the shaped carbon product was determined by mass balance [i.e., [(Weight$_{Shaped\ Carbon\ Product}$−Weight$_{Carbon\ Black\ (in\ formulation)}$/Weight$_{Shaped\ Carbon\ Product}$)×100]. Total binder content after pyrolysis (i.e., total carbonized binder) varied from 15-50 wt. %.

Additional extrudate pellets (Nos. 9-11 below) were prepared accordingly to the following procedure. Approximately 24.0 g of carbon black powder (Timcal Ensaco 250G, 65 $m^2/g$) was added in multiple portions to an aqueous solution (100.0 g) containing 25.0 wt. % Cerelose Dextrose from Ingredion. The mixture was stirred well using a spatula to produce a paste. This paste was loaded into a syringe and the material was extrudated into spaghetti-like strings with a 1.5 mm diameter. After drying in a 100° C. oven for 3 hours under a dry air purge, these strings were cut into smaller pieces (2-6 mm lengths). Then they were treated at one of the following conditions to produce carbon black extrudates: (1) 250° C. for 3 hours with 10° C./min temperature ramp rate under continuous $N_2$ flow; (2) 800° C. for 4 hours with 10° C./min temperature ramp rate under continuous $N_2$ flow; (3) 200° C. for 3 hours with 10° C./min temperature ramp rate in air. Binder content varied from 15 to 50 wt. %. Table 5 presents the crush strength data for the extrudates prepared.

TABLE 5

| No. | Extrudate Description | Mean Mechanical Piece Crush Strength (lb) | Mean Radial Piece Crush Strength (N/mm) | Mean Radial Piece Crush Strength (lb/mm) | Carbonized Binder Content (wt. %) |
|---|---|---|---|---|---|
| 1 | Cabot Monarch 120 (Glucose + Hydroxyethylcellulose binder, 350° C./2 h/$N_2$) | 8.7 | 9.2 | 2.1 | 15 |

TABLE 5-continued

| No. | Extrudate Description | Mean Mechanical Piece Crush Strength (lb) | Mean Radial Piece Crush Strength (N/mm) | Mean Radial Piece Crush Strength (lb/mm) | Carbonized Binder Content (wt. %) |
|---|---|---|---|---|---|
| 2 | Cabot Monarch 280 (Glucose + Hydroxyethylcellulose binder, 800° C./2 h/$N_2$) | 5.4 | 7.7 | 1.7 | 23 |
| 3 | Cabot Monarch 700 (Glucose + Hydroxyethylcellulose binder, 350° C./2 h/$N_2$) | 12.3 | 12.3 | 2.8 | 31 |
| 4 | Cabot Monarch 700 (Glucose + Hydroxyethylcellulose binder, 500° C./2 h/$N_2$) | 6.3 | 6.3 | 1.4 | 34 |
| 5 | Cabot Monarch 700 (Glucose + Hydroxyethylcellulose binder, 800° C./2 h/$N_2$) | 18.7 | 18.5 | 4.2 | 31 |
| 6 | Cabot Vulcan XC72 (Glucose + Hydroxyethylcellulose binder, 800° C./2 h/$N_2$) | 5.6 | 5.6 | 1.2 | 30 |
| 7 | Cabot Vulcan XC72R (Glucose + Hydroxyethylcellulose binder, 350° C./2 h/$N_2$) | 7.8 | 7.8 | 1.8 | 38 |
| 8 | Timcal Ensaco 250P (Glucose + Hydroxyethylcellulose binder, 350° C./2 h/$N_2$) | 8.6 | 8.6 | 1.9 | 50 |
| 9 | Timcal Ensaco 250G (Glucose binder, 800° C./4 h/$N_2$) | 10.9 | 10.9 | 2.5 | 32 |
| 10 | Timcal Ensaco 250G (Glucose binder, 200° C./3 h/Air) | 6.2 | 6.2 | 1.4 | 29 |
| 11 | Timcal Ensaco 250G (Glucose binder, 250° C./3 h/$N_2$) | 3.8 | 3.8 | 0.9 | 29 |

Example 5. Preparation of Catalyst Compositions

The Cabot Vulcan XC72 carbon black extrudates prepared in Example 1 were further cut into small pieces of about 0.5 cm long for testing. An aqueous solution (13 ml) containing 0.17 g Au in the form of $Me_4NAuO_2$ and 0.26 g Pt in the form of $PtO(NO_3)$ was mixed with 21.5 g of these extrudates. The mixture was agitated to impregnate the carbon black support and was dried in a 60° C. oven overnight under a dry air purge. The sample was then reduced at 350° C. under forming gas (5% $H_2$ and 95% $N_2$) atmosphere for 4 hours with 2° C./min temperature ramp rate. The final catalyst was composed of about 0.80 wt. % Au and 1.2 wt. % Pt.

By using other carbon black extrudates prepared from the method described above, a series of Pt—Au extrudate catalysts spanning ranges in Au and Pt loadings, Pt/Au ratios and metal distributions (e.g., eggshell, uniform, subsurface bands) could be prepared.

Figure 2:
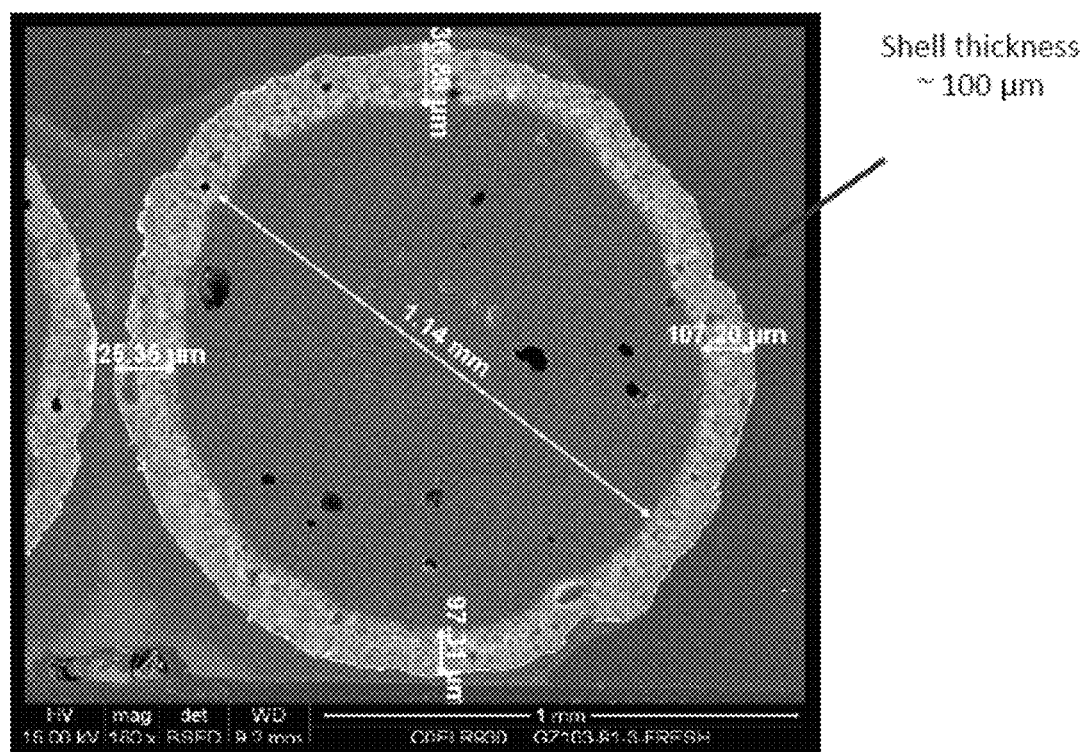
FIG. 2 provides a magnified view of one of catalyst extrudate cross-sections of FIG. 1.

The cross section of a sample of the catalyst extrudate prepared with Cabot Vulcan XC72 carbon black was analyzed using scanning electron microscopy. FIG. 1 provides an image of this analysis. The image shows that platinum and gold metal was deposited on the external surface of the carbon black extrudate forming a shell coating the outer surfaces the carbon black extrudate. FIG. 2 provides a magnified view of one of catalyst extrudate cross-sections with measurements of the diameter of the carbon black extrudate (i.e., 1.14 mm) and thickness of the platinum and gold shell (average of about 100 m) on the carbon black extrudate outer surface.

Example 6. Testing of Au/Pt Carbon Black Extrudate Catalysts (Using Cabot Monarch 700) In a Fixed-Bed Reactor for the Oxidation of Glucose to Glucaric Acid Extrudates based on carbon black Cabot Monarch 700 with glucose and hydroxyethylcellulose binder and subsequent catalyst with 0.80 wt. % Au and 1.20 wt. % Pt were prepared by mixing carbon black Cabot Monarch 700 (42.0 g) and a binder solution (145.8 g prepared by heating a solution containing 3.4 wt % hydroxyethylcellulose and 28.6 wt % glucose at 80° C. overnight)), The resultant paste was loaded into a syringe and the material was extrudated into spaghetti-like strings with a 1.5 mm diameter. After drying in a 100° C. oven for 3 hours under a dry air purge, these strings were cut into smaller pieces (2-6 mm lengths) and pyrolyzed at 350° C. for 2 hours under a nitrogen atmosphere. The final carbonized binder content in carbon extrudates was 31 wt %. The catalyst was then prepared using the method described in Example 5. Oxidation of glucose reactions were conducted in a 12.7 mm (0.5-inch) OD by 83 cm long 316 stainless steel tube with co-current down-flow of gas and liquid. Catalyst beds were vibration packed with 1.0 mm glass beads at the top to approximately 8 cm depth, followed by catalyst (67 cm bed depth containing 20.0 g, 0.80 wt. % Au+1.2 wt. % Pt on Cabot Monarch 700 carbon black pellets with a length of 0.5 cm and diameter of 1.5 mm prepared using the method described in Example 3), then 1.0 mm glass beads at the bottom to approximately 8 cm depth. Quartz wool plugs separated the catalyst bed from the glass beads.

The packed reactor tube was clamped in an aluminum block heater equipped with PID controller. Gas (compressed dry air) and liquid flows were regulated by mass flow controller and HPLC pump, respectively. A back pressure regulator controlled reactor pressure as indicated in Table 6. The catalyst was tested for approximately 350 hours of time on stream (TOS).

Table 6 describes the fixed bed reactor conditions and resultant extrudate catalyst performance. The catalyst productivity in Table 6 is 35 gram (glucaric acid) per gram $(Pt+Au)^{-1}$ $hr^{-1}$ or 0.70 gram (glucaric acid) per gram (catalyst)$^{-1}$ $hr^{-1}$.

TABLE 6

| Reactor block temperature/ °C. | Glucose feed concentration/ wt. % | Reactor pressure/ psi | Liquid flowrate/ mL min$^{-1}$ | Gas flowrate/ mL min$^{-1}$ (STP) | Glucose conversion/ % | Glucaric acid yield/ % | Selectivity/ % |
|---|---|---|---|---|---|---|---|
| 130 | 20 | 750 | 2.00 | 768 | >99 | 50 | 86 |

BET surface area measurements and BJM pore volume distribution measurements were made on the following carbon black and extrudate samples:

Sample 1: Monarch 700 carbon black material.

Sample 2: Fresh Monarch 700 extrudate prepared in accordance with this Example.

Sample 3: Monarch 700 extrudate of Example 4 following 350 hours on stream in a fixed bed reactor (described in Example 6).

Sample 4: An aqueous solution (915.0 g) containing 4.0 wt % hydroxyethylcellulose (Sigma-Aldrich, SKU54290, viscosity 80-125 cP, 2% in H$_2$O (20° C.)) and 56.0 wt % glucose (ADM Corn Processing, Dextrose Monohydrate 99.7DE with 91.2255 wt % Glucose content) was prepared by stirring 36.6 g hydroxyethylcellulose and 561.7 g Dextrose Monohydrate in 316.7 ml D.I. water at 80° C. for 16 hours. After cooling to ambient temperature, this viscous solution was added to 400.0 g carbon black powder (Cabot Monarch 700) in a blender/kneader and the material was mixed/kneaded for 1 hour. The material was then loaded into a 1" Bonnot BB Gun Extruder and extrudated into spaghetti like strings with ca. 1.5 mm diameter at cross section. These strings were dried under a dry air purge in a 120° C. oven for 16 hours and then pyrolyzed at 800° C. for 2 hours with 5° C./min ramp rate under a nitrogen purge. The final carbonized binder content was to be 36 wt %.

Sample 5: Prepared as described by Example 9.

Sample 6: Prepared as described by Example 12.

Sample 7: An aqueous solution (166.0 g) containing 4.0 wt % hydroxyethylcellulose (Sigma-Aldrich, SKU54290, viscosity 80-125 cP, 2% in H$_2$O (20° C.)) and 56.0 wt % glucose (ADM Corn Processing, Dextrose Monohydrate 99.7DE with 91.2255 wt % Glucose content) was prepared by stirring 6.64 g hydroxyethylcellulose and 84.8 g Dextrose Monohydrate in 74.6 ml D.I. water at 80° C. for 16 hours. After cooling to ambient temperature, this viscous solution was added to 60.0 g carbon powder (Asbury 5368) in a blender/kneader and the material was mixed/kneaded for 1 hour. The material was then loaded into a 1" Bonnot BB Gun Extruder and extrudated into spaghetti like strings with ca. 1.5 mm diameter at cross section. These strings were dried under a dry air purge in a 120° C. oven for 16 hours and then pyrolyzed at 800° C. for 2 hours with 5° C./min ramp rate under a nitrogen purge. The final carbonized binder content was 40 wt %.

Sample 8: Commercially available activated carbon extrudate Süd Chemie G32H-N-75.

Sample 9: Commercially available activated carbon extrudate Donau Supersorbon K4-35.

The results are presented in Table 7.

TABLE 7

| Sample | BET Surface Area (m$^2$/g) | Mean Pore Diameter (nm) | BJH Pore Volume (cm$^3$/g) | Pores < 3 nm (% of BJH pore volume) | Pores between 10 and 50 nm (% of BJH pore volume) | Pores between 10 and 100 nm (% of BJH pore volume) | Carbonized Binder Content (wt %) |
|---|---|---|---|---|---|---|---|
| Sample 1 | 180 | 12 | 0.38 | 5 | 40 | 75 | 0 |
| Sample 2 | 178 | 11 | 0.29 | 7 | 45 | 75 | 36 |
| Sample 3 | 98 | 18 | 0.31 | 3 | 50 | 90 | 36 |
| Sample 4 | 182 | 13 | 0.36 | 4 | 55 | 80 | 36 |
| Sample 5 | 194 | 11 | 0.29 | 6 | 45 | 75 | 36 |
| Sample 5 | 234 | 10 | 0.29 | 7 | 45 | 70 | 36 |
| Sample 6 | 218 | 12 | 0.33 | 5 | 60 | 80 | 40 |
| Sample 8 | 1164 | 3.4 | 0.63 | 40 | <15 | 15 | ** |
| Sample 9 | 1019 | 2.7 | 0.31 | 65 | 5 | 7 | ** |

Figure 3:
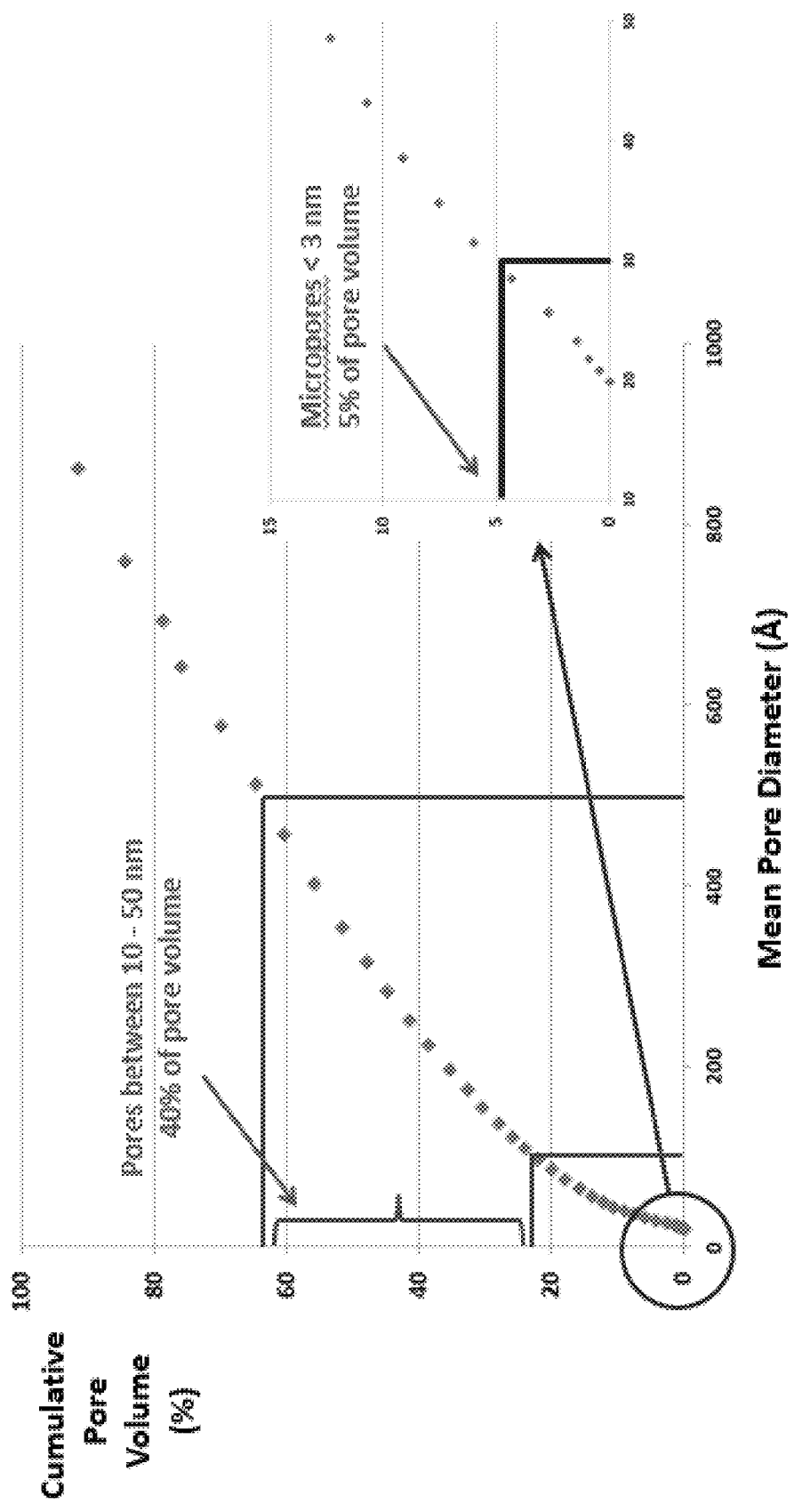
FIG. 3 presents a plot of the cumulative pore volume (%) as a function of mean pore diameter for a raw Monarch 700 carbon black material.
Figure 4:
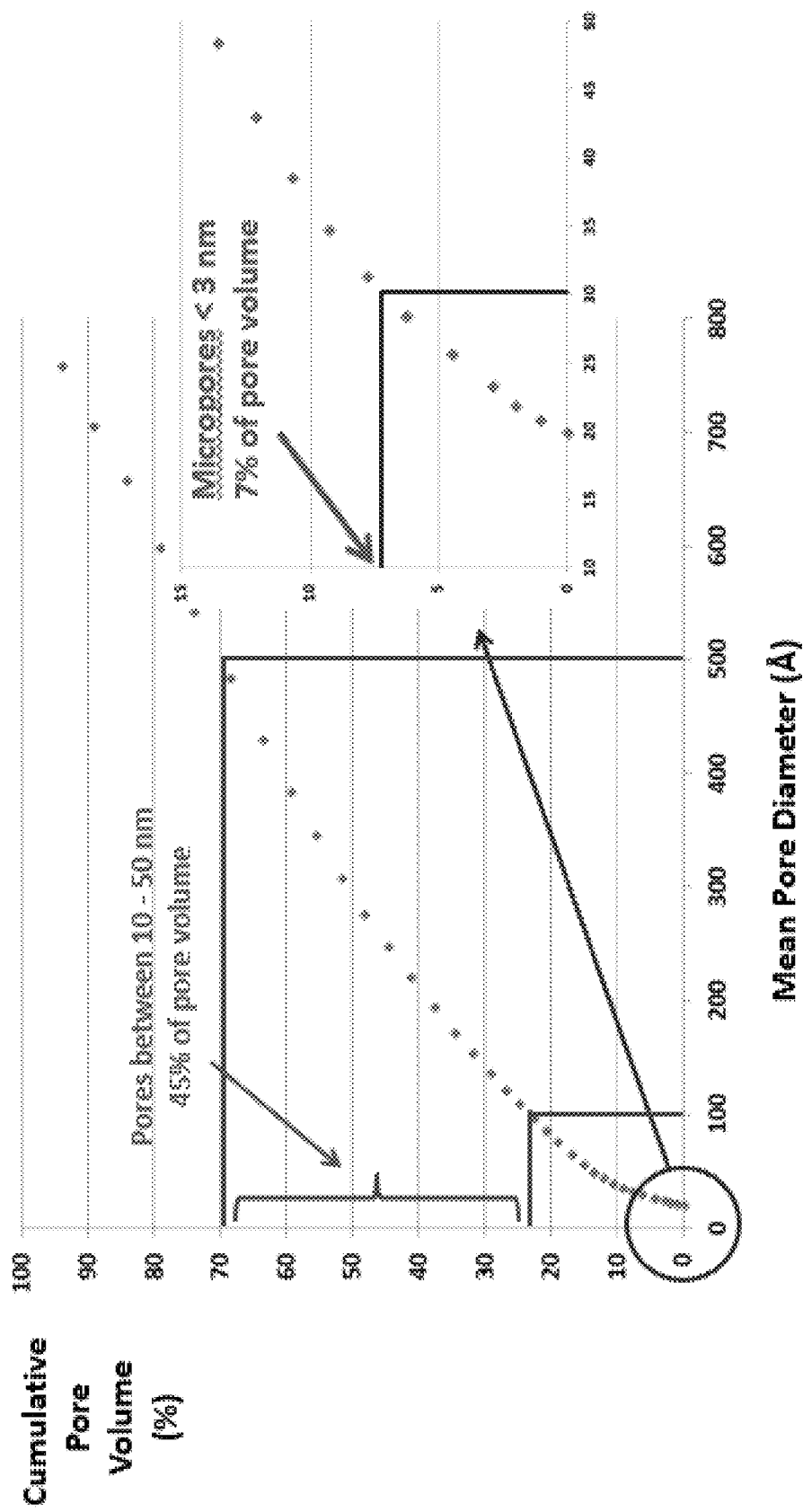
FIG. 4 presents a plot of the cumulative pore volume (%) as a function of mean pore diameter for a fresh catalyst extrudate including the Monarch 700 carbon black material.
Figure 5:
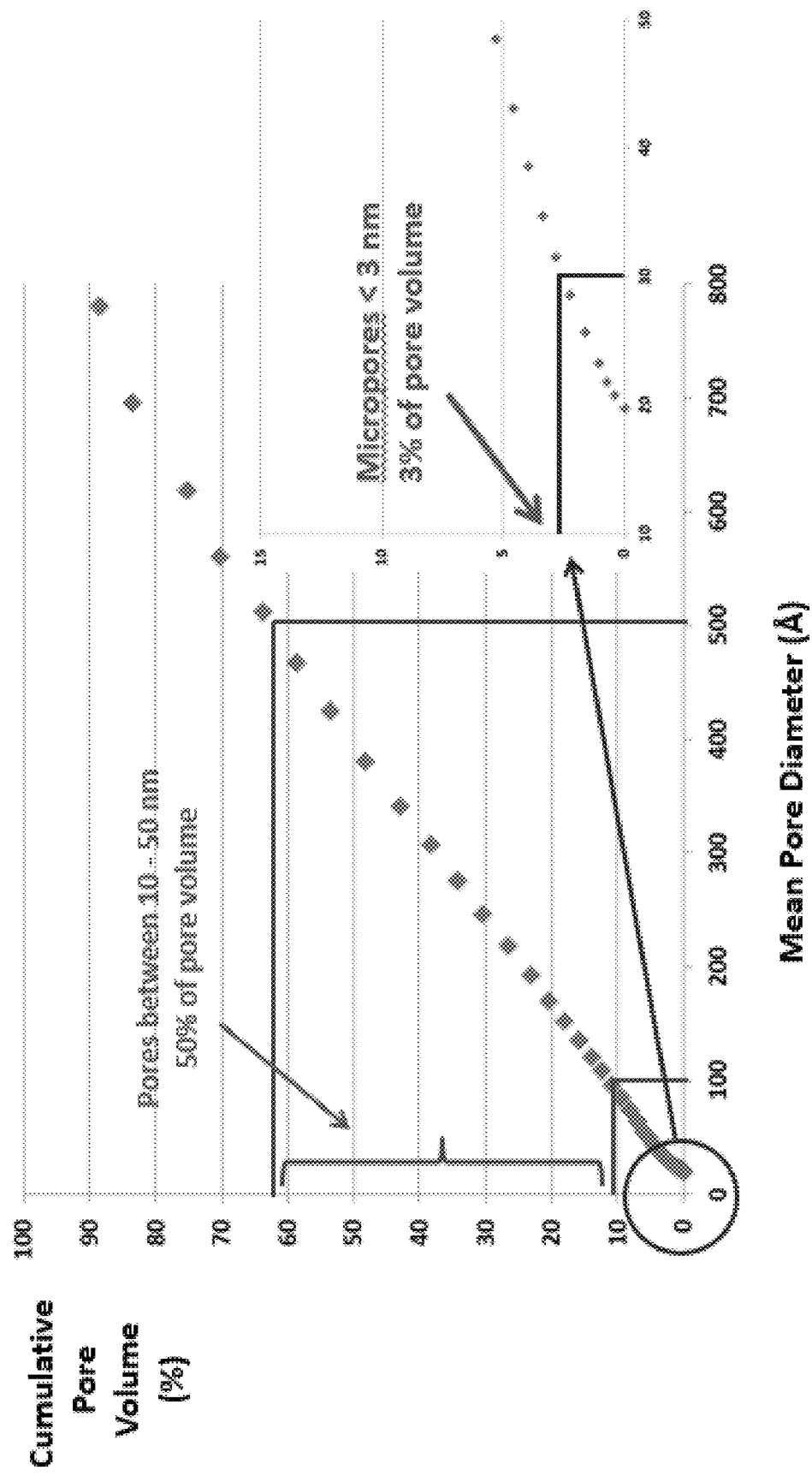
FIG. 5 presents a plot of the cumulative pore volume (%) as a function of mean pore diameter for a catalyst extrudate including the Monarch 700 carbon black material following 350 hours of use.
Figure 6:
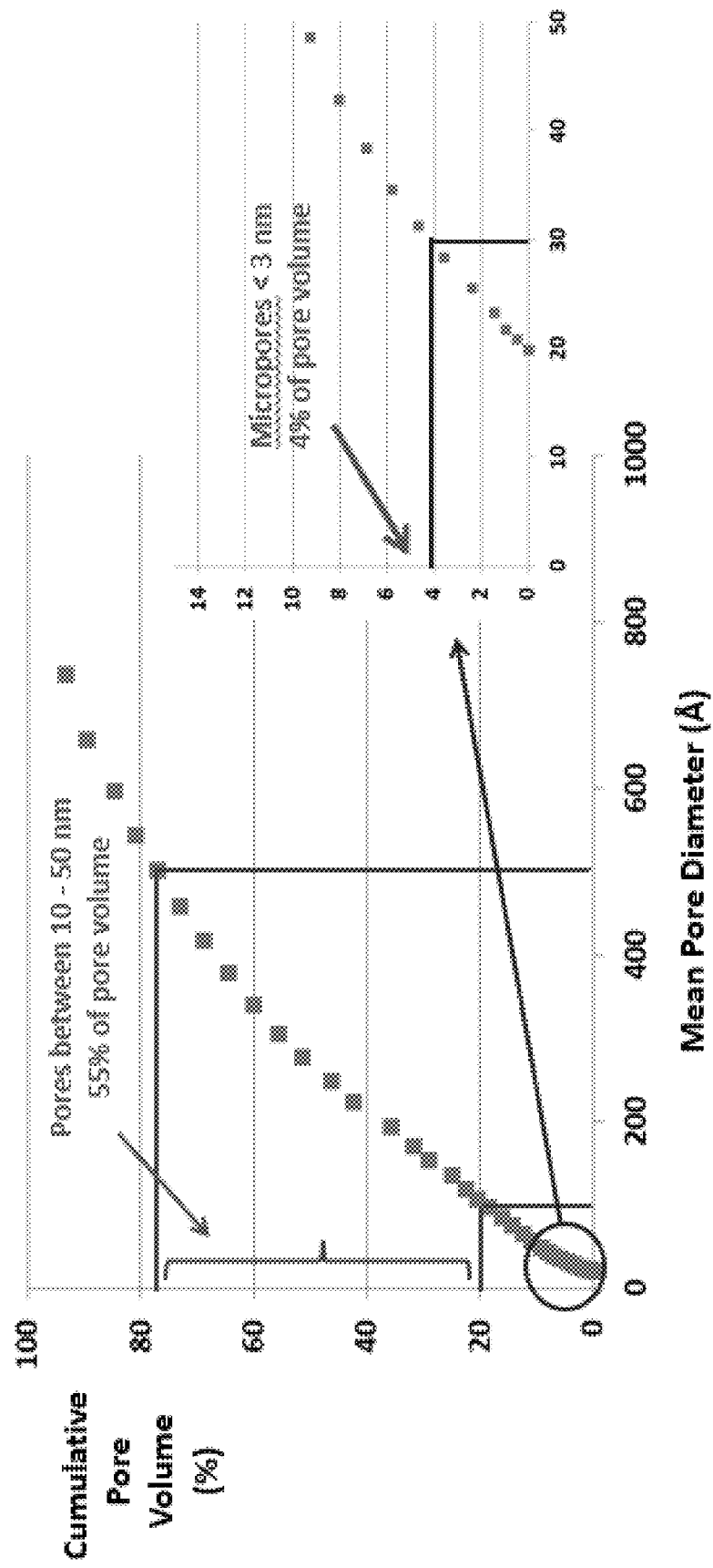
FIG. 6 presents a plot of the cumulative pore volume (%) as a function of mean pore diameter for an extrudate using Monarch 700 carbon black and a glucose/hydroxyethyl cellulose binder.
Figure 7:
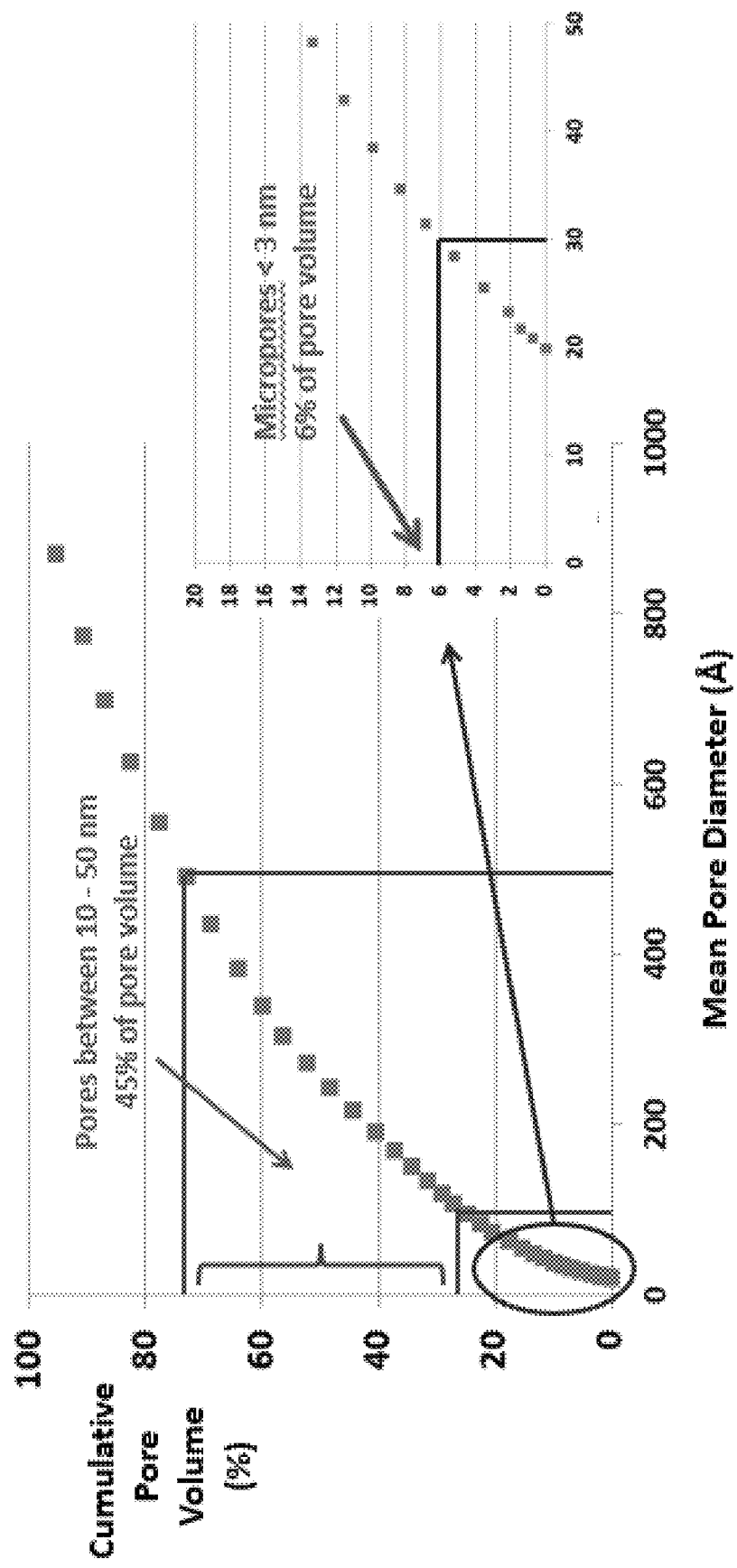
FIG. 7 presents a plot of the cumulative pore volume (%) as a function of mean pore diameter for an extrudate using Sid Richardson SC159 carbon black and a glucose/hydroxyethyl cellulose binder.
Figure 8:
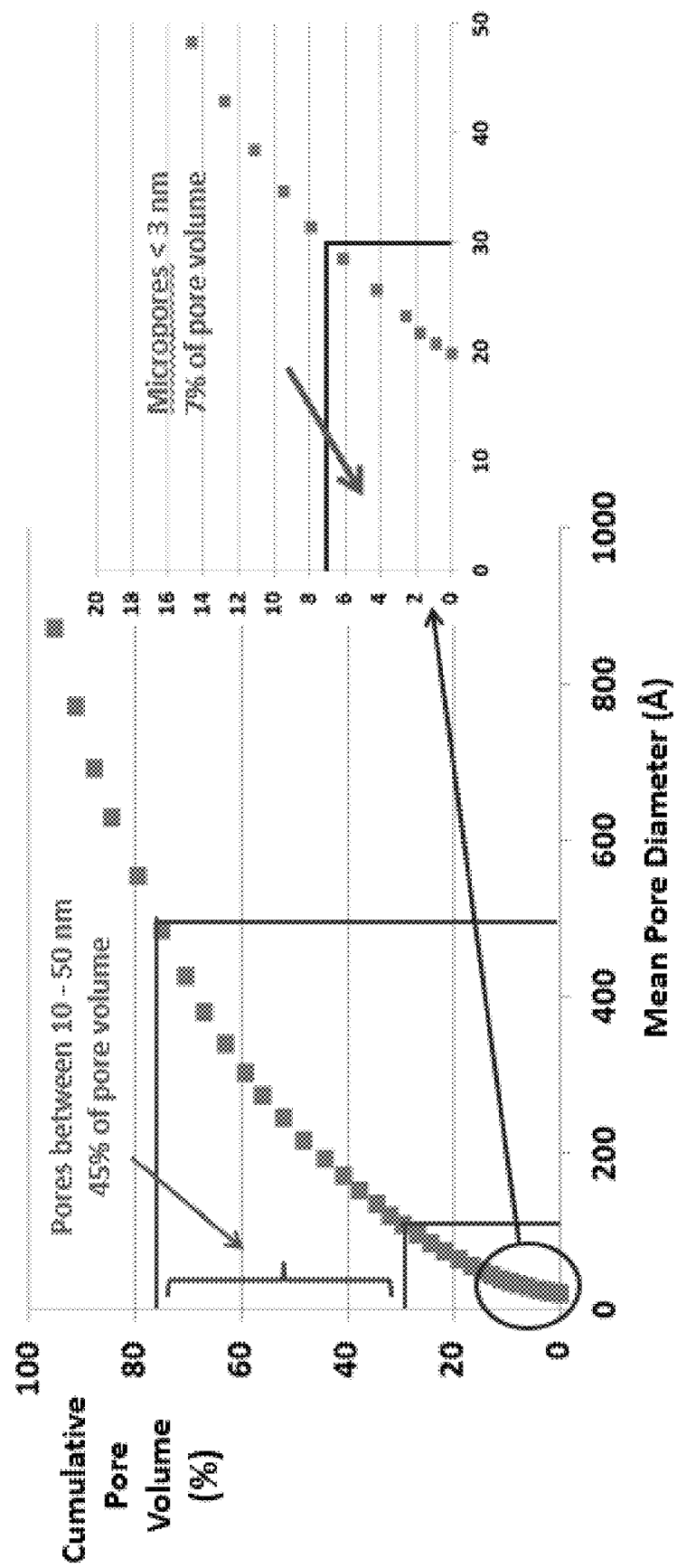
FIG. 8 presents a plot of the cumulative pore volume (%) as a function of mean pore diameter for a extrudate using Sid Richardson SC159 carbon black and a glucose/hydroxyethyl cellulose binder which has been exposed to oxygen at 300° C. for 3 hours.
Figure 9:
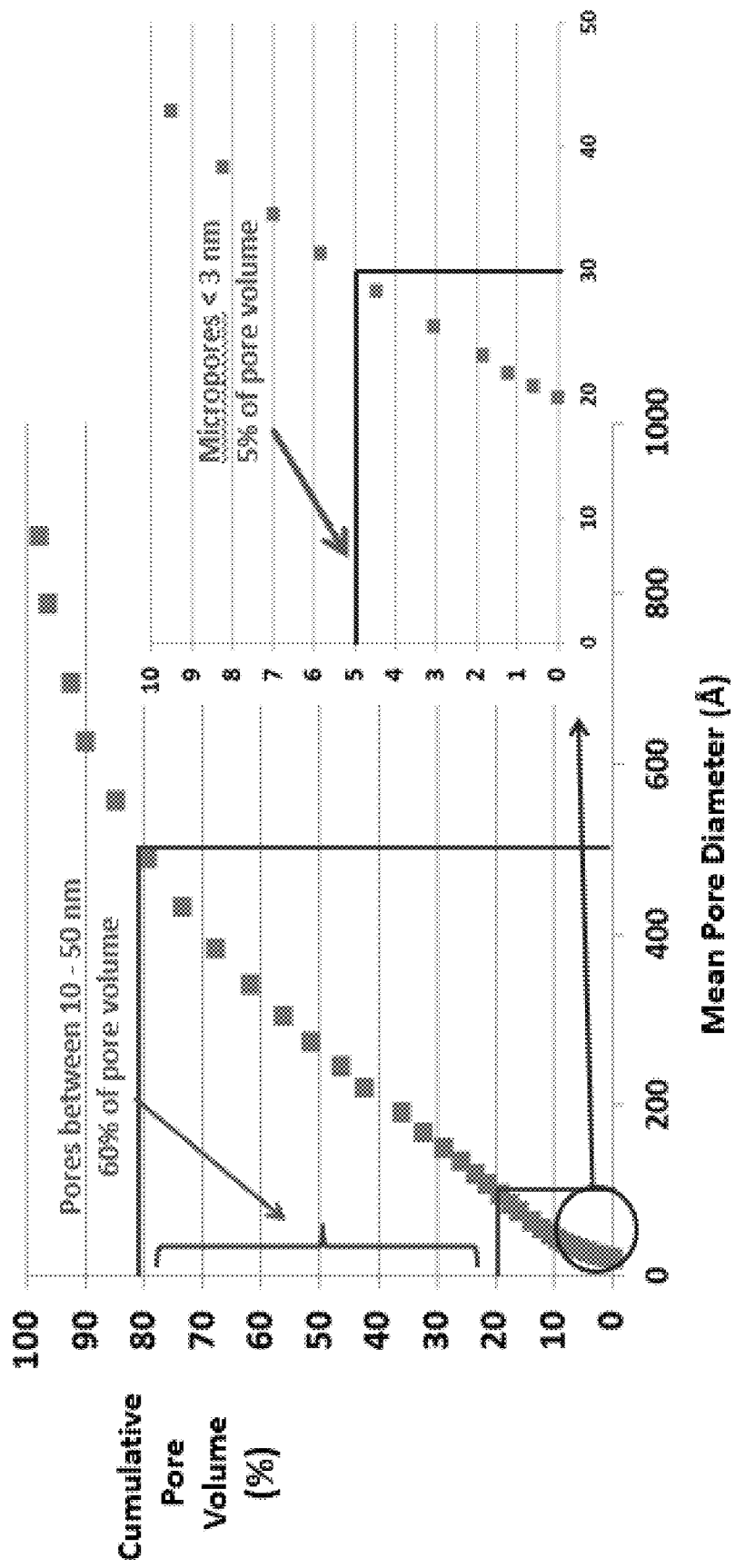
FIG. 9 presents a plot of the cumulative pore volume (%) as a function of mean pore diameter for an extrudate using Asbury 5368 carbon black and a glucose/hydroxyethyl cellulose binder.

FIG. 3 presents a plot of the cumulative pore volume (%) as a function of mean pore diameter for a raw Monarch 700 carbon black material. FIG. 4 presents a plot of the cumulative pore volume (%) as a function of mean pore diameter for a fresh catalyst prepared from a carbon black extrudate using Monarch 700 and a glucose/hydroxyethylcellulose binder. FIG. 5 presents a plot of the cumulative pore volume (%) as a function of mean pore diameter for the catalyst extrudate of FIG. 2 following 350 hours of use in a fixed bed reactor for the oxidation of glucose to glucaric acid. FIG. 6 presents a plot of the cumulative pore volume (%) as a function of mean pore diameter for a extrudate using Monarch 700 carbon black and a glucose/hydroxyethyl cellulose binder. FIG. 7 presents a plot of the cumulative pore volume (%) as a function of mean pore diameter for a extrudate using Sid Richardson SC 159 carbon black and a glucose/hydroxyethyl cellulose binder. FIG. 8 presents a plot of the cumulative pore volume (%) as a function of mean pore diameter for a extrudate using Sid Richardson SC 159 carbon black and a glucose/hydroxyethyl cellulose binder prepared in accordance with Example 12. FIG. 9 presents a plot of the cumulative pore volume (%) as a function of mean pore diameter for a extrudate using Asbury 5368 carbon black and a glucose/hydroxyethyl cellulose binder.

Example 7. Testing of Au/Pt Carbon Black Extrudate Catalysts (Using Cabot Vulcan XC72) in a Fixed-Bed Reactor for the Oxidation of Glucose to Glucaric Acid Extrudates based on carbon black Cabot Vulcan XC72 and subsequent catalyst with 0.80 wt. % Au and 1.20 wt. % Pt were prepared by mixing carbon black Cabot Vulcan XC72 (36.4 g) and a binder solution (136.5 g prepared by heating a solution containing 3.7 wt % hydroxyethylcellulose and 24.4 wt % glucose at 80° C. overnight). The resultant paste was loaded into a syringe and the material was extrudated into spaghetti-like strings with a 1.5 mm diameter followed by drying at 120° C. for 4 hours in air, and pyrolysis at 350° C. for 2 hours under a nitrogen atmosphere. The final binder content in pyrolyzed carbon extrudates was 30 wt %. The catalysts were prepared using the method described in Example 3. The catalyst was tested in the same 12.7 mm (0.5-inch) OD fixed-bed reactor as in Example 6. Table 8 describes the fixed bed reactor conditions and resultant extrudate catalyst performance. The catalyst productivity in Table 8 is 36 gram (glucaric acid) per gram $(Pt+Au)^{-1} hr^{-1}$ or 0.72 gram (glucaric acid) per gram $(catalyst)^{-1} hr^{-1}$.

TABLE 8

| Reactor block temperature/ ° C. | Glucose feed concentration/ wt. % | Reactor pressure/ psi | Liquid flowrate/ mL min$^{-1}$ | Gas flowrate/ mL min$^{-1}$ (STP) | Glucose conversion/ % | Glucaric acid yield/ % | Selectivity/ % |
|---|---|---|---|---|---|---|---|
| 130 | 20 | 750 | 2.00 | 768 | >99 | 52 | 87 |

Figure 10:
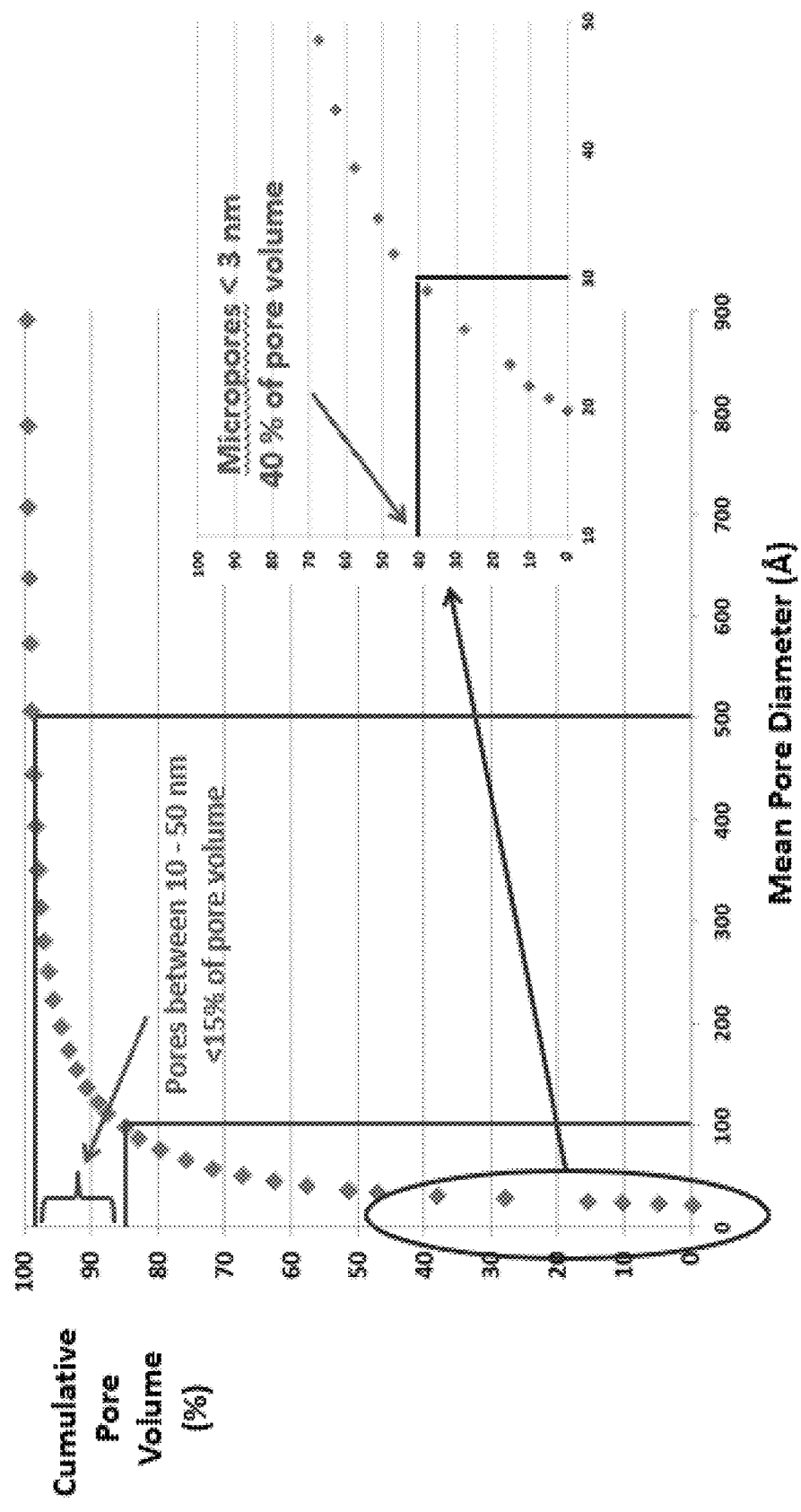
FIG. 10 presents a plot of the cumulative pore volume (%) as a function of mean pore diameter for an activated carbon extrudate of Süd Chemie G32H-N-75.
Figure 11:
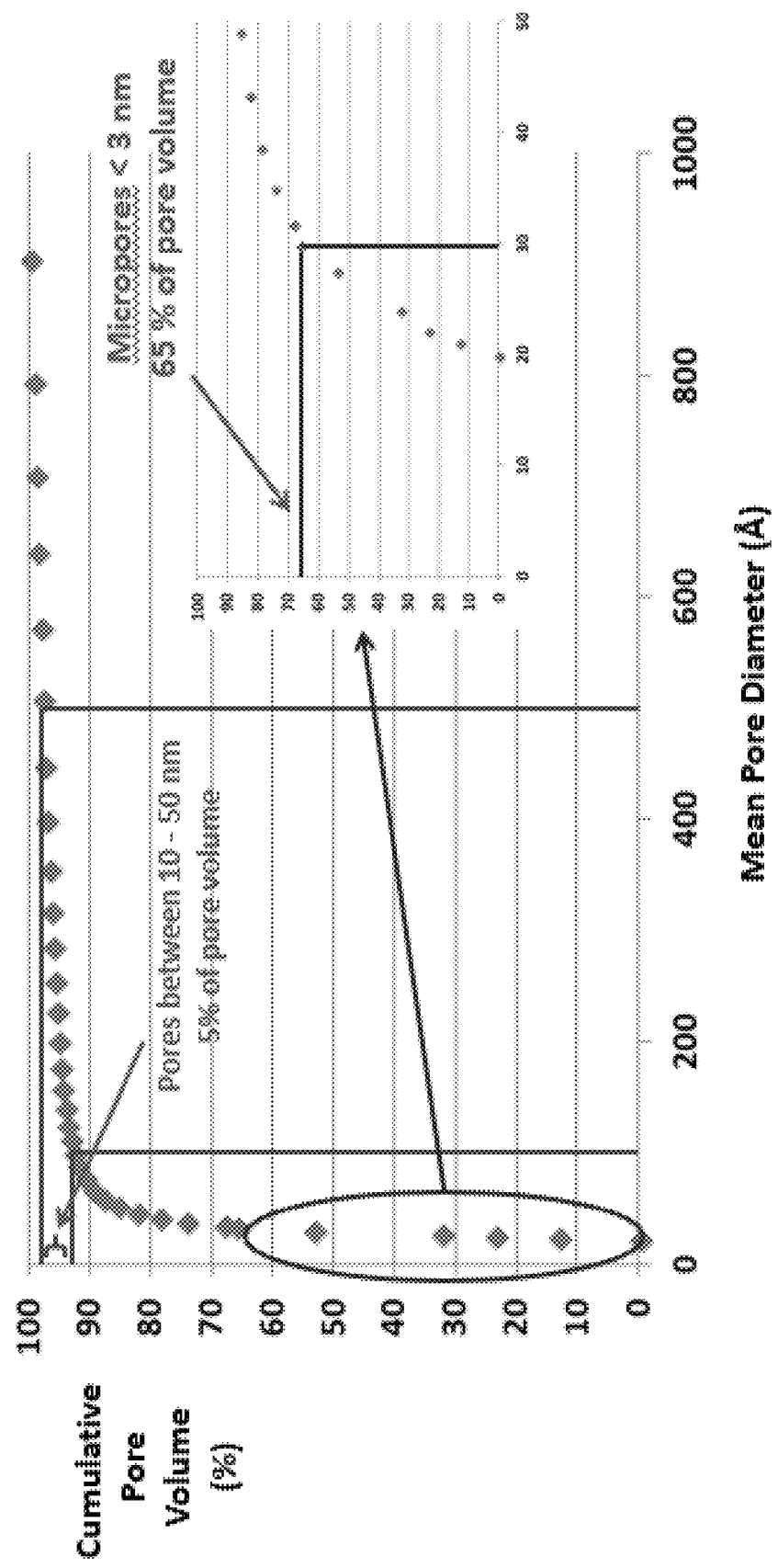
FIG. 11 presents a plot of the cumulative pore volume (%) as a function of mean pore diameter for an activated carbon extrudate of Donau Supersorbon K4-35.

FIG. 10 presents a plot of the cumulative pore volume (%) as a function of mean pore diameter for a commercially available activated carbon extrudate of Sd Chemie G32H-N-75. FIG. 11 presents a plot of the cumulative pore volume (%) as a function of mean pore diameter for a commercially available activated carbon extrudate of Donau Supersorbon K4-35.

Figure 12:
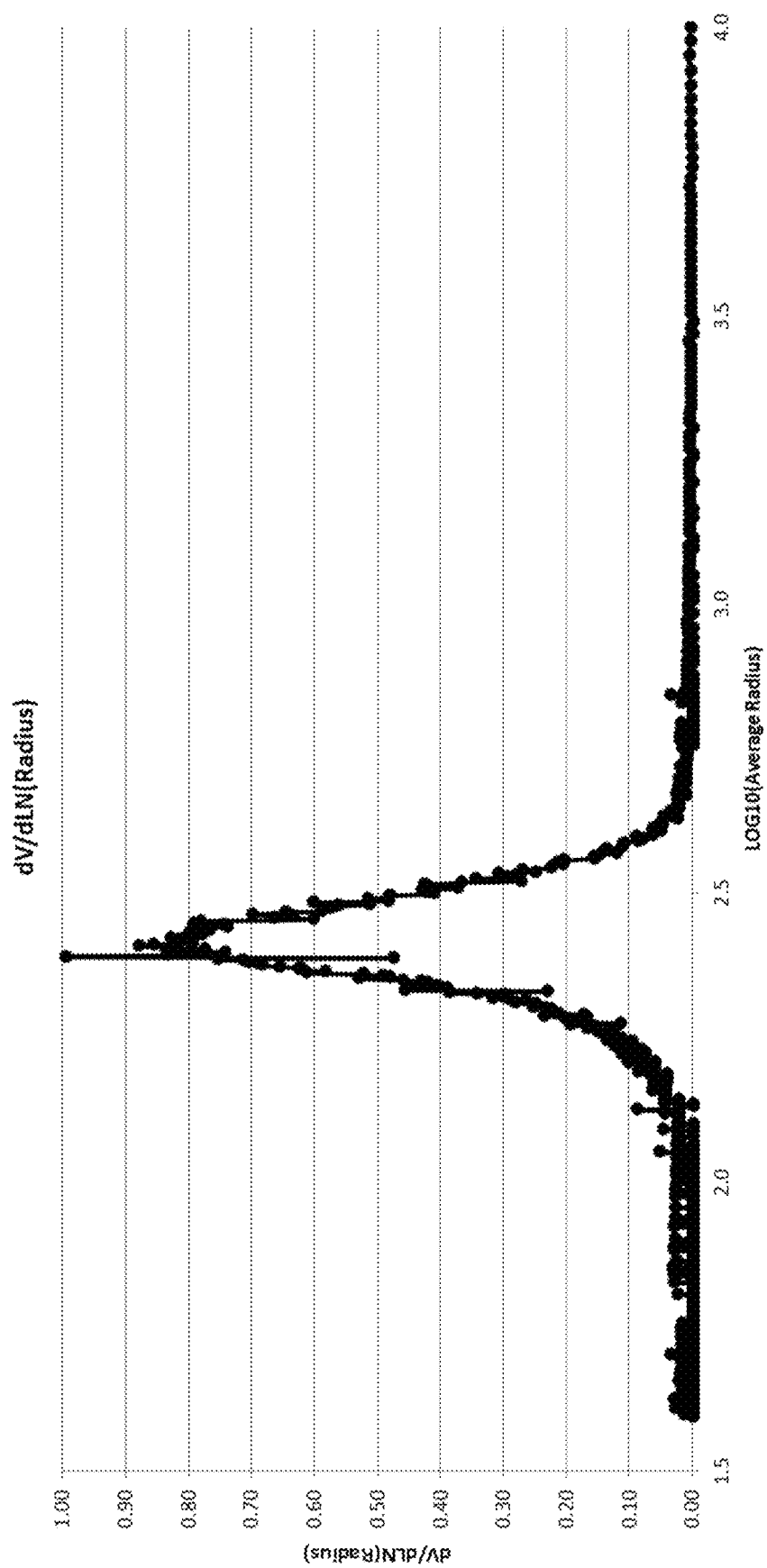
FIG. 12 presents the pore size distribution for an extrudate using Sid Richardson SC159 carbon black and a glucose/hydroxyethyl cellulose binder measured by mercury porosimetry.

FIG. 12 presents the pore size distribution for an extrudate using Sid Richardson SC159 carbon black and a glucose/hydroxyethyl cellulose binder measured by mercury porosimetry. These plots show that the micropore contribution to pore volume for carbon black extrudate catalysts (fresh and after use) is very low. In particular the plots show that the micropore contribution (pores <3 nm) is less than 10% of the BJH pore volume. In some instances the micropore contribution (pores <3 nm) is less than 6% of the BJH pore volume, and in some instances the micropore contribution (pores <3 nm) is less than 4% of the BJH pore volume. In contrast, the micropore contribution to pore volume for an activated carbon extrudate catalyst is exceedingly high at 40%. Also, the plots show that the contribution to pore volume from pores having a mean diameter from about 10 nm to 50 nm for the carbon black catalysts was about 40% or higher. On the other hand, the contribution to pore volume from pores having a mean diameter from about 10 nm to 50 nm for the activated carbon catalyst was less than 15%. The plots show that the contribution to pore volume from pores having a mean diameter from about 10 nm to 100 nm for the carbon black catalysts was about 70% or higher. On the other hand, the contribution to pore volume from pores having a mean diameter from about 10 nm to 100 nm for the activated carbon catalyst was 15% or less.

Example 8. Oxidation of Glucose to Glucaric Acid—Activated Carbons with High Surface Areas (Comparative)

The same synthesis procedure described in Example 6 was used to prepare Pt—Au catalysts supported on high surface area activated carbon. The activated carbon extrudates were crushed and sieved to <90 μm prior to the catalyst preparation and screening. The catalysts were screened in the same reactor under the same conditions described in Example 2(B)(ii). As shown in Table 9, the high surface area activated carbon carriers were found to exhibit lower activity and lower selectivity (as defined herein).

TABLE 9

| Support | Surface Area (m$^2$/g) | Mean Pore Diameter (Å) | Pore Volume (cm$^3$/g) | Glucaric Acid Yield (%) | Selectivity (%) |
|---|---|---|---|---|---|
| Donau Supersorbon K4-35 | 1019 | 27 | 0.31 | 22 | 66 |
| Donau Supersorbon SX30 | 1050 | 39 | 0.71 | 18 | 68 |
| Norit RX3 Extra | 1239 | 37 | 0.23 | 20 | 70 |

Example 9. Preparation of Carbon Black Extrudate Catalysts—Attrition and Abrasion Testing An aqueous solution (113 g) containing 4.0 wt % hydroxyethylcellulose (Sigma-Aldrich, SKU 54290, viscosity 80-125 cP, 2% in H$_2$O (20° C.)) and 56.0 wt % glucose (ADM Corn Processing, Dextrose Monohydrate 99.7DE with 91.2255 wt % Glucose content) was prepared by stirring 4.5 g hydroxyethylcellulose and 69.4 g Dextrose Monohydrate in 39.1 ml D.I. water at 80° C. overnight. After cooling to room temperature, this viscous solution was added to 50 g carbon black powder (Sid Richardson SC159, 231 m²/g) in a blender/kneader and the material was mixed/kneaded for 1 hour. The material was then loaded into a 1" Bonnot BB Gun Extruder and extrudated into spaghetti like strings with ca. 1.5 mm diameter at cross section. These strings were dried under a dry air purge in a 120° C. oven overnight and then pyrolyzed at 800° C. for 4 hours with 5° C./min ramp rate under a nitrogen purge. The extruded and pyrolyzed samples were cut into small pieces of about 0.5 cm long for testing.

The properties of the resultant extrudate are show in Table 10. BET and crush strength measurements performed as described in the current disclosure.

TABLE 10

| BET Surface Area (m²/g) | Mean Pore Diameter (Å) | Pore Volume (cm³/g) | Single Piece Crush Strength (N) | Mean Radial Piece Crush Strength (N/mm) |
|---|---|---|---|---|
| 194 | 112 | 0.29 | 90 | 30 |

Extrudates prepared in accordance with this example were tested for the determination of attrition index (ASTM D4058-96) and abrasion loss according to the procedure described below.

Measurement of Attrition Index.

The ASTM attrition index (ATTR) is a measurement of the resistance of a catalyst or extrudate particle to attrition wear, due to the repeated striking of the particle against hard surfaces within the specified test drum. The diameter and length of the drum is similar to that described in ASTM D4058, with a rolling apparatus capable of delivering 55 to 65 RPM of rotation to the test drum. The percentage of the original sample that remains on a 20-mesh sieve is called the "Percent Retained" result of the test. The results of the test can be used, on a relative basis, as a measure of fines production during the handling, transportation, and use of the catalyst or extrudate material. A percent retained result of >97% is desirable for an industrial application.

Approximately 100 g of the extrudate material prepared in Example 9 above was transferred to the test drum which was fastened and transferred to the rolling apparatus and rolled at 55 to 65 RPM for 35 minutes. The weight percent retained after the test was 99.7%.

Measurement of Abrasion Loss.

The abrasion loss (ABL) is an alternate measurement of the resistance of a catalyst or extrudate particle to wear, due to the intense horizontal agitation of the particles within the confines of a 30-mesh sieve. The results of this procedure can be used, on a relative basis, as a measure of fines production during the handling, transportation, and use of the catalyst or adsorbent material. An abrasion loss of <2 wt % is desired for an industrial application. Approximately 100 g of the extrudate material prepared in example 9 above was first de-dusted on a 20-mesh sieve by gently moving the sieve side-to-side at least 20 times. The de-dusted sample was then transferred to the inside of a clean, 30-mesh sieve stacked above a clean sieve pan for the collection of fines. The complete sieve stack was then assembled onto a RO-Tap RX-29 sieve shaker, covered securely and shaken for 30 minutes. The fines generated were weighed to provide a sample abrasion loss of 0.016 wt. %.

Example 10. Testing of Au/Pt Carbon Black Extrudate Catalysts of Example 9 in a Fixed-Bed Reactor for the Oxidation of Glucose to Glucaric Acid The carbon black extrudates prepared from the method described in Example 9 were further cut into small pieces of about 0.5 cm long for testing. To 27.0 g of these extrudates, an aqueous solution (8.0 ml) containing 0.16 g Au in the form of $Me_4NAuO_2$ and 0.24 g Pt in the form of $PtO(NO_3)$ was added. The mixture was agitated to impregnate the carbon black support and was dried in a 70° C. oven for 1 hour under a dry air purge. The sample was then reduced at 350° C. under forming gas (5% $H_2$ and 95% $N_2$) atmosphere for 4 hours with 2° C./min temperature ramp rate. The final catalyst was composed of ca. 0.60 wt. % Au and 0.90 wt. % Pt. By using other carbon black extrudates prepared from the methods described herein, a series of Pt—Au extrudate catalysts spanning ranges in Au and Pt loadings, Pt/Au ratios and metal distributions (e.g., eggshell, uniform, subsurface bands) can be prepared.

The glucose to glucaric acid oxidation reaction was conducted in a ½" OD by 83 cm long 316 stainless steel tube with co-current down-flow of gas and liquid. Catalyst beds were vibration packed with 1.0 mm glass beads at the top to approximately 10 cm depth, followed by catalyst (63 cm bed depth containing 27.4 g, 0.60 wt % Au+0.90 wt % Pt on Sid Richardson SC159 carbon black pellets with a length of 0.5 cm and diameter of 1.4 mm prepared using the method described, then 1.0 mm glass beads at the bottom to approximately 10 cm depth. Quartz wool plugs separated the catalyst bed from the glass beads.

The packed reactor tube was clamped in an aluminum block heater equipped with PID controller. Gas (compressed dry air) and liquid flows were regulated by mass flow controller and HPLC pump, respectively. A back pressure regulator controlled reactor pressure as indicated in Table 11. The catalyst was tested for ca. 920 hours on stream and showed stable performance. Table 11 describes the fixed bed reactor conditions and resultant extrudate catalyst performance. The catalyst productivity in Table 11 is 23 gram (glucaric acid) per gram $(Pt+Au)^{-1}$ $hr^{-1}$ or 0.35 gram (glucaric acid) per gram $(catalyst)^{-1}$ $hr^{-1}$.

TABLE 11

| Reactor block temperature/ °C. | Glucose feed concentration/ wt % | Reactor pressure/ psi | Liquid flowrate/ mL min⁻¹ | Gas flowrate/ mL min⁻¹ (STP) | Glucose conversion/ % | Glucaric acid yield/ % | Selectivity/ |
|---|---|---|---|---|---|---|---|
| 125 | 20 | 750 | 2.00 | 512 | >99 | 32 | 79 |

After 920 hours on stream the catalyst extrudate was removed and re-submitted for mechanical crush strength testing. The mean single piece crush strength and mean radial piece crush strength data were found be within experimental error unchanged from the data listed in Table 10, thereby illustrating that the extrudate catalyst prepared by the method described is productive, selective and stable under the continuous flow conditions described.

Example 11. Testing of Au/Pt Carbon Black Extrudate Catalysts (Using Asbury 5368) in a Fixed-Bed Reactor for the Oxidation of Glucose to Glucaric Acid Reactions were conducted in a ½" OD by 83 cm long 316 stainless steel tube with co-current down-flow of gas and liquid. Catalyst beds were vibration packed with 1.0 mm glass beads at the top to approximately 8 cm depth, followed by catalyst (73 cm bed depth containing 35.0 g, 0.50 wt % Au+0.85 wt % Pt on Asbury 5368 extruded pellets (as previously described for Sample 7 (Example 6) with a length of 0.5 cm and diameter of 1.4 mm prepared using the method described in previous example 9), then 1.0 mm glass beads at the bottom to approximately 8 cm depth. Quartz wool plugs separated the catalyst bed from the glass beads.

The packed reactor tube was clamped in an aluminum block heater equipped with PID controller. Gas (compressed dry air) and liquid flows were regulated by mass flow controller and HPLC pump, respectively. A back pressure regulator controlled reactor pressure as indicated in Table 12. The catalyst was tested for ca. 240 hours TOS and showed stable performance. Table 12 describes the fixed bed reactor conditions and resultant extrudate catalyst performance. The catalyst productivity in Table 12 is 20 gram (glucaric acid) per gram $(Pt+Au)^{-1}$ $hr^{-1}$ or 0.27 gram (glucaric acid) per gram $(catalyst)^{-1}$ $hr^{-1}$.

impregnate the carbon black support and was dried in a 60° C. oven overnight under a dry air purge. The sample was then reduced at 350° C. under forming gas (5% H2 and 95% N2) atmosphere for 4 hours with 2° C./min temperature ramp rate. The final catalyst was composed of ca. 0.50 wt % Au and 0.85 wt % Pt. By using other carbon black extrudates prepared from the method described herein, a series of Pt—Au extrudate catalysts spanning ranges in Au and Pt loadings, Pt/Au ratios and metal distributions (e.g., eggshell, uniform, subsurface bands) could be prepared. The glucose to glucaric acid oxidation reaction was conducted in a in a ½" OD by 83 cm long 316 stainless steel tube with co-current down-flow of gas and liquid. Catalyst beds were vibration packed with 1.0 mm glass beads at the top to approximately 6 cm depth, followed by catalyst (70.4 cm bed depth containing 34.5 g, 0.50 wt % Au+0.85 wt % Pt on partially oxidized Sid Richardson SC159 carbon black pellets with a length of 0.5 cm and diameter of 1.5 mm prepared using the method described in Example 2), then 1.0 mm glass beads at the bottom to approximately 6 cm depth. Quartz wool plugs separated the catalyst bed from the glass beads.

The packed reactor tube was clamped in an aluminum block heater equipped with PID controller. Gas (compressed dry air) and liquid flows were regulated by mass flow controller and HPLC pump, respectively. A back pressure regulator controlled reactor pressure as indicated in Table 13. The catalyst was tested for ca. 230 hours TOS and showed stable performance. Table 13 describes the fixed bed reactor conditions and resultant extrudate catalyst performance. The catalyst productivity in Table 13 is 26 gram (glucaric acid) per gram $(Pt+Au)^{-1}$ $hr^{-1}$ or 0.36 gram (glucaric acid) per gram $(catalyst)^{-1}$ $hr^{-1}$.

TABLE 12

0.50 wt % Au + 0.85 wt % Pt/Asbury 5368 Extrudate (stable performance over 240 hours on stream)

| Reactor block temperature/ ° C. | Glucose feed concentration/ wt % | Reactor pressure/ psi | Liquid flowrate/ mL min$^{-1}$ | Gas flowrate/ mL min$^{-1}$ (STP) | Glucose conversion/ % | Glucaric acid yield/ % | Selectivity |
|---|---|---|---|---|---|---|---|
| 125 | 20 | 750 | 2.00 | 512 | >99 | 31 | 76 |

Example 12. Preparation of Carbon Black Extrudate Catalysts on Partially Oxidized Support Sid Richardson SC159 carbon black extrudates prepared from the method described in example 9 were oxidized in air

TABLE 13

| Reactor block temperature/ ° C. | Glucose feed concentration/ wt % | Reactor pressure/ psi | Liquid flowrate/ mL min$^{-1}$ | Gas flowrate/ mL min$^{-1}$ (STP) | Glucose conversion/% | Glucaric acid yield/% |
|---|---|---|---|---|---|---|
| 125 | 20 | 750 | 2.00 | 512 | >99 | 42 | at 300° C. for 3 hours with 5° C./min ramp rate to give partially oxidized pellets. To 36.0 g of these partially oxidized extrudates, an aqueous solution (9.0 ml) containing 0.18 g Au in the form of Me4NAuO2 and 0.31 g Pt in the form of PtO(NO3) was added. The mixture was agitated to

Example 13. Preparation of Carbon Black Extrudates Using a Poly(Vinylalcohol) Porogen An aqueous solution (490.0 g) containing 8.0 wt % Mowiol 8-88 Poly(vinylalcohol) (Mw 67k, Sigma-Aldrich 81383) and 36.0 wt % glucose (ADM Corn Processing, Dextrose Monohydrate 99.7DE with 91.2255 wt % Glucose content) was prepared by stirring 39.2 g Mowiol 8-88 Poly(vinylalcohol) and 193.4 g Dextrose Monohydrate in 257.4 ml D.I. water at 70° C. overnight. After cooling to room temperature, this solution was added to 230 g carbon black powder (Sid Richardson SC159) in a blender/kneader and the material was mixed/kneaded for 1 hour. The material was then loaded into a 1" Bonnot BB Gun Extruder and extrudated into spaghetti like strings with ca. 1.5 mm diameter at cross section. These strings were further dried in a 90° C. oven overnight under a dry air purge and then pyrolyzed at 600° C. for 4 hours with 5° C./min ramp rate in a nitrogen atmosphere. The final carbonized binder content was 24 wt. %. The resultant extrudate (3-5 mm in length) possessed a surface area of 149 m²/g, a pore volume of 0.35 cm³/g and a mean pore diameter of 16 nm. The mean radial piece crush strength of these pellets was measured to be 11.5 N/mm. The single piece crush strength was measured to be 42N.

Example 14. Testing of Au/Pt Activated Carbon Extrudate Catalysts (Using Clariant Donau Supersorbon K4-35 Activated Carbon Extrudate) in a Fixed-Bed Reactor for the Oxidation of Glucose to Glucaric Acid Catalyst based on activated carbon Clariant Supersorbon K 4-35 was prepared using the same method described in Example 7. Oxidation of glucose reactions were conducted using the same method described in Example 2(B)(ii). A catalyst bed depth of 73 cm containing 27.0 g, 0.53 wt. % Au+0.90 wt. % Pt on Clariant Supersorbon K 4-35 activated carbon pellets with a length of 0.5 cm and diameter of 1.4 mm was tested for approximately 40 hours of time on stream (TOS). Table 14 describes the fixed bed reactor conditions and resultant extrudate catalyst performance. After 40 hours on stream the glucaric acid yield and the catalyst productivity were determined to be lower than the shaped carbon black catalysts of the invention.

TABLE 14

| Reactor block temperature/ ° C. | Glucose feed concentration/ wt % | Reactor pressure/ psi | Liquid flowrate/ mL min⁻¹ | Gas flowrate/ mL min⁻¹ (STP) |
|---|---|---|---|---|
| 125 | 20 | 750 | 2.00 | 512 |

Example 15. Preparation of Carbon Black Extrudates

An aqueous solution (915 g) containing 4.0 wt % hydroxyethylcellulose (HEC) (Sigma-Aldrich, SKU 54290, viscosity 80-125 cP at 2% in $H_2O$ (20° C.)) and 56.0 wt % glucose (ADM Corn Processing, Dextrose Monohydrate 99.7DE with 91.2 wt % Glucose content) was prepared by stirring 36.6 g hydroxyethylcellulose and 561.7 g Dextrose Monohydrate in 316.7 ml D.I. water at approximately 80° C. for 2 hours. To this viscous solution was added 400.1 g of Sid Richardson SC159 carbon black powder, the mixture was then mixed for a further 10 minutes. The material was then loaded into a 1" diameter Bonnot extruder, fitted with a ¼ inch spacer and a die with 1.6 mm cylindrical holes, and extruded into spaghetti-like strings. The extrudate was dried in a 110° C. oven overnight, then pyrolyzed in a stationary lab furnace under a nitrogen purge at 800° C. for 4 hours (after ramping the temperature up at 5° C./minute to reach the target temperature) (Table 15).

TABLE 15

Properties of the pyrolyzed extrudate from Example 15

| $N_2$ BET Surface Area (m²/g) | BJH $N_2$ Pore Volume (cm³/g) | Diameter at cross section (mm) | Radial Piece Crush Strength (N/mm) |
|---|---|---|---|
| 207 | 0.30 | 1.5 | 17 |

Example 16. Preparation of Carbon Black Extrudates

An aqueous solution (3813 g) containing 4.0 wt % hydroxyethylcellulose (HEC) (Sigma-Aldrich, SKU 54290, viscosity 80-125 cP at 2% in $H_2O$ (20° C.)) and 56.0 wt % glucose (ADM Corn Processing, Dextrose Monohydrate 99.7DE with 91.2 wt % Glucose content) was prepared by stirring 153 g hydroxyethylcellulose and 2340 g Dextrose Monohydrate in 1320 ml D.I. water at approximately 80° C. for 3 hours. This viscous solution was added over 3.5 minutes to 1670 g of Sid Richardson SC159 carbon black powder in a mix-muller, the mixture was then mixed for a further 20 minutes in the mix-muller. The material was then loaded into a 2" diameter Bonnot extruder, fitted with 5 dies with 26 cylindrical holes each ¹⁄₁₆" internal diameter (JMP Industries, part number 0388P062), and no spacer, and extruded into spaghetti-like strings. 1515 g of the extrudate was dried in a 110° C. oven overnight, to produce 1240 g of dried extrudate. The product was then pyrolyzed in a stationary tube furnace under a nitrogen purge at 800° C. for 4 hours (Table 16).

TABLE 16

Properties of the pyrolyzed extrudate from Example 2

| $N_2$ BET Surface Area (m²/g) | BJH $N_2$ Pore Volume (cm³/g) | Diameter at cross section (mm) | Radial Piece Crush Strength (N/mm) |
|---|---|---|---|
| 169 | 0.23 | 1.4 | 13 |

Example 17. Preparation of Carbon Black Extrudates, Using Batch Pyrolysis in a Rotary Tube Furnace An aqueous solution (3813 g) containing 4.0 wt % of Dow Cellosize HEC QP 40 hydroxyethylcellulose (viscosity 80-125 cP at 2% in $H_2O$ (20° C.)), and 56.0 wt % glucose (ADM Corn Processing, Dextrose Monohydrate 99.7DE with 91.2 wt % Glucose content) was prepared by stirring 153 g hydroxyethylcellulose and 2340 g Dextrose Monohydrate in 1320 ml D.I. water at approximately 80° C. for 3 hours. This viscous solution was added over 3.5 minutes to 1670 g of Sid Richardson SC159 carbon black powder in a mix-muller, the mixture was then mixed for a further 20 minutes in the mix-muller. The material was then loaded into a 2" diameter Bonnot extruder, fitted with 5 dies with 26 cylindrical holes each ¹⁄₁₆" internal diameter (JMP Industries, part number 0388P062), and no spacer, and extruded into spaghetti-like strings. 3.9 kg of the extrudate was dried in a 110° C. oven overnight, to produce 2.93 kg of dried extrudate. This dried extrudate was then screened over an 18 mesh screen, and 2.91 kg of screened material were collected.

The mixing, extrusion, drying and screening procedure above was repeated 3 more times to generate a total of 4 batches of dried, screened extrudate, which were combined, as summarized in Table 17.

TABLE 17

Production of Carbon Black Extrudate in a 2" Extruder

| Sample number | Mass of wet extrudate collected (kg) | Mass of dried extrudate (kg) | Mass of dried extrudate after screening (kg) |
|---|---|---|---|
| 17.1 | 3.90 | 2.93 | 2.91 |
| 17.2 | 4.66 | 3.80 | 3.76 |
| 17.3 | 5.17 | 4.24 | 4.20 |
| 17.4 | 4.85 | 3.74 | 3.71 |
| Combined Total | 18.58 | 14.71 | 14.58 |

650 g batches of the combined dried & screened extrudate of were then pyrolyzed in a rotary tube furnace under a nitrogen purge at 800° C. for 2 hours, each batch producing approximately 350 g of pyrolyzed product. For each batch, 650 g of the carbon black extrudates (prepared from Sid Richardson SC159 with glucose and hydroxyethylcellulose binders) were loaded into an MTI Corporation 5" Quartz Tube Three Zone Rotary Tube Furnace (OTF-1200X-5L-R—III-UL). The carbon black extrudates were pyrolyzed with the 5" quartz tube rotating at 4.0 rpm under a nitrogen atmosphere at 800° C. for 2 hours with the following temperature ramp: ambient temperature to 200° C. at 10° C./min, 200° C. to 600° C. at 5° C./min, 600° C. to 800° C. at 10° C./min, hold at 800° C. for 2 hours, then allowed to cool to ambient temperature, still under nitrogen purge. 350 g of pyrolyzed carbon black extrudates were recovered, with 51.5% yield by mass. The properties of the batch-pyrolyzed extrudate are shown in Table 18. Other carbon black extrudates can be pyrolyzed at various temperatures in a similar manner, or using a continuously operating rotary kiln as described in the next example.

TABLE 18

Properties of Carbon Black Extrudate Batch-Pyrolyzed in a Rotary Tube Furnace

| | $N_2$ BET Surface Area ($m^2/g$) | $N_2$ Mean Pore Diameter (Å) | BJH $N_2$ Pore Volume ($cm^3/g$) | Radial Piece Crush Strength (N/mm) |
|---|---|---|---|---|
| Combined Extrudates of Example 17 Batch-Pyrolyzed at 800° C. for 2 hours | 191 | 100 | 0.29 | 15 |

Example 18. Preparation of Carbon Black Extrudates, Using Continuous Pyrolysis in Rotary Kiln The mixing, extrusion, drying and screening procedure described in Example 17 was repeated 10 more times to generate an additional 33.4 kg of dried, screened extrudate, which were combined. 25.7 kg of the combined dried & screened extrudate was then pyrolyzed in a continuous rotary kiln, with a continuous nitrogen purge (counter current flow vs. the extrudate), with a continuous feed of dried extrudate at approximately 0.5 kg/hour, with product collected at a number of set point conditions summarized in Table 19. The rotary kiln was electrically heated; the temperature set points for the external heaters are shown in Table 19, along with the calculated residence time of the material in the heating zone. The temperature and residence time were adjusted to influence the surface area of the product. A total of 12.5 kg of pyrolyzed product was collected, for an overall mass-based yield of 48.5%.

TABLE 19

Properties of Carbon Black Extrudate Pyrolyzed in a Continuously Operated Rotary Kiln

| Continuous Rotary Kiln Pyrolyzed Extrudate Sample Number | Temperature Set Point in Heating Zone (° C.) | Calculated Residence Time in Heating Zone (minutes) | $N_2$ Specific Surface Area ($m^2/g$) |
|---|---|---|---|
| 18.1 | 820 | 63 | 219 |
| 18.2 | 820 | 44 | 208 |
| 18.3 | 800 | 44 | 202 |
| 18.4 | 780 | 44 | 188 |
| 18.5 | 760 | 44 | 188 |
| 18.6 | 780 | 33 | 176 |
| 18.7 | 820 | 33 | 181 |

Example 19. Hydrodeoxygenation of Glucaric Acid Dilactone to Adipic Acid

Suitably concentrated aqueous solutions of rhodium nitrate and platinum nitrate were added together to carbon black powder (crushed from carbon black pellets) by incipient wetness impregnation and agitated to impregnate supports. The samples were dried in an oven at 60° C. overnight, and reduced at 350° C. under a forming gas (5% $H_2$ and 95% $N_2$) atmosphere for 4 hours with 2° C./min temperature ramp rate to produce catalysts with a composition of 1.0 wt. % Rh and 2.0 wt. % Pt. By using other carbon blacks supports, Rh and Pt precursors, and adjusting amount of Rh and Pt in solution, different catalysts with various Rh and Pt loadings on a variety of particles from extrudates were prepared in a similar manner.

These catalysts were tested for hydrodeoxygenation of glucaric acid dilactone using the following testing protocol. Catalyst (16 mg) was weighed into a glass vial insert followed by addition of a solution (125 μl) containing glucaric acid dilactone (0.80 M), HBr (0.80 M), and water (2.0 M). The glass vial insert was loaded into a reactor and the reactor was closed. The atmosphere in the reactor was replaced with hydrogen and pressurized to 900 psig at room temperature. Reactor was heated to 120° C. and maintained at 120° C. for 1 hour while vials were shaken. Reactor was then heated to 160° C. and maintained at 160° C. for 2 hours while vials were shaken. After that, shaking was stopped and reactor was cooled to 40° C. Pressure in the reactor was slowly released. The glass vial insert was removed from reactor and centrifuged. The clear solution was hydrolyzed with NaOH, diluted with deionized water, and analyzed by ion chromatography to determine the yield of adipic acid. The properties of the carbon black starting materials and results of the reaction screening are presented in Table 20.

TABLE 20

| Support | Surface Area (m²/g) | Mean Pore Diameter (Å) | Pore Volume (cm³/g) | Adipic Acid Yield (%) | Adipic Acid Selectivity (%) |
|---|---|---|---|---|---|
| Cabot Monarch 120 | 25 | 277 | 0.1 | 75 | 83 |
| Cabot Monarch 280 | 30 | 176 | 0.1 | 81 | 91 |
| Timcal Ensaco 250P | 64 | 140 | 0.24 | 92 | 99 |
| Cabot Monarch 570 | 102 | 138 | 0.3 | 87 | 97 |
| Cabot Monarch 700 | 181 | 121 | 0.38 | 89 | 99 |
| Cabot Vulcan XC72 | 224 | 161 | 0.43 | 86 | 99 |
| Sid Richardson SC159 | 234 | 182 | 0.81 | 75 | 86 |

Example 20. Testing of Rh/Pt Carbon Black Extrudate Catalysts in a Fixed-Bed Reactor for Hydrodeoxygenation of Glucaric Acid to Adipic Acid Cabot Vulcan XC72 carbon black particles used in this experiment were 150 to 300 µm sized particles crushed and sieved from extrudate pellets prepared from the method described in previous examples. Reactions were conducted in a 6.4 mm (0.25 inch) OD by 38 cm long zirconium tube with co-current down-flow of gas and liquid. Catalyst beds were vibration packed with 200 to 300 µm sized glass beads at the top to approximately 5 cm depth, followed by catalyst (28 cm bed depth containing 1.9 g, 0.90 wt. % Rh+2.1 wt. % Pt on carbon black particles, 150 to 300 µm particle size), then 200 to 300 µm sized glass beads at the bottom to approximately 5 cm depth. Quartz wool plugs separated the catalyst bed from the glass beads.

The packed reactor tube was clamped in an aluminum block heater equipped with PID controller. Gas (compressed hydrogen) and liquid flows were regulated by mass flow controller and HPLC pump, respectively. Substrate solution contains 0.80M D-glucaric acid-1,4:6,3-dilactone, 0.40M HBr and 2.0 M water in acetic acid. A back pressure regulator controlled reactor pressure as indicated in Table 21. External temperature of top half reactor and bottom half reactor was controlled at 110° C. and 160° C. respectively. The catalyst was tested for 350 hours on stream and showed stable performance. Table 21 describes the fixed bed reactor conditions and resultant catalyst performance.

TABLE 21

| Test | Reactor block temperature/ ° C. | Glucaric acid dilactone concentration/M | Reactor pressure/ psi | Liquid flowrate/ mL min⁻¹ | Gas flowrate/ mL min⁻¹ (STP) | Glucaric acid dilactone conversion/% | Adipic acid yield/% |
|---|---|---|---|---|---|---|---|
| 1 | 110/160 | 0.80 | 1000 | 0.050 | 50 | 90 | 42 |

Example 21. Hydrodeoxygenation of 1,2,6-Hexanetriol to 1,6-Hexanediol

Suitably concentrated aqueous solutions of $Pt(NO_3)_x$ and $H_4SiO_4 \cdot 12WO3$ or $PtONO_3$ and $H_4SiO_4 \cdot 12WO3$ were added to approximately 50 mg of Ensaco 250G carbon and agitated to impregnate the supports. The samples were dried in an oven at 40° C. overnight under static air and then reduced at 350° C. under forming gas (5% $H_2$ and 95% $N_2$) atmosphere for 3 hours. The final catalysts had a metal content of approximately 4.09 wt. % Pt and 3.42 wt. % W.

These catalysts were tested for 1,2,6-hexanetriol hydrodeoxygenation using the following catalyst testing protocol. Catalyst (approximately 10 mg) was weighed into a glass vial insert followed by addition of an aqueous 1,2,6-hexanetriol solution (200 μl of 0.8 M). The glass vial insert was loaded into a reactor and the reactor was closed. The atmosphere in the reactor was replaced with hydrogen and pressurized to 670 psig at room temperature. The reactor was heated to 160° C. and maintained at the respective temperature for 150 minutes while vials were shaken. After 150 minutes, shaking was stopped and reactor was cooled to 40° C. Pressure in the reactor was then slowly released. The glass vial insert was removed from the reactor and centrifuged. The solution was diluted with methanol and analyzed by gas chromatography with flame ionization detection. The results are shown in Table 22.

TABLE 22

| Support | Surface Area ($m^2/g$) | Mean Pore Diameter (Å) | Pore Volume ($cm^3/g$) | Pt Precursor | W Precursor | Yield (%) | Selectivity (%) |
|---|---|---|---|---|---|---|---|
| Ensaco 250G | 64 | 140 | 0.24 | $Pt(NO_3)_2$ | $H_4SiO_4*12WO_3$ | 27 | 64 |
| Ensaco 250G | 64 | 140 | 0.24 | $PtONO_3$ | $H_4SiO_4*12WO_3$ | 47 | 69 |

Example 22. Hydrodeoxygenation of 1,2,6-Hexanetriol to 1,6-Hexanediol

A suitably concentrated aqueous solution of ammonium metatungstate, $H_{26}N6W_{12}O_{40}$ was added to approximately 500 mg of Ensaco 250G and agitated to impregnate the carbon black support. The sample was thermally treated at 600° C. under a nitrogen atmosphere for 3 hours with 5° C./min temperature ramp rate. Suitably concentrated aqueous solutions of $Pt(NMe_4)_2(OH)_6$ was added to 50 mg of the above sample and agitated to impregnate the carbon supports. The samples were dried in an oven at 40° C. overnight under static air and then reduced at 250° C. under forming gas (5% $H_2$ and 95% $N_2$) atmosphere for 3 hours with 5° C./min temperature ramp rate. The final catalysts had a metal content of approximately 4.5 wt. % Pt and 2 wt. % W.

These catalysts were tested for 1,2,6-hexanetriol hydrodeoxygenation using the following catalyst testing protocol. Catalyst (approximately 10 mg) was weighed into a glass vial insert followed by addition of an aqueous 1,2,6-hexanetriol solution (200 μl of 0.8 M). The glass vial insert was loaded into a reactor and the reactor was closed. The atmosphere in the reactor was replaced with hydrogen and pressurized to 670 psig at room temperature. The reactor was heated to 160° C. and maintained at the respective temperature for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are shown in Table 23.

TABLE 23

| Support | Surface Area ($m^2/g$) | Mean Pore Diameter (Å) | Pore Volume ($cm^3/g$) | Pt Precursor | W Precursor | Yield (%) | Selectivity (%) |
|---|---|---|---|---|---|---|---|
| Ensaco 250G | 64 | 140 | 0.24 | $Pt(NMe_4)_2(OH)_6$ | $H_{26}N_6W_{12}O_{40}$ | 38 | 88 |

Example 23. Hydrodeoxygenation of 1,2,6-Hexanetriol to 1,6-Hexanediol

Suitably concentrated aqueous solutions of ammonium metatungstate, $H_{26}N_6W_{12}O_{40}$ were added to approximately 500 mg of carbon black materials and agitated to impregnate the carbon black supports. The samples were thermally treated at 600° C. under a nitrogen atmosphere for 3 hours with 5° C./min temperature ramp rate. Suitably concentrated aqueous solutions of $Pt(NMe_4)_2(OH)_6$ were added to approximately 50 mg of the above samples and agitated to impregnate the carbon supports. The samples were dried in an oven at 60° C. under static air and then reduced at 350° C. under forming gas (5% $H_2$ and 95% $N_2$) atmosphere for 3 hours with 5° C./min temperature ramp rate. The final catalysts had a metal content of approximately 5.7 wt. % Pt and 1.8 wt. % W.

These catalysts were tested for 1,2,6-hexanetriol hydrodeoxygenation using the following catalyst testing protocol. Catalyst (approximately 10 mg) was weighed into a glass vial insert followed by addition of an aqueous 1,2,6-hexanetriol solution (200 μl of 0.8 M). The glass vial insert was loaded into a reactor and the reactor was closed. The atmosphere in the reactor was replaced with hydrogen and pressurized to 670 psig at room temperature. The reactor was heated to 160° C. and maintained at the respective temperature for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. Results are shown in Table 24.

TABLE 24

| Support | Surface Area ($m^2/g$) | Mean Pore Diameter (Å) | Pore Volume ($cm^3/g$) | Pt Precursor | W Precursor | Yield (%) | Selectivity (%) |
|---|---|---|---|---|---|---|---|
| Ensaco 250G | 64 | 140 | 0.24 | $Pt(NMe_4)_2(OH)_6$ | $H_{26}N_6W_{12}O_{40}$ | 52 | 71 |
| Orion HiBlack 40B2 | 109 | 155 | 0.32 | $Pt(NMe_4)_2(OH)_6$ | $H_{26}N_6W_{12}O_{40}$ | 28 | 68 |

Example 24. Small Scale Batch Reactor Experiments for Amination of 1,6-Hexanediol to Produce 1,6-Hexamethylenediamine Amination of 1,6-Hexanediol to Produce 1,6-Hexamethylenediamine—Analytical Details Product composition was determined by HPLC analysis using a Thermo Ultimate 3000 dual analytical chromatography system. Hexamethylenediamine (HMDA), hexamethyleneimine (HMI) and pentylamine were eluted with a mobile phase consisting of $H_2O$/MeCN/TFA and detected using a charged aerosol detector (CAD). 1,6-Hexanediol (HDO) was eluted with a mobile phase consisting of $H_2O$/MeCN/TFA and detected using a refractive index detector (RI). In certain examples an internal standard, N-methyl-2-pyrrolidone (NMP), was used in the substrate feed to correct for variations in product effluent concentration due to $NH_3$ off-gassing. NMP was eluted with a mobile phase consisting of $H_2O$/MeCN/TFA and detected by UV at 210 nm. All products were quantified by comparison to calibration standards. Selectivity is reported as the yield of HMDA divided by the sum of HMDA and pentylamine.

Experiment 1

Preparation of Supported Ru Catalysts

A suitably concentrated aqueous solution of Ru(NO)(NO$_3$)$_3$ was added to a 96 vial array of carbon supports containing 10 or 20 mg of support in each vial. The volume of ruthenium solution was matched to equal the pore volume of the support. Each sample was agitated to impregnate the support. The samples were dried in an oven at 60° C. for 12 hours under a dry air purge. The catalysts were reduced under forming gas (5% $H_2$ and 95% $N_2$) at 250° C. for 3 hours using a 2° C./min temperature ramp rate. The final catalysts were composed of 2 weight percent ruthenium.

Catalyst Screening Procedure

A substrate solution consisting of 0.7M 1,6-hexanediol in concentrated aqueous $NH_4OH$ was added to an array of catalysts prepared as described above. The vials were covered with a Teflon pinhole sheet, a silicone pinhole mat, and a steel gas diffusion plate. The reactor insert was placed in a pressure vessel and purged 2× with $NH_3$ gas. The pressure vessel was charged to 100 psi with $NH_3$ gas and then to 680 psi with $N_2$ at ambient temperature. The reactor was placed on a shaker and vortexed at 800 rpm at 160° C. After 3 hours, the reactor was cooled to room temperature, vented, and purged with nitrogen prior to being unsealed. The samples were diluted with water, mixed, and then centrifuged to separate catalyst particles. Aliquots were removed from the supernatant and diluted further with dilute aqueous trifluoroacetic acid for analysis by HPLC. Results are summarized below in Table 25.

TABLE 25

| Support | Surface Area ($m^2/g$) | Mean Pore Diameter (Å) | Pore Volume ($cm^3/g$) | Catalyst Amount (mg) | HDO Conversion (%) | HMDA Yield (%) | Pentylamine Yield (%) | Selectivity |
|---|---|---|---|---|---|---|---|---|
| Asbury 5346R | 80 | 145 | 0.28 | 10 | 79.8 | 16.5 | 0.0 | 99.8 |
| Asbury 5346R | 80 | 145 | 0.28 | 20 | 99.1 | 25.1 | 0.5 | 97.9 |
| Ensaco 150G | 47 | 136 | 0.17 | 10 | 80.8 | 16.4 | 0.1 | 99.5 |
| Ensaco 150G | 47 | 136 | 0.17 | 20 | 95.5 | 24.5 | 0.7 | 97.4 |
| Ensaco 250G | 64 | 140 | 0.24 | 10 | 78.6 | 16.3 | 0.0 | 100 |
| Ensaco 250G | 64 | 140 | 0.24 | 20 | 94.4 | 26.0 | 0.5 | 98.2 |
| Ensaco 260G | 63 | 104 | 0.18 | 10 | 74.7 | 15.4 | 0.0 | 100 |
| Ensaco 260G | 63 | 104 | 0.18 | 20 | 93.3 | 24.0 | 0.5 | 98.1 |
| HP160 | 158 | 208 | 0.87 | 10 | 81.7 | 11.9 | 0.0 | 100 |
| HP160 | 158 | 208 | 0.87 | 20 | 98.3 | 18.3 | 0.1 | 99.2 |
| Orion HI-Black 50L | 193 | 157 | 0.66 | 10 | 91.0 | 18.8 | 0.2 | 99.1 |
| Orion HI-Black 50L | 193 | 157 | 0.66 | 20 | 100 | 21.7 | 0.7 | 96.8 |
| Sid Richardson SC159 | 234 | 182 | 0.81 | 10 | 90.3 | 14.7 | 0.0 | 100 |
| Sid Richardson SC159 | 234 | 182 | 0.81 | 20 | 99.3 | 17.3 | 0.4 | 97.9 |
| Sid Richardson SR155 | 146 | 222 | 0.87 | 10 | 93.2 | 19.5 | 0.1 | 99.5 |
| Sid Richardson SR155 | 146 | 222 | 0.87 | 20 | 100 | 19.7 | 0.4 | 98.1 |

Experiment 2

Preparation of Supported Ru/Re Catalysts

Suitably concentrated aqueous solutions of $Ru(NO)(N_3)_3$ containing varying amounts of $HReO_4$ were added to 0.15 g of a support and agitated to impregnate the support. The volume of metal solution was matched to equal the pore volume of the support. The samples were dried in an oven at 60° C. for 3 hours under a dry air purge. Catalyst amounts from 10-20 mg were weighed in to glass vials of a 96 vial array. The catalysts were reduced under forming gas (500$H_2$ and 95%0$N_2$) at 60° C. for 3 hours then at 250° C. for 3 hours using a 2° C./min temperature ramp rate. The final catalysts were composed of 4.04 weight percent ruthenium containing various rhenium loadings of 0, 0.4, 0.7, and 1.9 wt. %.

Catalyst Screening Procedure

A substrate solution consisting of 1.549M 1,6-hexanediol in concentrated aqueous $NH_4OH$ was added to an array of catalysts prepared as described above. The vials were covered with a Teflon pinhole sheet, a silicone pinhole mat, and a steel gas diffusion plate. The reactor insert was placed in a pressure vessel and purged 2× with $NH_3$ gas. The pressure vessel was charged to 100 psi with $NH_3$ gas and then to 680 psi with $N_2$ at ambient temperature. The reactor was placed on a shaker and vortexed at 800 rpm at 160° C. After 3 hours, the reactor was cooled to room temperature, vented, and purged with nitrogen prior to being unsealed. The samples were diluted with water, mixed, and then centrifuged to separate catalyst particles. Aliquots were removed from the supernatant and diluted further with dilute aqueous trifluoroacetic acid for analysis by HPLC. Results are outline below in Table 26.

TABLE 26

Hexanediol to Hexamethylenediamine using Ru/Re/Carbon HP-160 Catalysts

| Entry | Catalyst Amount (mg) | Ru (wt. %) | Re (wt. %) | HDO Conversion (%) | HMDA Yield (%) | Pentylamine Yield (%) | HMDA/ Pentylamine |
|---|---|---|---|---|---|---|---|
| 1 | 20 | 4.04 | 0.0 | 95.8 | 20.2 | 1.4 | 14.5 |
| 2 | 20 | 4.04 | 0.4 | 98.7 | 23.2 | 1.3 | 18.1 |
| 3 | 20 | 4.04 | 0.7 | 99.4 | 23.4 | 1.0 | 23.3 |
| 4 | 20 | 4.04 | 1.9 | 97.4 | 20.3 | 0.4 | 51.8 |
| 5 | 10 | 4.04 | 0.0 | 79.5 | 14.4 | 0.6 | 26.1 |
| 6 | 10 | 4.04 | 0.4 | 90.4 | 20.1 | 0.7 | 27.9 |
| 7 | 10 | 4.04 | 0.7 | 92.6 | 20.7 | 0.6 | 35.8 |
| 8 | 10 | 4.04 | 1.9 | 78.3 | 11.5 | 0.0 | |

Experiment 3

Preparation of Ni/Ru Catalysts Supported on Ensaco 250G

Suitably concentrated aqueous solutions containing $Ni(NO_3)_2$ and/or $Ru(NO)(NO_3)_3$ were added by incipient wetness impregnation to approximately 0.4 g of a carbon black support and agitated to impregnate the support. The volume of metal solution was matched to equal the pore volume of the support. Each catalyst was thermally treated under $N_2$ in a tube furnace at 60° C. for 12 hours then at 300° C. for 3 hours using a 5° C./min temperature ramp rate.

Catalyst amounts from 15-25 mg were weighed in to glass vials of a 96 vial array. The catalysts were reduced under forming gas (5% $H_2$ and 95% $N_2$) at 450° C. for 3 hours using a 2° C./min temperature ramp rate. Catalysts were passivated with 1% $O_2$ in $N_2$ at room temperature before removing from the tube furnace.

Catalyst Screening Procedure A

A substrate solution consisting of 0.7M 1,6-hexanediol in concentrated aqueous $NH_4OH$ was added to an array of catalysts prepared as described above. The vials were covered with a Teflon pinhole sheet, a silicone pinhole mat, and a steel gas diffusion plate. The reactor insert was placed in a pressure vessel and purged 2× with $NH_3$ gas. The pressure vessel was charged to 100 psi with $NH_3$ gas and then to 680 psi with $N_2$ at ambient temperature. The reactor was placed on a shaker and vortexed at 800 rpm at 160° C. After 3 hours, the reactor was cooled to room temperature, vented, and purged with nitrogen prior to being unsealed. The samples were diluted with water, mixed, and then centrifuged to separate catalyst particles. Aliquots were removed from the supernatant and diluted further with dilute aqueous trifluoroacetic acid for analysis by HPLC. Results are summarized below in Table 27.

TABLE 27

| Entry | Catalyst Amount (mg) | Ni (wt. %) | Ru (wt. %) | HDO Conversion (%) | HMDA Yield (%) | Pentylamine Yield (%) | Selectivity |
|---|---|---|---|---|---|---|---|
| 1 | 15 | 12 | 0 | 35.8 | 1.9 | 0.0 | 98.4 |
| 2 | 15 | 0 | 0.56 | 66.1 | 9.6 | 0.3 | 97.4 |
| 3 | 15 | 4 | 0.56 | 74.3 | 17.3 | 0.3 | 98.5 |
| 4 | 15 | 8 | 0.56 | 77.3 | 22.7 | 0.3 | 98.7 |
| 5 | 15 | 12 | 0.56 | 85.9 | 25.3 | 0.4 | 98.6 |
| 6 | 25 | 12 | 0 | 54.0 | 7.7 | 0.1 | 99.1 |
| 7 | 25 | 0 | 0.56 | 82.7 | 18.9 | 0.5 | 97.2 |
| 8 | 25 | 4 | 0.56 | 89.1 | 29.0 | 0.8 | 97.5 |
| 9 | 25 | 8 | 0.56 | 92.8 | 31.4 | 0.7 | 97.7 |
| 10 | 25 | 12 | 0.56 | 94.7 | 30.1 | 0.7 | 97.6 |

Catalyst Screening Procedure B

Passivated catalysts were reactivated in water under $H_2$ at 180° C. for 3 hours. Most of the water was removed from each catalyst leaving behind enough to act as a protective layer. The catalysts were then screened as described above in Procedure A. Results are summarized below in Table 28.

TABLE 28

| Entry | Catalyst Amount (mg) | Ni (wt. %) | Ru (wt. %) | HDO Conversion (%) | HMDA Yield (%) | Pentylamine Yield (%) | Selectivity |
|---|---|---|---|---|---|---|---|
| 1 | 15 | 12 | 0 | 49.2 | 7.2 | 0.00 | 100.0 |
| 2 | 15 | 0 | 0.56 | 67.0 | 11.2 | 0.06 | 99.5 |
| 3 | 15 | 4 | 0.56 | 73.7 | 18.2 | 0.07 | 99.7 |
| 4 | 15 | 8 | 0.56 | 86.8 | 25.5 | 0.38 | 98.5 |
| 5 | 15 | 12 | 0.56 | 86.0 | 23.8 | 0.33 | 98.7 |
| 6 | 25 | 12 | 0 | 73.3 | 16.0 | 0.00 | 100.0 |

TABLE 28-continued

| Entry | Catalyst Amount (mg) | Ni (wt. %) | Ru (wt. %) | HDO Conversion (%) | HMDA Yield (%) | Pentylamine Yield (%) | Selectivity |
|---|---|---|---|---|---|---|---|
| 7 | 25 | 0 | 0.56 | 83.8 | 18.3 | 0.84 | 95.6 |
| 8 | 25 | 4 | 0.56 | 93.5 | 28.1 | 1.22 | 95.9 |
| 9 | 25 | 8 | 0.56 | 94.0 | 27.8 | 1.07 | 96.3 |
| 10 | 25 | 12 | 0.56 | 96.1 | 27.3 | 1.15 | 96.0 |

Fixed Bed Experiments

Preparation of 2 wt. % Ru on Carbon Ensaco 250G

A carbon extrudate, prepared from carbon black Ensaco 250G and a carbohydrate binder, was crushed and sized to 150-300 um. A suitably concentrated aqueous solution of Ru(NO)(NO$_3$)$_3$ was added to 4.77 g of the crushed extrudate and agitated to impregnate the support. The volume of metal solution was matched to equal the pore volume of the support. The samples were dried in an oven at 60° C. for 12 hours under a dry air purge. The catalyst was reduced under forming gas (5% H$_2$ and 95% N$_2$) at 250° C. for 3 hours using a 2° C./min temperature ramp rate. The catalyst was washed with water and again sized to 106-300 um to remove any fines that may have been generated during the metal impregnation step.

Preparation of 10.5 wt. % Ni and 0.45 wt. % Ru on Carbon Ensaco 250G

A carbon extrudate, prepared from carbon black Ensaco 250G and a carbohydrate binder, was crushed and sized to 106-300 um. A suitably concentrated aqueous solution containing Ni(NO$_3$)$_2$.6H$_2$O and Ru(NO)(NO$_3$)$_3$ was added to 10 g of the crushed extrudate and agitated to impregnate the support. The volume of metal solution was matched to equal the pore volume of the support. The catalyst was dried in an oven at 60° C. for 12 hours under a dry air purge then thermally treated under N$_2$ at 300° C. for 3 hours. The catalyst was reduced under forming gas (5% H$_2$ and 95% N$_2$) at 450° C. for 3 hours using a 2° C./min temperature ramp rate. After cooling to room temperature the catalyst was passivated with 1% 02 in N$_2$ at room temperature before removing from the tube furnace. The catalyst was washed with water and again sized to 106-300 um to remove any fines that may have been generated during the metal impregnation step.

2 wt. % Ru on Carbon Catalyst

The reaction was performed in a 0.25 inch OD by 570 mm long 316 stainless steel tube with a 2 um 316 stainless steel frit at the bottom of the catalyst bed. The reactor was vibration packed with 1 g of SiC beads (90-120 um) followed by 3 g of a 2% by weight ruthenium on carbon Ensaco 250G catalyst (100-300 um) and finally 2.5 g of SiC beads at the top. A ¼ inch layer of glass wool was used between each layer. The packed reactor tube was vertically mounted in an aluminum block heater equipped with PID controller. An HPLC pump was used to deliver liquid feed to the top of the reactor and a back pressure regulator was used to control reactor pressure. The reaction was run at 160° C. Product effluent was collected periodically for analysis by HPLC. No decline in catalyst activity was observed after 1650 h.

Three different feed compositions were investigated at 160° C. with a reactor pressure ranging from 800-1000 psi. In all cases N-methyl-2-pyrrolidone (NMP) was used as an internal standard.

Feed 1: 0.7M 1,6-hexanediol and 0.14M NMP in concentrated NH4OH.

Feed 2: 0.7M 1,6-hexanediol, 0.14M hexamethyleneimine, and 0.14M NMP in concentrated NH4OH.

Feed 3: 1.54M 1,6-hexanediol, 0.308M hexamethyleneimine, and 0.308M NMP in concentrated NH4OH.

The results are summarized below in Table 29.

10.5 wt. % Ni/0.45 wt. % Ru on Carbon Catalyst

The reaction was performed as described above for the Ru only catalyst. A total of 3 g of Ni/Ru catalyst was loaded into the reactor and reactivated at 180° C. under H$_2$ before introduction of the feed solution. No decline in catalyst activity was observed after 650 h. Results are summarized below in Table 29.

TABLE 29

| Catalyst | Source | Feed Rate (mL/min) | Reactor Pressure (psi) | HDO Conversion (%) | HMDA Yield (%) | HMI Yield (%) | Pentylamine Yield (%) | Selectivity |
|---|---|---|---|---|---|---|---|---|
| 2 wt. % Ru | Feed 1 | 0.2 | 800 | 85 | 23 | 11 | 1.5 | 93.9 |
| 2 wt. % Ru | Feed 2 | 0.2 | 800 | 83 | 29 | 18 | 1.6 | 94.8 |
| 2 wt. % Ru | Feed 3 | 0.15 | 1000 | 90 | 36 | 21 | 2.6 | 93.3 |
| 10.5 wt. % Ni/0.45% Ru | Feed 2 | 0.2 | 800 | 83 | 26 | 17 | 0.5 | 98.1 |

Example 25. Preparation of Carbon Black Extrudate

A carbon black extrudate was prepared according to the following procedure. To prepare a binder solution, 552.67 grams of dextrose monohydrate (ADM Corn Processing, 91.22 wt % glucose content) was dissolved in 455.63 grams of DI water at 70° C. The solution was then cooled to 50° C. 20.51 grams of hydroxyethylcellulose we added to the mixture and stirred overnight.

Subsequently, 450 grams of the binder solution was mixed with 200.6 grams of carbon black powder (approx. 1 hour mixing) using a Winkworth Mixer (Model 1Z) and extruded using a Diamond America 1-inch single-screw extruder (Model TT100CS). This same mixing/extruding procedure was repeated again the same day with another 450 gram portion of the carbon. The strings were dried in a forced air oven at 120° C. for approx. 2 hours, and then broken up by hand. The extrudates were then dried overnight.

The carbon was split into 4 approx. 250 gram portions and pyrolyzed in a rotary kiln. Each portion was treated separately in the rotary kiln. The temperature of the kiln was ramped at a rate of 30° C./min until reaching a maximum 800° C. This temperature is held for 2 hours before cooling. The kiln was set to rotate at 6.6 rpms. During the temperature ramp, a large amount of water vapor and other pyrolysis products were formed. From approximately 350° C.–450° C. a large amount of gas was formed.

Following pyrolysis and cooling, the extrudates were washed. The desired amount of DI water was heated up to 60° C. in a beaker. The extrudates were then added and the slurry was stirred at 300-350 rpm for 4 h while the water temperature was kept at 60° C. The beaker was covered with a watch glass to avoid excess evaporation. The initial water to carbon ratio was kept at 10:1 (vol/wt). Extrudates were separated and rinsed with DI water and dried in an oven at 80° C. overnight.

Figure 13:
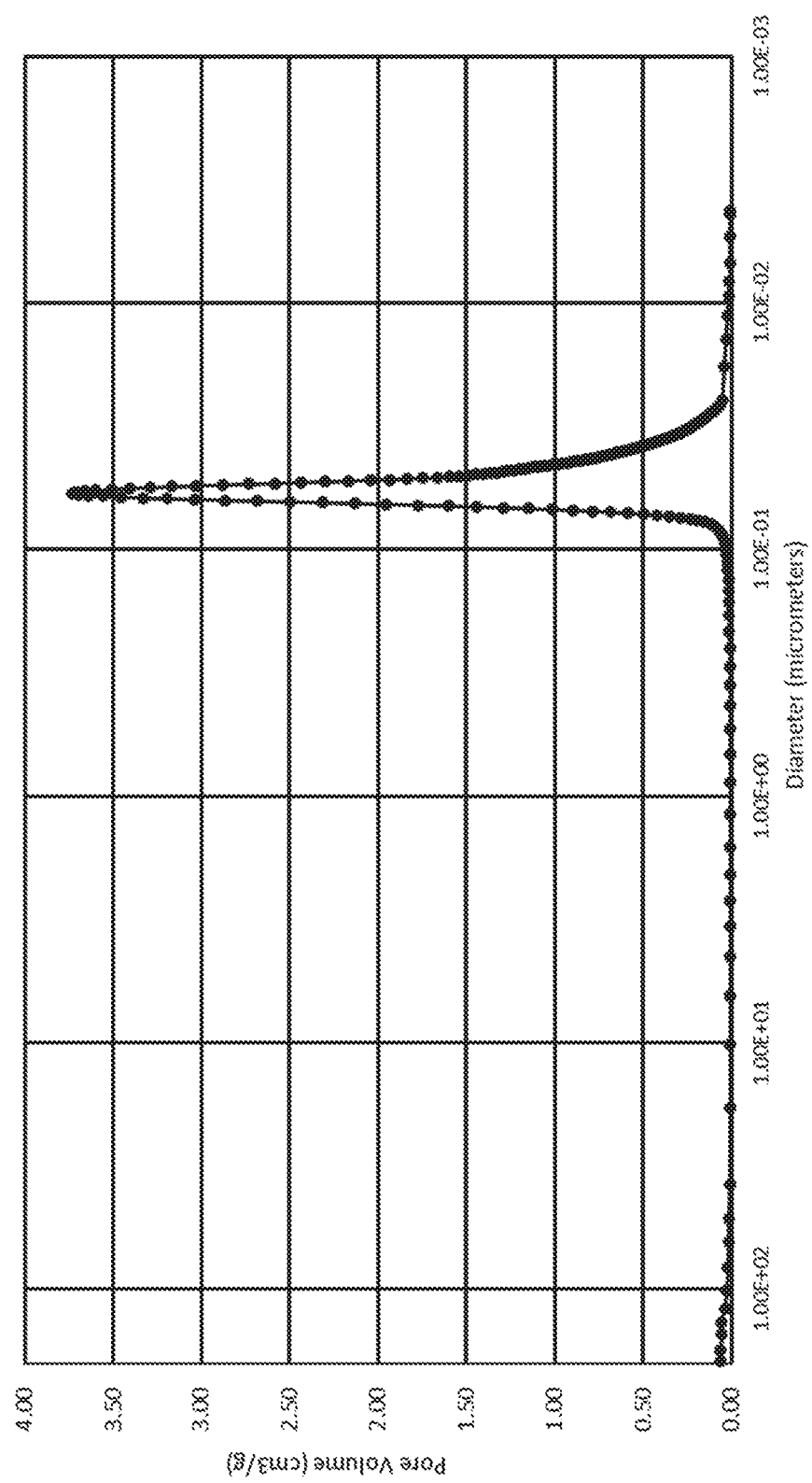
FIG. 13 presents a plot of the pore diameter vs pore volume for a carbon black extrudate.

A 0.31 gram sample (bulk volume of 0.33 cm$^3$) of the extrudate was analyzed for various physical properties by mercury porosimetry. Table 30 presents the full results of the analysis. A plot of the pore diameter vs pore volume is presented in FIG. 13.

TABLE 30

| Pressure [PSI] | Pore Diameter [μm] | Volume Intruded [cc/g] | Delta Volume [cc/g] | Volume Intruded % | Dv(d) [cc/(μm-g)] | dV/d(log d) [cc/g] |
| --- | --- | --- | --- | --- | --- | --- |
| 0.984 | 2.57E+02 | 0.0073 | 0.0073 | 1.21 | 1.20E−04 | 8.13E−02 |
| 1.064 | 2.37E+02 | 0.0145 | 0.0072 | 2.4 | 1.20E−04 | 7.72E−02 |
| 1.176 | 2.15E+02 | 0.02 | 0.0056 | 3.32 | 1.31E−04 | 7.26E−02 |
| 1.283 | 1.97E+02 | 0.023 | 0.0029 | 3.81 | 1.42E−04 | 6.63E−02 |
| 1.432 | 1.76E+02 | 0.0251 | 0.0021 | 4.16 | 1.57E−04 | 6.07E−02 |
| 1.651 | 1.53E+02 | 0.0268 | 0.0017 | 4.44 | 1.85E−04 | 5.60E−02 |
| 1.849 | 1.37E+02 | 0.0294 | 0.0026 | 4.87 | 2.39E−04 | 5.69E−02 |
| 2.101 | 1.20E+02 | 0.0316 | 0.0023 | 5.24 | 1.80E−04 | 3.84E−02 |
| 2.493 | 1.01E+02 | 0.0328 | 0.0012 | 5.44 | 1.50E−04 | 2.70E−02 |
| 3.087 | 8.18E+01 | 0.0337 | 0.0009 | 5.59 | 1.44E−04 | 2.02E−02 |
| 3.931 | 6.42E+01 | 0.0347 | 0.0009 | 5.75 | 1.65E−04 | 1.66E−02 |
| 4.871 | 5.18E+01 | 0.0356 | 0.0009 | 5.9 | 2.06E−04 | 1.46E−02 |
| 6.68 | 3.78E+01 | 0.0365 | 0.0009 | 6.05 | 1.98E−04 | 1.03E−02 |
| 13.715 | 1.84E+01 | 0.0374 | 0.0009 | 6.2 | 2.83E−04 | 7.29E−03 |
| 24.938 | 1.01E+01 | 0.0382 | 0.0008 | 6.34 | 6.19E−04 | 6.56E−03 |
| 39.16 | 6.45E+00 | 0.039 | 0.0008 | 6.47 | 1.13E−03 | 6.23E−03 |
| 56.165 | 4.49E+00 | 0.0398 | 0.0008 | 6.6 | 1.59E−03 | 5.92E−03 |
| 75.077 | 3.36E+00 | 0.0406 | 0.0008 | 6.73 | 1.48E−03 | 5.52E−03 |
| 95.519 | 2.64E+00 | 0.0414 | 0.0008 | 6.86 | 1.22E−03 | 5.48E−03 |
| 120.183 | 2.10E+00 | 0.0421 | 0.0008 | 6.99 | 1.45E−03 | 5.85E−03 |
| 156.383 | 1.61E+00 | 0.0429 | 0.0008 | 7.11 | 1.92E−03 | 6.27E−03 |
| 212.97 | 1.19E+00 | 0.0436 | 0.0007 | 7.23 | 2.80E−03 | 6.70E−03 |
| 286.447 | 8.81E−01 | 0.0444 | 0.0007 | 7.35 | 4.18E−03 | 7.11E−03 |
| 374.248 | 6.74E−01 | 0.0451 | 0.0007 | 7.47 | 5.89E−03 | 7.45E−03 |
| 475.002 | 5.31E−01 | 0.0458 | 0.0007 | 7.59 | 7.57E−03 | 7.76E−03 |
| 587.472 | 4.30E−01 | 0.0465 | 0.0007 | 7.71 | 9.10E−03 | 8.11E−03 |
| 710.405 | 3.55E−01 | 0.0472 | 0.0007 | 7.83 | 1.10E−02 | 8.68E−03 |
| 846.917 | 2.98E−01 | 0.048 | 0.0007 | 7.95 | 1.39E−02 | 9.57E−03 |
| 1004.088 | 2.51E−01 | 0.0487 | 0.0007 | 8.07 | 1.79E−02 | 1.06E−02 |
| 1174.217 | 2.15E−01 | 0.0494 | 0.0007 | 8.19 | 2.30E−02 | 1.17E−02 |
| 1357.222 | 1.86E−01 | 0.0502 | 0.0007 | 8.31 | 2.94E−02 | 1.30E−02 |
| 1542.737 | 1.64E−01 | 0.0509 | 0.0007 | 8.43 | 3.72E−02 | 1.45E−02 |
| 1719.073 | 1.47E−01 | 0.0516 | 0.0007 | 8.55 | 4.58E−02 | 1.61E−02 |
| 1893.314 | 1.33E−01 | 0.0523 | 0.0007 | 8.67 | 5.60E−02 | 1.81E−02 |
| 2067.439 | 1.22E−01 | 0.053 | 0.0007 | 8.79 | 6.92E−02 | 2.07E−02 |
| 2235.627 | 1.13E−01 | 0.0537 | 0.0007 | 8.91 | 8.59E−02 | 2.38E−02 |
| 2397.15 | 1.05E−01 | 0.0545 | 0.0007 | 9.03 | 1.07E−01 | 2.77E−02 |
| 2551.342 | 9.89E−02 | 0.0552 | 0.0007 | 9.15 | 1.34E−01 | 3.25E−02 |
| 2695.282 | 9.36E−02 | 0.0559 | 0.0008 | 9.27 | 1.68E−01 | 3.84E−02 |
| 2819.66 | 8.95E−02 | 0.0567 | 0.0007 | 9.4 | 2.13E−01 | 4.63E−02 |
| 2932.549 | 8.61E−02 | 0.0574 | 0.0008 | 9.52 | 2.76E−01 | 5.76E−02 |
| 3031.196 | 8.33E−02 | 0.0582 | 0.0008 | 9.65 | 3.64E−01 | 7.34E−02 |
| 3118.625 | 8.09E−02 | 0.059 | 0.0008 | 9.79 | 4.83E−01 | 9.44E−02 |
| 3197.594 | 7.89E−02 | 0.0599 | 0.0009 | 9.93 | 6.38E−01 | 1.21E−01 |
| 3264.71 | 7.73E−02 | 0.0609 | 0.0009 | 10.09 | 8.37E−01 | 1.54E−01 |
| 3319.679 | 7.60E−02 | 0.0619 | 0.001 | 10.26 | 1.07E+00 | 1.93E−01 |
| 3365.369 | 7.50E−02 | 0.063 | 0.0012 | 10.45 | 1.35E+00 | 2.39E−01 |
| 3404.708 | 7.41E−02 | 0.0643 | 0.0013 | 10.66 | 1.67E+00 | 2.91E−01 |
| 3440.807 | 7.34E−02 | 0.0658 | 0.0015 | 10.9 | 2.04E+00 | 3.52E−01 |
| 3473.631 | 7.27E−02 | 0.0674 | 0.0016 | 11.18 | 2.47E+00 | 4.21E−01 |
| 3506.323 | 7.20E−02 | 0.0693 | 0.0019 | 11.49 | 2.96E+00 | 5.00E−01 |
| 3538.793 | 7.13E−02 | 0.0715 | 0.0022 | 11.85 | 3.51E+00 | 5.86E−01 |
| 3571.123 | 7.07E−02 | 0.074 | 0.0025 | 12.27 | 4.12E+00 | 6.82E−01 |
| 3603.18 | 7.00E−02 | 0.0769 | 0.0028 | 12.74 | 4.79E+00 | 7.85E−01 |
| 3635.014 | 6.94E−02 | 0.0801 | 0.0032 | 13.27 | 5.53E+00 | 8.97E−01 |
| 3666.519 | 6.88E−02 | 0.0837 | 0.0036 | 13.87 | 6.33E+00 | 1.02E+00 |
| 3697.735 | 6.83E−02 | 0.0877 | 0.004 | 14.54 | 7.21E+00 | 1.15E+00 |
| 3728.588 | 6.77E−02 | 0.0922 | 0.0045 | 15.28 | 8.18E+00 | 1.29E+00 |
| 3759.178 | 6.71E−02 | 0.0971 | 0.0049 | 16.1 | 9.23E+00 | 1.44E+00 |
| 3789.413 | 6.66E−02 | 0.1025 | 0.0054 | 17 | 1.04E+01 | 1.61E+00 |
| 3819.359 | 6.61E−02 | 0.1084 | 0.0059 | 17.97 | 1.15E+01 | 1.78E+00 |
| 3849.106 | 6.56E−02 | 0.1149 | 0.0065 | 19.04 | 1.28E+01 | 1.95E+00 |

TABLE 30-continued

| Pressure [PSI] | Pore Diameter [μm] | Volume Intruded [cc/g] | Delta Volume [cc/g] | Volume Intruded % | Dv(d) [cc/(μm-g)] | dV/d(log d) [cc/g] |
|---|---|---|---|---|---|---|
| 3878.714 | 6.51E−02 | 0.1219 | 0.007 | 20.21 | 1.41E+01 | 2.13E+00 |
| 3908.091 | 6.46E−02 | 0.1295 | 0.0076 | 21.46 | 1.54E+01 | 2.32E+00 |
| 3937.336 | 6.41E−02 | 0.1376 | 0.0081 | 22.81 | 1.68E+01 | 2.50E+00 |
| 3966.383 | 6.36E−02 | 0.1463 | 0.0086 | 24.24 | 1.82E+01 | 2.69E+00 |
| 3995.29 | 6.32E−02 | 0.1554 | 0.0092 | 25.76 | 1.96E+01 | 2.87E+00 |
| 4024.148 | 6.27E−02 | 0.165 | 0.0096 | 27.36 | 2.09E+01 | 3.04E+00 |
| 4053.187 | 6.23E−02 | 0.1752 | 0.0102 | 29.04 | 2.21E+01 | 3.19E+00 |
| 4082.538 | 6.18E−02 | 0.186 | 0.0108 | 30.83 | 2.33E+01 | 3.34E+00 |
| 4112.509 | 6.14E−02 | 0.1974 | 0.0114 | 32.72 | 2.43E+01 | 3.46E+00 |
| 4143.305 | 6.09E−02 | 0.2094 | 0.012 | 34.71 | 2.52E+01 | 3.56E+00 |
| 4174.859 | 6.05E−02 | 0.2219 | 0.0125 | 36.78 | 2.60E+01 | 3.64E+00 |
| 4207.205 | 6.00E−02 | 0.2348 | 0.0129 | 38.91 | 2.66E+01 | 3.70E+00 |
| 4240.45 | 5.95E−02 | 0.248 | 0.0132 | 41.1 | 2.71E+01 | 3.73E+00 |
| 4274.618 | 5.90E−02 | 0.2614 | 0.0135 | 43.33 | 2.74E+01 | 3.73E+00 |
| 4309.801 | 5.86E−02 | 0.2751 | 0.0136 | 45.59 | 2.74E+01 | 3.71E+00 |
| 4346.081 | 5.81E−02 | 0.2888 | 0.0137 | 47.87 | 2.73E+01 | 3.67E+00 |
| 4383.45 | 5.76E−02 | 0.3026 | 0.0138 | 50.16 | 2.71E+01 | 3.60E+00 |
| 4421.511 | 5.71E−02 | 0.3162 | 0.0136 | 52.4 | 2.67E+01 | 3.51E+00 |
| 4460.001 | 5.66E−02 | 0.3293 | 0.0131 | 54.58 | 2.62E+01 | 3.41E+00 |
| 4498.516 | 5.61E−02 | 0.3418 | 0.0125 | 56.66 | 2.55E+01 | 3.29E+00 |
| 4536.627 | 5.56E−02 | 0.3536 | 0.0117 | 58.6 | 2.47E+01 | 3.17E+00 |
| 4574.07 | 5.52E−02 | 0.3645 | 0.0109 | 60.41 | 2.39E+01 | 3.03E+00 |
| 4610.845 | 5.47E−02 | 0.3745 | 0.0101 | 62.08 | 2.29E+01 | 2.88E+00 |
| 4646.943 | 5.43E−02 | 0.3838 | 0.0093 | 63.62 | 2.19E+01 | 2.73E+00 |
| 4682.366 | 5.39E−02 | 0.3923 | 0.0085 | 65.02 | 2.08E+01 | 2.58E+00 |
| 4717.078 | 5.35E−02 | 0.4 | 0.0077 | 66.31 | 1.98E+01 | 2.43E+00 |
| 4751.024 | 5.31E−02 | 0.407 | 0.007 | 67.47 | 1.88E+01 | 2.30E+00 |
| 4784.187 | 5.28E−02 | 0.4134 | 0.0063 | 68.52 | 1.79E+01 | 2.17E+00 |
| 4816.822 | 5.24E−02 | 0.4192 | 0.0058 | 69.48 | 1.70E+01 | 2.04E+00 |
| 4849.003 | 5.21E−02 | 0.4245 | 0.0053 | 70.36 | 1.62E+01 | 1.93E+00 |
| 4880.936 | 5.17E−02 | 0.4295 | 0.005 | 71.19 | 1.54E+01 | 1.83E+00 |
| 4912.844 | 5.14E−02 | 0.4342 | 0.0047 | 71.97 | 1.47E+01 | 1.74E+00 |
| 4945.009 | 5.10E−02 | 0.4388 | 0.0046 | 72.73 | 1.42E+01 | 1.66E+00 |
| 4977.677 | 5.07E−02 | 0.4433 | 0.0045 | 73.48 | 1.37E+01 | 1.60E+00 |
| 5010.823 | 5.04E−02 | 0.4477 | 0.0044 | 74.2 | 1.33E+01 | 1.54E+00 |
| 5044.381 | 5.00E−02 | 0.4519 | 0.0043 | 74.91 | 1.29E+01 | 1.49E+00 |
| 5078.369 | 4.97E−02 | 0.4561 | 0.0042 | 75.6 | 1.26E+01 | 1.44E+00 |
| 5112.784 | 4.94E−02 | 0.4601 | 0.0041 | 76.27 | 1.23E+01 | 1.40E+00 |
| 5147.662 | 4.90E−02 | 0.4641 | 0.004 | 76.93 | 1.21E+01 | 1.36E+00 |
| 5182.928 | 4.87E−02 | 0.468 | 0.0039 | 77.58 | 1.18E+01 | 1.33E+00 |
| 5218.664 | 4.84E−02 | 0.4719 | 0.0038 | 78.21 | 1.16E+01 | 1.29E+00 |
| 5254.811 | 4.80E−02 | 0.4756 | 0.0038 | 78.84 | 1.14E+01 | 1.26E+00 |
| 5291.38 | 4.77E−02 | 0.4793 | 0.0037 | 79.45 | 1.12E+01 | 1.23E+00 |
| 5328.254 | 4.74E−02 | 0.4829 | 0.0036 | 80.05 | 1.10E+01 | 1.20E+00 |
| 5364.905 | 4.70E−02 | 0.4864 | 0.0035 | 80.63 | 1.08E+01 | 1.17E+00 |
| 5401.358 | 4.67E−02 | 0.4898 | 0.0034 | 81.18 | 1.06E+01 | 1.15E+00 |
| 5437.671 | 4.64E−02 | 0.493 | 0.0032 | 81.72 | 1.04E+01 | 1.12E+00 |
| 5473.844 | 4.61E−02 | 0.4962 | 0.0031 | 82.24 | 1.03E+01 | 1.09E+00 |
| 5509.876 | 4.58E−02 | 0.4992 | 0.003 | 82.74 | 1.01E+01 | 1.06E+00 |
| 5545.727 | 4.55E−02 | 0.5021 | 0.0029 | 83.23 | 9.86E+00 | 1.04E+00 |
| 5581.446 | 4.52E−02 | 0.5049 | 0.0028 | 83.69 | 9.67E+00 | 1.01E+00 |
| 5616.984 | 4.49E−02 | 0.5076 | 0.0027 | 84.14 | 9.47E+00 | 9.81E−01 |
| 5652.333 | 4.47E−02 | 0.5102 | 0.0026 | 84.57 | 9.28E+00 | 9.55E−01 |
| 5687.556 | 4.44E−02 | 0.5127 | 0.0025 | 84.99 | 9.08E+00 | 9.28E−01 |
| 5723.003 | 4.41E−02 | 0.5151 | 0.0024 | 85.39 | 8.88E+00 | 9.03E−01 |
| 5758.929 | 4.38E−02 | 0.5175 | 0.0024 | 85.78 | 8.68E+00 | 8.77E−01 |
| 5795.291 | 4.36E−02 | 0.5198 | 0.0023 | 86.16 | 8.49E+00 | 8.53E−01 |
| 5832.107 | 4.33E−02 | 0.5221 | 0.0023 | 86.54 | 8.31E+00 | 8.29E−01 |
| 5869.632 | 4.30E−02 | 0.5243 | 0.0022 | 86.91 | 8.14E+00 | 8.07E−01 |
| 5907.875 | 4.27E−02 | 0.5265 | 0.0022 | 87.28 | 7.98E+00 | 7.86E−01 |
| 5946.827 | 4.24E−02 | 0.5287 | 0.0022 | 87.63 | 7.83E+00 | 7.66E−01 |
| 5986.464 | 4.22E−02 | 0.5308 | 0.0021 | 87.99 | 7.68E+00 | 7.47E−01 |
| 6026.81 | 4.19E−02 | 0.5329 | 0.0021 | 88.34 | 7.54E+00 | 7.28E−01 |
| 6067.939 | 4.16E−02 | 0.535 | 0.0021 | 88.68 | 7.40E+00 | 7.10E−01 |
| 6109.711 | 4.13E−02 | 0.5371 | 0.0021 | 89.03 | 7.27E+00 | 6.92E−01 |
| 6151.55 | 4.10E−02 | 0.5391 | 0.002 | 89.36 | 7.14E+00 | 6.75E−01 |
| 6193.76 | 4.08E−02 | 0.5411 | 0.002 | 89.68 | 7.02E+00 | 6.59E−01 |
| 6236.678 | 4.05E−02 | 0.543 | 0.0019 | 90 | 6.89E+00 | 6.43E−01 |
| 6280.258 | 4.02E−02 | 0.5449 | 0.0019 | 90.32 | 6.76E+00 | 6.26E−01 |
| 6323.952 | 3.99E−02 | 0.5467 | 0.0018 | 90.62 | 6.62E+00 | 6.10E−01 |
| 6368.05 | 3.96E−02 | 0.5485 | 0.0018 | 90.92 | 6.48E+00 | 5.92E−01 |
| 6412.882 | 3.94E−02 | 0.5503 | 0.0018 | 91.21 | 6.34E+00 | 5.76E−01 |
| 6458.449 | 3.91E−02 | 0.552 | 0.0017 | 91.5 | 6.21E+00 | 5.59E−01 |
| 6504.766 | 3.88E−02 | 0.5537 | 0.0017 | 91.77 | 6.07E+00 | 5.43E−01 |
| 6551.783 | 3.85E−02 | 0.5553 | 0.0016 | 92.05 | 5.93E+00 | 5.27E−01 |
| 6599.593 | 3.82E−02 | 0.5569 | 0.0016 | 92.31 | 5.80E+00 | 5.11E−01 |

TABLE 30-continued

| Pressure [PSI] | Pore Diameter [µm] | Volume Intruded [cc/g] | Delta Volume [cc/g] | Volume Intruded % | Dv(d) [cc/(µm-g)] | dV/d(log d) [cc/g] |
|---|---|---|---|---|---|---|
| 6648.764 | 3.80E−02 | 0.5585 | 0.0016 | 92.57 | 5.66E+00 | 4.95E−01 |
| 6699.023 | 3.77E−02 | 0.5601 | 0.0016 | 92.83 | 5.52E+00 | 4.79E−01 |
| 6749.752 | 3.74E−02 | 0.5616 | 0.0015 | 93.08 | 5.39E+00 | 4.64E−01 |
| 6801 | 3.71E−02 | 0.563 | 0.0015 | 93.33 | 5.26E+00 | 4.50E−01 |
| 6853.338 | 3.68E−02 | 0.5645 | 0.0015 | 93.57 | 5.13E+00 | 4.36E−01 |
| 6906.451 | 3.65E−02 | 0.5659 | 0.0014 | 93.8 | 5.02E+00 | 4.23E−01 |
| 6959.746 | 3.63E−02 | 0.5673 | 0.0014 | 94.03 | 4.89E+00 | 4.09E−01 |
| 7013.229 | 3.60E−02 | 0.5686 | 0.0013 | 94.24 | 4.76E+00 | 3.95E−01 |
| 7067.2 | 3.57E−02 | 0.5698 | 0.0013 | 94.45 | 4.64E+00 | 3.82E−01 |
| 7121.97 | 3.54E−02 | 0.5711 | 0.0012 | 94.66 | 4.51E+00 | 3.68E−01 |
| 7177.821 | 3.52E−02 | 0.5723 | 0.0012 | 94.86 | 4.38E+00 | 3.55E−01 |
| 7234.513 | 3.49E−02 | 0.5735 | 0.0012 | 95.05 | 4.26E+00 | 3.42E−01 |
| 7292.045 | 3.46E−02 | 0.5746 | 0.0011 | 95.24 | 4.14E+00 | 3.30E−01 |
| 7351.047 | 3.43E−02 | 0.5757 | 0.0011 | 95.42 | 4.01E+00 | 3.18E−01 |
| 7411.772 | 3.41E−02 | 0.5768 | 0.0011 | 95.6 | 3.90E+00 | 3.06E−01 |
| 7473.949 | 3.38E−02 | 0.5778 | 0.0011 | 95.78 | 3.78E+00 | 2.94E−01 |
| 7537.659 | 3.35E−02 | 0.5789 | 0.001 | 95.95 | 3.66E+00 | 2.83E−01 |
| 7603.497 | 3.32E−02 | 0.5799 | 0.001 | 96.12 | 3.55E+00 | 2.72E−01 |
| 7671.785 | 3.29E−02 | 0.5809 | 0.001 | 96.28 | 3.45E+00 | 2.62E−01 |
| 7742.192 | 3.26E−02 | 0.5819 | 0.001 | 96.45 | 3.34E+00 | 2.51E−01 |
| 7814.463 | 3.23E−02 | 0.5828 | 0.001 | 96.61 | 3.24E+00 | 2.42E−01 |
| 7888.302 | 3.20E−02 | 0.5838 | 0.0009 | 96.77 | 3.14E+00 | 2.32E−01 |
| 7963.633 | 3.17E−02 | 0.5847 | 0.0009 | 96.92 | 3.04E+00 | 2.22E−01 |
| 8040.489 | 3.14E−02 | 0.5856 | 0.0009 | 97.07 | 2.93E+00 | 2.12E−01 |
| 8118.533 | 3.11E−02 | 0.5865 | 0.0009 | 97.21 | 2.82E+00 | 2.02E−01 |
| 8197.51 | 3.08E−02 | 0.5873 | 0.0008 | 97.34 | 2.71E+00 | 1.92E−01 |
| 8284.824 | 3.05E−02 | 0.5881 | 0.0008 | 97.49 | 2.60E+00 | 1.82E−01 |
| 8380.518 | 3.01E−02 | 0.589 | 0.0009 | 97.63 | 2.48E+00 | 1.72E−01 |
| 8484.352 | 2.98E−02 | 0.5898 | 0.0009 | 97.77 | 2.36E+00 | 1.62E−01 |
| 8596.11 | 2.94E−02 | 0.5907 | 0.0009 | 97.91 | 2.24E+00 | 1.52E−01 |
| 8715.813 | 2.90E−02 | 0.5915 | 0.0008 | 98.05 | 2.12E+00 | 1.41E−01 |
| 8843.548 | 2.85E−02 | 0.5924 | 0.0008 | 98.19 | 1.98E+00 | 1.30E−01 |
| 8987.074 | 2.81E−02 | 0.5932 | 0.0008 | 98.33 | 1.81E+00 | 1.17E−01 |
| 9146.553 | 2.76E−02 | 0.5941 | 0.0008 | 98.47 | 1.61E+00 | 1.02E−01 |
| 9329.939 | 2.71E−02 | 0.5949 | 0.0008 | 98.61 | 1.43E+00 | 8.77E−02 |
| 9545.491 | 2.64E−02 | 0.5958 | 0.0009 | 98.75 | 1.25E+00 | 7.47E−02 |
| 9801.678 | 2.58E−02 | 0.5966 | 0.0009 | 98.89 | 1.08E+00 | 6.27E−02 |
| 10275.9 | 2.46E−02 | 0.5974 | 0.0008 | 99.03 | 9.31E−01 | 5.18E−02 |
| 13869.13 | 1.82E−02 | 0.5982 | 0.0008 | 99.16 | 1.05E+00 | 4.17E−02 |
| 17913.18 | 1.41E−02 | 0.5989 | 0.0007 | 99.28 | 1.34E+00 | 3.22E−02 |
| 22424.16 | 1.13E−02 | 0.5997 | 0.0007 | 99.4 | 1.49E+00 | 2.39E−02 |
| 26977.73 | 9.36E−03 | 0.6003 | 0.0007 | 99.51 | 1.39E+00 | 1.77E−02 |
| 30811.12 | 8.19E−03 | 0.6011 | 0.0007 | 99.63 | 9.84E−01 | 1.20E−02 |
| 36676.23 | 6.88E−03 | 0.6018 | 0.0007 | 99.75 | 6.35E−01 | 8.95E−03 |
| 46884.64 | 5.38E−03 | 0.6024 | 0.0007 | 99.85 | 9.09E−01 | 9.32E−03 |
| 57328.51 | 4.40E−03 | 0.603 | 0.0006 | 99.95 | 1.33E+00 | 9.69E−03 |
| 59520.29 | 4.24E−03 | 0.6033 | 0.0003 | 100 | 1.58E+00 | 1.01E−02 |

Samples of the extrudate were also analyzed for various physical properties by nitrogen adsorption (BJH method). Shaped carbon black extrudates were added to a tared Tristar II sample holder and placed under vacuum at 120 overnight to remove any volatiles. The mass of the carbon support after this pretreatment was 154.7 mg. Nitrogen isotherm data was collected at 77.3 K. Data was collected using a TriStar 113020 instrument from micromeritics and analyzed using vendor supplied software (version 3.02). For the BJH analysis of all desorption data for pore sizes between 1.7 and 300 nm, a Faas correction was applied and the following Halsey thickness equation was used with the default parameters: t=3.54*[(−5.000/ln(p/p))^0.333]. The BET specific surface area was determined to be 178.5 m²/g. Table 31 presents the nitrogen isotherm data collected during analysis. Table 32 presents t-Plot data. Table 33 presents BJH desorption pore distribution.

TABLE 31

| Relative Pressure (p/p°) | Absolute Pressure (kPa) | Quantity Adsorbed (mmol/g) | Elapsed Time (h:min) | Saturation Pressure (kPa) |
|---|---|---|---|---|
| | | | 02:31 | 100.3624890 |
| 0.000974927 | 0.0977043 | 1.40903 | 04:08 | 100.2169931 |
| 0.001937495 | 0.1941442 | 1.51972 | 04:20 | 100.2037130 |
| 0.002972380 | 0.2977996 | 1.59005 | 04:29 | 100.1889437 |
| 0.004036246 | 0.4044198 | 1.63889 | 04:35 | 100.1970159 |
| 0.005021868 | 0.5031704 | 1.67570 | 04:41 | 100.1958604 |
| 0.005866942 | 0.5877733 | 1.70299 | 04:52 | 100.1839311 |
| 0.007016406 | 0.7028952 | 1.73138 | 04:58 | 100.1788127 |
| 0.007789426 | 0.7803261 | 1.74898 | 05:04 | 100.1776083 |
| 0.009001330 | 0.9016390 | 1.77222 | 05:08 | 100.1673064 |
| 0.009822558 | 0.9839312 | 1.78733 | 05:14 | 100.1705695 |
| 0.048704151 | 4.8789781 | 2.04400 | 05:27 | 100.1758181 |
| 0.103826751 | 10.4014704 | 2.18728 | 05:31 | 100.1810260 |
| 0.145225131 | 14.5482342 | 2.26876 | 05:34 | 100.1771120 |
| 0.192754485 | 19.3103468 | 2.35357 | 05:37 | 100.1810504 |
| 0.240741154 | 24.1180641 | 2.43457 | 05:39 | 100.1825558 |

TABLE 31-continued

| Relative Pressure (p/p°) | Absolute Pressure (kPa) | Quantity Adsorbed (mmol/g) | Elapsed Time (h:min) | Saturation Pressure (kPa) |
|---|---|---|---|---|
| 0.288102609 | 28.8628674 | 2.51259 | 05:42 | 100.1825965 |
| 0.335010554 | 33.5594956 | 2.59087 | 05:44 | 100.1744429 |
| 0.380104756 | 38.0768905 | 2.66742 | 05:47 | 100.1747277 |
| 0.404476842 | 40.5178605 | 2.70787 | 05:49 | 100.1734990 |
| 0.428597203 | 42.9339140 | 2.75040 | 05:52 | 100.1731084 |
| 0.473408523 | 47.4241708 | 2.83157 | 05:55 | 100.1759971 |
| 0.521271957 | 52.2160833 | 2.92721 | 05:57 | 100.1705207 |
| 0.568655161 | 56.9662919 | 3.03166 | 06:00 | 100.1772177 |
| 0.615350087 | 61.6399687 | 3.15330 | 06:03 | 100.1705695 |
| 0.662477027 | 66.3617739 | 3.30038 | 06:07 | 100.1721889 |
| 0.709351611 | 71.0575517 | 3.47868 | 06:10 | 100.1725388 |
| 0.756040447 | 75.7337958 | 3.70141 | 06:14 | 100.1716192 |
| 0.802282304 | 80.3619482 | 3.99350 | 06:19 | 100.1666717 |
| 0.857515027 | 85.8876018 | 4.48845 | 06:28 | 100.1587134 |
| 0.902473903 | 90.3738225 | 5.19371 | 06:37 | 100.1400951 |
| 0.943716713 | 94.4849518 | 6.49700 | 06:47 | 100.1200366 |
| 0.988640202 | 98.9655414 | 11.92837 | 07:19 | 100.1026877 |
| 0.984326480 | 98.5353602 | 11.76369 | 07:24 | 100.1043477 |
| 0.979467556 | 98.0580230 | 11.47040 | 07:29 | 100.1135999 |
| 0.975787847 | 97.6842744 | 11.14086 | 07:35 | 100.1081072 |
| 0.971289083 | 97.2176379 | 10.67770 | 07:42 | 100.0913524 |
| 0.961833993 | 96.2645340 | 9.38756 | 07:53 | 100.0843543 |
| 0.939899759 | 94.0597995 | 6.85730 | 08:12 | 100.0742884 |
| 0.925218349 | 92.5791917 | 6.15428 | 08:19 | 100.0619928 |
| 0.898179403 | 89.8688264 | 5.46669 | 08:28 | 100.0566547 |
| 0.862566086 | 86.2997425 | 5.06268 | 08:34 | 100.0500065 |
| 0.821872624 | 82.2334174 | 4.83462 | 08:37 | 100.0561583 |
| 0.764130128 | 76.4539353 | 4.66144 | 08:41 | 100.0535544 |
| 0.682580833 | 68.2902005 | 4.51865 | 08:44 | 100.0470526 |
| 0.610060063 | 61.0364090 | 4.42836 | 08:47 | 100.0498356 |
| 0.475415888 | 47.5380734 | 3.09876 | 09:18 | 99.9926056 |
| 0.317164437 | 31.7113989 | 2.51882 | 09:22 | 99.9840939 |

TABLE 32

Micropore Volume: 0.044058 $cm^3/g$ Micropore Area: 91.6410 $m^2/g$
External Surface Area: 86.8680 $m^2/g$
Slope: 0.250556 ± 0.001644 mmol/g · Å
Y-Intercept: 1.270784 ± 0.010200 mmol/g
Correlation Coefficient: 0.999742 Surface Area Correction Factor: 1.000
Density Conversion Factor: 0.0015468
Total Surface Area (BET): 178.5090 $m^2/g$
Thickness Range: 4.0000 Å to 9.0000 Å
Thickness Equation: Harkins and Jura
Thickness Curve
$t = [13.99/(0.034 - \log(p/p°))]^{0.5}$

| Relative Pressure (p/p°) | Statistical Thickness (Å) | Quantity Adsorbed (mmol/g) | Fitted |
|---|---|---|---|
| 0.000974927 | 2.1434 | 1.40903 | |
| 0.001937495 | 2.2568 | 1.51972 | |
| 0.002972380 | 2.3373 | 1.59005 | |
| 0.004036246 | 2.4004 | 1.63889 | |
| 0.005021868 | 2.4487 | 1.67570 | |
| 0.005866942 | 2.4850 | 1.70299 | |
| 0.007016406 | 2.5287 | 1.73138 | |
| 0.007789426 | 2.5553 | 1.74898 | |
| 0.009001330 | 2.5936 | 1.77222 | |
| 0.009822558 | 2.6176 | 1.78733 | |
| 0.048704151 | 3.2234 | 2.04400 | |
| 0.103826751 | 3.7077 | 2.18728 | |
| 0.145225131 | 4.0055 | 2.26876 | * |
| 0.192754485 | 4.3218 | 2.35357 | * |
| 0.240741154 | 4.6306 | 2.43457 | * |
| 0.288102609 | 4.9349 | 2.51259 | * |
| 0.335010554 | 5.2429 | 2.59087 | * |
| 0.380104756 | 5.5505 | 2.66742 | * |
| 0.404476842 | 5.7232 | 2.70787 | * |
| 0.428597203 | 5.8996 | 2.75040 | * |
| 0.473408523 | 6.2446 | 2.83157 | * |
| 0.521271957 | 6.6439 | 2.92721 | * |
| 0.568655161 | 7.0793 | 3.03166 | * |
| 0.615350087 | 7.5585 | 3.15330 | * |
| 0.662477027 | 8.1076 | 3.30038 | * |
| 0.709351611 | 8.7402 | 3.47868 | * |
| 0.756040447 | 9.4865 | 3.70141 | |
| 0.802282304 | 10.3869 | 3.99350 | |
| 0.857515027 | 11.7833 | 4.48845 | |
| 0.902473903 | 13.3442 | 5.19371 | |
| 0.943716713 | 15.3780 | 6.49700 | |
| 0.988640202 | 18.9491 | 11.92837 | |

TABLE 33

Faas Correction Halsey
$t = 3.54 [-5/\ln(p/p°)]^{0.333}$
Width Range: 17.000 Å to 3,000.000 Å
Adsorbate Property Factor: 9.53000 Å
Density Conversion Factor: 0.0015468
Fraction of Pores Open at Both Ends: 0.00

| Pore Width Range (Å) | Average width (nm) | Incremental Pore Volume ($cm^3/g$) | Cumulative Pore Volume ($cm^3/g$) | Normalized Cumulative Pore Volume | Incremental Pore Area ($m^2/g$) | Cumulative Pore Area ($m^2/g$) |
|---|---|---|---|---|---|---|
| 1721.4-1254.1 | 141.47 | 0.01 | 0.006114 | 0.02 | 0.173 | 0.17 |
| 1254.1-962.1 | 106.94 | 0.011009 | 0.02 | 0.04 | 0.412 | 0.585 |
| 962.1-818.7 | 87.86 | 0.012498 | 0.03 | 0.07 | 0.569 | 1.154 |
| 818.7-693.0 | 74.51 | 0.017722 | 0.05 | 0.12 | 0.951 | 2.105 |
| 693.0-524.9 | 58.53 | 0.050203 | 0.10 | 0.24 | 3.431 | 5.536 |
| 524.9-337.5 | 39.06 | 0.101324 | 0.20 | 0.50 | 10.375 | 15.911 |
| 337.5-273.0 | 29.81 | 0.027624 | 0.23 | 0.57 | 3.707 | 19.618 |
| 273.0-202.3 | 22.67 | 0.026721 | 0.25 | 0.63 | 4.715 | 24.333 |
| 202.3-151.2 | 16.89 | 0.014713 | 0.27 | 0.67 | 3.484 | 27.817 |
| 151.2-117.4 | 12.97 | 0.007358 | 0.28 | 0.69 | 2.270 | 30.086 |
| 117.4-89.0 | 9.89 | 0.004636 | 0.28 | 0.70 | 1.875 | 31.961 |
| 89.0-66.0 | 7.37 | 0.003069 | 0.28 | 0.71 | 1.666 | 33.627 |
| 66.0-53.3 | 5.81 | 0.001758 | 0.28 | 0.71 | 1.211 | 34.838 |

TABLE 33-continued

Faas Correction Halsey
t = 3.54 [−5/ln(p/p°)] ^ 0.333
Width Range: 17.000 Å to 3,000.000 Å
Adsorbate Property Factor: 9.53000 Å
Density Conversion Factor: 0.0015468
Fraction of Pores Open at Both Ends: 0.00

| Pore Width Range (Å) | Average width (nm) | Incremental Pore Volume (cm³/g) | Cumulative Pore Volume (cm³/g) | Normalized Cumulative Pore Volume | Incremental Pore Area (m²/g) | Cumulative Pore Area (m²/g) |
|---|---|---|---|---|---|---|
| 53.3-38.4 | 4.30 | 0.086837 | 0.37 | 0.93 | 80.736 | 115.57 |
| 38.4-27.6 | 3.08 | 0.028668 | 0.40 | 1.00 | 37.198 | 152.77 |

Example 26. Preparation of a Nickel-Rhenium Catalyst

Approximately 8.87 grams of nickel nitrate hexahydrate, 1.79 g of perrhenic acid and nitric acid were added to water and brought to a volume of 5.81 mL. Carbon extrudate prepared in Example 25 was poured into a small tumbler and the solution containing the nickel and rhenium precursors was sprayed gradually onto the carbon with a Sonaer nozzle and syringe pump. The beaker and spraying device were rinsed to obtain any residual metal solution and bring the total volume to 9.96 mL. The catalyst was allowed to spin for approximately 30 minutes under air flow, then vacuum dried overnight at 80° C. and 75 torr in a furnace.

A second catalyst was prepared using the same method, except that nitric acid was not added during the metal deposition.

Example 27. Hydrogenolysis of Glycerol

The first nickel-rhenium catalyst (w/nitric acid addition during metal deposition) prepared in Example 26 was evaluated for hydrogenolysis of glycerol. The catalyst was loaded into a 30 cc reactor. The reactor was then purged with hydrogen at a flow rate of 100 ml/min. Following purging of the reactor, the reactor was pressurized to 1800 psi with hydrogen. Subsequently, hydrogen and glycerol supplied to the reactor as a 40 wt. % solution with sodium hydroxide co-catalyst. Details of the evaluation are provided in Table 34. The catalyst was evaluated over various reaction temperatures, various hydrogen flowrates and various co-catalyst concentrations. Periodic liquid samples were analyzed by HPLC and GC. The pH of all samples was between 7.5-9.9. Propylene glycol yield and selectivity as well as glycerol conversion was enhanced with this catalyst.

TABLE 34

| Time on Stream (h) | Jacket Temp. (° C.) | $H_2$ Pressure (psi) | LHSV | $H_2$ Flow (ml/min) | NaOH Co-Catalyst Conc. (M) | Propylene Glycol Yield (%) | Propylene Glycol Selectivity (%) | Glycerol Conversion (%) |
|---|---|---|---|---|---|---|---|---|
| 16 | 205.0 | 1798.26 | 0.7 | 1997.43 | 0.4 | 54.9 | 84.2 | 78.9 |
| 40 | 205.0 | 1800.67 | 0.7 | 1996.76 | 0.4 | 59.9 | 87.2 | 83.1 |
| 64 | 205.0 | 1799.39 | 0.7 | 2995.62 | 0.4 | 72.4 | 88.4 | 99.1 |
| 136 | 205.0 | 1799.85 | 0.7 | 2996.03 | 0.4 | 76.4 | 92.4 | 100.0 |
| 160 | 205.0 | 1800.13 | 0.7 | 2994.40 | 0.4 | 77.7 | 94.0 | 100.0 |
| 184 | 205.0 | 1800.21 | 0.7 | 2996.06 | 0.3 | 79.6 | 96.4 | 100.0 |
| 208 | 205.0 | 1800.96 | 0.7 | 2996.33 | 0.3 | 77.3 | 93.6 | 100.0 |
| 214 | 202.5 | 1800.00 | 0.7 | 2996.33 | 0.3 | 79.5 | 96.4 | 99.7 |
| 232 | 202.5 | 1800.00 | 0.7 | 2996.33 | 0.3 | 77.3 | 93.6 | 99.9 |
| 238 | 200.0 | 1800.00 | 0.7 | 2996.33 | 0.3 | 80.0 | 97.3 | 99.5 |
| 310 | 200.0 | 1800.00 | 0.7 | 2996.33 | 0.3 | 80.6 | 98.4 | 99.1 |
| 334 | 200.0 | 1800.00 | 0.7 | 2996.33 | 0.3 | 80.0 | 97.6 | 99.2 |
| 358 | 200.0 | 1800.00 | 0.7 | 2996.33 | 0.3 | 79.6 | 97.2 | 99.1 |
| 382 | 200.0 | 1800.00 | 0.7 | 2996.33 | 0.3 | 80.0 | 97.7 | 99.1 |
| 406 | 200.0 | 1800.00 | 0.7 | 2996.33 | 0.3 | 80.0 | 97.8 | 98.9 |
| 478 | 200.0 | 1800.00 | 0.7 | 2996.33 | 0.3 | 79.7 | 97.2 | 99.2 |
| 526 | 200.0 | 1800.00 | 0.7 | 2996.33 | 0.3 | 80.1 | 97.5 | 99.4 |
| 550 | 200.0 | 1800.00 | 0.7 | 2996.33 | 0.3 | 79.1 | 96.5 | 99.2 |

Select samples from the evaluation above were analyzed for various products (EG=ethyleneglycol; PG=propyleneaglycol) and, byproducts (BDO=butanediol). The results of this analysis are shown in Table 35. These samples were also analyzed for metals of the catalyst, where the presence of which would indicate leaching from the catalyst. The results show that nickel and rhenium were not detected above the limits of detection (0.5 mg/kg). Thus, no leaching of catalyst metals was observed in this evaluation.

TABLE 35

| Sample | EG (mg/kg) | PG (mg/kg) | 2,3-BDO (mg/kg) | Lactic Acid (mg/kg) | Glycolic acid (mg/kg) | 1,2-BDO (mg/kg) | 1,3-BDO (mg/kg) | 1,4-BDO (mg/kg) | Glycerol (mg/kg) |
|---|---|---|---|---|---|---|---|---|---|
| @238 | 12670 | 316824 | 1646 | 6005 | 300 | 225 | <100 | 152 | 2057 |
| @310 | 12736 | 316437 | 1444 | 5043 | 206 | 244 | <100 | 114 | 3331 |
| @334 | 12710 | 317836 | 1469 | 5004 | 222 | 241 | <100 | 145 | 3146 |

The second nickel-rhenium catalyst prepared in Example 26 was also evaluated for glycerol hydrogenolysis. Details of the evaluation are provided in Table 36. Periodic liquid samples were analyzed by HPLC and GC. Conversion increased significantly with increased hydrogen flow.

TABLE 36

| Time on Stream (h) | Jacket Temp. (° C.) | $H_2$ Pressure (psi) | LHSV | $H_2$ Flow (ml/min) | NaOH Co-Catalyst Conc. (M) | Propylene Glycol Yield (%) | Propylene Glycol Selectivity (%) | Glycerol Conversion (%) |
|---|---|---|---|---|---|---|---|---|
| 16 | 205.14 | 1799.66 | 0.7 | 1995.61 | 0.5 | 51.33 | 87.50 | 71.00 |
| 40 | 195.17 | 1798.79 | 0.7 | 1995.41 | 0.5 | 43.18 | 91.48 | 57.13 |
| 64 | 200.25 | 1800.06 | 0.7 | 1995.56 | 0.5 | 51.00 | 88.99 | 69.36 |
| 88 | 200.10 | 1801.38 | 0.7 | 1995.15 | 0.7 | 56.07 | 85.81 | 79.08 |
| 136 | 200.06 | 1801.19 | 0.7 | 1995.55 | 0.7 | 62.61 | 88.66 | 85.47 |
| 160 | 195.18 | 1801.43 | 0.7 | 1998.25 | 0.7 | 59.47 | 91.36 | 78.78 |
| 184 | 200.17 | 1800.07 | 0.7 | 2994.44 | 0.7 | 73.37 | 90.21 | 98.44 |
| 208 | 200.06 | 1799.45 | 0.7 | 2994.84 | 0.5 | 74.39 | 93.02 | 96.79 |
| 232 | 202.39 | 1800.28 | 0.7 | 2994.11 | 0.5 | 75.84 | 93.57 | 98.09 |
| 328 | 202.49 | 1800.25 | 0.7 | 2994.54 | 0.5 | 76.86 | 94.04 | 98.92 |
| 352 | 202.68 | 1799.63 | 0.7 | 2994.34 | 0.4 | 74.64 | 92.54 | 97.62 |
| 368 | 205.30 | 1800.00 | 0.7 | 2994.47 | 0.4 | 69.88 | 91.08 | 92.86 |
| 392 | 205.32 | 1799.86 | 0.7 | 2994.55 | 0.4 | 70.02 | 91.58 | 92.54 |
| 416 | 203.33 | 1799.85 | 0.7 | 2994.05 | 0.5 | 68.62 | 94.04 | 88.31 |
| 440 | 205.34 | 1799.69 | 0.7 | 2973.49 | 0.5 | 71.22 | 93.49 | 92.20 |
| 464 | 207.31 | 1800.11 | 0.7 | 2993.57 | 0.5 | 72.38 | 91.73 | 95.50 |
| 488 | 209.31 | 1799.77 | 0.7 | 2997.04 | 0.5 | 71.20 | 88.73 | 97.11 |
| 512 | 209.19 | 1800.04 | 0.7 | 2995.18 | 0.5 | 75.02 | 92.26 | 98.41 |
| 584 | 209.47 | 1799.75 | 0.7 | 2996.31 | 0.5 | 73.90 | 90.33 | 99.00 |
| 608 | 207.39 | 1799.98 | 0.7 | 2993.94 | 0.5 | 73.97 | 91.72 | 97.59 |

Example 28. Analysis of Ni—Re on Carbon Black Extrudate

The Ni—Re catalysts prepared in Example 26 were analyzed using energy dispersive X-ray spectroscopy (EDX) with scanning electron microscopy (SEM).

Figure 14:
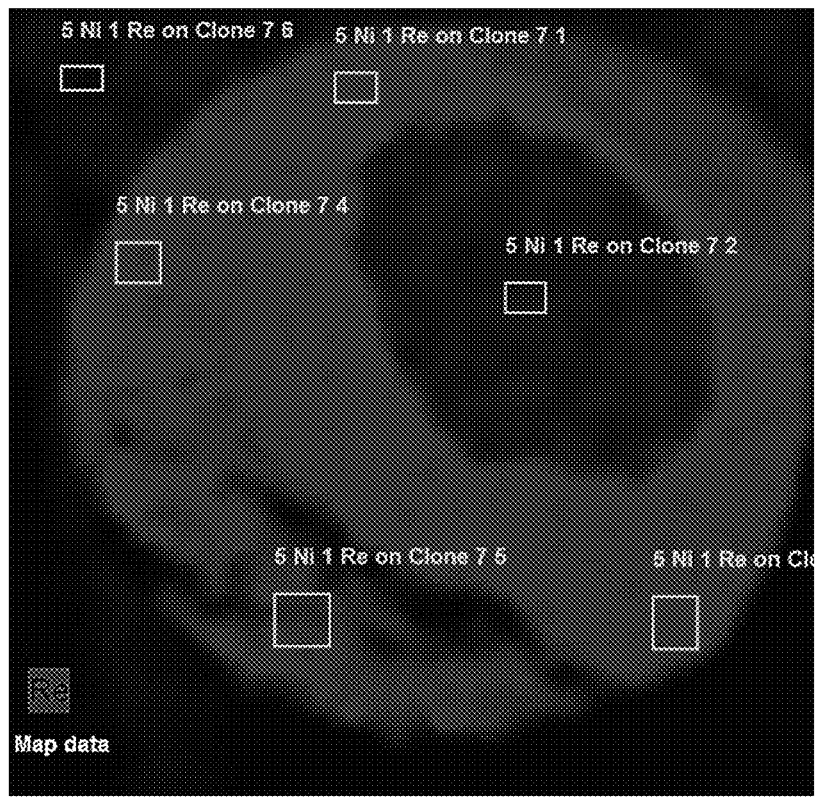
FIG. 14 presents a SEM image of a Ni—Re on carbon black extrudate catalyst (without nitric acid addition).
Figure 14:
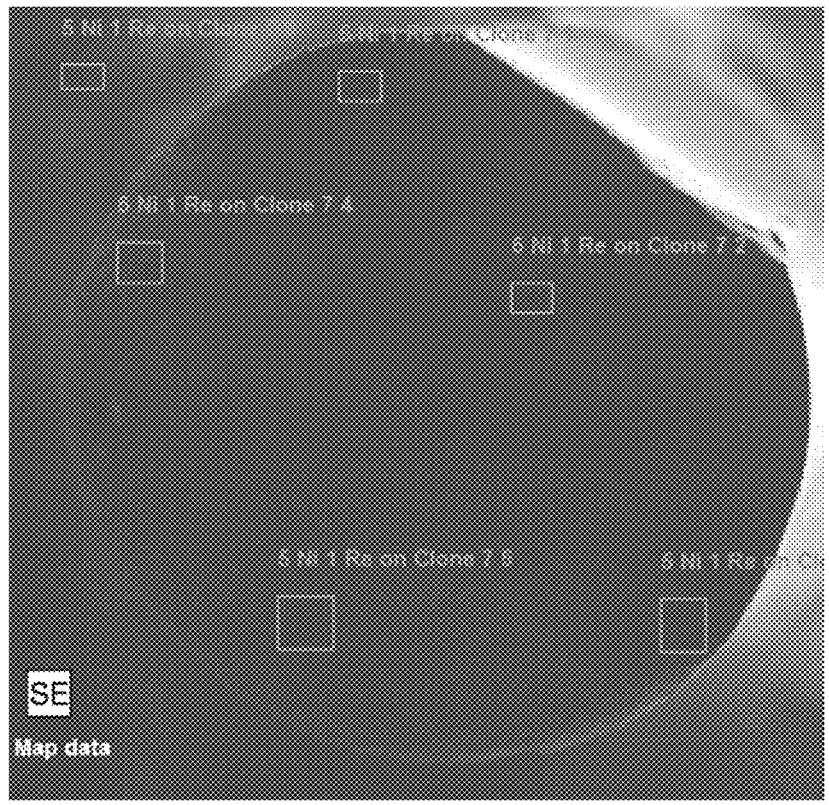

FIG. 14 presents a SEM image of the Ni—Re on carbon black extrudate catalyst Nitric acid was not added during nickel deposition for this catalyst. FIG. 15 presents the results of EDX analysis for this catalyst. The EDX results show that nickel reaches inner regions of the extrudate support (see Sample 2).

Figure 16:
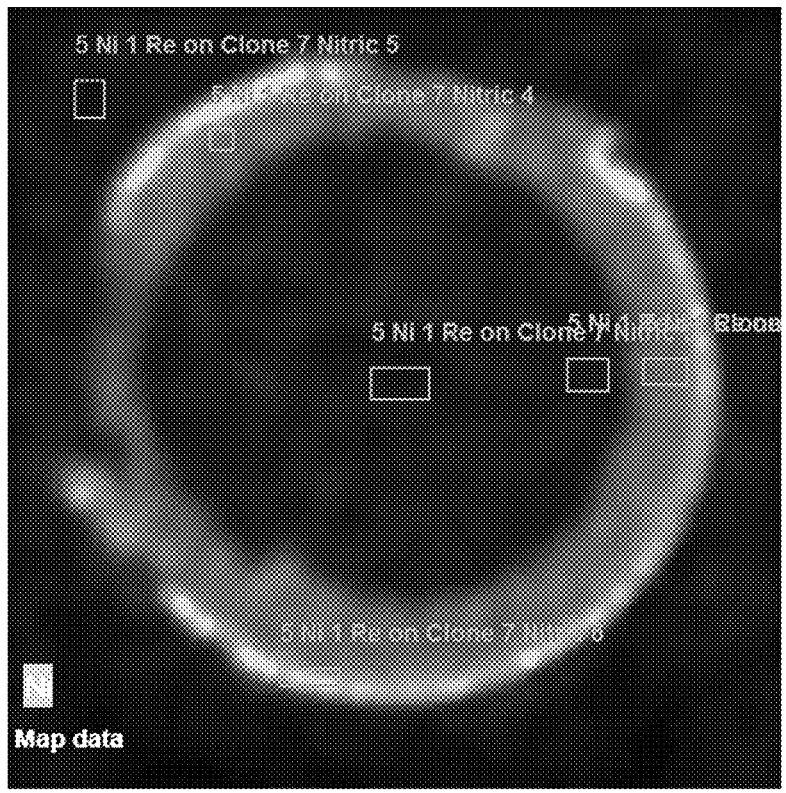
FIG. 16 presents a SEM image of a Ni—Re on carbon black extrudate catalyst (with nitric acid addition).
Figure 16:
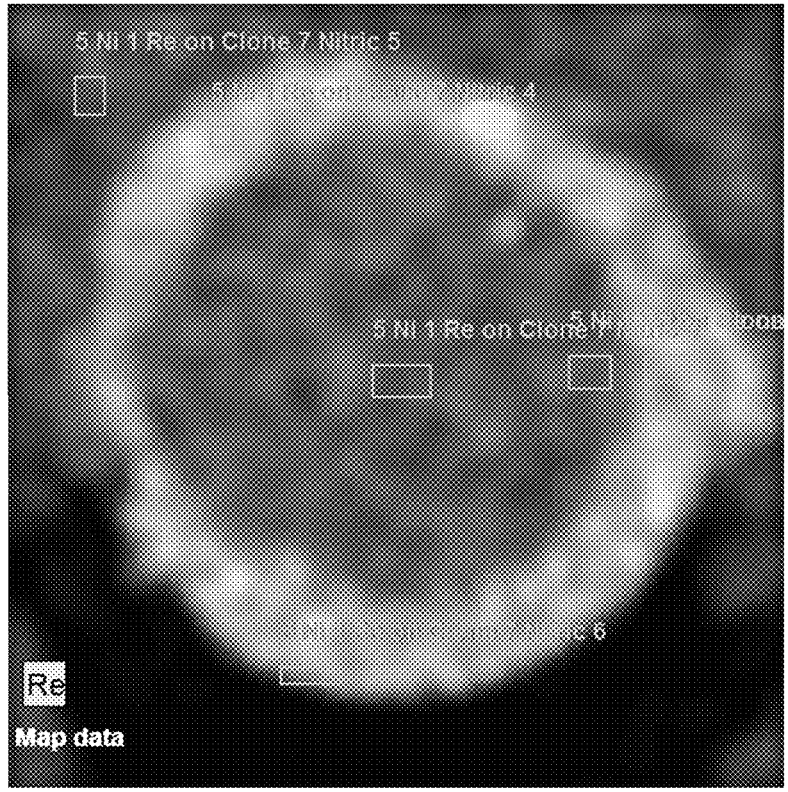

FIG. 16 presents a SEM image of the second Ni—Re on carbon black extrudate catalyst. Nitric acid was added during nickel deposition for this catalyst. FIG. 17 presents the results of EDX analysis for this catalyst. The EDX results show that nickel did not deposit on inner regions of the extrudate support (see Samples 2 and 3). Instead, nickel concentrated as a shell on the outer regions of the catalyst.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions, methods, and processes without departing from the scope of the invention, it is intended that all matter contained in the above description and shown in the accompanying drawing[s] shall be interpreted as illustrative and not in a limiting sense.

Having described the invention in detail, it will be apparent that modifications and variations are possible without departing from the scope of the invention defined in the appended claims.

What is claimed is:

1. A process for the hydrogenolysis of glycerol comprising feeding a feed composition comprising glycerol to a reaction zone and reacting the glycerol with hydrogen in the presence of a catalyst composition in the reaction zone to form a reaction product comprising propylene glycol and/or ethylene glycol, wherein the catalyst composition comprises a shaped porous carbon product as a catalyst support and a catalytically active component or precursor thereof, wherein the shaped porous carbon product comprises:
  (a) carbon black and
  (b) a carbonized binder comprising a carbonization product of a water soluble organic binder and wherein the shaped porous carbon product has a BET specific surface area from about 20 m$^2$/g to about 500 m$^2$/g, a mean pore diameter greater than about 5 nm, a specific pore volume greater than about 0.1 cm$^3$/g, a carbon black content of at least about 35 wt. %, and a carbonized binder content from about 20 wt. % to about 50 wt. %, and
  wherein the shaped porous carbon product has a radial piece crush strength greater than about 4.4 N/mm (1 lb/mm) and/or a mechanical piece crush strength greater than about 22 N (5 lbs).

2. The process of claim 1 wherein the catalytically active component comprises a metal selected from the group consisting of chromium, cobalt, nickel, copper, zinc, ruthenium, rhodium, palladium, silver, rhenium, osmium, iridium, platinum, gold, and any combination thereof.

3. A process for the hydrogenolysis of glycerol comprising feeding a feed composition comprising glycerol to a reaction zone and reacting the glycerol with hydrogen in the presence of a catalyst composition in the reaction zone to form a reaction product comprising propylene glycol and/or ethylene glycol, wherein the catalyst composition comprises a catalytically active component comprising a metal selected from the group consisting of chromium, cobalt, nickel, copper, zinc, ruthenium, rhodium, palladium, silver, rhenium, osmium, iridium, platinum, gold, and any combination thereof and a catalyst support comprising a shaped porous carbon product comprising carbon black.

4. The process of claim 3 wherein about 10% or less of the pore volume of the shaped porous carbon product as measured by mercury porosimetry is attributable to pores having a mean pore diameter of about 100 nm or greater.

5. The process of claim 3 wherein from about 0.1% to about 10% of the pore volume of the shaped porous carbon product as measured by mercury porosimetry is attributable to pores having a mean pore diameter of about 100 nm or greater.

6. The process of claim 3 wherein the partial pressure of hydrogen in reaction zone is from about 2.1 MPa (300 psi) to about 13.8 MPa (2000 psi).

7. The process of claim 3 wherein the yield of propylene glycol is at least about 50%.

8. The process of claim 3 wherein the catalytically active component comprises rhenium.

9. The process of claim 3 wherein the catalytically active component comprises nickel.

10. The process of claim 3 wherein the catalytically active component comprises copper.

11. The process of claim 3 wherein the catalytically active component comprises a combination of metals selected from the group consisting of nickel and rhenium, copper and rhenium, and cobalt and rhenium.

12. The process of claim 3 wherein the catalyst composition further comprises manganese, molybdenum, and/or zinc.

13. The process of claim 3 wherein the catalyst composition has a loading of the catalytically active component of about 0.1 wt. % or greater.

14. The process of claim 3 wherein the catalytically active component is primarily present on surficial pores of the shaped porous carbon product to form a shell layer with a thickness of from about 10 μm to about 400 μm.

15. The process of claim 3 wherein the catalyst composition comprises an inner region and outer region and the outer region has a greater concentration of the catalytically active component than the inner region.

16. The process of claim 15 wherein the outer region concentration of the catalytically active component is at least 2 times greater than the inner region concentration of the catalytically active component.

17. The process of claim 15 wherein the catalyst composition has an average diameter and the outer region constitutes from about 5% to 50% of the average diameter and/or the inner region constitutes from about 20% to about 80% of the average diameter.

18. The process of claim 3 wherein the reaction zone further comprises a co-catalyst comprising a base.

19. The process of claim 3 wherein the reaction is conducted at a pH of from about 7 to about 11.

20. The process of claim 3 wherein the reaction is conducted at a temperature of from about 150° C. to about 300° C.

21. The process of claim 3 wherein the feed composition comprises an aqueous glycerol solution.

22. The process of claim 3 wherein the feed composition has a glycerol concentration of about 10 wt % or greater.

23. The process of claim 3 wherein the feed composition further comprises at least one other polyol selected from the group consisting of five- and six-carbon sugars and sugar alcohols.

24. The process of claim 3 wherein at least about 35% of the pore volume of the shaped porous carbon product, as measured by the BJH method on the basis of pores having a diameter from 1.7 nm to 100 nm, is attributable to pores having a mean pore diameter of from about 20 nm to about 90 nm.

25. The process of claim 3 wherein about 10% or less of the pore volume of the shaped porous carbon product as measured by mercury porosimetry is attributable to pores having a mean pore diameter of about 100 nm or greater.

26. The process of claim 3 wherein the reaction is conducted at a pH of from about 8 to about 14.

\* \* \* \* \*